US012139730B2

(12) United States Patent
Nishida

(10) Patent No.: US 12,139,730 B2
(45) Date of Patent: Nov. 12, 2024

(54) COMPLEX FOR GENOME EDITING HAVING STABILITY AND FEW SIDE-EFFECTS, AND NUCLEIC ACID CODING SAME

(71) Applicant: NATIONAL UNIVERSITY CORPORATION KOBE UNIVERSITY, Kobe (JP)

(72) Inventor: Keiji Nishida, Kobe (JP)

(73) Assignee: NATIONAL UNIVERSITY CORPORATION KOBE UNIVERSITY, Kobe (JP)

( * ) Notice: Subject to any disclaimer, the term of this patent is extended or adjusted under 35 U.S.C. 154(b) by 477 days.

(21) Appl. No.: 16/764,799

(22) PCT Filed: Nov. 21, 2018

(86) PCT No.: PCT/JP2018/042915

§ 371 (c)(1), (2) Date: May 15, 2020

(87) PCT Pub. No.: WO2019/103020

PCT Pub. Date: May 31, 2019

(65) Prior Publication Data

US 2021/0024906 A1 Jan. 28, 2021

(30) Foreign Application Priority Data

Nov. 22, 2017 (JP) ................................ 2017-225221

(51) Int. Cl.

*C12N 9/22* (2006.01)
*C12N 9/24* (2006.01)
*C12N 9/78* (2006.01)
*C12N 15/113* (2010.01)

(52) U.S. Cl.

CPC ............ *C12N 9/22* (2013.01); *C12N 9/2497* (2013.01); *C12N 9/78* (2013.01); *C12N 15/113* (2013.01); *C07K 2319/40* (2013.01); *C07K 2319/80* (2013.01); *C12N 2310/20* (2017.05)

(58) Field of Classification Search

CPC ...................................................... C12N 9/22

See application file for complete search history.

(56) References Cited

U.S. PATENT DOCUMENTS

2016/0362667 A1 12/2016 Donohoue et al.
2017/0073670 A1 3/2017 Nishida et al.
2018/0230494 A1 8/2018 Joung et al.
2018/0245075 A1* 8/2018 Khalil ................. C12Y 201/01
2020/0370058 A1* 11/2020 Davis ................ C12N 15/1079

FOREIGN PATENT DOCUMENTS

CN 104531632 A 4/2015
EP 3201340 A1 8/2017
WO WO 2015/133554 A1 9/2015
WO WO 2016/054326 A1 4/2016
WO WO 2016/205613 A1 12/2016

OTHER PUBLICATIONS

Hentschel et al., "Destabilized eYFP variants for dynamic gene expression studies in Corynebacterium glutamicum," Microb. Biotechnol., 6(2): 196-201 (2012).

Canadian Patent Office, Examination Report in Canadian Patent Application No. 3,082,922 (Jun. 18, 2021).

European Patent Office, Extended European Search Report in European Patent Application No. 18882051.8 (Jul. 21, 2021).

Andersen et al., "New Unstable Variants of Green Fluorescent Protein for Studies of Transient Gene Expression in Bacteria," *Appl. Environ. Microbiol.*, 64(6): 2240-2246 (1998).

Banno et al., "Deaminase-mediated multiplex genome editing in *Escherichia coli*," *Nat. Microbiol.*, 3(4): 423-429 (2018).

Bowater et al., "Making Ends Meet: Repairing Breaks in Bacterial DNA by Non-Homologous End-Joining," *PLoS Genet.*, 2(2): e8 (2006).

Cong et al., "Multiplex Genome Engineering Using CRISPR/Cas Systems," *Science*, 339(6121): 819-823 (2013).

Costantino et al., "Enhanced levels of λ Red-mediated recombinants in mismatch repair mutants," *Proc. Natl. Acad. Sci. U.S.A.*, 100(26): 15748-15753 (2003).

Cui et al., "Consequences of Cas9 cleavage in the chromosome of *Escherichia coli*," *Nucleic Acids Res.*, 44(9): 4243-4251 (2016).

Datsenko et al., "One-step inactivation of chromosomal genes in *Escherichia coli* K-12 using PCR products," *Proc. Natl. Acad. Sci. U.S.A.*, 97(12): 6440-6445 (2000).

Jiang et al., "RNA-guided editing of bacterial genomes using CRISPR-Cas systems," *Nat. Biotechnol.*, 31(3): 233-239 and Online Methods (2013).

Komor et al., "Programmable editing of a target base in genomic DNA without double-stranded DNA cleavage," *Nature*, 533(7603): 420-424 and Online Methods (2016).

Li et al., "Metabolic engineering of *Escherichia coli* using CRISPR—Cas9 meditated genome editing," *Metab. Eng.*, 31: 13-21 (2015).

Ma et al., "Targeted AID-mediated mutagenesis (TAM) enables efficient genomic diversification in mammalian cells," *Nat. Methods*, 13(12): 1029-1035 and Online Methods (2016).

Mali et al., "RNA-Guided Human Genome Engineering via Cas9," *Science*, 339 (66121): 823-826 (2013).

(Continued)

*Primary Examiner* — Suzanne M Noakes

(74) *Attorney, Agent, or Firm* — Leydig, Voit & Mayer, Ltd.

(57) ABSTRACT

The present invention provides a complex containing a nucleic acid sequence-recognizing module and a proteolysis tag, wherein the module is linked to the proteolysis tag, the module specifically binds to a target nucleotide sequence in a double stranded DNA, and the tag consists of (i) a peptide containing 3 hydrophobic amino acid residues at the C-terminal, or (ii) a peptide containing 3 amino acid residues at the C-terminal wherein at least a part of the amino acid residues is substituted by serine.

15 Claims, 13 Drawing Sheets

Specification includes a Sequence Listing.

(56) References Cited

OTHER PUBLICATIONS

Nishida et al., "Targeted nucleotide editing using hybrid prokaryotic and vertebrate adaptive immune systems," *Science*, 353(6305): aaf8729 (2016).
Nishida et al., "Base conversion-type genome editing technology, Usage of Target-AID," *Experimental Medicine*, 35(4): 613-618 (2017).
Wang et al., "An Improved Recombineering Approach by Adding RecA to λ Red Recombination," *Mol. Biotechnol.*, 32(1): 43-53 (2006).
Japanese Patent Office, International Search Report in International Patent Application No. PCT/JP2018/042915 (Feb. 5, 2019).
Canadian Intellectual Property Office, Examination Report in Canadian Patent Application No. 3,082,922 (Apr. 29, 2022).
Japan Patent Office, Notice of Reasons for Refusal in Japanese Patent Application No. 2019-555327 (Sep. 30, 2022).
China National Intellectual Property Administration, First Office Action in Chinese Patent Application No. 201880075854.2 (Feb. 10, 2023).
U.S. Appl. No. 18/634,640, filed Apr. 12, 2024.
Brazil National Institute of Industrial Property, Written Opinion in Brazilian Patent Application No. BR112020010036 (Mar. 1, 2024).

* cited by examiner

Fig. 3

```
                 310                329
galK_9      5' GCGTGGTGAAACATCTGCAACTGCGTAACAACAGCTTCGGCGGCGTGGACAT 3'
            3' CGCACCACTTTGTAGACGTTGACGCATTGTTGTCGAAGCCGCCGCACCTGTA 5'
translation     V  V  K  H  L  Q  L  R  N  N  S  F  G  G  V  D

(4/8)          GCGTGGTGAAACATCTGTAATTGCGTAACAACAGCTTCGGCGGCGTGGACAT
                V  V  K  H  L  *

(2/8)          GCGTGGTGAAACATCTGTAACTGCGTAACAACAGCTTCGGCGGCGTGGACAT
                V  V  K  H  L  *

(2/8)          GCGTGGTGAAACATCTGCAACTGCGTAACAACAGCTTCGGCGGCGTGGACAT
clone           V  V  K  H  L  Q  L  R  N  N  S  F  G  G  V  D
count
```

Fig. 4
a
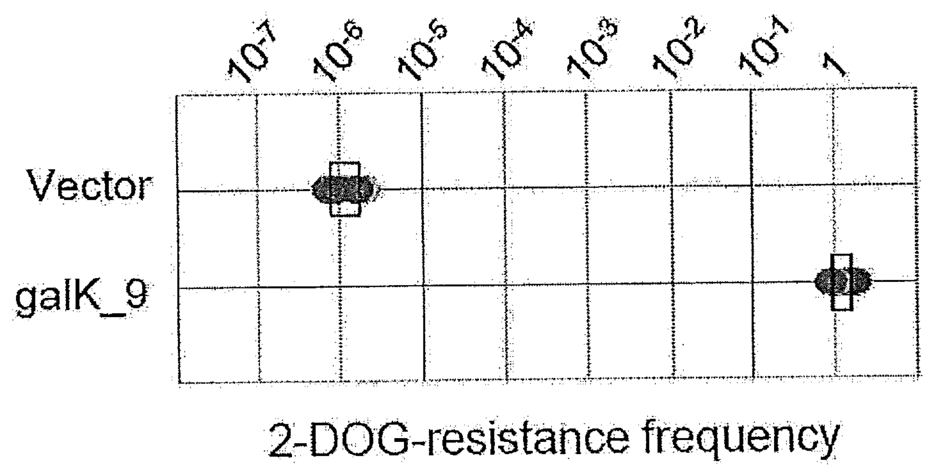
b
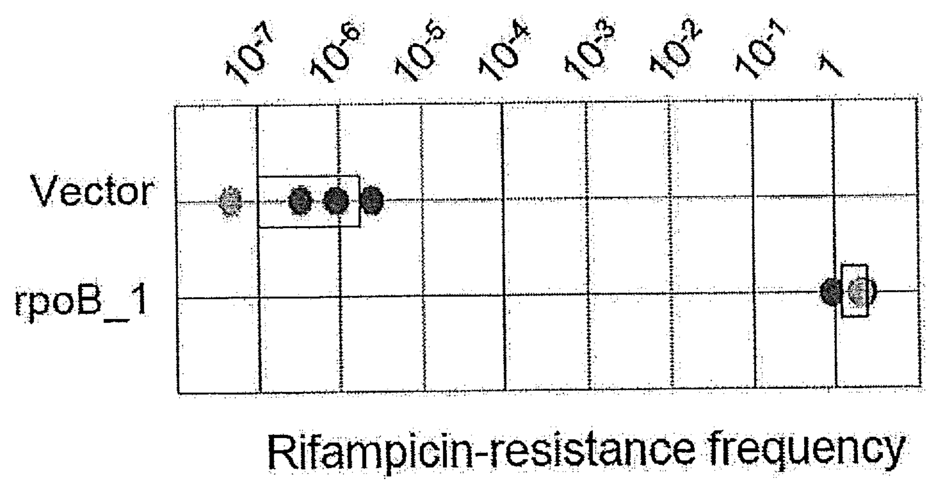

Fig 5 a

```
                 1530                 1549
          5' CTTCGGTTCCAGCCAGCTGTCTCAGTTTATGGACCAGAACAACCCGCTGT 3'
rpoB_1    3' GAAGCCAAGGTCGGTCGACAGAGTCAAATACCTGGTCTTGTTGGGCGACA 5'
translation  F  G  S  S  Q  L  S  Q  F  M  D  Q  N  N  P  L

(7/8)  CTTCGGTTCCAGCCAGCTGTCTCAGTTTATGAACCAGAACAACCCGCTGT
        F  G  S  S  Q  L  S  Q  F  M  N  Q  N  N  P  L

(1/8)  CTTCGGTTCCAGCCAGCTGTCTCAGTTTATAAACCAGAACAACCCGCTGT
clone   F  G  S  S  Q  L  S  Q  F  I  N  Q  N  N  P  L
count
```

b

| Strain | Clone | Sequence coverage | Parental/ variable mutation | Detected mutation | | | | |
|---|---|---|---|---|---|---|---|---|
| | | | | count | region | gene | reference | allele |
| dCas-CDA /rpoB_1 | 1 | 27.9 | 2 | 2 | 1591287<br>4172717 | *yneO*<br>*rpoB* | C<br>GG | T<br>AA |
| | 2 | 22.1 | 3 | 3 | 2170816<br>4056442<br>4172717 | *gatC*<br>*yihN*<br>*rpoB* | G<br>C<br>GG | A<br>A<br>AA |
| | 3 | 51.1 | 1 | 1 | 4172717 | *rpoB* | GG | AA |

c

*yneO* 5' ACATTAAGTTCACCGTCGCCAGCATCACCGATATAGATATAGCGGAAAGCT 3'

*gatC* 5' GTGAAAGGCAAAAAAACGGGCTCCCGATAGGGAAGCCGTAGCAAAGTGCGG 3'

*yihN* 5' GGTGGACCGATTGGTGGCATGATTTCAGATAAGATGCTGAAATCGCCAAGT 3'

Fig. 7

| Name | Position | Strand | GC contents | Missense or Nonsense | Mutation frequency (%) | Sequence (5'->3') | PAM |
|---|---|---|---|---|---|---|---|
| galK_1 | 25-44 | + | 9/20 | M | 71.8 | TCT**C**TGTTTGCCAACGCATT | TGG |
| galK_2 | 51-70 | + | 12/20 | M | 90.4 | CC**C**TGCCACTCACACCATTC | AGG |
| galK_3 | 58-77 | + | 12/20 | M | 93.9 | ACT**C**ACACCATTCAGGCGCC | TGG |
| galK_4 | 76-95 | + | 11/20 | M | 13.9 | C**C**TGGCCGCGTGAATTTGAT | TGG |
| galK_5 | 186-205 | - | 10/20 | M | 1.4 | CTG**C**CATCACGCGAACTTTA | CGG |
| galK_6 | 239-258 | - | 12/20 | M | 95.1 | TG**C**GACAATGGGCGCATCGA | GGG |
| galK_7 | 254-273 | + | 7/20 | M | 22.0 | TCG**C**ACATGAAAACTATCAA | TGG |
| galK_8 [20 nt] | 271-290 | + | 10/20 | N | 49.0 | **C**AATGGGCTAACTACGTTCG | TGG |
| galK_8 [21 nt] | 270-290 | + | 10/21 | N | 91.8 | T**C**AATGGGCTAACTACGTTCG | TGG |
| galK_9 [20 nt] | 310-329 | + | 9/20 | N, M | 90.4 | CAA**C**TGCGTAACAACAGCTT | CGG |
| galK_9 [21 nt] | 309-329 | + | 10/21 | N, M | 1.1 | G**C**AACTGCGTAACAACAGCTT | CGG |
| galK_10 | 392-411 | - | 12/20 | M | 2.8 | GAC**C**GCGACTTCCAGTGAAG | CGG |
| galK_11 [20 nt] | 426-445 | + | 11/20 | N, M | 35.5 | G**C**AGCTTTATCATCTGCCGC | TGG |
| galK_11 [23 nt] | 423-445 | + | 13/23 | N, M | 9.2 | GCAG**C**AGCTTTATCATCTGCCGC | TGG |
| galK_12 | 456-475 | + | 10/20 | N | 3.2 | A**C**AAATCGCGCTTAACGGTC | AGG |
| galK_13 [20 nt] | 490-509 | + | 9/20 | N | 17.2 | **C**AGTTTGTAGGCTGTAACTG | CGG |
| galK_13 [21 nt] | 489-509 | + | 10/21 | N | 42.9 | C**C**AGTTTGTAGGCTGTAACTG | CGG |
| galK_14 | 520-539 | + | 10/20 | N | 61.7 | GAT**C**AGCTAATTTCCGCGCT | CGG |

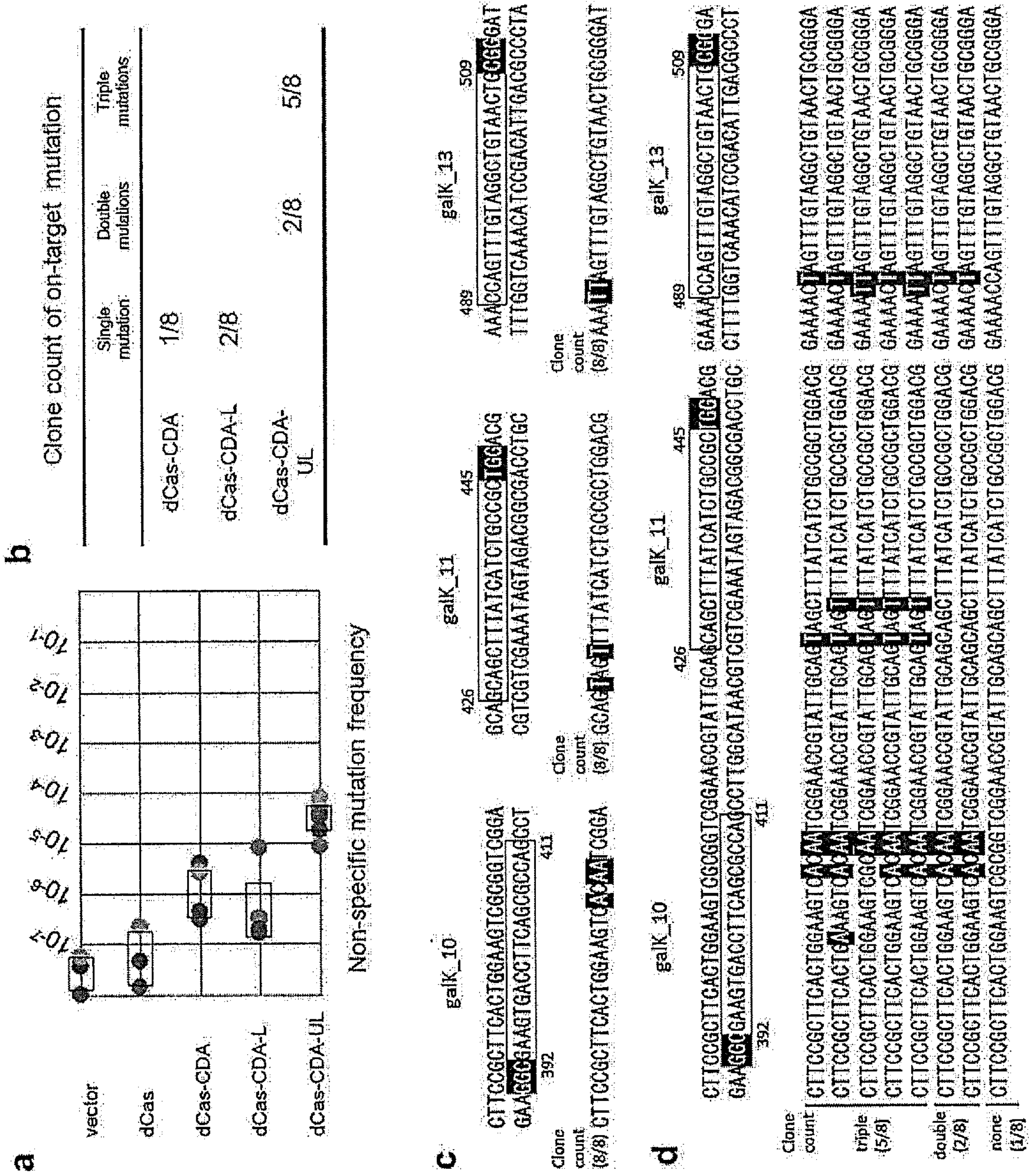
Fig. 9
a
vector
dCas
dCas-CDA
dCas-CDA-L
dCas-CDA-UL
10-7
10-6
10-5
10-4
10-3
10-2
10-1
Non-specific mutation frequency
b
Clone count of on-target mutation
Single mutation
Double mutations
Triple mutations
dCas-CDA 1/8
dCas-CDA-L 2/8
dCas-CDA-UL 2/8 5/8
c
galK_10
CTTCCGCTTCACTGGAAGTCGCGGTCGGA
GAAGGCGAAGTGACCTTCAGCGCCAGCCT
392
411
Clone count
(8/8) CTTCCGCTTCACTGGAAGTCACAATCGGA
galK_11
426
445
GCAGCAGCTTTATCATCTGCCGCTGGACG
CGTCGTCGAAATAGTAGACGGCGACCTGC
Clone count
(8/8) GCAGTAGTTTTATCATCTGCCGCTGGACG
galK_13
489
509
AAACCAGTTTGTAGGCTGTAACTGCGGGAT
TTTGGTCAAACATCCGACATTGACGCCCTA
Clone count
(8/8) AAATTAGTTTGTAGGCTGTAACTGCGGGAT
d
galK_10
galK_11
galK_13
426
445
489
509
CTTCCGCTTCACTGGAAGTCGCGGTCGGAACCGTATTGCAGCAGCTTTATCATCTGCCGCTGGACG
GAAGGCGAAGTGACCTTCAGCGCCAGCCTTGGCATAACGTCGTCGAAATAGTAGACGGCGACCTGC
GAAAACCAGTTTGTAGGCTGTAACTGCGGGA
CTTTTGGTCAAACATCCGACATTGACGCCCT
392
411
Clone count
triple (5/8)
double (2/8)
none (1/8)
CTTCCGCTTCACTGGAAGTCACAATCGGAACCGTATTGCAGTAGCTTTATCATCTGCCGCTGGACG GAAAACTAGTTTGTAGGCTGTAACTGCGGGA
CTTCCGCTTCACTGAAAGTCACAATCGGAACCGTATTGCAGTAGTTTTATCATCTGCCGCTGGACG GAAAACTAGTTTGTAGGCTGTAACTGCGGGA
CTTCCGCTTCACTGGAAGTCGCAATCGGAACCGTATTGCAGTAGTTTTATCATCTGCCGCTGGACG GAAAATTAGTTTGTAGGCTGTAACTGCGGGA
CTTCCGCTTCACTGGAAGTCACAATCGGAACCGTATTGCAGTAGTTTTATCATCTGCCGCTGGACG GAAAACTAGTTTGTAGGCTGTAACTGCGGGA
CTTCCGCTTCACTGGAAGTCACAATCGGAACCGTATTGCAGTAGTTTTATCATCTGCCGCTGGACG GAAAATTAGTTTGTAGGCTGTAACTGCGGGA
CTTCCGCTTCACTGGAAGTCACAATCGGAACCGTATTGCAGCAGCTTTATCATCTGCCGCTGGACG GAAAACTAGTTTGTAGGCTGTAACTGCGGGA
CTTCCGCTTCACTGGAAGTCACAATCGGAACCGTATTGCAGCAGCTTTATCATCTGCCGCTGGACG GAAAACTAGTTTGTAGGCTGTAACTGCGGGA
CTTCCGCTTCACTGGAAGTCGCGGTCGGAACCGTATTGCAGCAGCTTTATCATCTGCCGCTGGACG GAAAACCAGTTTGTAGGCTGTAACTGCGGGA

| | Position | Sequence |
|---|---|---|
| IS1 targeted sequence | | CGACGCTGGGGCGTCTTATGAGCCTGCTGTCACCCTTTGACGTGGTGATATGGATGACGGATGGCTGGCCGCTGTATGAATCCCGCCTGA |
| 1-1 | 20037 to 20018 | CGACGCTGGGGCGTCTTATGAGCCTGCTGTCACCCTTTGACGTGGTGATATAAATAACGGATGGCTGGCCGCTGTATGAATCCCGCCTGA |
| 1-3 | 252732 to 252713 | CGACGCTGGGGCGTCTTATGAGCCTGCTGTCACCCTTTGACGTGGTAATATAAATAACGGATGGCTGGCCGCTGTATGAATCCCGCCTGA |
| 1-5 | 265649 to 265630 | CGACGCTGGGGCGTCTTATGAGCCTGCTGTCACCCTTTGACGTGGTAATATAAATGACGGATGGCTGGCCGCTGTATGAATCCCGCCTGA |
| 1-6 | 1103455 to 1103474 | CGACGCTGGGGCGTCTTATGAGCCTGCTGTCACCCTTTGACGTGGTAATATAAATAACGGATGGCTGGCCGCTGTATGAATCCCGCCTGA |
| 1-7 | 3679722 to 3679741 | CGACGCTGGGGCGTCTTATGAGCCTGCTGTCACCCTTTGACGTAGTGATATAAATAACGGATGGCTGGCCGCTGTATGAATCCCGCGTGA |
| 1-8 | 1339869 to 1339850 | CGACGCTGGGGCGTCTTATGAGCCTGCTGTCACCCTTTGACGTGGTAATATAAATAACGGATGGCTGGCCGCTGTATGAATCCCGCCTGA |
| 1-9 | 2472071 to 2472052 | CGACGCTGGGGCGTCTTATGAGCCTGCTGTCACCCTTTGACGTGGTAATATAAATAACGGATGGCTGGCCGCTGTATGAATCCCGCGTGA |
| 1-10 | 2896143 to 2896124 | CGACGCTGGGGCGTCTTATGAGCCTGCTGTCACCCTTTGACGTGGTGATATAAATAACGGATGGCTGGCCGCTGTATGAATCCCGCCTGA |
| 1-11 | 4166876 to 4166857 | CGACGCTGGGGCGTCTTATGAGCCTGCTGTCACCCTTTGACGTGGTGATATAAATAACGGATGGCTGGCCGCTGTATGAATCCCGCCTGA |
| 1-12 | 4387721 to 4387702 | CGACGCTGGGGCGTCTTATGAGCCTGCTGTCACCCTTTGACGTGGTAATATAAATAACGGATGGCTGGCCGCTGTATGAATCCCGCCTGA |

G A V E R R F G N D L P S S P V E W L T D N G S C Y R A N

| | Position | Sequence |
|---|---|---|
| IS2 targeted sequence | | GGAGCGGTGGAACGCCGCTTCGGCAACGATCTTCCGTCGTCTCCAGTGGAGTGGCTGACGGATAATGGTTCATGCTACCGGGCTAATGAA |
| 2-1 | 3282844 to 3282863 | GGAGCGGTGGAACGCCGCTTCGGCAACGATCTTCCGTCGTCTCCAGTGAAATAACTGACGGATAATGGTTCATGCTACCGGGCTAATGAA |
| 2-2 | 2158322 to 2158303 | GGAGCGGTGGAACGCCGCTTCGGCAACGATCTTCCGTCGTCTCCAGTGGAATAACTAACGGATAATGGTTCATGCTACCGGGCTAATGAA |
| 2-4 | 320796 to 320815 | GGAGCGGTGGAACGCCGCTTCGGCAAGGATCTTCCGTCGTCTCCAGTGAAATAACTGACGGATAATGGTTCATGCTACCGGGCTAATGAA |
| 2-5 | 1556878 to 1556859 | GGAGCGGTGGAACGCCGCTTCGGCAACGATCTTCCGTCGTCTCCAGTGGAATAACTGACGGATAATGGTTCATGCTACCGGGCTAATGAA |
| 2-6 | 1738848 to 1738867 | GGAGCGGTGGAACGCCGCTTCGGCAACGATCTTCCGTCGTCTCCAGTGAAATAACTGACGGATAATGGTTCATGCTACCGGGCTAATGAA |
| 2-7 | 4598993 to 4599012 | GGAGCGGTGGAACGCCGCTTCGGCAACGATCTTCCGTCGTCTCCAGTGAAATAACTGACGGATAATGGTTCATGCTACCGGGCTAATGAA |
| 2-8 | 841962 to 841981 | GGAGCGGTGGAACGCCGCTTCGGCAACGATCTTCCGTCGTCTCCAGTGAAATAACTGACGGATAATGGTTCATGCTACCGGGCTAATGAA |
| 2-9 | 1147637 to 1147618 | GGAGCGGTGGAACGCCGCTTCGGCAACGATCTTCCGTCGTCTCCAGTGAAATAACTGACGGATAATGGTTCATGCTACCGGGCTAATGAA |
| 2-10 | 1739835 to 1739854 | GGAGCGGTGGAACGCCGCTTCGGCAACGATCTTCCGTCGTCTCCAGTGAAATAACTGACGGATAATGGTTCATGCTACCGGGCTAATGAA |
| 2-11 | 3004291 to 3004310 | GGAGCGGTGGAACGCCGCTTCGGCAACGATCTTCCGTCGTCTCCAGTGAAATAACTGACGGATAATGGTTCATGCTACCGGGCTAATGAA |
| 2-12 | 3088583 to 3088602 | GGAGCGGTGGAACGCCGCTTCGGCAACGATCTTCCGTCGTCTCCAGTAAAATAACTGACGGATAATGGTTCATGCTACCGGGCTAATGAA |
| 2-13 | 4034925 to 4034944 | GGAGCGGTGGAACGCCGCTTCGGCAACGATCTTCCGTCGTCTCCAGTGAAATAACTAACGGATAATGGTTCATGCTACCGGGCTAATGAA |

I K A M C R V L R V A R S G W Y T W C G R R T R I S T R Q A

| | Position | Sequence |
|---|---|---|
| IS3 targeted sequence | | CATCAAAGCAATGTGCCGCGTGCTCCGGGTGGCCCGCAGCGGCTGGTATACGTGGTGTCAGCGGCGGACAAGGATAAGCACGCGTCAGCA |
| 3-1 | 290438 to 290457 | CATCAAAGCAATGTGCCGCGTGCTCCGGGTGGCCCGCAGCGGCTAGTATACATAATGTCAGCGGGGGACAAGGATAAGCACGCGTCAGCA |
| 3-2 | 331083 to 331064 | CATCAAAGCAATGTGCCGCGTGCTCCGGGTGGCCCGCAGCGGCTAGTATACATAATGTCAGCGGCGGACAAGGATAAGCACGCGTCAGCA |
| 3-3 | 505770 to 808789 | CATCAAAGCAATGTGCCGCGTGCTCCGGGTGGCCCGCAGCGGCTGGTATACATAATGTCAGCGGCGGACAAGGATAAGCACGCGTCAGCA |
| 3-4 | 1149551 to 1149551 | CATCAAAGCAATGTGCCGCGTGCTCCGGGTGGCCCGCAGCGGCTGGTATACATAGTGTCAGCGGCGGACAAGGATAAGCACGCGTCAGCA |
| 3-5 | 2259641 to 2259660 | CATCAAAGCAATGTGCCGCGTGCTCCGGGTGGCCCGCAGCGGCTGGTATACATAATGTCAGCGGCGGACAAGGATAAGCACGCGTCAGCA |

K E Q Q R D P E M H Q T K K G N Q W H F G M K A H I G V D

| | Position | Sequence |
|---|---|---|
| IS5 targeted sequence | | AAGAGCAGCAACGCGATCCGGAGATGCATCAGACCAAGAAAGGCAATCAGTGGCACTTTGGCATGAAGGCCCACATTGGTGTCGATGCCA |
| 5-1 | 2478907 to 247888 | AAGAGCAGCAACGCGATCCGGAGATGCATCAGACCAAGAAAGGCAATCAGTAACACTTTGGCATGAAGGCCCACATTGGTGTCGATGCCA |
| 5-2 | 513770 to 513770 | AAGAGCAGCAACGCGATCCGGAGATGCATCAGACCAAGAAAGGCAATCAGTAACACTTTGGCATGAAGGCCCACATTGGTGTCGATGCCA |
| 5-3 | 740290 to 740290 | AAGAGCAGCAACGCGATCCGGAGATGCATCAGACCAAGAAAGGCAATCAATAACACTTTGGCATGAAGGCCCACATTGGTGTCGATGCCA |
| 5-4 | 1515644 to 1515625 | AAGAGCAGCAACGCGATCCGGAGATGCATCAGACCAAGAAAGGCAATCAGTAACACTTTGGCATGAAGGCCCACATTGGTGTCGATGCCA |
| 5-5 | 2155815 to 2155796 | AAGAGCAGCAACGCGATCCGGAGATGCATCAGACCAAGAAAGGCAATCAGTGACACTTTGGCATGAAGGCCCACATTGGTGTCGATGCCA |
| 5-6 | 2191405 to 2191386 | AAGAGCAGCAACGCGATCCGGAGATGCATCAGACCAAGAAAGGCAATCAGTAACACTTTGGCATGAAGGCCCACATTGGTGTCGATGCCA |
| 5-7 | 2378553 to 2378534 | AAGAGCAGCAACGCGATCCGGAGATGCATCAGACCAAGAAAGGCAATCAGTGACACTTTGGCATGAAGGCCCACATTGGTGTCGATGCCA |
| 5-8 | 3461947 to 3461928 | AAGAGCAGCAACGCGATCCGGAGATGCATCAGACCAAGAAAGGCAATCAGTGACACTTTGGCATGAAGGCCCACATTGGTGTCGATGCCA |
| 5-9 | 3748428 to 3748409 | AAGAGCAGCAACGCGATCCGGAGATGCATCAGACCAAGAAAGGCAATCAGTAACACTTTGGCATGAAGGCCCACATTGGTGTCGATGCCA |
| 5-11 | 1484034 to 1484053 | AAGAGCAGCAACGCGATCCGGAGATGCATCAGACCAAGAAAGGCAATCAGTGACACTTTGGCATGAAGGCCCACATTGGTGTCGATGCCA |
| 5-12 | 3226483 to 3226502 | AAGAGCAGCAACGCGATCCGGAAATGCATCAGACCAAGAAAGGCAATCAATAACACTTTGGCATGAAGGCCCACATTGGTGTCGATGCCA |
| 5-13 | 1522356 to 1522337 | AAGAGCAGCAACGCGATCCGGAGATGCATCAGACCAAGAAAGGCAATCAGTAACACTTTGGCATGAAGGCCCACATTGGTGTCGATGCCA |
| 5-14 | 2067709 to 2067728 | AAGAGCAGCAACGCGATCCGGAGATGCATCAGACCAAGAAAGGCAATCAGTAACACTTTGGCATGAAGGCCCACATTGGTGTCGATGCCA |
| 5-15 | 3171208 to 3171189 | AAGAGCAGCAACGCGATCCGGAGATGCATCAGACCAAGAAAGGCAATCAGTAACACTTTGGCATGAAGGCCCACATTGGTGTCGATGCCA |

Fig. 12

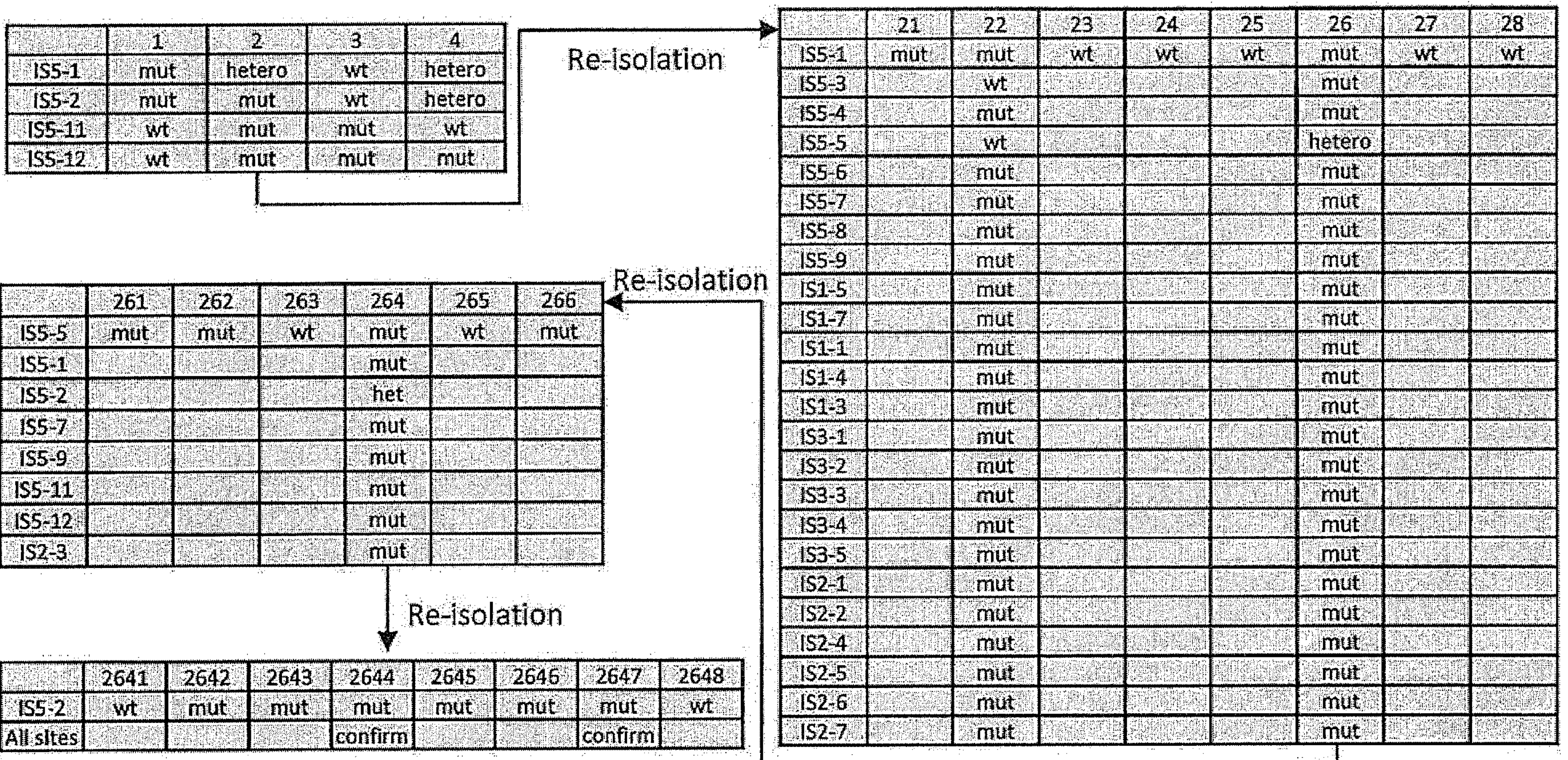

| | 1 | 2 | 3 | 4 |
|---|---|---|---|---|
| IS5-1 | mut | hetero | wt | hetero |
| IS5-2 | mut | mut | wt | hetero |
| IS5-11 | wt | mut | mut | wt |
| IS5-12 | wt | mut | mut | mut |

| | 21 | 22 | 23 | 24 | 25 | 26 | 27 | 28 |
|---|---|---|---|---|---|---|---|---|
| IS5-1 | mut | mut | wt | wt | wt | mut | wt | wt |
| IS5-3 | | wt | | | | mut | | |
| IS5-4 | | mut | | | | mut | | |
| IS5-5 | | wt | | | | hetero | | |
| IS5-6 | | mut | | | | mut | | |
| IS5-7 | | mut | | | | mut | | |
| IS5-8 | | mut | | | | mut | | |
| IS5-9 | | mut | | | | mut | | |
| IS1-5 | | mut | | | | mut | | |
| IS1-7 | | mut | | | | mut | | |
| IS1-1 | | mut | | | | mut | | |
| IS1-4 | | mut | | | | mut | | |
| IS1-3 | | mut | | | | mut | | |
| IS3-1 | | mut | | | | mut | | |
| IS3-2 | | mut | | | | mut | | |
| IS3-3 | | mut | | | | mut | | |
| IS3-4 | | mut | | | | mut | | |
| IS3-5 | | mut | | | | mut | | |
| IS2-1 | | mut | | | | mut | | |
| IS2-2 | | mut | | | | mut | | |
| IS2-4 | | mut | | | | mut | | |
| IS2-5 | | mut | | | | mut | | |
| IS2-6 | | mut | | | | mut | | |
| IS2-7 | | mut | | | | mut | | |

| | 261 | 262 | 263 | 264 | 265 | 266 |
|---|---|---|---|---|---|---|
| IS5-5 | mut | mut | wt | mut | wt | mut |
| IS5-1 | | | | mut | | |
| IS5-2 | | | | het | | |
| IS5-7 | | | | mut | | |
| IS5-9 | | | | mut | | |
| IS5-11 | | | | mut | | |
| IS5-12 | | | | mut | | |
| IS2-3 | | | | mut | | |

| | 2641 | 2642 | 2643 | 2644 | 2645 | 2646 | 2647 | 2648 |
|---|---|---|---|---|---|---|---|---|
| IS5-2 | wt | mut | mut | mut | mut | mut | mut | wt |
| All sites | | | | confirm | | | confirm | |

COMPLEX FOR GENOME EDITING HAVING STABILITY AND FEW SIDE-EFFECTS, AND NUCLEIC ACID CODING SAME

CROSS-REFERENCE TO RELATED APPLICATIONS

This patent application is the U.S. national phase of International Patent Application No. PCT/JP2018/042915, filed on Nov. 21, 2018, which claims the benefit of Japanese Patent Application No. 2017-225221 filed on Nov. 22, 2017, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 183,521 bytes ASCII (Text) file named "749459-ReplacementSequenceListing.txt" created Feb. 28, 2023.

TECHNICAL FIELD

The present invention relates to a complex for genome editing which is stable and causes few side effects, a nucleic acid encoding same, and a genome editing method using the complex.

BACKGROUND ART

Genome editing that does not require incorporation of a selection marker gene and can minimize the effect on expression of downstream genes in the same operon is particularly advantageous in prokaryotes. Phage-derived RecET and λ-Red recombinases have been used as recombinant techniques and facilitate homology-dependent incorporation/substitution of donor DNA or oligonucleotides (e.g., non-patent literature 1). By combining with a strain deficient in methyl-directed mismatch repair (MMR), highly efficient recombination can be achieved without incorporating a selectable marker (non-patent literature 2), and genetic diversity at multiple target loci can be achieved within several days. Thus, the technique is utilized in multiplex automated genome engineering (MAGE). However, the aforementioned recombination technique relies on MMR deficiency and host-dependent factors such as RecA, which is a central constituent element of the recombinant DNA repair system, and damages most *Escherichia coli* used as a host for cloning. Therefore, it cannot be easily applied to bacterial species with a different background (non-patent literature 3).

CRISPR (clustered regularly interspaced short palindromic repeats) and CRISPR-associated (Cas) protein are known to work as a bacterial adaptive immune system by cleaving target DNA in a manner dependent on a single guide RNA (sgRNA) and protospacer is adjacent motif (PAM). Cas9 nuclease from Streptococcus pyogenes is widely used as a powerful genome editing tool in eukaryotes having a double-stranded DNA break (DSB) repair pathway (e.g., non-patent literatures 4, 5). During the repair of DSB by the non-homologous end joining (NHEJ) pathway, a small insertion and/or deletion (indels) are/is introduced into the target DNA, and site-specific mutation or gene destruction occurs. Even though the efficiency depends on the host cell, homologous recombination repair (HDR) can be promoted by providing a donor DNA containing a homology arm to the target region for more accurate editing.

However, since the genome editing technique at present relies on the DNA repair system of the host, application to prokaryotes requires further designing. In most bacteria, DNA cleavage by artificial nucleases results in cell death due to the lack of the NHEJ pathway (non-patent literatures 6, 7). Therefore, CRISPR/Cas9 is used only as a counter-selector for cells with altered genes in other methods, such as the λ-Red recombination system (e.g., non-patent literatures 8, 9).

Recently, deaminase-mediated target base editing has been demonstrated in which nucleotides are directly edited at the target gene locus without using donor DNA containing a homology arm for the target region (e.g., patent literature 1, non-patent literatures 10-12). Since this technique utilizes DNA deamination instead of nuclease-mediated DNA cleavage, it does not induce bacterial cell death and is applicable to genome editing of bacteria. However, its mutation efficiency, especially the efficiency of simultaneous editing of multiple sites, is not sufficient.

CITATION LIST

Patent Literature patent literature 1: WO 2015/133554

Non-Patent Literature non-patent literature 1: Datsenko, K. A. & Wanner, B. L., Proc. Natl. Acad. Sci. U. S. A. 97, 6640-5 (2000).

non-patent literature 2: Costantino, N. & Court, D. L., Proc. Natl. Acad. Sci. U. S. A. 100, 15748-53 (2003).

non-patent literature 3: Wang, J. et al., Mol. Biotechnol. 32, 43-53 (2006).

non-patent literature 4: Mali, P. et al., Science 339, 823-827 (2013).

non-patent literature 5: Cong, L. et al., Science 339, 819-823 (2013).

non-patent literature 6: Bowater, R. & Doherty, A. J., PLoS Genet. 2, 93-99 (2006).

non-patent literature 7: Cui, L. & Bikard, D., Nucleic Acids Res. 44, 4243-4251 (2016).

non-patent literature 8: Jiang, W. et al., Nat Biotechnol 31, 233-239 (2013).

non-patent literature 9: Li, Y. et al., Metab. Eng. 31, 1-9 (2015).

non-patent literature 10: Komor, A. C. et al., Nature 61, 5985-91 (2016) .

non-patent literature 11: Nishida, K. et al., Science 102, 553-563 (2016).

non-patent literature 12: Ma, Y. et al., Nat. Methods 1-9 (2016). doi:10.1038/nmeth.4027

SUMMARY OF INVENTION

Technical Problem

Conventional vectors for genome editing impose heavy burden on hosts, particularly bacteria, and may make the vector unstable in the host, due to a high toxicity of the complex for genome editing that is expressed from the vector and acts on the genomic DNA of the host. In genome editing, side effects such as non-specific mutation, off-target mutation and the like occur. Particularly, when the mutation efficiency is increased using uracil DNA glycosylase inhibitor (UGI) and the like, a strong toxicity to the host occurs in response, and cell death, an increase in the non-specific mutation rate and the like occur. Therefore, an object of the present invention is to provide a nucleic acid such as a vector having low toxicity that can be stably amplified even in a host, and a complex for genome editing encoded by the nucleic acid, and a method for genome editing using the vector, and a nucleic acid altering enzyme as necessary, which method does not rely on host-dependent factors such as RecA, can alter DNA of bacterium while suppressing non-specific mutation and the like, and is applicable to a wide range of bacteria.

Solution to Problem

The present inventor had an idea that a vector in a bacterium may be stabilized and non-specific mutation of bacterial DNA and the like may be reduced by suppressing the amount of a complex for genome editing present in the bacterium which has high toxicity to the bacterium as a host. To suppress the amount of a complex for genome editing, the inventor took note of LVA tag which is a proteolysis tag known to promote degradation of proteins in bacteria and shorten the half-life, and proceeded with the research. As a result, the inventor has demonstrated that non-specific mutation can be reduced while maintaining mutation efficiency into the target site by adding a proteolysis tag to a complex for genome editing and that even when UGI is combined, non-specific mutation can be reduced and the target sequence can be altered with high efficiency (FIG. 9, FIG. 10). The present inventor conducted further studies and completed the present invention.

Accordingly, the present invention provides the following.

[1] A complex comprising a nucleic acid sequence-recognizing module and a proteolysis tag, wherein the module is linked to the proteolysis tag, the module specifically binds to a target nucleotide sequence in a double stranded DNA, and the tag consists of (i) a peptide containing 3 hydrophobic amino acid residues at the C-terminal, or (ii) a peptide containing 3 amino acid residues at the C-terminal wherein at least a part of the amino acid residues is substituted by serine.

[2] The complex of [1], wherein the aforementioned complex is further bound with a nucleic acid altering enzyme, and converts one or more nucleotides in the targeted site to other one or more nucleotides or deletes them, or insert one or more nucleotides in the targeted site.

[3] The complex of [1] or [2], wherein the aforementioned 3 amino acid residues are leucine-valine-alanine, leucine-alanine-alanine, alanine-alanine-valine or alanine-serine-valine.

[4] The complex of any of [1] to [3], wherein the aforementioned nucleic acid sequence-recognizing module is a CRISPR-Cas system in which only one of the two DNA cleavage abilities of Cas or both DNA cleavage abilities are inactivated.

[5] The complex of any of [1] to [3], wherein the aforementioned complex is a complex in which the proteolysis tag is bound to a CRISPR-Cas system.

[6] The complex of any of [2] to [4], wherein the aforementioned nucleic acid altering enzyme is a nucleic acid base converting enzyme or a DNA glycosylase.

[7] The complex of [6], wherein the aforementioned nucleic acid base converting enzyme is deaminase.

[8] The complex of [6] or [7] , wherein a base excision repair inhibitor is further bound to the complex.

[9] A nucleic acid encoding the complex of any of [1] to [8].

[10] A method for altering a targeted site of a double stranded DNA of a bacterium, or regulating an expression of a gene encoded by a double-stranded DNA near the site, comprising a step of bringing a complex comprising a nucleic acid sequence-recognizing module specifically binding to a target nucleotide sequence in a selected double stranded DNA and a proteolysis tag, wherein the proteolysis tag consists of (i) a peptide containing 3 hydrophobic amino acid residues at the C-terminal, or (ii) a peptide containing 3 amino acid residues at the C-terminal wherein at least a part of the amino acid residues is substituted by serine into contact with the double stranded DNA.

[11] The method of [10], comprising a step of converting one or more nucleotides in the targeted site to other one or more nucleotides or delete one or more nucleotides, or inserting one or more nucleotides into said targeted site, wherein the aforementioned complex is further bound with a nucleic acid altering enzyme.

[12] The method of [10] or [11], wherein the aforementioned 3 amino acid residues are leucine-valine-alanine, leucine-alanine-alanine, alanine-alanine-valine or alanine-serine-valine.

[13] The method of any of [10] to [12], wherein the aforementioned nucleic acid sequence-recognizing module is a CRISPR-Cas system in which only one of the two DNA cleavage abilities of Cas or both DNA cleavage abilities are inactivated.

[14] The method of any of [10] to [12], wherein the aforementioned complex is a complex in which the proteolysis tag is bound to a CRISPR-Cas system.

[15] The method of any of [10] to [14], wherein two or more kinds of nucleic acid sequence-recognizing modules each specifically binding to a different target nucleotide sequence are used.

[16] The method of [15], wherein the aforementioned different target nucleotide sequence is present in a different gene.

[17] The method of any of [10] to [13] , [15] and [16], wherein the aforementioned nucleic acid altering enzyme is a nucleic acid base converting enzyme or a DNA glycosylase.

[18] The method of [17], wherein the aforementioned nucleic acid base converting enzyme is deaminase.

[19] The method of [17] or [18], wherein the complex is further bound with a base excision repair inhibitor.

[20] The method of any of [10] to [19] , wherein the double stranded DNA is brought into contact with the complex by introduction the nucleic acid encoding the complex into the bacterium having the double stranded DNA.

Advantageous Effects of Invention

According to the present invention, a nucleic acid (e.g., vector) which is stable and amplifiable even in a host bacterium and has low toxicity, and a complex for genome editing which is encoded by the nucleic acid are provided. According to the method for genome editing using the nucleic acid and nucleic acid altering enzyme of the present invention, it is possible to alter the gene of a host bacterium while suppressing non-specific mutation and the like, or regulate the expression of a gene encoded by a double stranded DNA. Since this method does not rely on host dependent factors such as RecA, it can be applied to a wide range of bacteria.

BRIEF DESCRIPTION OF DRAWINGS

FIG. 3 shows a mutation induced in a specific site of the galK9 gene (5' to 3' is SEQ ID NO: 202, 3' to 5' is SEQ ID NO: 203, and amino acid translation below is SEQ ID NO: 204) by dCas-CDA. DH5α cells expressing dCas-CDA with galK_9 targeting sgRNA were spotted onto the LB agar plate to isolate single colonies. Randomly selected eight clones were sequenced and sequences were aligned. Translated amino acid sequences are shown on the bottom of each nucleotide sequences. Frequency of the aligned sequence is indicated as clone count. Box and inverted box indicate target sequence and PAM sequence, respectively. ORF number is indicated on the top. Mutated sites are highlighted in black shade and mutated bases and amino acids are shown in bold. Mutated codons are underlined. The clones in descending order are SEQ ID NO: 205 (amino acid translation SEQ ID NO: 207), SEQ ID NO: 206 (amino acid translation SEQ ID NO: 207), and SEQ ID NO: 202 (amino acid translation SEQ ID NO: 204).

FIG. 4 shows the mutation frequency assessed by drug resistance. (a) shows the galK mutagenesis and 2-DOG-resistance frequency. DH5α cells expressing dCas-CDA with non-targeting sgRNA (vector) or galK_9 target ssRNA were spotted onto the M63 medium agar plate with or without 2-DOG in serial dilutions, and colonies were counted. (b) shows the rpoB mutagenesis and rifampicin-resistance frequency. Cells expressing dCas-CDA with non-targeting sgRNA (vector) or rpoB_1 target ssRNA were spotted onto the LB agar plate with or without rifampicin in serial dilutions, and colonies were counted. Drug resistance frequency is calculated as a number of drug resistant colonies over that of non-selected colonies. Dots represent four independent experiments and box indicates 95% confidence interval for a geometric mean by t-test analysis.

FIG. 5 shows the gain-of-function mutagenesis of rpoB gene. (a) shows the sequence alignment of rpoB mutations induced by dCas-CDA. DH5a cells expressing dCas-CDA with rpoB_1 targeting sgRNA were spotted onto the LB agar plate to isolate single colonies. Randomly selected eight clones were sequenced and sequences were aligned. Translated amino acid sequences are shown on the bottom of each nucleotide sequences. Frequency of the aligned sequences is indicated as clone count. Box and inverted box indicate target sequence and PAM sequence. ORF number is indicated on the top. Mutated sites are highlighted in black shade and mutated bases and amino acids are shown in bold. Mutated codons are underlined. The rpoB_1 gene 5' to 3' is SEQ ID NO: 208. The rpoB_1 gene 3' to 5' is SEQ ID NO: 209. The amino acid translation of the rpoB_1 gene is SEQ ID NO: 210. The top clone is SEQ ID NO: 211, and the amino acid translation is SEQ ID NO: 212. The bottom clone is SEQ ID NO: 213, and the amino acid translation is SEQ ID NO: 214. (b) shows the results of the whole genome sequencing analyses of rpoB-targeted cells. Rifampicin-selected independent three clones were subjected to whole genome sequencing. Sequence coverage was calculated as sum base pair of mapped sequence over 4,631 Mbp of *Escherichia coli* BW25113 genome sequence. Parental/variable mutation is shown by the number of variants obtained by subtracting common parental mutations from detected variants over 50%frequency including insertions, deletions, single nucleotide variants (SNV) and multiple nucleotide variants (MNV). Detected mutation indicates the number of mutations (count), genomic locus (region/gene), reference genome sequence (reference) and mutant allele (allele). Variant calling was performed as described in Examples. (c) shows the sequences around detected mutations listed in (b). Mutated sites are highlighted in gray shade and mutated bases and amino acid are highlighted in bold. yne0 is SEQ ID NO: 215, gatC is SEQ ID NO: 216, yihN is SEQ ID NO: 217.

FIG. 7 shows the effect of target sequence properties on mutational positions and frequencies for Target-AID. Cells expressing dCas-CDA and each targeting sgRNA were analyzed by deep sequencing. Targeting sequences (20nt length or as indicated) were (+) DNA strand on galK ORF or (−) DNA strand below galK ORF, and expectedly introduced missense (M) or nonsense (N) mutations. Corresponding ORF number is indicated (Position). Mutation frequencies of the peak base position (highlighted in gray shade in the sequence) were obtained as averages of three independent experiments. Mutation frequencies in>50%, 10-50% or <10% are highlighted in shades of gray. The sequence (5'->3') of galK_1 is SEQ ID NO: 226, galK_2 is SEQ ID NO: 227, galK_3 is SEQ ID NO: 228, galK_4 is SEQ ID NO: 229, galK_5 is SEQ ID NO: 230, galK_6 is SEQ ID NO: 231, galK_7 is SEQ ID NO: 232, galK_8 [20 nt] is SEQ ID NO: 233, galK_8 [21 nt] is SEQ ID NO: 234, galK_9 [20 nt] is SEQ ID NO: 235, galK_9 [21 nt] is SEQ ID NO: 236, galK_10 is SEQ ID NO: 237, galK_11 [20 nt] is SEQ ID NO: 238, galK_11 [23 nt] is SEQ ID NO: 239, galK_12 is SEQ ID NO: 240, galK_13 [20 nt] is SEQ ID NO: 241, galK_13 [21 nt] is SEQ ID NO: 242, and galK_14 is SEQ ID NO: 243.

FIG. 9 shows the multiple mutagenesis in the galK gene. (a) shows the non-specific mutagenic effect assessed by rifampicin resistance. Cells expressing each protein (vector, dCas, dCas-CDA, dCas-CDA-LVA or dCas-CDA1-UGI-LVA) with tandem-sgRNA-unit containing galK_10-galK_11-galK_13 targets were spotted onto the LB agar plate with or without rifampicin to assess the frequency of non-specific mutations. Dots represent at least three independent experiments and box indicates 95% confidence interval for a geometric mean by t-test analysis. (b) shows frequency of on-target multiplex mutation induced in the target region. Randomly selected eight clones in (a) were sequenced at the targeted three loci. Frequencies of the single-, double-or triple-mutant clone are indicated. (c) and (d) show the sequence alignments of the mutants. Single targets (galK 10, galK 11 or galK 13) (c) or triple targets (d) were mutated using dCas-CDA-UGI-LVA. Randomly selected eight clones were sequenced and sequences were aligned. Box and inverted box indicate target sequence and PAM sequence, respectively. Mutation sites and mutated bases are highlighted in black shade and bold, respectively. In (c), galK_10 is 5' to 3' SEQ ID NO: 251 and 3' to 5' SEQ ID NO: 252, and the galK_10 clone is SEQ ID NO: 253. galK_11 is 5' to 3' SEQ ID NO: 254 and 3' to 5' SEQ ID NO: 255, and the galK_11 clone is SEQ ID NO: 256. galK_13 is 5' to 3' SEQ ID NO: 224 and 3' to 5' SEQ ID NO: 258, and the galK_13 clone is SEQ ID NO: 259. In (d), the combined galK_10 and galK_11 is 5' to 3' SEQ ID NO: 331 and 3' to 5' SEQ ID NO: 332. The combined galK_10 and galK_11 clones from top to bottom are SEQ ID NO: 333, SEQ ID NO: 334, SEQ ID NO: 335, SEQ DI NO: 336, SEQ ID NO: 336, SEQ ID NO: 337, SEQ ID NO: 337, and SEQ ID NO: 331. galK_13 is 5' to 3' SEQ ID NO: 262 and 3' to 5' SEQ ID NO: 263. The galK_13 clones from top to bottom are SEQ ID NO: 269, SEQ ID NO: 269, SEQ ID NO: 270, SEQ ID NO: 269, SEQ ID NO: 270, SEQ ID NO: 269, SEQ ID NO: 269, and SEQ ID NO: 262.

FIG. 11 shows the simultaneous disruption of multi-copy transposase genes. IS1, 2, 3 and 5 are simultaneously targeted using dCas-CDA-UGI-LVA. sgRNAs are designed to introduce stop codons in the common sequence of the same type of transposase. All but the sequences which cannot be amplified from DH10B reference genome are aligned. Translated amino acid sequences are shown on the top of each common sequence. Genomic regions of each sequence are shown on the left. All target sequences are designed on the complementary strands and corresponding regions are squared with complementary PAM sequences (inverted). Mutated bases are highlighted in black shade. The IS1 targeted sequence is SEQ ID NO: 301 and the amino acid translation is SEQ ID NO: 302, 1-1 is SEQ ID NO: 303, 1-3 is SEQ ID NO: 304, 1-5 is SEQ ID NO: 339, 1-6 is SEQ ID NO: 304, 1-7 is SEQ ID NO: 305, 1-8 is SEQ ID NO: 304, 1-9 is SEQ ID NO: 304, 1-10 is SEQ ID NO: 303, 1-11 is SEQ ID NO: 303, and 1-12 is SEQ ID NO: 304. The IS2 targeted sequence is SEQ ID NO: 306 and the amino acid translation is SEQ ID NO: 307, 2-1 is SEQ ID NO: 308, 2-2 is SEQ ID NO: 309, 2-4 is SEQ ID NO: 308, 2-5 is SEQ ID NO: 310, 2-6 is SEQ ID NO: 308, 2-7 is SEQ ID NO: 308, 2-8 is SEQ ID NO: 308, 2-9 is SEQ ID NO: 308, 2-10 is SEQ ID NO: 308, 2-11 is SEQ ID NO: 308, 2-12 is SEQ ID NO: 311, and 2-13 is SEQ ID NO: 312. The IS3 targeted sequence is SEQ ID NO: 313 and the amino acid translation is SEQ ID NO: 314, 3-1 is SEQ ID NO: 340, 3-2 is SEQ ID NO: 340, 3-3 is SEQ ID NO: 315, 3-4 is SEQ ID NO: 317, and 3-5 is SEQ ID NO: 315. The IS5 targeted sequence is SEQ ID NO: 318 and the translation is SEQ ID NO: 319. 5-1 is SEQ ID NO: 320, 5-2 is SEQ ID NO: 320, 5-3 is SEQ ID NO: 321, 5-4 is SEQ ID NO: 320, 5-5 is SEQ ID NO: 322, 5-6 is SEQ ID NO: 320, 5-7 is SEQ ID NO: 322, 5-8 is SEQ ID NO: 322, 5-9 is SEQ ID NO: 320, 5-11 is SEQ ID NO: 322, 5-12 is SEQ ID NO: 323, 5-13 is SEQ ID NO: 320, 5-14 is SEQ ID NO: 320, and 5-15 is SEQ ID NO: 320.

FIG. 12 shows an isolation and verification procedure for IS-edited cells. Clone isolation and sequence verification as done in stages. Isolated clones are numbered as indicated on the top row of each table and sequence-analyzed at the IS sites indicated on the left column. Genotype was determined as targeted mutation verified (mut), not mutated (wt) or hetero of mut and wt (hetero) based on the Sanger sequencing spectrum.

DESCRIPTION OF EMBODIMENTS

Figure 1:
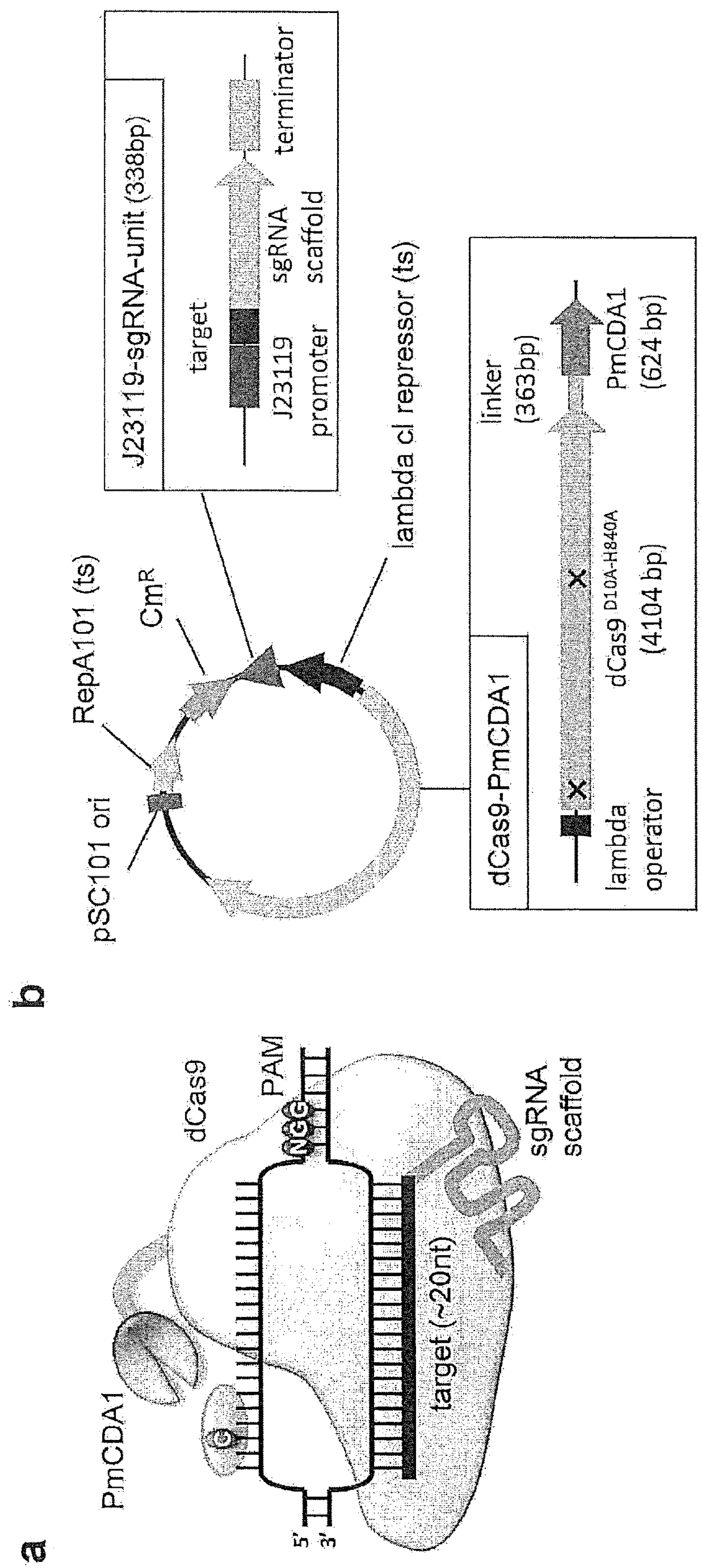
FIG. 1 shows the outline of the Target-AID system in a bacterium. (a) is a schematic model of Target-AID (dCas9-PmCDA1/sgRNA) base editing. dCas9-PmCDA1/sgRNA complex binds to the double-stranded DNA to form an R-loop in sgRNA-and PAM-dependent manner. PmCDA1 catalyzes deamination of cytosine located at a top (non-complementary) strand within 15-20 bases upstream from PAM, which results in C-to-T mutagenesis. (b) shows a single Target-AID plasmid of bacterium. The plasmid contains the chloramphenicol-resistant ($Cm^R$) gene, temperature-sensitive (ts) λ cI repressor, the pSC101 origin (ori) and RepA101 (ts). λ operator expresses dCas9-PmCDA1 fusion at high temperature (>37° C.) as cI repressor (ts) gets inactivated. sgRNA is expressed by a constitutive promoter J23119. dCas9 is a nuclease-deficient Cas9 with D10A H840A mutations, and PmCDA1 is *Petromyzon marinus* cytosine deaminase.

1. Complex for Genome Editing and Nucleic Acid Encoding Same

The present invention provides a complex for genome editing in which a nucleic acid sequence-recognizing module specifically binding to a target nucleotide sequence in a double stranded DNA and a proteolysis tag are linked, and a nucleic acid encoding the complex. In one embodiment of the complex for genome editing of the present invention, a complex wherein a nucleic acid altering enzyme is further linked (i.e., a complex in which a nucleic acid sequence-recognizing module, a nucleic acid altering enzyme and a proteolysis tag are linked), which can alter the nucleic acid in the targeted site is provided. In one embodiment, to improve the alteration efficiency of the double stranded DNA, a base excision repair inhibitor may be further linked to the complex. In another embodiment of the complex for genome editing of the present invention, a complex wherein at least a nucleic acid sequence-recognizing module and a proteolysis tag are linked, which can regulation the expression of a gene double stranded DNA in the vicinity of the targeted site, is provided. In one embodiment, a transcriptional regulatory factor may be further linked to the complex. In the following, a complex in which at least any of a nucleic acid altering enzyme, a base excision repair inhibitor and a transcriptional regulatory factor is linked and a complex in which none of them is linked are sometimes collectively referred to as "the complex of the present invention" or "the complex for genome editing", and particularly, a complex in which a nucleic acid altering enzyme is linked is sometimes referred to as "the nucleic acid altering enzyme complex". The nucleic acids encoding these complexes are sometimes collectively referred to as "the nucleic acid of the present invention".

When the nucleic acid of the present invention is introduced into a host bacterium (e.g., *Escherichia coli*) and cultured for the purpose of replication, rather than alteration of DNA, and a complex is expressed unintendedly from the nucleic acid, the toxicity to host bacterium can be suppressed low because the complex is degraded rapidly by the proteolysis tag. In fact, when the nucleic acid of the present invention is introduced into a host bacterium for the purpose of replication of the nucleic acid, the transformation efficiency of the host bacterium is high as demonstrated in the Examples described below as compared to when one not containing a nucleic acid encoding proteolysis tag is introduced. Therefore, the nucleic acid of the present invention containing a sequence encoding proteolysis tag can be replicated stably in a bacterium as a nucleic acid for genome editing of a host other than bacteria (e.g., eukaryote). Therefore, it is useful to add a sequence encoding the proteolysis tag of the present invention to a vector aiming at genome editing in a host other than bacteria.

In the present invention, the "alteration" of a double stranded DNA means that a nucleotide (e.g., dC) on a DNA strand is converted to another nucleotide (e.g., dT, dA or dG), or deleted, or a nucleotide or a nucleotide sequence is inserted between certain nucleotides on a DNA strand. The double stranded DNA to be altered is not particularly limited as long as it is a DNA present in the cell, preferably a genomic DNA. The "targeted site" of a double stranded DNA means the whole or partial "target nucleotide sequence", which a nucleic acid sequence-recognizing module specifically recognizes and binds to, or the vicinity of the target nucleotide sequence (one or both of 5' upstream and 3' downstream). The "target nucleotide sequence" means a sequence to which a nucleic acid sequence-recognizing module in the double stranded DNA binds. In the present invention, the term "genome editing" is used to mean not only altering a double stranded DNA but also promoting or suppressing the expression of a gene encoded by a double stranded DNA in the vicinity of the targeted site.

In the present invention, the "nucleic acid sequence-recognizing module" means a molecule or molecule complex having an ability to specifically recognize and bind to a particular nucleotide sequence (i.e., target nucleotide sequence) on a DNA strand. When a nucleic acid altering enzyme complex is used, binding of the nucleic acid sequence-recognizing module to a target nucleotide sequence enables a nucleic acid altering enzyme and/or a base excision repair inhibitor linked to the module to specifically act on a targeted site of a double stranded DNA.

In the present invention, the "nucleic acid altering enzyme" means an enzyme that modifies DNA, and the modification directly or indirectly causes alteration of DNA. The enzyme may be a peptide fragment thereof as long as it has a catalytic activity. Examples of such DNA modification reaction include a reaction to cleave DNA (hereinafter to be also referred to as "DNA strand cleavage reaction") which is catalyzed by a nucleolytic enzyme, a reaction to convert a substituent on the purine or pyrimidine ring of a nucleic acid base to other group or atom, which is a reaction catalyzed by a nucleic acid base converting enzyme and not directly involving cleavage of DNA strand (hereinafter to be also referred to as "nucleic acid base conversion reaction") (e.g., deamination reaction of base), a reaction to hydrolyze N-glycoside linkage of DNA (hereinafter to be also referred to as "base excision reaction") which is catalyzed by DNA glycosylase and the like. As shown in the Examples described below, the toxicity of a nucleic acid altering enzyme complex containing a nucleic acid base converting enzyme to the host bacterium can be reduced by adding a proteolysis tag. Therefore, the technique of the present invention can be applied to genome editing using not only a nucleic acid base converting enzyme but also nucleolytic enzymes conventionally difficult for application to bacteria due to the strong toxicity thereof. Therefore, the nucleic acid altering enzyme to be used in the present invention includes a nucleolytic enzyme, a nucleic acid base converting enzyme, a DNA glycosylase and the like. From the aspect of reduction of cytotoxicity, nucleic acid base converting enzyme and DNA glycosylase are preferable, and the targeted site can be altered using these enzymes in the targeted site, without cleaving at least one the strands of the double stranded DNA.

In the present invention, the "proteolysis tag" mainly consists of a peptide containing not less than 3 hydrophobic amino acid residues, wherein the peptide shows a shortened half-life of protein when added to a complex for genome editing as compared to that without addition to the complex. As such amino acid, glycine, alanine, valine, leucine, isoleucine, methionine, proline, phenylalanine, and tryptophan can be mentioned. The proteolysis tag of the present invention only needs to contain any three of these amino acid residues at the C-terminal, and other constitution is not particularly limited. It may be a peptide consisting of the three amino acid residues. A peptide in which a part or all of the aforementioned hydrophobic amino acid residues is/are substituted by serine or threonine is also encompassed in the proteolysis tag of the present invention. While preferable aforementioned three amino acid residues are not particularly limited, leucine-valine-alanine (LVA), leucine-alanine-alanine (LAA), alanine-alanine-valine (AAV) and the like, whose high effects were acknowledged in Escherichia coli and Pseudomonas putida (Andersen J. B. et al., Apll. Environ. Microbiol., 64:2240-2246 (1998)), can be mentioned and, as one containing serine, alanine-serine-valine (ASV) and the like can be mentioned. In addition, the data base of tm RNA tag peptide (e.g., tmRDB, ag.auburn.edu/mirror/tmRDB/peptide/peptidephylolist.html) and the like can be referred to for the proteolysis tag containing these three amino acid residues. Specifically, YAASV (SEQ ID NO: 324), YALAA (SEQ ID NO: 325), ANDENYALAA (SEQ ID NO: 181) and AANDENYALAA (SEQ ID NO: 182) known as tmRNA tag peptides of *Escherichia coli*, GKQNNLSLAA (SEQ ID NO: 183), GKSNNNFALAA (SEQ ID NO: 184), GKENNNFALAA (SEQ ID NO: 185), GKTNSFNQNVALAA (SEQ ID NO: 186), GKSNQNLA-LAA (SEQ ID NO: 187) and GKQNYALAA (SEQ ID NO: 188) known as tmRNA tag peptides of genus *Bacillus*, ANDDNYALAA (SEQ ID NO: 189), ANDDQYGAALAA (SEQ ID NO: 190), ANDENYGQEFALAA (SEQ ID NO: 191), ANDETYGDYALAA (SEQ ID NO: 192), ANDETY-GEYALAA (SEQ ID NO: 193), ANDETYGEETYALAA (SEQ ID NO: 194), ANDENYGAEYKLAA (SEQ ID NO: 195) and ANDENYGAQLAA (SEQ ID NO: 196) known as tmRNA tag peptides of genus Pseudomonas, AKNTNSYA-LAA (SEQ ID NO: 197), AKNTNSYAVAA (SEQ ID NO: 198), AKNNTTYALAA (SEQ ID NO: 199), AKNTNTYA-LAA (SEQ ID NO: 200) and AKNNTSYALAA (SEQ ID NO: 201) known as tmRNA tag peptides of genus *Streptococcus* and the like can be unlimitatively mentioned. The proteolysis tag typically consists of 3-15 amino acid residues, but is not limited to this range. In one embodiment, proteolysis tag consists of 3-5 amino acid residues. Those of ordinary skill in the art can appropriately select the proteolysis tag according to the kind of host bacterium and the like. In the present specification, unless otherwise specified, the capital letter of the alphabet indicates a one- letter code for the amino acid, and the amino acid sequence is indicated from left to right, from N-terminal to C-terminal.

In the present invention, the "complex for genome editing" means a molecular complex having nucleic acid alteration activity or expression regulation activity and imparted with a particular nucleotide sequence recognition, which includes the above-mentioned complex in which a nucleic acid sequence-recognizing module and a proteolysis tag are linked. The "nucleic acid altering enzyme complex" means a molecular complex having a nucleic acid alteration activity and imparted with a particular nucleotide sequence recognition ability, which includes the above-mentioned complex in which a nucleic acid sequence-recognizing module, a nucleic acid altering enzyme, and a proteolysis tag are linked. The complex may be linked with a base excision repair inhibitor. The "complex" here encompasses not only one constituted of plural molecules but also one having, in a single molecule, a molecule constituting the above-mentioned complex of the present invention such as fusion proteins. Furthermore, a molecule or molecular complex that functions due to a nucleic acid sequence-recognizing module and a nucleic acid altering enzyme in integration such as restriction enzyme and CRISPR/Cas system, and is bound with a proteolysis tag is also encompassed in the complex of the present invention. In addition, "encoding a complex" encompasses both encoding respective molecules constituting the complex, and encoding a fusion protein having constituting molecules in a single molecule.

The nucleolytic enzyme used in the present invention is not particularly limited as long as it catalyzes the above-mentioned reaction, and, for example, nuclease (e.g., Cas effector protein (e.g., Cas9, Cpf1), endonuclease (e.g., restriction enzyme), exonuclease etc.), recombinase, DNA gyrase, DNA topoisomerase, transposase and the like can be mentioned.

The nucleic acid base converting enzyme to be used in the present invention is not particularly limited as long as it can catalyze the above-mentioned reaction, and examples thereof include deaminase belonging to the nucleic acid/nucleotide deaminase superfamily, which catalyzes a deamination reaction that converts an amino group to a carbonyl group. Preferable examples thereof include cytidine deaminase capable of converting cytosine or 5-methylcytosine to uracil or thymine, respectively, adenosine deaminase capable of converting adenine to hypoxanthine, guanosine deaminase capable of converting guanine to xanthine and the like. As cytidine deaminase, more preferred is activation-induced cytidine deaminase (hereinafter to be also referred to as AID) which is an enzyme that introduces a mutation into an immunoglobulin gene in the acquired immunity of vertebrata or the like.

While the derivation of nucleic acid base converting enzyme is not particularly limited, for example, PmCDA1 (Petromyzon marinus cytosine deaminase 1) derived from Petromyzon marinus, or AID (Activation-induced cytidine deaminase; AICDA) derived from mammal (e.g., human, swine, bovine, horse, monkey etc.) can be used. For example, GenBank accession Nos. EF094822 and ABO15149 can be referred to for the base sequence and amino acid sequence of cDNA of PmCDA1, GenBank accession No. NM_020661 and NP_065712 can be referred to for the base sequence and amino acid sequence of cDNA of human AID. From the aspect of enzyme activity, PmCDA1 is preferred.

The DNA glycosylase to be used in the present invention is not particularly limited as long as it can catalyze the above-mentioned reaction, and thymine DNA glycosylase, oxoguanine glycosylase, alkyladenine DNA glycosylase (e.g., yeast 3-methyladenine-DNA glycosylase (MAG1) etc.) and the like can be mentioned. The present inventor previously reported that use of a DNA glycosylase with sufficiently low reactivity with DNA having a double helix structure without distortion (unrelaxed DNA) as DNA glycosylase can reduce cytotoxicity and efficiently alter a target sequence (WO 2016/072399). Therefore, as DNA glycosylase, a DNA glycosylase with sufficiently low reactivity with DNA having a double helix structure without distortion is preferably used. Examples of such DNA glycosylase include a mutant of UNG having cytosine-DNA glycosylase (CDG) activity and/or thymine-DNA glycosylase (TDG) activity (uracil-DNA glycosylase), and UDG mutant from vaccinia virus, which are described in WO 2016/072399.

Specific examples of the aforementioned mutant of UNG include yeast UNG1 N222D/L304A double mutant, N222D/R308E double mutant, N222D/R308C double mutant, Y164A/L304A double mutant, Y164A/R308E double mutant, Y164A/R308C double mutant, Y164G/L304A double mutant, Y164G/R308E double mutant, Y164G/

R308C double mutant, N222D/Y164A/L304A triple mutant, N222D/Y164A/R308E triple mutant, N222D/Y164A/R308C triple mutant, N222D/Y164G/L304A triple mutant, N222D/Y164G/R308E triple mutant, N222D/Y164G/R308C triple mutant and the like. When another UNG is used in place of the yeast UNG1, a mutant in which a similar mutation has been introduced into the amino acid corresponding to each mutant described above may be used. As UDG mutant from vaccinia virus, N120D mutant, Y70G mutant, Y70A mutant, N120D/Y70G double mutant, N120D/Y70A double mutant and the like can be mentioned. Alternatively, it may be a DNA glycosylase divided into two segments which is a split enzyme designed such that each segment is bound to either of two divided nucleic acid sequence-recognizing modules to form two complexes, the nucleic acid sequence-recognizing module can specifically bind to a target nucleotide sequence when both complexes are refolded, and the DNA glycosylase can catalyze a base excision reaction by the specific binding. The split enzyme can be designed and produced by referring to the descriptions of, for example, WO 2016/072399, Nat Biotechnol. 33(2): 139-142 (2015), PNAS 112(10): 2984-2989 (2015).

In the present invention, the "base excision repair" is one of the DNA repair mechanisms of living organisms, and means a mechanism for repairing damages of bases by cutting off damaged parts of the bases by enzymes and rejoining them. Excision of damaged bases is performed by DNA glycosylase, which is an enzyme that hydrolyzes the N-glycoside linkage of DNA. An abasic site (apurinic/apyrimidic (AP) site) resulting from the abasic reaction by the enzyme is treated by an enzyme at the downstream of the base excision repair (BER) pathway such as an AP endonuclease, DNA polymerase, DNA ligase and the like. Examples of such gene or protein involved in the BER pathway include, but are not limited to, UNG (NM_003362), SMUG1 (NM_014311), MBD4 (NM_003925), TDG (NM_003211), OGG1 (NM_002542), MYH (NM_012222), NTHL1 (NM_002528), MPG (NM_002434), NEIL1 (NM_024608), NEIL2 (NM_145043), NEIL3 (NM_018248), APE1 (NM_001641), APE2 (NM_014481), LIG3 (NM_013975), XRCC1 (NM_006297), ADPRT (PARP1) (NM_0016718), ADPRTL2 (PARP2) (NM_005484) and the like (parentheses indicate refseq number in which the base sequence information of each gene (cDNA) is registered).

In the present invention, the "base excision repair inhibitor" means a substance that inhibits any stage of the above-mentioned BER pathway, or a protein that eventually inhibits BER by inhibiting the expression of molecules mobilized in the BER pathway. While the base excision repair inhibitor to be used in the present invention is not particularly limited as long as it consequently inhibits BER, from the aspect of efficiency, an inhibitor of DNA glycosylase located at the upstream of the BER pathway is preferable. Examples of the inhibitor of DNA glycosylase to be used in the present invention include, but are not limited to, a thymine DNA glycosylase inhibitor, an uracil DNA glycosylase inhibitor, an oxoguanine DNA glycosylase inhibitor, an alkylguanine DNA glycosylase inhibitor and the like. For example, when cytidine deaminase is used as a nucleic acid altering enzyme, it is suitable to use a uracil DNA glycosylase inhibitor to inhibit repair of U:G or G:U mismatch of DNA generated by mutation.

Examples of such uracil DNA glycosylase inhibitor include, but are not limited to, a uracil DNA glycosylase inhibitor (Ugi) derived from *Bacillus subtilis* bacteriophage, PBS1, and a uracil DNA glycosylase inhibitor (Ugi) derived from *Bacillus subtilis* bacteriophage, PBS2 (Wang, Z., and Mosbaugh, D. W. (1988) J. Bacteriol. 170, 1082-1091). The above-mentioned inhibiter of the repair of DNA mismatch can be used in the present invention. Particularly, Ugi derived from PBS2 is also known to have an effect of making it difficult to cause mutation, cleavage and recombination other than T from C on DNA, and thus the use of Ugi derived from PBS2 is suitable.

As mentioned above, in the base excision repair (BER) mechanism, when a base is excised by DNA glycosylase, AP endonuclease puts a nick in the abasic site (AP site), and exonuclease completely excises the AP site. When the AP site is excised, DNA polymerase produces a new base by using the base of the opposing strand as a template, and DNA ligase finally seals the nick to complete the repair. Mutant AP endonuclease that has lost the enzyme activity but maintains the binding capacity to the AP site is known to competitively inhibit BER. Therefore, these mutation AP endonucleases can also be used as the base excision repair inhibitor in the present invention. While the derivation of the mutant AP endonuclease is not particularly limited, for example, AP endonucleases derived from *Escherichia coli,* yeast, mammal (e.g., human, mouse, swine, bovine, horse, monkey etc.) and the like can be used. For example, UniprotKB No. P27695 can be referred to for the amino acid sequence of human Apel. Examples of the mutant AP endonuclease that has lost the enzyme activity but maintains the binding capacity to the AP site include proteins having mutated activity site and mutated Mg (cofactor)-binding site. For example, E96Q, Y171A, Y171F, Y171H, D210N, D210A, N212A and the like can be mentioned for human Apel.

In the present invention, the "transcriptional regulatory factor" means a protein or a domain thereof which has an activity of promoting or suppressing target gene transcription. In the following, one having a transcription promoting activity is sometimes referred to as a "transcription activation factor", and one having a transcription suppressing activity is sometimes referred to as a "transcription inhibitory factor".

The transcription activation factor to be used in the present invention is not particularly limited as long as it can promote transcription of the target gene and, for example, an activated domain of HSV (Herpes simplex virus) VP16, p65 subunit of NFκB, VP64, VP160, HSF, P300 and EB virus (Epstein-Barr Virus) RTA, fusion proteins of these and the like can be mentioned. The transcription inhibitory factor to be used in the present invention is not particularly limited as long as it can suppress transcription of the target gene and, for example, KRAB, MBD2B, v-ErbA, SID (including SID concatemer (SID4X)), MBD2, MBD3, DNMT family (e.g., DNMT1, DNMT3A, DNMT3B), Rb, MeCP2, ROM2 and AtHD2A, fusion proteins of these and the like can be mentioned.

A target nucleotide sequence in a double-stranded DNA to be recognized by the nucleic acid sequence-recognizing module in the complex of the present invention is not particularly limited as long as the module specifically binds to, and may be any sequence in the double-stranded DNA. The length of the target nucleotide sequence only needs to be sufficient for specific binding of the nucleic acid sequence-recognizing module. For example, when mutation is introduced into a particular site in the genomic DNA of a mammal, it is not less than 12 nucleotides, preferably not less than 15 nucleotides, more preferably not less than 17 nucleotides, according to the genome size thereof.

While the upper limit of the length is not particularly limited, it is preferably not more than 25 nucleotides.

As the nucleic acid sequence-recognizing module in the complex of the present invention, a CRISPR-Cas system wherein at least one DNA cleavage ability of the Cas effector protein is inactivated (hereinafter to be also referred to as "CRISPR-mutant Cas"), zinc finger motif, TAL effector and PPR motif and the like, as well as a fragment which contains a DNA binding domain of a protein that specifically binds to DNA, such as restriction enzyme, transcriptional regulatory factor, RNA polymerase and the like, and the like can be used, but the module is not limited thereto. When a nucleic acid altering enzyme is used, the CRISPR-Cas system in which a nucleic acid sequence-recognizing module and a nucleic acid altering enzyme are integrated (Cas effector protein of the system maintains both activities of the DNA cleavage ability) may also be used. Preferably, CRISPR-mutant Cas, zinc finger motif, TAL effector, PPR motif and the like can be mentioned.

A zinc finger motif is constituted by linkage of 3-6 different Cys2His2 type zinc finger units (1 finger recognizes about 3 bases), and can recognize a target nucleotide sequence of 9-18 bases. A zinc finger motif can be produced by a known method such as Modular assembly method (Nat Biotechnol (2002) 20: 135-141), OPEN method (Mol Cell (2008) 31: 294-301), CoDA method (Nat Methods (2011) 8: 67-69), *Escherichia coli* one-hybrid method (Nat Biotechnol (2008) 26:695-701) and the like. JP-B-4968498 can be referred to as for the detail of the zinc finger motif production.

A TAL effector has a module repeat structure with about 34 amino acids as a unit, and the 12th and 13th amino acid residues (called RVD) of one module determine the binding stability and base specificity. Since each module is highly independent, TAL effector specific to a target nucleotide sequence can be produced by simply connecting the module. For TAL effector, a production method utilizing an open resource (REAL method (Curr Protoc Mol Biol (2012) Chapter 12: Unit 12.15), FLASH method (Nat Biotechnol (2012) 30: 460-465), and Golden Gate method (Nucleic Acids Res (2011) 39: e82) etc.) have been established, and a TAL effector for a target nucleotide sequence can be designed comparatively conveniently. National Publication of International Patent Application No. 2013-513389 can be referred to as for the detail of the production of a TAL effector.

PPR motif is constituted such that a particular nucleotide sequence is recognized by a continuation of PPR motifs each consisting of 35 amino acids and recognizing one nucleic acid base, and recognizes a target base only by 1, 4 and ii(−2) amino acids of each motif. Motif constitution has no dependency, and is free of interference of motifs on both sides. Therefore, like TAL effector, a PPR protein specific to the target nucleotide sequence can be produced by simply connecting PPR motifs. JP-A-2013-128413 can be referred to as for the detail of the production of a PPR motif.

When a fragment of restriction enzyme, transcriptional regulatory factor, RNA polymerase and the like is used, since the DNA binding domains of these proteins are well known, a fragment which contains the domain and does not have a DNA double strand cleavage ability, can be easily designed and constructed.

When a nucleic acid altering enzyme is used, any of the above-mentioned nucleic acid sequence-recognizing modules can be provided as a fusion protein with the above-mentioned nucleic acid altering enzyme and/or a base excision repair inhibitor, or a protein binding domain such as SH3 domain, PDZ domain, GK domain, GB domain and the like and a binding partner thereof may be fused with a nucleic acid sequence-recognizing module and/or a base excision repair inhibitor, respectively, and provided as a protein complex via an interaction of the domain and a binding partner thereof. Alternatively, a nucleic acid sequence-recognizing module and/or a base excision repair inhibitor may be each fused with intein, and they can be linked by ligation after protein synthesis. The proteolysis tag may be bound with any of the constituent molecules of a nucleic acid altering enzyme complex (nucleic acid sequence-recognizing module, nucleic acid altering enzyme and base excision repair inhibitor), and may be bound with plural constituent molecules. Also, when a transcriptional regulatory factor is used, the transcriptional regulatory factor may be provided as a fusion protein with a nucleic acid sequence-recognizing module in the same manner as described above, or may be bound with a nucleic acid recognition module via the above-mentioned protein binding domain and a binding partner thereof. In the same manner as described above, the proteolysis tag may be bound as a fusion protein, or may be bound with a complex for genome editing or a constituent molecule thereof via the above-mentioned protein binding domain and a binding partner thereof. The proteolysis tag is preferably bound with the C-terminal of a complex for genome editing or a constituent molecule thereof.

In the nucleic acid of the present invention, a nucleic acid sequence-recognizing module, a proteolysis tag, a nucleic acid altering enzyme and/or a base excision repair inhibitor as necessary, or a transcriptional regulatory factor can be prepared as a nucleic acid encoding a fusion protein thereof, or in a form capable of forming a complex in a host cell after translation into a protein by utilizing a binding domain, intein and the like, or as a nucleic acid encoding each of them. The nucleic acid here may be a DNA or an RNA. When it is a DNA, it is preferably a double stranded DNA, and provided in the form of an expression vector placed under regulation of a functional promoter in a host cell. When it is an RNA, it is preferably a single strand RNA.

A DNA encoding a nucleic acid sequence-recognizing module such as zinc finger motif, TAL effector, PPR motif and the like can be obtained by any method mentioned above for each module. A DNA encoding a sequence-recognizing module of restriction enzyme, transcriptional regulatory factor, RNA polymerase and the like can be cloned by, for example, synthesizing an oligoDNA primer covering a region encoding a desired part of the protein (part containing DNA binding domain) based on the cDNA sequence information thereof, and amplifying by the RT-PCR method using, as a template, the total RNA or mRNA fraction prepared from the protein-producing cells.

A DNA encoding a nucleic acid altering enzyme and base excision repair inhibitor can also be cloned similarly by synthesizing an oligoDNA primer based on the cDNA sequence information thereof, and amplifying by the RT-PCR method using, as a template, the total RNA or mRNA fraction prepared from the enzyme-producing cells. For example, a DNA encoding PBS2-derived UGI can be cloned by designing suitable primers for the upstream and downstream of CDS based on the cDNA sequence (accession No. J04434) registered in the NCBI/GenBank database, and cloning from PBS2-derived mRNA by the RT-PCR method.

The cloned DNA may be directly, or after digestion with a restriction enzyme when desired, or after addition of a suitable linker (e.g., GS linker, GGGAR linker etc.), spacer (e.g., FLAG sequence etc.) and/or a nuclear localization signal (NLS) (each organelle transfer signal when the double-stranded DNA of interest is mitochondria or chloroplast DNA), to prepare a DNA encoding a fusion protein. In addition, a DNA encoding a fusion protein can be prepared by ligating with a DNA encoding a nucleic acid sequence-recognizing module.

A DNA encoding the complex for genome editing of the present invention can be obtained by chemically synthesizing the DNA strand, or by connecting synthesized partly overlapping oligoDNA short strands by utilizing the PCR method and the Gibson Assembly method to construct a DNA encoding the full length thereof. The advantage of constructing a full-length DNA by chemical synthesis or a combination of PCR method or Gibson Assembly method is that the codon to be used can be designed in CDS full-length according to the host into which the DNA is introduced. In the expression of a heterologous DNA, the protein expression level is expected to increase by converting the DNA sequence thereof to a codon highly frequently used in the host organism. As the data of codon use frequency in host to be used, for example, the genetic code use frequency database disclosed in the home page of Kazusa DNA Research Institute (kazusa.or.jp/codon/index.html) can be used, or documents showing the codon use frequency in each host may be referred to. By reference to the obtained data and the DNA sequence to be introduced, codons showing low use frequency in the host from among those used for the DNA sequence may be converted to a codon coding the same amino acid and showing high use frequency.

An expression vector containing a DNA encoding the complex for genome editing of the present invention can be produced, for example, by linking the DNA to the downstream of a promoter in a suitable expression vector.

As the expression vector, plasmids from *Escherichia coli* (e.g., pBR322, pBR325, pUC12, pUC13); plasmids from *Bacillus subtilis* (e.g., pUB110, pTP5, pC194); plasmids from yeast (e.g., pSH19, pSH15); insect cell expression plasmids (e.g., pFast-Bac); animal cell expression plasmids (e.g., pA1-11, pXT1, pRc/CMV, pRc/RSV, pcDNAI/Neo); bacteriophages such as Aphage and the like; insect virus vectors such as baculovirus and the like (e.g., BmNPV, AcNPV); animal virus vectors such as retrovirus, vaccinia virus, adenovirus and the like, and the like are used.

As the promoter, any promoter appropriate for a host used for gene expression can be used. When a nucleolytic enzyme is used as a nucleic acid altering enzyme, since the survival rate of the host cell sometimes decreases markedly due to the toxicity, it is desirable to increase the number of cells by the start of the induction by using an inductive promoter. On the other hand, when a nucleic acid base converting enzyme and DNA glycosylase are used as a nucleic acid altering enzyme, or when a nucleic acid altering enzyme is not used, since sufficient cell proliferation can also be achieved by expressing the nucleic acid-altering enzyme complex of the present invention, a constitutive promoter can also be used without limitation.

For example, when the host is an animal cell, SRα promoter, SV40 promoter, LTR promoter, CMV (cytomegalovirus) promoter, RSV (Rous sarcoma virus) promoter, MoMuLV (Moloney mouse leukemia virus) LTR, HSV-TK (simple herpes virus thymidine kinase) promoter and the like are used. Of these, CMV promoter, SRα promoter and the like are preferable.

When the host is *Escherichia coli,* J23 series promoters (e.g., J23119 promoter), trp promoter, lac promoter, recA promoter, $\lambda P_L$ promoter, lpp promoter, T7 promoter and the like are preferable.

When the host is genus *Bacillus,* SPO1 promoter, SPO2 promoter, penP promoter and the like are preferable.

When the host is a yeast, the Gall/10 promoter, PHO5 promoter, PGK promoter, GAP promoter, ADH promoter and the like are preferable.

When the host is an insect cell, a polyhedrin promoter, P10 promoter and the like are preferable.

When the host is a plant cell, CaMV35S promoter, CaMV19S promoter, NOS promoter and the like are preferable.

As the expression vector, besides those mentioned above, one containing an enhancer, a splicing signal, a terminator, a polyA addition signal, a selection marker such as drug resistance gene, an auxotrophic complementary gene and the like, a replication origin and the like on demand can be used.

An RNA encoding the complex of the present invention can be prepared by, for example, transcription to mRNA an in vitro transcription system known per se by using the above-mentioned expression vector containing a DNA encoding each protein as a template.

The host bacterium used for replication of the nucleic acid of the present invention is not particularly limited as long as it is a bacterium having a proteolysis system using tmRNA (ssrA). For example, genus *Escherichia,* genus *Bacillus,* genus *Pseudomonas* (e.g., *Pseudomonas putida*), genus *Streptococcus* (e.g., *Streptococcus*), genus *Streptomyces,* genus *Staphylococcus,* genus *Yersinia,* genus *Acinetobacter,* genus *Klebsiella,* genus *Bordetella,* genus *Lactococcus,* genus *Neisseria,* genus *Aeromonas,* genus *Francisella,* genus *Corynebacterium,* genus *Citrobacter,* genus *Chlamydiae,* genus *Haemophilus,* genus *Brucella,* genus *Mycobacterium,* genus *Legionella,* genus *Rhodococcus,* genus *Pseudomonas,* genus *Helicobacter,* genus *Salmonella,* genus *Staphylococcus,* genus *Vibrio,* and genus *Erysipelothrix* and the like are used.

As the genus *Escherichia, Escherichia coli* K12·DH1 [Proc. Natl. Acad. Sci. USA, 60, 160 (1968)], *Escherichia coli* JM103 [Nucleic Acids Research, 9, 309 (1981)], *Escherichia coli* JA221 [Journal of Molecular Biology, 120, 517 (1978)], *Escherichia coli* HB101 [Journal of Molecular Biology, 41, 459 (1969)], *Escherichia coli* C600 [Genetics, 39, 440 (1954)], *Escherichia coli* DH5α, *Escherichia coli* BW25113 and the like are used.

As the genus *Bacillus, Bacillus subtilis* MI114 [Gene, 24, 255 (1983)], *Bacillus subtilis* 207-21 [Journal of Biochemistry, 95, 87 (1984)] and the like are used.

When a nucleic acid base converting enzyme or DNA glycosylase is used as a nucleic acid altering enzyme, the nucleic acid altering enzyme and/or a base excision repair inhibitor are/is provided as a complex with mutant Cas by a method similar to the coupling scheme with the above-mentioned zinc finger and the like. Alternatively, a nucleic acid base converting enzyme and/or a base excision repair inhibitor, and mutant Cas can also be bound by utilizing RNA aptamers MS2F6, PP7 and the like and RNA scaffold by binding proteins thereto. The guide RNA forms a complementary strand with the target nucleotide sequence, mutant Cas is recruited by the tracrRNA attached and mutant Cas recognizes DNA cleavage site recognition sequence PAM (protospacer adjacent motif) (when SpCas9 is used, PAM has 3 bases of NGG (N is any base), and theoretically can target any site on the genome). One or both DNAs cannot be cleaved and, due to the action of the nucleic acid base converting enzyme or DNA glycosylase linked to the mutant Cas, nucleic acid base conversion or base excision occurs in the targeted site (appropriately adjusted within several hundred bases including whole or partial target nucleotide sequence) and a mismatch (e.g., when cytidine deaminase such as PmCDA1, AID or the like is used as the nucleic acid base converting enzyme, cytosine on the sense strand or antisense strand at the targeted site is converted to uracil to cause U:G or G:U mismatch), or apurinic/apyrimidinic site (AP site) occurs in the double stranded DNA. Various mutations are introduced due to an error in the BER system of the cell attempting to repair this. For example, the mismatch or AP site is not correctly repaired, and when repaired such that a base of the opposite strand forms a pair with a base of the converted strand (T-A or A-T in the above-mentioned example), or when other nucleotide is further substituted (e.g., UA, G) or when one to several dozen bases are deleted or inserted during repair, various mutations are introduced. By using a base excision repair inhibitor in combination, the intracellular BER mechanism is inhibited, the frequency of repair mis increases, and the mutation introduction efficiency can be improved.

As for zinc finger motifs, production of many actually functionable zinc finger motifs is not easy, since production efficiency of a zinc finger that specifically binds to a target nucleotide sequence is not high and selection of a zinc finger having high binding specificity is complicated. While TAL effectors and PPR motifs have a high degree of freedom of target nucleic acid sequence recognition as compared to zinc finger motifs, a problem remains in the efficiency since a large protein needs to be designed and constructed every time according to the target nucleotide sequence.

In contrast, since the CRISPR-Cas system recognizes the double-stranded DNA sequence of interest with a guide RNA complementary to the target nucleotide sequence, any sequence can be targeted by simply synthesizing an oligoDNA capable of specifically hybridizing with the target nucleotide sequence.

Therefore, in a more preferable embodiment of the present invention, a CRISPR-Cas system maintaining both activities of the DNA cleavage ability, or a CRISPR-Cas system wherein DNA cleavage ability of only one or both of the Cas is inactivated (CRISPR-mutant Cas) is used as a nucleic acid sequence-recognizing module.

The nucleic acid sequence-recognizing module of the present invention using CRISPR-mutant Cas is provided as a complex of a CRISPR-RNA (crRNA) containing a sequence complementary to the target nucleotide sequence and, where necessary, trans-activating RNA (tracrRNA) necessary for recruiting mutant Cas effector protein (when tracrRNA is necessary, possibly provided as chimeric RNA with crRNA) and mutant Cas effector protein. An RNA molecule consisting of crRNA alone or a chimeric RNA of crRNA and tracrRNA that constitutes a nucleic acid sequence-recognizing module in combination with a mutant Cas effector protein is collectively referred to as a “guide RNA”. The same also applies when a CRISPR/Cas system without introduction of mutation is used.

While the Cas effector protein to be used in the present invention is not particularly limited as long as it can form a complex with guide RNA and recognize and bind to the target nucleotide sequence in the gene of interest and a protospacer adjacent motif (PAM) adjacent thereto, it is preferably Cas9 or Cpf1. Examples of Cas9 include, but are not limited to, Cas9 derived from Streptococcus pyogenes (SpCas9; PAM sequence NGG (N is A, G, T or C, hereinafter the same)), Cas9 derived from *Streptococcus thermophilus* (StCas9; PAM sequence NNAGAAW), Cas9 derived from Neisseria meningitidis (NmCas9; PAM sequence NNNNGATT) and the like. Preferred is SpCas9 with less restriction by PAM (substantially 2 bases, and can target theoretically any site in the genome). Examples of the Cpf1 include, but are not limited to, Cpf1 derived from *Francisella novicida* (FnCpf1; PAM sequence NTT), Cpf1 derived from *Acidaminococcus* sp. (AsCpf1; PAM sequence NTTT), Cpf1 derived from *Lachnospiraceae bacterium* (LbCpf1; PAM sequence NTTT) and the like. As a mutant Cas effector protein (sometimes to be abbreviated as mutant Cas) to be used in the present invention, any of Cas effector protein wherein the cleavage ability of the both strands of the double-stranded DNA is inactivated and one having nickase activity wherein at least one cleavage ability of one strand alone is inactivated can be used. For example, in the case of SpCas9, a D10A mutant in which the 10th Asp residue is converted to an Ala residue and lacking cleavage ability of a strand opposite to the strand forming a complementary strand with a guide RNA (thus having nickase activity for a strand forming complementary strand with guide RNA), or H840A mutant in which the 840th His residue is converted to an Ala residue and lacking cleavage ability of a strand forming a complementary strand to guide RNA (thus having nickase activity for a strand forming complementary strand with guide RNA, or a double mutant thereof (dCas9) can be used. In the case of FnCpf1, a mutant in which the 917th Asp residue is converted to an Ala residue (D917A) or the 1006th Glu residue is converted to an Ala residue (E1006A), and lacking cleavage ability of both strands can be used. As long as at least one of the strands of double-stranded DNA lacks cleavage ability, other mutant Cas can also be used similarly.

A DNA encoding Cas effector protein (including mutant Cas, hereinafter the same) can be cloned by a method similar to the above-mentioned method for a DNA encoding a base excision repair inhibitor, from a cell producing the enzyme. A mutant Cas can be obtained by introducing a mutation to convert an amino acid residue of the site important for the DNA cleavage activity (e.g., 10th Asp residue and 840th His residue for SpCas9, 917th Asp residue and 1006th Glu residue for FnCpf1 and the like, though not limited thereto) to other amino acids, into a DNA encoding cloned Cas, by a site specific mutation induction method known per se.

Alternatively, a DNA encoding Cas effector protein can also be constructed as a DNA with codon usage suitable for expression in a host cell to be used, by a method similar to those mentioned above for a DNA encoding a nucleic acid sequence-recognizing module and a DNA encoding DNA glycosylase, and in a combination of chemical synthesis or PCR method or Gibson Assembly method.

The obtained DNA encoding a Cas effector protein, nucleic acid altering enzyme, base excision repair inhibitor, and/or transcriptional regulatory factor can be inserted into the downstream of a promoter of an expression vector similar to the one mentioned above, according to the target cell.

On the other hand, a DNA encoding guide RNA can be obtained by designing an oligoDNA sequence linking a coding sequence of crRNA sequence containing a nucleotide sequence complementary to the target nucleotide sequence (to be also referred to as “targeting sequence” in the present specification) (e.g., when FnCpf1 is recruited as Cas effector protein, crRNA containing SEQ ID NO: 19; AAUUUCUACUGUUGUAGAU at the 5'-side of the targeting sequence can be used, and the underlined sequences form base pairs to form a stem-loop structure), or a crRNA coding sequence and, where necessary, a known tracrRNA coding sequence (e.g., as tracrRNA coding sequence when Cas is recruited as Cas9 effector protein, gttttagagctagaaatagcaagttaaaataaggctagtccgttatcaacttgaaaaagtggca ccgagtcggtgcttttttt; SEQ ID NO: 18) and chemically synthesizing using a DNA/RNA synthesizer.

The "targeted strand" here means a strand forming a hybrid with crRNA of the target nucleotide sequence, and the opposite strand, which becomes single-stranded after hybridization of the targeted strand and crRNA, is referred to as a "non-targeted strand". Since a nucleic acid base conversion reaction is generally assumed to frequently occur on a single stranded non-targeted strand, when the target nucleotide sequence is to be expressed by one of the strands (e.g., when PAM sequence is indicated, when positional relationship of target nucleotide sequence and PAM is shown etc.), it is represented by a sequence of the non-targeted strand.

While the length of the targeting sequence is not particularly limited as long as it can specifically bind to a target nucleotide sequence, for example, it is 15-30 nucleotides, preferably 18-25 nucleotides. The selection of the target nucleotide sequence is restricted by the presence of an adjacent PAM on the 3'-side (in the case of Cas9) or 5'-side (in the case of Cpf1) of the sequence. According to the finding verified in the below-mentioned Examples, in the system of the present invention in which CRISPR-mutated Cas and cytidine deaminase are combined, the regularity exists that easily substituted C shifts toward the 5'-end as the target nucleotide sequence becomes longer. Therefore, by appropriately determining the length of the target nucleotide sequence (targeting sequence as a complementary strand thereof), the site of a base into which a mutation can be introduced can be shifted. As a result, restriction by PAM (NGG in SpCas9) can be removed at least partially, and the degree of freedom of mutation introduction is expected to be still higher.

When Cas9 is used as a Cas effector protein, a targeting sequence can be designed, for example, using a guide RNA design website open to public (CRISPR Design Tool, CRISPRdirect etc.) by listing up 20 mer sequences having PAM (e.g., NGG in the case of SpCas9) adjacent to the 3'-side from the CDS sequences of the gene of interest, and selecting a sequence that causes an amino acid change in the protein encoded by the target gene when C within 7 nucleotides from the 5' end thereof toward 3' direction is converted to T. An appropriate sequence can be selected even when a targeting sequence with a length other than 20 mer is used. A candidate sequence having a small number of off-target sites in the host genome of interest can be used as a targeting sequence. When the guide RNA design software to be used does not have a function to search off-target sites in the genome of the host, for example, off-target sites can be searched by applying a Blast search against the genome of the host, for example, 8-12 nucleotides on the 3'-side of the candidate sequence (seed sequence with high discrimination ability of target nucleotide sequence).

While a DNA encoding guide RNA can also be inserted into an expression vector similar to the one mentioned above. As the promoter, pol III system promoter (e.g., SNR6, SNR52, SCR1, RPR1, U3, U6, H1 promoter etc.) and terminator (e.g., polyT sequence ($T_6$ sequence etc.)) are preferably used.

A DNA encoding guide RNA (crRNA or crRNA-tracrRNA chimera) can be obtained by designing an oligoRNA sequence linking a sequence complementary to the target strand of the target nucleotide sequence and a known tracrRNA sequence (when Cas9 is recruited) or a direct repeat sequence of crRNA (when Cpf1 is recruited) and chemically synthesizing using a DNA/RNA synthesizer.

2. Alteration Method of Targeted Site of Double Stranded DNA of Host Bacterium

The targeted site of the double stranded DNA of the host can be altered, or the expression of a gene encoded by the double stranded DNA in the vicinity of the targeted site can be regulated by introducing the complex and the nucleic acid of the present invention described in 1. into a host, particularly a bacterium, and culturing the host. Therefore, in another embodiment, a method for altering a targeted site of a double stranded DNA of a bacterium, including a step of bringing the nucleic acid altering enzyme complex into contact with the double stranded DNA of the host bacterium to convert one or more nucleotides in the targeted site to other one or more nucleotides or delete one or more nucleotides, or insert one or more nucleotides into said targeted site (hereinafter to be also referred to as "the alteration method of the present invention") is provided. Using a nucleic acid base converting enzyme or DNA glycosylase as a nucleic acid altering enzyme, the targeted site can be altered without cleaving at least one of the strands of the double stranded DNA in the targeted site. In still another embodiment, a method including contacting the complex of the present invention with a double stranded DNA of the host bacterium and regulating transcription of a gene in the vicinity of the targeted site is provided.

The complex of the present invention is contacted with the double stranded DNA by introducing the complex or a nucleic acid encoding same into a bacterium having the desired double stranded DNA (e.g., genomic DNA). In consideration of the introduction and expression efficiency, it is desirable to introduce the complex for genome editing into the bacterium in the form of a nucleic acid encoding the complex, rather than as the complex itself, and express the complex in the bacterium.

Examples of the bacterium used for the alteration method of the present invention include those similar to the bacteria used for nucleic acid replication in 1.

An expression vector can be introduced by a known method (e.g., lysozyme method, competent method, PEG method, $CaCl_2$ coprecipitation method, electroporation method, the microinjection method, the particle gun method, lipofection method, *Agrobacterium* method and the like) according to the kind of the bacterium.

*Escherichia coli* can be transformed according to the methods described in, for example, Proc. Natl. Acad. Sci. USA, 69, 2110 (1972), Gene, 17, 107 (1982) and the like.

The genus *Bacillus* can be introduced into a vector according to the methods described in, for example, Molecular & General Genetics, 168, 111 (1979) and the like.

A bacterium introduced with a vector can be cultured according to a known method according to the kind of the bacterium.

For example, when *Escherichia coli* or genus *Bacillus* is cultured, a liquid medium is preferable as a medium to be used for the culture. The medium preferably contains a carbon source, nitrogen source, inorganic substance and the like necessary for the growth of the transformant. Examples of the carbon source include glucose, dextrin, soluble starch, sucrose and the like; examples of the nitrogen source include inorganic or organic substances such as ammonium salts, nitrate salts, corn steep liquor, peptone, casein, meat extract, soybean cake, potato extract and the like; and examples of the inorganic substance include calcium chloride, sodium dihydrogen phosphate, magnesium chloride and the like. The medium may contain yeast extract, vitamins, growth promoting factor and the like. The pH of the medium is preferably about 5 to about 8.

As a medium for culturing *Escherichia coli,* for example, M9 medium containing glucose, casamino acid [Journal of Experiments in Molecular Genetics, 431-433, Cold Spring Harbor Laboratory, New York 1972] is preferable. Where necessary, for example, agents such as 3β-indolylacrylic acid may be added to the medium to ensure an efficient function of a promoter. *Escherichia coli* is cultured at generally about 15 to about 43° C. Where necessary, aeration and stirring may be performed.

The genus *Bacillus* is cultured at generally about 30 to about 40° C. Where necessary, aeration and stirring may be performed.

The present inventors confirmed that when PmCDA1 is used as the nucleic acid altering enzyme, the mutation introduction efficiency is increased by culturing animal cells and plant cells at a temperature lower (e.g., 20 to 26° C., preferably, about 25° C.) than usual. When a bacterium is cultured, it is also preferable to culture at the above-mentioned low temperature.

An RNA encoding the complex of the present invention can be introduced into a host cell by microinjection method, lipofection method and the like. RNA introduction can be performed once or repeated multiple times (e.g., 2-5 times) at suitable intervals.

The present inventors also confirmed using a budding yeast that when sequence-recognizing modules are produced corresponding to the adjacent multiple target nucleotide sequences, and simultaneously used, the mutation introduction efficiency drastically increases than using a single nucleotide sequence as a target, and similar effects can also be expected in the bacterium. The effect can occur both when the nucleotide sequences are in the same direction (targeted strands are the same), and when they are opposed (both strands of double stranded DNA are targeted strands).

In a preferable embodiment, it was demonstrated that mutation can be simultaneously introduced into 6 sites of the genomic DNA of a bacterium by the method of the present invention (FIG. 10), and the mutation introduction efficiency is extremely high. Therefore, in the genome sequence alteration method, or target gene expression regulating method of the present invention, alteration of multiple DNA regions at completely different positions as targets, or regulation of expression of plural target genes can also be performed. Therefore, in one preferable embodiment of the present invention, two or more kinds of nucleic acid sequence-recognizing modules that specifically bind to different target nucleotide sequences (which, when target DNA is cell-endogenous DNA, may be present in one object gene, or two or more different object genes, and these object genes may be present on the same chromosome or plasmid, or different chromosome or plasmid) can be used. In this case, each one of these nucleic acid sequence-recognizing modules, and a nucleic acid altering enzyme and/or a base excision repair inhibitor, or a transcriptional regulatory factor form a complex added with a proteolysis tag. Here, a common nucleic acid base converting enzyme, a common base excision repair inhibitor and a common transcriptional regulatory factor can be used. For example, when CRISPR-Cas system is used as a nucleic acid sequence-recognizing module, a common complex (including fusion protein) of a Cas effector protein and a nucleic acid altering enzyme and/or a base excision repair inhibitor, or transcriptional regulatory factor is used, and two or more kinds of chimeric RNAs of each of two or more guide RNAs that respectively form a complementary strand with a different target nucleotide sequence, and tracrRNA are produced and used as guide RNA-tracrRNA. On the other hand, when zinc finger motif, TAL effector and the like are used as nucleic acid sequence-recognizing modules, for example, a nucleic acid altering enzyme and/or a base excision repair inhibitor, or a transcriptional regulatory factor can be fused with a nucleic acid sequence-recognizing module that specifically binds to a different target nucleotide.

To express the complex of the present invention in a host bacterium, as mentioned above, an expression vector containing a DNA encoding the complex is introduced into the host bacterium. For efficient introduction of mutation or sufficient regulation of the expression of a target gene, it is desirable to maintain an expression of the complex for genome editing at a given level or above for not less than a given period. From such viewpoint, it is certain that the expression vector is incorporated into the host genome. Since continuous expression of the complex for genome editing increases the risk of off-target cleavage, it is preferably removed immediately after achieving mutation introduction. Examples of the means for removing DNA incorporated into the host genome include a method using a Cre-loxP system, a method using transposon and the like.

Alternatively, editing of host genome can be efficiently realized while avoiding the risk of off-target cleavage by causing a nucleic acid reaction in a desired stage, and transiently expressing the complex of the present invention in a host bacterium for a period necessary for stabilizing the alteration of the targeted site. While a period necessary for the nucleic acid alteration reaction and stabilizing the alteration of the targeted site varies depending on the kind of the host bacterium, culture conditions and the like, about 2 to 3 days are considered to be necessary since at least several generations of cell division are generally necessary. Those of ordinary skill in the art can appropriately determine a preferable expression induction period based on the culture conditions and the like to be used. The expression induction period of a nucleic acid encoding the complex of the present invention may be extended beyond the above-mentioned "period necessary for stabilizing the alteration of the targeted site" as long as the host bacterium is free of side effects.

As a means for transiently expressing the complex of the present invention at a desired stage for a desired period, a method including producing a construct (expression vector) containing a DNA encoding the complex (in mutant CRISPR-Cas system, a DNA encoding a guide RNA, a DNA encoding a Cas effector protein, and, as necessary, a DNA encoding a nucleic acid altering enzyme and/or a base excision repair inhibitor, or a transcriptional regulatory factor) in a form permitting regulation of the expression period of the complex and introducing same into the host cell can be mentioned. The "form capable of regulating the expression period" is specifically, for example, a nucleic acid encoding the complex of the present invention placed under regulation of an inducible regulatory region. While the "inducible regulatory region" is not particularly limited, it is, for example, an operon of a temperature sensitive (ts) mutation repressor and an operator regulated thereby. Examples of the ts mutation repressor include, but are not limited to, ts mutation of cI repressor from Aphage. In the case of Aphage cI repressor (ts), it is linked to an operator to suppress expression of gene in the downstream at not more than 30° C. (e.g., 28° C.). At a high temperature of not less than 37° C. (e.g., 42° C.), it is dissociated from the operator to allow for induction of gene expression. Therefore, the period when the expression of the target gene is suppressed can be minimized by culturing a host bacterium is introduced with a nucleic acid encoding the complex of the present invention generally at not more than 30° C., raising the temperature to not less than 37° C. at an appropriate stage, performing culture for a given period to carry out nucleic acid conversion reaction and, after introduction of mutation into the target gene, rapidly lowering the temperature to not more than 30° C. Thus, even when an essential gene for the host cell is targeted, it can be efficiently edited while suppressing the side effects.

When temperature sensitive mutation is utilized, for example, a temperature sensitive mutant of a protein necessary for autonomous replication of a vector is included in a vector containing a DNA encoding the complex of the present invention. As a result, autonomous replication becomes impossible rapidly after expression of the complex, and the vector naturally falls off during the cell division. Examples of the temperature sensitive mutant protein include, but are not limited to, a temperature sensitive mutant of Rep101 ori necessary for the replication of pSC101 ori. Rep101 ori (ts) acts on pSC101 ori to enable autonomous replication of plasmid at not more than 30° C. (e.g., 28° C.), but loses function at not less than 37° C. (e.g., 42° C.), and plasmid cannot replicate autonomously. Therefore, a combined use with cI repressor (ts) of the above-mentioned λphage simultaneously enables transient expression of the complex of the present invention, and removal of the plasmid.

In addition, a DNA encoding the complex of the present invention is introduced into a host bacterium under regulation of inducible promoter (e.g., lac promoter (induced by IPTG), cspA promoter (induced by cold shock), araBAD promoter (induced by arabinose) etc.), the inducing substance is added to the medium (or removed from the medium) at an appropriate stage to induce expression of the complex, culture is performed for a given period to carry out a nucleic acid alteration reaction and, is introduction of mutation into the target gene, expression induction discontinuation, whereby transient expression of the complex can be realized.

The present invention is explained in the following by referring to Examples, which are not to be construed as limitative.

EXAMPLE

In the below-mentioned Examples, experiments were performed as follows.

<Design of Strain, Plasmid, Primer and Targeted gRNA>

*Escherichia coli* DH5α (($F^-$ endA1supE44 thi-1 recA1 relA1 gyrA96 deoR phoA Φ80dlacZ ΔM15 Δ(lacZYA-argF) U169, hsdR17 ($rK^-$, $mK^+$), $\lambda^-$) (TaKaRa-Bio) , BW25113 ($lacI^+$ $rrnB_{T14}$ $\Delta lacZ_{WJ16}$hsdR514 $\Delta araBAD_{AH33}$ $\Delta rhaBAD_{LD78}$ rph-1 Δ(araB-D)567 Δ(rhaD-B) 568ΔlacZ4787(::rrnB-3) hsdR514 rph-1) and Top10 (F-mcrA Δ(mrr-hsdRMS-mcrBC) φ80 lacZΔM15 ΔlacX74 nupG recA1 araD139 Δ(ara-leu)7697 galE15 galK16 rpsL ($Str^R$) endA1 $\lambda^-$) (Invitrogen) were used. The plasmids and primers used in the Examples are respectively shown in Table 1 and Table 2. An oligo DNA pair for constructing the targeted gRNA vector was designed as follows: 5'-tagc-(target sequence)-3' and 5'-aaac-(reverse complementary sequence of target sequence)-3'.

TABLE 1

Plasmids used in Example
Editing target is shown in italics.

| Plasmids | Characteristics | Reference |
|---|---|---|
| General plasmids | | |
| pSC101 | $Tc^r$ repA 101(Ts), | Lab stock |
| pWTY121 | $Amp^r$, $Erm^r$, B. subtilis recombination vector encoding λ cI857, λ β λ exo and cre recombinase genes | Wang, 2012 (23) |
| pTAKN2 | $Kan^r$, pMBI ori, cloning vector | Lab stock |
| Cas/CRISPR plasmids | | |
| pCas9 | $Cm^r$, p15A ori, cas9, tracrRNA, repeat-BsaI_spacer-repeat | Jiang, 2013 (13) |
| pCRISPR | $Kan^r$, repeat-BsaI_spacer-repeat | Jiang, 2013 (13) |
| pScI_dCas9-PmCDA1_J23119-sgRNA | $Cm^r$, repA 101(Ts), λ cI857, dCas9-PmCDA1, J23119-sgRNA-unit | This study |
| pSBP307 | pScI_dCas9-PmCDA1_J23110-*galK_9* | This study |
| pSBP304 | pScI_dCas9-PmCDA1_J23119-*rpoB_1* | This study |
| pScI | $Cm^r$, repA 101(Ts) λ cI857, | This study |
| pScI_dCas | $Cm^r$, repA 101(Ts) λ cI857, dCas9 | This study |
| PScI_dCas9-PmCDA1 | $Cm^r$, repA 101(Ts) λ cI857, dCas9-PmCDA1 | This study |
| pScI_dCas9-PmCDA1-LVA | $Cm^r$, repA 101(Ts) λ cI857, dCas9-PmCDA1-LVA | This study |
| pScI_dCas9-PmCDA1-UGI-LVA | $Cm^r$, repA 101(Ts) λ cI857, dCas9-PmCDA1-UGI-LVA | This study |
| pTAKN2_J23119-sgRNA | $Kan^r$, pTAKN2, J23119-sgRNA-units | This study |
| pSBP804 | pTAKN2_J23119-*galK_10-galK_11-galK_13* | This study |
| pSBP806 | pTAKN2_J23110-*galK_2-xylB_1-manA_1* | This study |
| pSBP808 | pTAKN2_J23119-*pta_1-adhE_3-tpA_2* | This study |
| pSBP80608 | pTAKN2_J23119-*galK_2-xylB_1-manA_1-pta_1-adhE_3-tpiA_2* | This study |
| pTAKN-IS1235 | pTAKN2_J23119-*IS1-IS2-IS3-IS5* | This study |
| pSBP8001 | $Kan^r$, pTAKN2_J23119-*galK_1* | This study |
| pSBP8003 | pTAKN2_J23119-*galK_2* | This study |
| pSBP8004 | pTAKN2_J23119-*galK_3* | This study |
| pSBP8005 | pTAKN2_J23119-*galK_4* | This study |
| pSBP8006 | pTAKN2_J23119-*galK_5* | This study |
| pSBP8007 | pTAKN2_J23119-*galK_6* | This study |
| pSBP8008 | pTAKN2_J23119-*galK_7* | This study |
| pSBP8009 | pTAKN2_J23119-*galK_8* [*20 nt*] | This study |
| pSBP8010 | pTAKN2_J23119-*galK_8* [*21 nt*] | This study |
| pSBP8011 | pTAKN2_J23119-*galK_9* [*20 nt*] | This study |
| pSBP8012 | pTAKN2_J23119-*galK_9* [*21 nt*] | This study |

TABLE 1-continued

Plasmids used in Example
Editing target is shown in italics.

| Plasmids | Characteristics | Reference |
|---|---|---|
| pSBP8013 | pTAKN2_J23119-*galK_10* | This study |
| pSBP8014 | pTAKN2_J23119-*galK_11* [*20 nt*] | This study |
| pSBP8015 | pTAKN2_J23119-*galK_11* [*23 nt*] | This study |
| pSBP8016 | pTAKN2_J23119-*galK_12* | This study |
| pSBP8017 | pTAKN2_J23119-*galK_13* [*20 nt*] | This study |
| pSBP8018 | pTAKN2_J23119-*galK_13* [*21 nt*] | This study |
| pSBP8019 | pTAKN2_J23119-*galK_14* | This study |
| pSBP8025 | pTAKN2_J23119-*gsiA* [*A18 nt*] | This study |
| pSBP8021 | pTAKN2_J23119-*gsiA* [*A20 nt*] | This study |
| pSBP8022 | pTAKN2_J23119-*gsiA* [*A22 nt*] | This study |
| pSBP8023 | pTAKN2_J23119-*gsiA* [*A24 nt*] | This study |
| pSBP8029 | pTAKN2_J23119-*gsiA* [*B18 nt*] | This study |
| pSBP8027 | pTAKN2_J23119-*gsiA* [*B20 nt*] | This study |
| pSBP8040 | pTAKN2_J23119-*gsiA* [*B22 nt*] | This study |
| pSBP8042 | pTAKN2_J23119-*gsiA* [*B24 nt*] | This study |
| pSBP8043 | pTAKN2_J23119-*gsiA* [*C18 nt*] | This study |
| pSBP8030 | pTAKN2_J23119-*gsiA* [*C20 nt*] | This study |
| pSBP8045 | pTAKN2_J23119-*gsiA* [*C22 nt*] | This study |
| pSBP8047 | pTAKN2_J23119-*gsiA* [*C24 nt*] | This study |
| pSBPS048 | pTAKN2_J23119-*ycbF* [*18 nt*] | This study |
| pSBP8050 | pTAKN2_J23119-*ycbF* [*20 nt*] | This study |
| pSBPS052 | pTAKN2_J23119-*ycbF* [*22 nt*] | This study |
| pSBP8037 | pTAKN2_J23119-*yfiH* [*18 nt*] | This study |
| pSBP8035 | pTAKN2_J23119-*yfiH* [*20 nt*] | This study |
| pSBP8056 | pTAKN2_J23119-*yfiH* [*22 nt*] | This study |

TABLE 2

Primers used in Example

| Name | Sequence (5' → 3') | SEQ ID NO | Purpose |
|---|---|---|---|
| p346 | GCTACTCTAGAAAAAAAAAACCCCGCCCTGTCAGGGGCGGGGTTTTTTTTTCGGGGTT TAGCAAGATGGCAGCGC | 20 | Xba1-rhoTer-chmrUnit_R |
| p426 | GCCTGATCGATGCATCAGAAAATTATTTTAAATTTCCTCTTGACAGCTAGCTCAGTC CTAGGTATAATGCTAGCAGAGACCCGGGATGGTC | 21 | Cla1-upE-P3-chmrUnit_F2 |
| p597 | GATCCTTTTTGATAATCTCGTCGACATAACAATTGAGCAAGAATCTTCATCG | 22 | Sal1-gRNArepeat_F |
| p598 | CTCACGTTAAGGGATTTTGGTCATCTGCAGTGTATGCGTATTTGCGCGCTG | 23 | Pst1_gRNArepeat_R |
| p599 | GAAGATTCTTGCTCAATTGTTATGTCGACGAGATTATCAAAAAGGATCTTCACCTAG | 24 | Sal1-pTAEN2-Kan-down |
| p600 | CAGCGCGCAAATACGCATACACTGCAGATGACCAAAATCCCTTAACGTGAG | 25 | Pst1-pTAKN2-colE1-up |
| p669 | CTGCACGCGCACTTTTCC | 26 | galK_up150_F |
| p260 | CTCTGTTTGCCAACGCATTTG | 27 | galK_50_F |
| p259 | CAATGGTGACATCACGCAGG | 28 | galK_600_R |
| p141 | CCTGGGCGATAACGTAGTTGC | 29 | rpoB_2K_R |
| p143 | CCTCGGCAACCGTCGTATCC | 30 | rpoB_1.5K_F |
| p490 | CCGGTTATCGGTAGCGATAC | 31 | xylB_up_F |
| p491 | GCCTGGGGATTATTGTGTGG | 32 | xylB_1K_R |
| p470 | GCGGCTCCAGGTTACTTCC | 33 | manA_up50_F |
| p471 | GCCATCACTTCCAGCGC | 34 | manA_0.9K_R |
| p496 | GCCAAATCGGCGGTAACG | 35 | pta_up_F |
| p497 | CCATTTCGTAACCGCCAGTC | 36 | pta_0.9K_R |
| p502 | CTCTCGTATTCGAGCAGATG | 37 | adhE_up_F |
| p503 | CCGCCCATAGCAACCAG | 38 | adhE_1K_R |

TABLE 2-continued

Primers used in Example

| Name | Sequence (5' → 3') | SEQ ID NO | Purpose |
|---|---|---|---|
| p508 | GGGGCGGCCATCTTCC | 39 | tpiA_up_F |
| p509 | CAGCCGAGGAAATTCAGG | 40 | tpiA_down_R |
| p685 | TCTTTCCCTACACGACGCTCTTCCGATCTCCGCAGAACAGGCAGCAGAG | 41 | NGSadaptor-galK_F1 |
| p686 | GTGACTGGAGTTCAaACGTGTGCTCTTCCGATCTGACAATGGGCGCATCGAGGG | 42 | NGSadaptor-galK_R1 |
| p687 | TCTTTCCCTACACGACGCTCTTCCGATCTCACACCGACTACAACGACGG | 43 | NGSadaptor-galK_F2 |
| p688 | GTGACTGGAGTTCAaACGTGTGCTCTTCCGATCTGCTGCTGCAATACGGTTCCG | 44 | NGSadaptor-galK_R2 |
| p689 | TCTTTCCCTACACGACGCTCTTCCGATCTCTTCGGCGGCGTGGACATGG | 45 | NGSadaptor-galK_F3 |
| p690 | GTGACTGGAGTTCAGACGTGTGCTCTTCCGATCTACGACAGCCACACCTTTGGGC | 46 | NGSadaptor-galK_R3 |
| p691 | TCTTTCCCTACACGACGCTCTTCCGATCTGGCGGTGGAAACGGGTACCGTCG | 47 | NGSadaptor-gisA_F |
| p692 | GTGACTGGAGTTCAGACGTGTGCTCTTCCGATCTCGCCCACCAGCGATAGCGTT | 48 | NGSadaptor-gsiA_R |
| p693 | TCTTTCCCTACACGACGCTCTTCCGATCTGGCGCTCTTGATTTTCGCCG | 49 | NGSadaptor-ycbF_F |
| p694 | GTGACTGGAGTTCAGACGTGTGCTCTTCCGATCTGGATGGCACGCTGGCAATGC | 50 | NGSadaptor-ycbF_R |
| p695 | TCTTTCCCTACACGACGCTCTTCCGATCTGCCTCCCTGTGCTGTTTTGC | 51 | NGSadaptor-yfiH_F |
| p696 | GTGACTGGAGTTCAGACGTGTGCTCTTCCGATCTGCTCAACACCCACGTTCGCC | 52 | NGSadaptor-yfiH_R |

| Name | Sequence (5' → 3') | SEQ ID NO | Purpose |
|---|---|---|---|
| 1631 | GCTCATTATTTGCCCGCTTG | 53 | IS1-1_F |
| 1632 | TGCCGGTTGCCAGATAGTC | 54 | IS1-1_R |
| 1683 | GGTCTTCAGGAAATCACCG | 55 | IS1-2_F |
| 1684 | CGTTCAACCACTTCAGTGTC | 56 | IS1-2_R |
| 1639 | CACAAAGCTGTAAATCAGCG | 57 | IS1-3_F |
| 1640 | GTCAATGCAACACCCCTTTC | 58 | IS1-3_R |
| 1635 | CTACAACCAGGTCGAGTCAG | 59 | IS1-4_F |
| 1636 | GTAATCCTGCACCTCCATCAC | 60 | IS1-4_R |
| 1628 | GCCAGTAGTACCCGTCGTTG | 61 | IS1-5_F |
| 1627 | CACAAGTCGTATTTCCAGAGG | 62 | IS1-5_R |
| 1637 | CTGCAATAAGCAGAACCACC | 63 | IS1-6_F |
| 1638 | TGTTGTGCGGTAAGTGTCTG | 64 | IS1-6_R |
| 1629 | GAGCAATGGATGGATTCGAAG | 65 | IS1-7_F |
| 1630 | TGAACAACTGTCCATGATTTCG | 66 | IS1-7_R |
| 703 | GGTACTTTCCGGGCAACCG | 67 | IS1-8_F |
| 708 | CTGCCATTAGCGCAGCCA | 68 | IS1-8_R |
| 704 | CATAGCTCTACACGCCAGG | 69 | IS1-9_F |
| 709 | ATCATGGGCTCCTTTTAGTTGC | 70 | IS1-9_R |
| 705 | GATATTGCCCGCCGGACAC | 71 | IS1-10_F |
| 710 | CGATCTAAAGCGCGCAGC | 72 | IS1-10_R |
| 706 | GACGTTGTTGAAAATGTAGGGT | 73 | IS1-11_F |
| 711 | GCCTAACGCCTTTAATTCAGG | 74 | IS1-11_R |
| 707 | TGTTGTGGAGCCTGAACGG | 75 | IS1-12_F |

TABLE 2-continued

| Primers used in Example | | |
|---|---|---|
| 712 GCAACTGTTCCGGCAGATG | 76 | IS1-12_R |
| 1556 CGGATTAATGATAAGTGGATCAG | 77 | IS2-1_F |
| 1563 CTTAGTGAATATTTGCCGACG | 78 | IS2-1_R |
| 1557 GCTGATAAGTTACCTCCTGACC | 79 | IS2-2_F |
| 1564 GCGACTATACAGGTTATTGACC | 80 | IS2-2_R |
| 1685 ACATTACAGAGAAGCCGATG | 81 | IS2-3_F |
| 1686 GTGATAGTTAGCGATGCCG | 82 | IS2-3_R |
| 1559 GGACGAATAAACGCATAATTAC | 83 | IS2-4_F |
| 1566 TCCCAACCTTCTGTCACAG | 84 | IS2-4_R |
| 1560 CAATTTTCGCACCGGAATC | 85 | IS2-5_F |
| 1567 ATGGAGATACGACAATCAGC | 86 | IS2-5_R |
| 1561 CAATTCCTGGAACATTATCCG | 87 | IS2-6_F |
| 1568 TGAGTGATGTTTTGGCGAC | 88 | IS2-6_R |
| 1562 CTGTACTCACAGGGTGATG | 89 | IS2-7_F |
| 1569 GGCAGACAGTTTGAAACC | 90 | IS2-7_R |
| 713 CGCCACGAACGTAGTTAGC | 91 | IS2-8_F |
| 719 GATTGGTGAACACACCGACTAC | 92 | IS2-8_R |
| 714 GGTCAGGTGGTTTGGAAAGC | 93 | IS2-9_F |
| 720 AAGTGGACACGCTATACCTGC | 94 | IS2-9_R |
| 715 CACTCAACACATACCGTGCC | 95 | IS2-10_F |
| 721 CAACACCAAACTGGAACACGG | 96 | IS2-10_R |
| 716 CGGAGGAAACAGAATCAGTGTG | 97 | IS2-11_F |
| 722 GAGATGGTGGAGATCCTCTCG | 98 | IS2-11_R |
| 717 GATAGTTAGCGATGCCGGG | 99 | IS2-12_F |
| 723 GGAGAATCCCCAGGTTATCTGG | 100 | IS2-12_R |
| 718 TGAAACGTGCGGGTCTCAAC | 101 | IS2-13_F |
| 724 GGATAGTGGTTAATGGTGGCGTC | 102 | IS2-13_R |
| 1641 CGTGCTGAGGGCTATTTACC | 103 | IS3-1_F |
| 1642 GACGTCATCATTTAGCCAGATG | 104 | IS3-1_R |
| 1643 GGTTCTCAGGTTAATGTTTCGG | 105 | IS3-2_F |
| 1644 CACCAGATACTACGTTACCG | 106 | IS3-2_R |
| 1645 TTCGGACTGAAAGGAGCAAG | 107 | IS3-3_F |
| 1646 AGATTCGTGCTCACCTTTCC | 108 | IS3-3_R |
| 1647 GATTAGTATTGGCGCTGTTGTG | 109 | IS3-4_F |
| 1648 CAGTCCATTTCACCGTATGAG | 110 | IS3-4_R |
| 1649 ACAGACGACCAGAGTAATGTC | 111 | IS3-5_F |
| 1650 TGGTTACGCGCTTTCATGG | 112 | IS3-SR |
| 1651 CAGGCTGAACATGGATAAGAC | 113 | IS5-1_F |
| 1652 ACGTATGGACATCTAAACATCC | 114 | IS5-1_R |

TABLE 2-continued

| Primers used in Example | | |
|---|---|---|
| 1653 GCAAGGTTGTGCTTCTAAAGG | 115 | IS5-2_F |
| 1654 CCTGCAATCTAAAGGTAAGGATC | 116 | IS5-2_R |
| 1655 GATTGCTGTGGCAGGTTTAC | 117 | IS5-3_F |
| 1656 CAGTACAACCTAGTTGCACC | 118 | IS5-3_R |
| 1657 TGAAGATTCCGTGCGTAACC | 119 | IS5-4_F |
| 1658 CACGATGAAACCGTCAGTG | 120 | IS5-4_R |
| 1659 ATGCTACTGCCGGAACAAC | 121 | IS5-5_F |
| 1660 TGATGTCAGCGAGAAGATGG | 122 | IS5-5_R |
| 1661 AGCACAGGTCAATATCTTCAC | 123 | IS5-6_F |
| 1662 AATATAGACCCGCAGATGATG | 124 | IS5-6_R |
| 1663 TCCGCCAGGATTGATTTTCG | 125 | IS5-7_F |
| 1664 CTCCGGGTATGGAGCTATG | 126 | IS5-7_R |
| 1665 GATCAGGACGCTCATATTCG | 127 | IS5-8_F |
| 1666 CTGTCATGTCGGTTAGTTCC | 128 | IS5-8_R |
| 1667 ACAGGATGAAAGTCTTTGCC | 129 | IS5-9_F |
| 1668 GCAATTTCCGCTTTTGCTCG | 130 | IS5-9_R |
| 1681 AACTGCTTCTCCTCACCATC | 131 | IS5-10_F |
| 1682 AGAATCGTCTGGCGGTTG | 132 | IS5-10_R |
| 1671 CATCAGAATCAATGCTGCG | 133 | IS5-11_F |
| 1672 TCGCTGACTTCAGTTTCGC | 134 | IS5-11_R |
| 1673 GCCTGCCAGATGATATGGTC | 135 | IS5-12_F |
| 1674 ACCAGACCGTGGTTGTTAG | 136 | IS5-12_R |
| 725 TTTGTTATCCAGCCATGATGTTTTC | 137 | IS5-13_F |
| 728 TTCCTGTATACCTGAAACGACAATG | 138 | IS5-13_R |
| 726 CACGCACATACAACGGAGGG | 139 | IS5-14_F |
| 729 TTGACTGTGCGCAACATCCC | 140 | IS5-14_R |
| 727 CCTATTCCGCCCATGACC | 141 | IS5-15_F |
| 730 CAAAGGTCCAGGCTTTTGGG | 142 | IS5-15_R |

<Plasmid Construction> pCas9 and pCRISPR plasmids were obtained from the Marraffini lab (non-patent literature 8) via Addgene. Nickase Cas9:nCas9 (D10A or H840A) and nuclease lack Cas9: dCas9 (D10A and H840A) (SEQ ID NO: 1 and 2) (Jinek, M. et al., Science 337, 816-822 (2012).) were produced by the PCR method. PmCDA1 (SEQ ID NO: 3 and 4) was fused to the C-terminus of nCas9 or dCas9 with 121 amino acid peptide linkers (SEQ ID NO: 5 and 6) (FIG. 1).

A plasmid pScI_dCas9-PmCDA1_J23119-sgRNA carries sgRNA unit (SEQ ID NO: 15) driven by synthetic constitutive promoter J23119 (BBa_J23119 in the registry for standard biological parts) (parts.igem.org/Part:BBa_J23119) (SEQ ID NO: 16) amplified by PCR using p346/p426. sgRNA-expression unit contains two BsaI restriction sites for insertion target sequence. A pair of oligo DNA that contains target sgRNA sequence was annealed and ligated into BsaI-digested pScI_dCas9-PmCDA1_sgRNA.

pScI and pScI_dCas9 are carrying only λ operator and operator-dCas9, respectively. pScI_dCas9-PmCDA1 is carrying dCas9-PmCDA1 gene. The degradation tag (LVA tag) and UGI gene are added to the C-terminus of the dCas9-PmCDA1 gene, resulting plasmid pScI_dCas9-PmCDA1-LVA and pScI_dCas9-PmCDA1-UGI-LVA, respectively.

The vector plasmid pTAKN-2 has pMB1 origin compatible with pSC101. sgRNA-unit with the promoter J23119 was digested from synthetic oligonucleotide by EcoRI-HindIII, followed by ligation to the cloning vector pTAKN2. The plasmid harboring tandem three target sequences (pSBP804, galK_10-galK_11-gal_13; pSBP806, galK_2-xylB_1-manA_1; pSBP808, pta_1-adhE_3-tpiA_2) were constructed using Golden Gate assembly of the PCR product using BsaI digestion-ligation (Engler, C. et al., PLoS One 4, (2009).). The plasmid harboring different six target sequences (pSBP80608) was constructed using Gibson Assembly of the PCR products amplified from pSBP808 (pta_1-adhE_3-tpiA_2 tandem-sequence) by primers p597/598 and from pSBP806 (vector and galK_2-xylB_1-manA_1 tandem-sequence) by primers p599/p600. For IS-editing plasmid, sgRNA-expressing units were tandemly aligned in the order of IS1, IS2, IS3 and IS5.

<Mutagenesis Assay>

DH5α or BW25113 cells chemically transformed with objective plasmid(s) were pre-cultured with 1 mL SOC medium (2% Bacto Tryptone, 0.5% Yeast Extract, 10 mM NaCl, 2.5 mM KCl, 1 mM $MgSO_4$ and 20 mM glucose). After incubation for 2-3hr at 28° C., cell cultures were diluted 1:10 into 1 ml of Luria-Bertani (LB) broth or terrific broth (TB), supplemented with the following antibiotics as needed: chloramphenicol (25 μg/ml) and/or kanamycin (30 μg/ml), and grown overnight at 28° C. in 100K rpm using maximizer (TAITEC, Saitama, Japan). Next day, cell cultures were diluted 1:10 into 1 ml media again and cultured for 6hr at 37° C. for induction, followed by overnight incubation at 28° C. The cell cultures were then spotted in serial dilution onto LB or TB agar plates supplemented with appropriate antibiotics, incubated overnight at 28° C. to form single colonies.

For positive-selection for galK gene disruption, cells were grown in M63 minimal medium (2 g/L $(NH_4)_2SO_4$, 13.6 g/L $KH_2PO_4$, 0.5 mg/L $FeSO_4$-$7H_2O$, 1 mM $MgSO_4$, 0.1 mM $CaCl_2$ and 10 μg/ml thiamine) containing 0.2% glycerol and 0.2% 2-deoxy-galctose (2-DOG) (Warming, S. et al., Nucleic Acids Res. 33, 1-12 (2005).). For selection for rifampicin-resistant mutation of rpoB gene, cells were grown in LB broth containing 50 μg/ml rifampicin. For the sequencing analysis, colonies were randomly collected and directly amplified using appropriate primers by PCR and were analyzed by Sanger sequencing using a 3130XL Genetic Analyzer (Applied Biosystems). The t-test statistical analysis was done using Excel software (Microsoft).

<Whole Genome Sequencing>

BW25113 cells harboring each expression construct (dCas9, dCas9-PmCDA1, dCas9-PmCDA1-LVA-UGI and dCas9-PmCDA1 with rpoB_1 target) were pre-incubated overnight, diluted 1:10 into 1 mL LB media and grown for 6 hr at 37° C. for induction, followed by overnight incubation at 28° C. Cells were spread onto rifampicin-containing plate medium to isolate single colonies. Each three independent colonies were inoculated into TB medium. Genomic DNA was extracted using Wizard Genomic DNA Purification Kit (Promega) and then fragmented by sonication using Bioruptor UCD-200 TS Sonication System (Diagenote) to obtain fragments with size distribution at 500-1000 bp. Genomic DNA library was prepared by using NEBNext Ultra DNA Library Prep Kit for Illumina (New England Biolabs) and labeled by Dual Index Primers. Size selection of the library was done using Agencourt AMPure XP (Beckman Coulter) to obtain tagged fragments with length ranging from 600 to 800 bp. Size distribution was evaluated by the Agilent 2100 Bioanalyzer system (Agilent Technologies). DNA was quantified using Qibit HS dsDNA HS Assay Kit and fluorometer (Thermo Fisher Scientific). Sequencing was performed using MiSeq sequencing system (Illumina) and MiSeq Reagent Kit v3 to obtain 2×300 bp read length, expecting approximately 20-fold coverage for the genome size. Data analysis was done by using CLC Genomic Workbench 9.0. (CLC bio). The sequence reads were paired and overlapping reads within a read pair were merged then trimmed based on a quality limit of 0.01 with a maximum of 2 ambiguities. Reads were mapped to *Escherichia coli* BW25113 reference genome by the following setting (Masking mode=no masking, Mismatch cost=2, Insertion cost=3, Deletion cost=3, Length fraction=0.5, Similarity fraction=0.8, Global alignment=No, Auto-detect paired distances=Yes, Nonspecific match handling=ignore). Local realignment was done with defaults settings (Realign unaligned ends=Yes, Multi-pass realignment=2). The variant calling was performed with the following settings (Ignore positions with coverage=1,000,000, Ignore broken pairs=Yes, Ignore Nonspecific matches=Reads, Minimum coverage=5, Minimum count=2, Minimum frequency=50%, Base quality filter=No, Read detection filter=No, Relative read direction filter=Yes, Significance=1%, Read position filter=No, Remove pyro-error variants=No). Output file was arranged using Excel (Microsoft).

<Deep Sequencing of Target Regions>

DH5α cells expressed dCas9-PmCDA1 or dCas9-PmCDA1-UGI-LVA with gRNA targeting galK, gsiA, ycbF or yfiH genes were incubated overnight, diluted 1:10 into 1 mL LB media and grown for 6 hr at 37° C. for induction. Cell cultures were collected and genomic DNA was extracted. Target region-containing fragment (~0.3 kb) was directly amplified using primer pairs (p685-p696) from the extracted genomic DNA. The amplicon was labeled by Dual Index Primers. More than 30,000 reads per sample on average were analyzed by MiSeq sequencing system. The sequence reads were paired and trimmed based on a quality limit of 0.01 with a maximum of 2 ambiguities and then overlapping reads within a read pair were merged. Reads were mapped to each reference sequence by the following settings (Masking mode=no masking, Mismatch cost=2, Insertion cost=3, Deletion cost=3, Length fraction=0.5, Similarity fraction=0.8, Global alignment=No, Auto-detect paired distances=Yes, Nonspecific match handling=Map randomly). Output file was arranged using Excel.

Example 1

Deaminase-Mediated Target Mutagenesis in *Escherichia coli*

Figure 2:
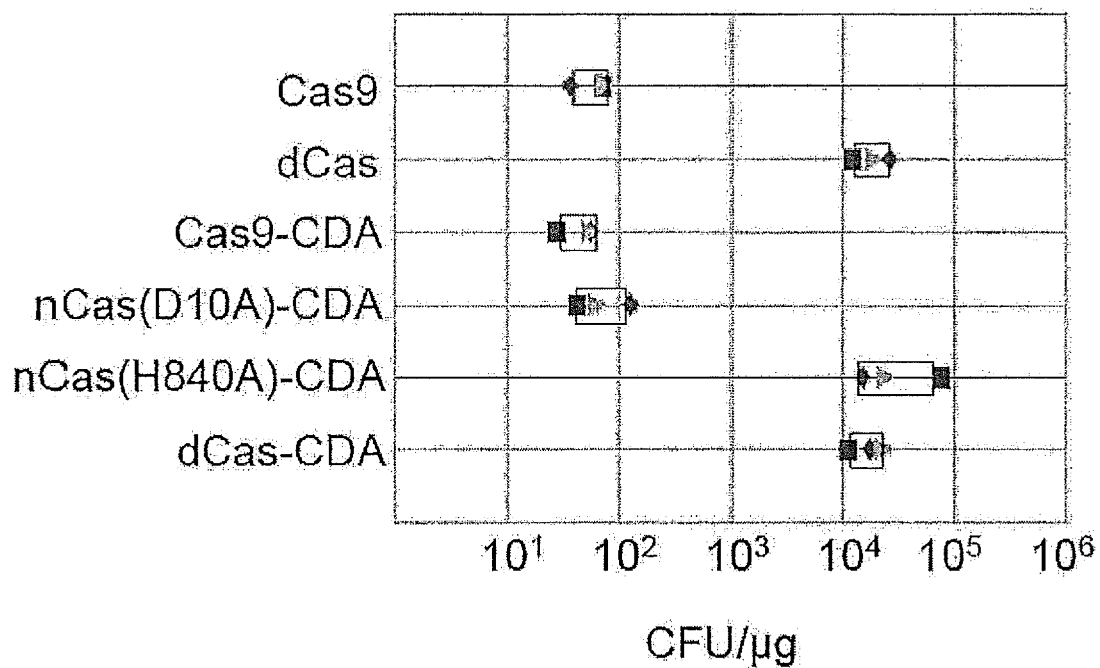
FIG. 2 shows the transformation efficiency of the Cas9 and Target-AID vectors in *Escherichia coli*. Plasmids expressing each protein for alteration (Cas9, dCas, Cas9-CDA, nCas-CDA or dCas-CDA) with sgRNA targeting galK gene were transformed into *Escherichia coli* DH5α strain and selected for chloramphenicol resistance marker. Viable cells were counted and calculated as colony forming unit (CFU) per amount of transformed plasmid DNA. Dots represent three independent experiments and box indicates 95% confidence interval for a geometric mean by t-test analysis.

To assess whether the deaminase-mediated targeted mutagenesis is applicable in bacteria, a bacterial Target-AID vector was constructed that expresses catalytically inactivated Cas9 (dCas: D10A and H840A mutations) fused to the cytosine deaminase PmCDA1 from P. marinus (sea lamprey) (non-patent literature 11) (CDA) under temperature-inducible A operator system (Wang, Y. et al., Nucleic Acids Res. 40, (2012).) and 20-nucleotides (nt) target sequence-gRNA scaffold hybrid (sgRNA) under a synthetic constitutive promoter J23119 (FIG. 1*b*). While nickase Cas9 (nCas: a D10A mutation) in combination with the deaminase can be used in eukaryotes to perform higher mutational efficiency (non-patent literatures 10, 11), the plasmid expressing nCas (D10A)-CDA showed poor transformation efficiency, suggesting that it causes severe cell growth and/or cell death in *Escherichia coli,* similarly to full Cas9 nuclease (FIG. 2). On the other hand, nCas (H840)-CDA showed transformation efficiency similarly as high as dCas and dCas-CDA, and was advantageous for cell proliferation and cell survival.

To assess the efficacy of targeted mutagenesis quantitatively, galK gene was used as a target whose loss of function can be positively selected by a galactose analog 2-deoxi-D-galactose (2-DOG), which is catalyzed by the galK gene product galactokinase to form a toxic compound (Warming, S. et al., Nucleic Acids Res. 33, 1-12 (2005).). As Target-AID is known to induce mutations at cytosine nucleotides (C) located around 15-20 bases with core region of 16-19 bases upstream of the protospacer adjacent motif (PAM) sequence (non-patent literature 11) (FIG. 1(*a*)). Targeting sequence was selected in the galK gene to introduce a stop codon (FIG. 3) and induced nearly 100% viability against 2-DOG, suggesting highly efficient mutagenesis (FIG. 4(*a*)). Six out of eight colonies were mutated as expected when sequencing analysis was performed on the cells from non-2-DOG selective medium. C to T substitutions were observed at -17 and/or -20 positions as expected.

Next, an essential gene rpoB was targeted that encodes the β-subunit of RNA polymerase. While disturbing gene function of rpoB would cause cell growth suppression or cell death, specific point mutations in rpoB gene are known to confer rifampicin resistance (Jin, D. J. et al., J. Mol. Biol. 202, 245-253 (1988).). A targeting sequence was designed to induce a point mutation that confers rifampicin resistance (FIG. 5(*a*)). With no obvious growth suppression, transformed cells gained rifampicin resistance in nearly 100% frequency (FIG. 4(*b*)). Sequencing analysis of the non-rifampicin selected clones confirmed the C to T substitutions at −16 and/or −17 positions from the PAM sequence (position 1545 and 1546 of the rpoB gene) as expected (FIG. 5(*a*)). Whole genome sequencing was performed to assess the possible non-specific mutagenesis effect of the Target-AID in *Escherichia coli*. Three independent clones expressing dCas-CDA and the rpoB 1 targeting sgRNA were analyzed and found to contain zero to two unique single nucleotide variants (SNVs) at apparently unrelated genomic position (FIG. 5(*b*)). Adjacent sequences of the detected SNVs did not show any similarity to the rpoB target sequence (FIG. 5(*c*)).

Example 2

Figure 6:
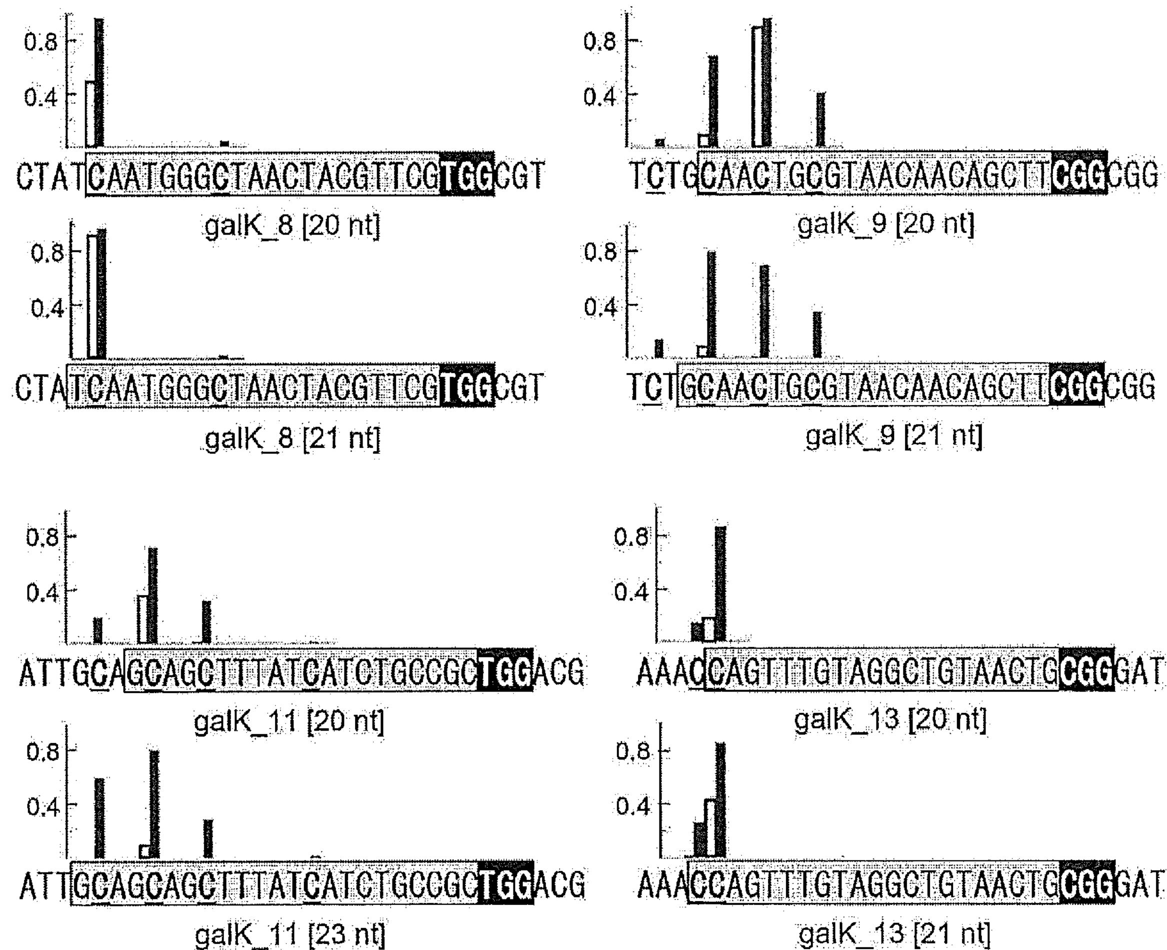
FIG. 6 shows the presence or absence of UGI-LVA, and mutation position and frequency when sgRNA with a different length was used. Target sequences (galK_8, 9, 11 and 13) with 20 nt length and longer were tested by using dCas-CDA (blue bar) or dCas-CDA-UGI-LVA (red bar) and analyzed by deep sequencing. Average of three independent experiments was plotted. Gray shade and inverted box indicate galK targeting sequences and PAM, respectively. Mutated bases are underlined. galK_8 is SEQ ID NO: 218, galK_9 is SEQ ID NO: 222, galK_11 is SEQ ID NO: 220, and galK_13 is SEQ ID NO: 224.

Effect of sgRNA Length and Uracil DNA Glycosylase Inhibitor on the Mutational Frequency and Positions To comprehensively analyze mutational efficiency and position, deep sequencing analysis was performed using 18 targeting sequences at galK gene (FIG. 6, FIG. 7). Seven targets showed highly efficient (61.7-95.1%) mutagenesis while five showed poor (1.4-9.2%) mutagenesis. The most effective mutational positions were at 17-20 bases upstream of PAM, which was consistent with the previous study in higher organisms. The mutation frequency also varied depending on the length of the target sequence, as appreciated from the higher efficiency at galK_8 and galK_13, and lower at galK_9 and galK_11, of sgRNA with longer target sequences (FIG. 6, left bars).

To improve mutational efficiency, uracil DNA glycosylase inhibitor (UGI) from bacteriophage PBS2 (Zhigang, W. et al., Gene 99, 31-37 (1991).) and protein degradation tag (LVA-tag) (Andersen, J. B. et al., Appl. Environ. Microbiol. 64, 2240-2246 (1998).) were introduced by fusing at the C-terminus of dCas-CDA. UGI boosts the mutagenesis by cytidine deamination because it inhibits removal of uracil (immediate product of cytosine deamination) from DNA (non-patent literatures 10, 11). Use of the LVA-tag is expected to protect cells from injury and suppress the occurrence of escaper cells by decreasing the half-life of the dCas-CDA-UGI protein, which could be potentially harmful when expressed in excess. To assess the non-specific mutagenesis effect, whole genome sequencing analysis was performed on the cells expressing dCas, dCas-CDA and dCas-CDA-UGI-LVA. While dCas-CDA induced 0 to 2 SNV mutations, dCas-CDA-UGI-LVA induced 21-30 mutations with no positional bias in the entire genome (Table 3 and Table 4).

TABLE 3

Whole genome sequencing analysis of rifampicin resistance variant

| Strain | Clone | Sequence coverage | rpoB mutation Position | rpoB mutation Amino acid | Number of other variants | C:G to T:A SNV |
|---|---|---|---|---|---|---|
| dCas | 1 | 22.8 | 4172707 | S512F | 0 | 0 |
| dCas-CDA | 1 | 34.7 | 4172764 | S531F | 2 | 1 |
| | 2 | 28.1 | 4172718 | D516N | 0 | 0 |
| | 3 | 20.5 | 4172718 | D516N | 0 | 0 |
| dCas-CDA-UGI-LVA | 1 | 17.3 | 4172737 | S522F | 21 | 21 |
| | 2 | 23.3 | 4172737 | S522F | 30 | 29 |
| | 3 | 24.0 | 4172863 | P564L | 29 | 29 |

Rifampicin selected clones expressing each constructs (dCas, dCas-CDA or dCas-CDA-LVA-UGI) without sgRNA were subjected to whole genome sequencing. Biological triplicate was shown for dCas-CDA and dCas-CDA-LVA-UGI. Sequence coverage was calculated as sum base pair of mapped sequence over 4,631 Mbp of *Escherichia coli* BW25113 genome sequence. List of unique mutation is shown in Table 4.

TABLE 4

List of unique SNV mutations The detail of SNV detected by whole genome sequencing is shown in Table 3.

| Strain_Clone | Region | Gene | Reference | Allele |
|---|---|---|---|---|
| dCas-CDA_1 | 883372 | rcdA | C | T |
| | 1371764 | ycjS | T | A |
| dCas-CDA--UGI-LVA_1 | 31518 | carB | C | T |
| | 97137 | marG | C | T |
| | 290595 | intergenic | C | T |
| | 652855 | espE | C | T |
| | 689724 | miaB | C | T |
| | 896435 | artM | C | T |
| | 1267335 | intergenic | C | T |
| | 2054913 | nac | G | A |
| | 2062420 | yoaA | G | A |
| | 2072468 | intergenic | G | A |
| | 2110764 | wcaK | G | A |
| | 2550667 | intergenic | C | T |
| | 3322221 | intergenic | G | A |
| | 3681689 | yhjK | G | C |
| | 3692110 | bcsG | G | A |
| | 3983269 | hemC | C | T |
| | 4110323 | intergenic | G | A |
| | 4335067 | yjdF | C | T |
| | 4480068 | idnR | C | T |
| | 4596191 | tRNA-Leu | G | A |
| | 4596193 | tRNA-Leu | G | A |
| dCas-CDA--UGI-LVA_2 | 800029 | ybhJ | C | T |
| | 1024591 | 23S rRNA | C | T |
| | 1050689 | torS | G | A |
| | 1199523 | ymfM | C | T |
| | 1644392 | ydfE | G | A |
| | 1723279 | intergenic | G | A |
| | 1728672 | intergenic | C | T |
| | 1761805 | ydiJ | G | A |
| | 2063321 | IS2 transposase | G | A |
| | 2072468 | intergenic | G | A |
| | 2208318 | mlrA | C | T |
| | 2245059 | nfo | C | T |
| | 2249454 | yeiL | G | A |
| | 2261905 | yeiR | G | A |
| | 2416291 | yfcI | A | C |
| | 2438584 | yfcA | G | A |
| | 2563453 | eutJ | G | A |

TABLE 4-continued

List of unique SNV mutations The detail of SNV detected by whole genome sequencing is shown in Table 3.

Figure 8:
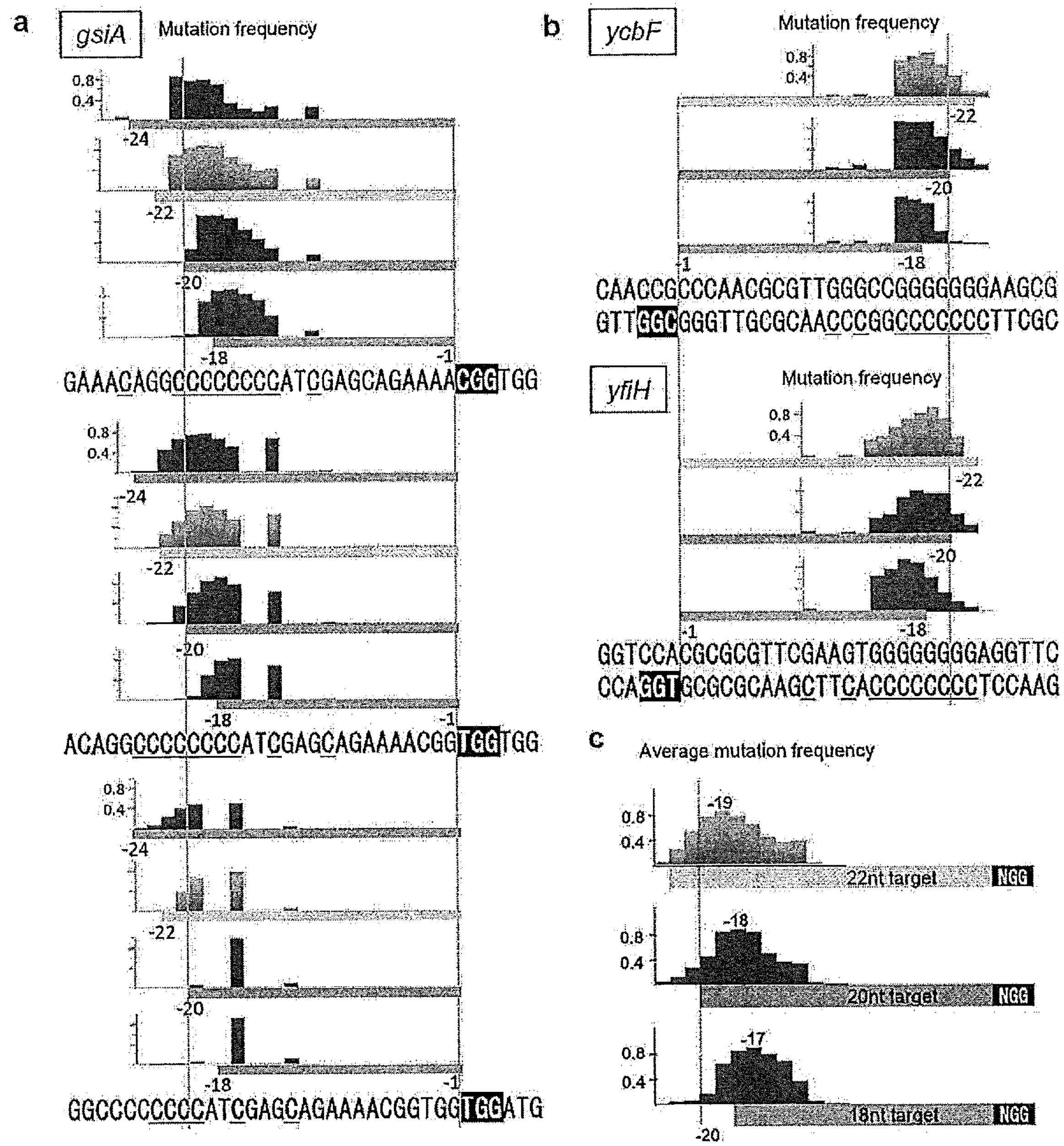
FIG. 8 shows the Effect of target lengths on the mutational spectrum. (a) shows the mutation frequencies using various lengths of target sequences in the gsiA. Target sequences that contain poly-C on the distal site was edited by dCas-CDA-UGI-LVA and analyzed by deep sequencing. Mutational spectra for sgRNAs with 18nt, 20nt, 22nt or 24nt length were distinguished by the shade of gray. Averages for three independent experiments are shown. Inverted box indicates PAM. Mutated bases are underlined. The sequences in FIG. 8A top to bottom are SEQ ID NO: 244, SEQ ID NO: 245 and SEQ ID NO: 246. (b) shows the mutation frequencies for targets in ycbF (5'->3' is SEQ ID NO: 247 and 3' to 5' is SEQ ID NO: 248) and yfiH (5'->3' is SEQ ID NO: 249 and 3'->5' is SEQ ID NO: 250). Targets are set on the bottom strands. Mutational spectra for sgRNAs with 18nt, 20nt or 22nt length are used and shown as in (a). (c) shows averaged mutational spectra for each sgRNA length of (a) and (b). Peak positions are numbered.

| Strain_Clone | Region | Gene | Reference | Allele |
|---|---|---|---|---|
| | 2668799 | yphC | G | A |
| | 2957527 | ppdA | G | A |
| | 3168170 | parE | G | A |
| | 3365636 | nanT | G | A |
| | 3374392 | degQ | C | T |
| | 3441395 | 50S rRNA | G | A |
| | 3521736 | yrfF | G | A |
| | 3787020 | yibB | G | A |
| | 3921738 | viaA | C | T |
| | 4233085 | malG | C | T |
| | 4291989 | mdrO | C | T |
| | 4357531 | aspA | C | T |
| | 4486193 | intergenic | C | T |
| dCas-CDA-- | 124371 | intergenic | C | T |
| UGI-LVA_3 | 268728 | ykfC | C | T |
| | 701013 | nagE | C | T |
| | 1094697 | ycdX | C | T |
| | 1253681 | pth | C | T |
| | 1356138 | puuD | C | T |
| | 1513742 | curA | G | A |
| | 1552442 | ddpD | G | A |
| | 1771594 | ydtO | G | A |
| | 1950273 | torZ | G | A |
| | 2025444 | dcm | G | A |
| | 2221782 | mdtQ | G | A |
| | 2298519 | intergenic | G | A |
| | 2312704 | resC | G | A |
| | 2730338 | intergenic | C | T |
| | 2769113 | ypjI | G | A |
| | 2811281 | intergenic | G | A |
| | 3009344 | ygfK | G | A |
| | 3055007 | scpA | G | A |
| | 3542313 | malQ | G | A |
| | 3572324 | yhhW | G | A |
| | 3574775 | yhhY | G | A |
| | 3601990 | zniA | G | A |
| | 4111319 | hslU | G | A |
| | 4133803 | frwB | C | T |
| | 4347276 | codA | C | T |
| | 4384586 | unr | C | T |
| | 4386604 | omiB | C | T |
| | 4492813 | IS4 transposase | C | T |

dCas-CDA-UGI-LVA showed robust mutagenesis at the all targeted sites regardless of the length and position of the target sequence (FIG. 5, right bars) and allowed for comparison of mutational spectra using different length of sgRNA. As a result, galK_9 and galK_11 showed extended mutational spectra towards 5' ends (FIG. 6). To further characterize the effect of length of sgRNA target sequence, C-rich target sequences with 18 nt, 20 nt, 22 nt and 24 nt length were tested (FIGS. 8(*a*) and (*b*)). Mutational spectra for each of 5 target sites consistently showed the peak shift and expansion of window towards 5' end as target sequence lengthened (FIG. 8(*c*)).

Example 3

Multiplex Mutagenesis

For multiplex editing, tandem repeat of sgRNA expression units was assembled onto a separate plasmid from the plasmid for alteration. A plasmid targeting three sites in the galK gene (galK_10, galK_11 and galK_13) was constructed and co-introduced into cells with the vector for alteration expressing dCas, dCas-CDA, dCas-CDA-LVA or dCas-CDA1-UGI-LVA. First, non-specific mutagenesis effect was assessed by analyzing occurrence of rifampicin resistance mutation (FIG. 9). While dCas-CDA showed approximately 10-fold increase over background mutational frequency, dCas-CDA-UGI-LVA showed another 10-fold increase over the mutational frequency of dCas-CDA. However, mutation at one site occurred in both and the mutation rate of at least the target did not show a significant difference between the presence or absence of LVA. Therefore, it was shown that non-specific mutagenesis can be suppressed by adding LVA, while maintaining mutation efficiency, and dCas-CDA and dCas-CDA-LVA were not efficient enough to obtain triple mutant at once, dCas-CDA-UGI-LVA succeeded in triple mutagenesis in five out of eight clones analyzed (FIG. 9(*b*) and (d)), although mutational frequency seemed lower when compared with the result of each single targeting that yielded 100% (8/8) for each targets (FIGS. 9(*c*) and (*d*)). Therefore, it was shown that non-specific mutagenesis can be suppressed by a combination of UGI and LVA, while achieving high mutation efficiency.

Figure 10:
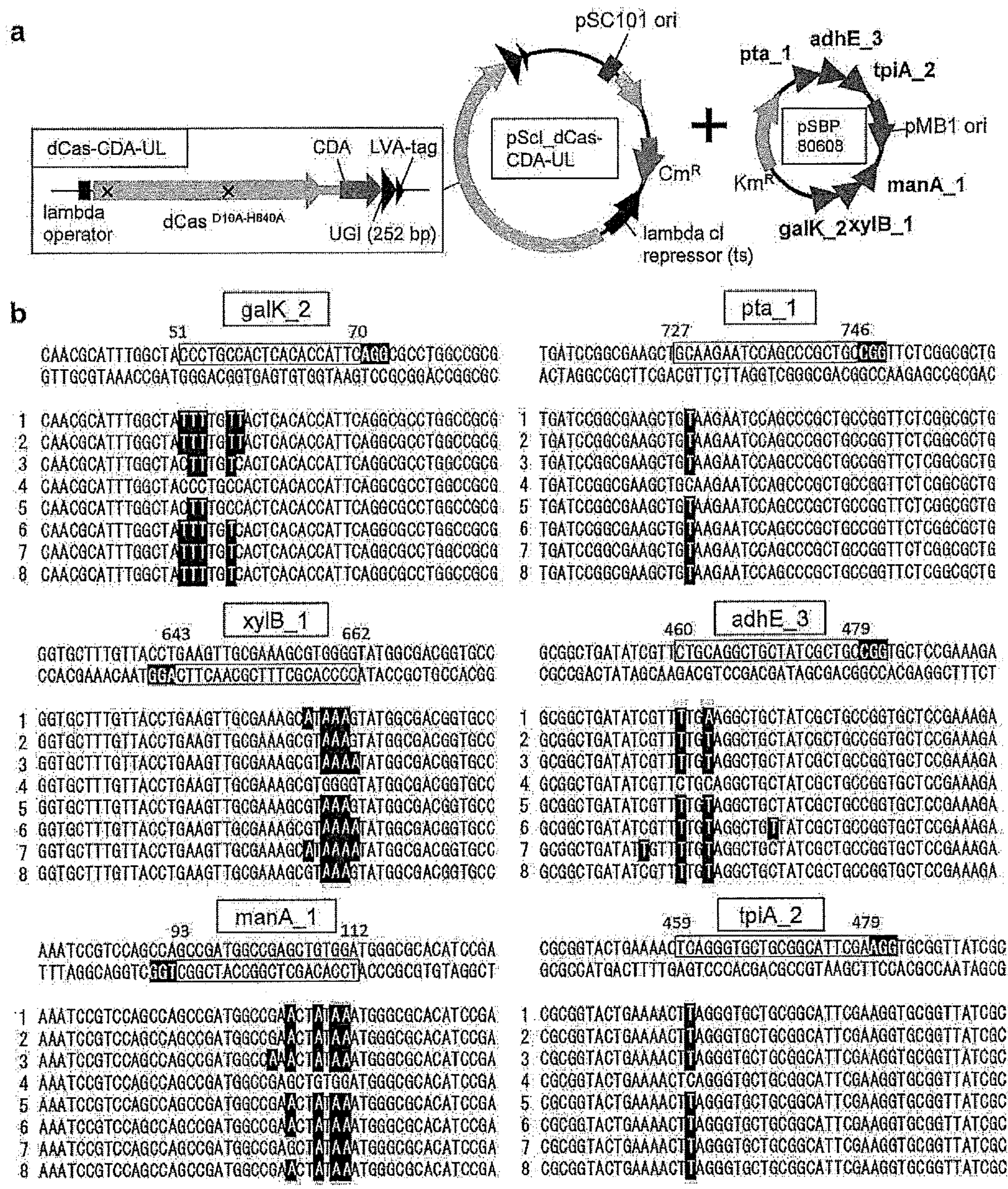
FIG. 10 shows the multiplex mutagenesis. (a) shows a schematic drawing of two plasmids for multiplex mutagenesis; a vector for alteration expressing dCas-CDA-UGI-LVA and a plasmid pSBP80608 containing two tandem-repeated sgRNA-units containing three targeting sgRNA. (b) shows the sequence alignments of the targeted regions. Randomly selected eight clones were sequenced and aligned at each targeted region. Clone numbers are indicated on the left of the sequences. Box and inverted box indicate targeted sequence and PAM. Mutated sites and bases are highlighted in black shade and bold. galK_2 is 5' to 3' SEQ ID NO: 271 and 3' to 5' SEQ ID NO: 272. The galK_2 clones are from 1-8, SEQ ID NO: 273, SEQ ID NO: 273, SEQ ID NO: 274, SEQ ID NO: 271, SEQ ID NO: 275, SEQ ID NO: 276, SEQ ID NO: 276, and SEQ ID NO: 276, respectively. xylB_1 is 5' to 3' SEQ ID NO: 277 and from 3' to 5' SEQ ID NO: 278. The xylB_1 clones are from 1-8, SEQ ID NO: 279, SEQ ID NO: 282, SEQ ID NO: 281, SEQ ID NO: 277, SEQ ID NO: 282, SEQ ID NO: 281, SEQ ID NO: 283, and SEQ ID NO: 282, respectively. manA_1 is 5' to 3' SEQ ID NO: 285 and 3' to 5' SEQ ID NO: 285. The manA_1 clones are from 1-8, SEQ ID NO: 286, SEQ ID No: 286, SEQ ID NO: 287, SEQ ID NO: 284, SEQ ID NO: 286, SEQ ID NO: 288, SEQ ID NO: 286. pta_1 is 5' to 3' SEQ ID NO: 289 and 3' to 5' SEQ ID NO: 290. The pta_1 clones from 1-8 are SEQ ID NO: 291, SEQ ID NO: 291 SEQ ID NO: 291, SEQ ID NO: 289, SEEQ ID NO: 291, SEQ ID NO: 291, SEQ ID NO: 291, and SEQ ID NO: 291, respectively. adhE_3 is 5' to 3' SEQ ID NO: 292 and 3' to 5' SEQ ID NO: 293. The adhE_3 clones are from 1-8, SEQ ID NO: 338, SEQ ID NO: 294, SEQ ID NO: 294, SEQ ID NO: 292, SEQ ID NO: 294, SEQ ID NO: 296, SEQ ID NO: 297, AND SEQ ID NO: 294. tpiA_2 is 5' to 3' SEQ ID NO: 298 and 3' to 5' SEQ ID NO: 299. The tpiA_2 clones are from 1-8, SEQ ID NO: 300, SEQ ID NO: 300, SEQ ID NO: 300, SEQ ID NO: 298, SEQ ID NO: 300, SEQ ID NO: 300, SEQ ID NO: 300, and SEQ ID NO: 300, respectively.

Six different genes; galK, xylB (xylulokinase), manA (mannose-6-phosphate isomerase), pta (Phosphate acetyltransferase), adhE (Aldehyde-alcohol dehydrogenase), and tpiA (Triosephosphate isomerase) were then targeted to introduce stop codons (FIG. 10). Cells expressing dCas-CDA-UGI-LVA with six different genes targeting sgRNAs found seven out of eight clones were successfully mutated at all targeted loci (FIG. 10).

Example 4

Multiple-Copy Gene Editing by Target-AID

Multi-copy elements occupy a substantial amount of genome sequence. Unlike other methods that involves recombination or genomic cleavages, Target-AID may edit multiple loci at once using the same sgRNA sequence without inducing genomic instability. For a proof of concept, the four major transposable elements (TEs: IS1, 2, 3, and 5) in *Escherichia coli* genome were targeted simultaneously by using four sgRNAs. Ten, twelve, five and fourteen loci for IS1, 2, 3, and 5, respectively, were able to be amplified specifically by unique PCR primers for each locus. The sgRNAs were designed to contain the common sequences of the transposase genes of each TE to introduce stop codons (FIG. 11). *Escherichia coli* Top10 cells were transformed with two plasmids respectively expressing dCas-CDA-UGI-LVA and the four target sgRNAs. Isolation and verification procedure for IS-edited cell is depicted in FIG. 12 and described as follows. After double transformation and selection, colonies were PCR-amplified and sequenced at IS5-1, IS5-2, IS5-11, IS5-12 sites first. IS5 targets turned out to be less efficient. Out of four colonies analyzed, one contained three mutated sites and one heterogenic site (IS5-1). The cells were then suspended in liquid medium and spread onto plates to re-isolate colonies. Three out of eight colonies contained mutation at IS5-1, two of which were then further sequenced for the rest of 24 IS loci, showing that one contained all mutated sites but one incomplete, heterogenic site (IS5-5). The cells were then suspended and spread to obtain four out of six re-isolated clones that contain mutation at IS5-5. One of the clones was sequenced at IS5 sites and found to contain one heterogenic site (IS5-2). Eight clones were re-isolated and 6 contained mutation at IS5-2. Two of the clones were spread onto non-selection medium to obtain cells that lost plasmids. The cells were then genome-extracted and sequenced to confirm mutations at all the IS sites (FIG. 11) and further subjected to whole genome sequencing to assess genome-wide off-target effect. Among 34 potential off target sites from the reference genome that contain matched sequences at 1-8 bases proximal to the PAM, two sites were found to be mutated (Table 5).

TABLE 5

List of IS_off-target candidate sites assessed by whole genome sequencing.

| Target | Region | Strand | Mis-match | Sequence | SEQ ID NO | PAM | gene | Frequency (%) Clone_1 | Clone_2 |
|---|---|---|---|---|---|---|---|---|---|
| IS1 | | | 0 | *CATCCATATCACCACGTCAA* | 143 | AGG | insA | | |
| IS1_off-1 | 459398-459420 | − | 10 | GGTGGCATCGCCCACGTCAA | 144 | TGG | ybbA | <0.1 | <0.1 |
| IS1_off-2 | 2084230-2084252 | + | 6 | GTCCATTAGCACCACGTCAA | 145 | CGG | uvrY | 100 | 100 |
| IS1_off-3 | 2617074-2617096 | + | 11 | TGCAATCGCCTTCACGTCAA | 146 | TGG | yfeH | <0.1 | <0.1 |
| IS1_off-4 | 2965681-2965703 | + | 10 | ATAGCGGTAGGCCACGTCAA | 147 | TGG | cysN | <0.1 | <0.1 |
| IS1_off-5 | 3677105-3677127 | − | 11 | TGGGCGCTGTTGCACGTCAA | 148 | TGG | rimL | <0.1 | <0.1 |
| IS1_off-6 | 4615816-4615838 | + | 9 | ACCACCGCGTACCACGTCAA | 149 | TGG | fecA | <0.1 | <0.1 |
| IS2 | | | 0 | *AGCCACTCCACTGGAGACGA* | 150 | CGG | insD1 | | |
| IS2_off-1 | 2664330-2664352 | − | 9 | GATCTTGTGACCGGAGACGA | 151 | CGG | eutQ | <0.1 | <0.1 |
| IS2_off-2 | 2797547-2797569 | + | 9 | CCCGTTTTGCCAGGAGACGA | 152 | CGG | rseC | <0.1 | <0.1 |
| IS2_off-3 | 3478902-3478924 | + | 6 | CATCTCTGCTCTGGAGACGA | 153 | TGG | degS | <0.1 | <0.1 |
| IS3 | | | 0 | *ACCACGTATACCAGCCGCTG* | 154 | CGG | insE1 | | |
| IS3_off-1 | 229782-229804 | − | 10 | AATTATCTCCACAGCCGCTG | 155 | TGG | pepD | <0.1 | <0.1 |
| IS3_off-2 | 297081-297103 | + | 9 | GAAGTGTTGATGAGCCGCTG | 156 | AGG | ykgE | <0.1 | <0.1 |
| IS3_off-3 | 828708-828730 | + | 9 | AAAAGCCGAGGCAGCCGCTG | 157 | CGG | tolA | <0.1 | <0.1 |
| IS3_off-4 | 992936-992958 | + | 8 | AACGTTGAAGTCAGCCGCTG | 158 | GGG | serS | <0.1 | <0.1 |
| IS3_off-5 | 1031011-1031033 | + | 10 | CAGAGCAGGTTCAGCCGCTG | 159 | CGG | mukB | <0.1 | <0.1 |
| IS3_off-6 | 2009292-2009314 | + | 7 | CATGCCAATATCAGCCGCTG | 160 | TGG | rsmL | 100 | 100 |
| IS3_off-7 | 2236079-2236101 | + | 7 | TCTGCTGCTGCCAGCCGCTG | 161 | AGG | alkA | <0.1 | <0.1 |
| IS3_off-8 | 2381447-2381469 | − | 8 | AAGAAGAGATCAAGCCGCTG | 162 | TGG | camH | <0.1 | <0.1 |
| IS3_off-9 | 2417471-2417493 | − | 9 | GACAACAGTCTTAGCCGCTG | 163 | GGG | yfaQ | <0.1 | <0.1 |
| IS3_off-10 | 2484639-2484661 | − | 9 | AGACATACAGCCAGCCGCTG | 164 | TGG | nuoL | <0.1 | <0.1 |
| IS3_off-11 | 2495424-2495446 | + | 10 | TTACTAAAAAAAAGCCGCTG | 165 | GGG | intergenic | <0.1 | <0.1 |
| IS3_off-12 | 2495435-2495457 | − | 9 | GTGTAAAAAACGAGCCGCTG | 166 | GGG | internenic | <0.1 | <0.1 |
| IS3_off-13 | 2517513-2517535 | + | 9 | CGCATAGCTGGAAGCCGCTG | 167 | TGG | argT | <0.1 | <0.1 |
| IS3_off-14 | 2629660-2629682 | − | 8 | AATTAGTGGTGCAGCCGCTG | 168 | GGG | cysA | <0.1 | <0.1 |
| IS3_off-15 | 3232817-3232839 | − | 8 | TGCTGGTCTTTGAGCCGCTG | 169 | TGG | gss | <0.1 | <0.1 |
| IS3_off-16 | 3251435-3251457 | − | 10 | TTCCGGATAGTTAGCCGCTG | 170 | CGG | yqhD | <0.1 | <0.1 |
| IS3_off-17 | 3382350-3382372 | + | 7 | AGCATATCGTGCAGCCGCTG | 171 | GGG | agaI | <0.1 | <0.1 |
| IS3_off-18 | 3393244-3393266 | − | 8 | GGCGGGTTTTTTAGCCGCTG | 172 | GGG | yraQ | <0.1 | <0.1 |
| IS3_off-19 | 4109690-4109712 | − | 10 | CGGCTCGCTCGCAGCCGCTG | 173 | CGG | yigM | <0.1 | <0.1 |
| IS3_off-20 | 4378317-4378339 | + | 10 | CTGCGATTCCTCAGCCGCTG | 174 | GGG | yjcE | <0.1 | <0.1 |
| IS3_off-21 | 4418352-4418374 | + | 10 | ACACGTCGATATAGCCGCTG | 175 | CGG | phnI | <0.1 | <0.1 |
| IS5 | | | 0 | *GTGCCACTGATTGCCTTTCT* | 176 | TGG | insH1 | | |
| IS5_off-1 | 1632093-1632115 | − | 5 | GTACCTGTATTTGCCTTTCT | 177 | CGG | narU | <0.1 | <0.1 |
| IS5_off-2 | 3273904-3273926 | + | 10 | TTATCGGCCTGAGCCTTTCT | 178 | GGG | tolC | <0.1 | <0.1 |
| IS5_off-3 | 3775233-3775255 | − | 10 | CTTAACGTCCGCGCCTTTCT | 179 | CGG | kdgK | <0.1 | <0.1 |
| IS5_off-4 | 4553528-4553550 | + | 7 | CTGACCGATAATGCCTTTCT | 180 | TGG | ytfT | 1.2 | <0.1 |

Region indicates the target sites in DH10B database. Strand indicates orientation of the target sites. Probable off-target sequences were determined as described in the present specification. Mismatch indicates number of mismatches between on-target and off-target sequences. Mismatch nucleotides are highlighted in bold. Frequencies of C-to-T mutations at each sequence highlighted in italics are shown.

Example 5

Figure 13:
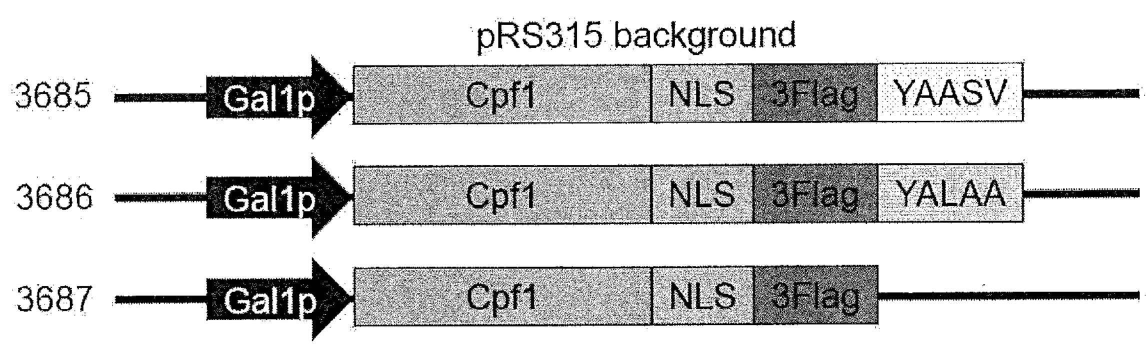
FIG. 13 is a schematic showing of the vectors for yeast is expression (background: pRS315 vector) used in Example 5. In the Figure, Gallp is a GAL1-10 promoter.

Comparison of Transformation Efficiency of *Escherichia coli* by Vector for Yeast Expression Vectors for yeast expression encoding LbCpf1 (SEQ ID NO: 326 and 327) as Cas effector protein, YAASV or YALAA as proteolysis tag (vector 3685:Cpf1-NLS-3xFlag-YAASV (SEQ ID NO: 328), vector 3687:Cpf1-NLS-3xFlag-YALAA (SEQ ID NO: 329)), and a control vector free of nucleic acid encoding proteolysis tag (vector 3687: Cpf1-NLS-3xFlag(SEQ ID NO: 330)) were generated using pRS315 vector as the base. Using these vectors, the transformation efficiency of *Escherichia coli* was verified. Schematic drawing of each vector is shown in FIG. 13. As shown in the following Table 6, a DNA solution containing each vector was adjusted to 2 ng/μl, 20 μl of *Escherichia coli* Top10 competent cells were transform by adding 1 μl (2 ng) of the DNA solution. Thereafter, 200 μl of SOC was added, the mixture was recovery cultured at 37° C. for 1 hr and stood on ice for 5 min to discontinue proliferation, and 1 μl of 50 mg/ml Amp was added. A part of the culture medium (1 μl or 10 μl) was diluted with TE, applied onto LB+Amp plate, cultured overnight at 37° C. and the number of colonies was counted. The results are shown in Table 6.

TABLE 6

| | 3685 | 3686 | 3687 |
|---|---|---|---|
| Plasmid conc (ng/ul) | 13 | 13.5 | 17 |
| Dilution (to 2 ng/ul) | 3.1 ± 16.9 | 3.0 ± 17 | 2.4 ± 17.6 |
| Colony in 10 ul | 39 | 96 | 28 |
| Colony in 1 ul | 3 | 4 | 1 |

It was shown that the transformation efficiency of *Escherichia coli* was high when vector 3685 and vector 3686 having a nucleic acid encoding a proteolysis tag were used, as compared to the use of the control vector 3687. Therefore, use of a proteolysis tag is expected to improve replication efficiency when replicating vectors in bacteria such as *Escherichia coli* and the like even if the vector is for expressing a heterologous organism.

This application is based on Japanese patent application No. 2017-225221 filed in Japan (filing date: Nov. 22, 2017), the contents of which are encompassed in full herein.

INDUSTRIAL APPLICABILITY

According to the present invention, a vector which is stable and amplifiable even in a host bacterium and has low toxicity, and a complex for genome editing which is encoded by the vector are provided. According to the method for genome editing using the nucleic acid and nucleic acid altering enzyme of the present invention, it is possible to alter the gene of a host bacterium while suppressing non-specific mutation and the like. Since this method does not rely on host dependent factors such as RecA, it can be applied to a wide range of bacteria, and is extremely useful.

The invention claimed is:

1. A complex comprising a nucleic acid sequence-recognizing module and a proteolysis tag, wherein the module is linked to the proteolysis tag, the module specifically binds to a target nucleotide sequence in a double stranded DNA, and the tag consists of a peptide at the C-terminal of the module containing 3 hydrophobic amino acid residues, wherein the 3 hydrophobic amino acid residues are leucine-valine-alanine, leucine-alanine-alanine, alanine-alanine-valine, or alanine-serine-valine, wherein the complex is further bound with a nucleic acid altering enzyme that converts one or more nucleotides in the target nucleotide sequence to a different nucleotide, deletes one or more nucleotides in the target nucleotide sequence, or inserts one or more nucleotides in the target nucleotide sequence, wherein the nucleic acid altering enzyme is a deaminase or a DNA glycosylase, and wherein the nucleic acid sequence-recognizing module is selected from the group consisting of CRISPR-mutant Cas, zinc finger motif, TAL effector and PPR motif.

2. The complex according to claim 1, wherein the nucleic acid sequence-recognizing module is a CRISPR-Cas system in which only one of the two DNA cleavage abilities of Cas or both DNA cleavage abilities are inactivated.

3. The complex according to claim 1, wherein the complex is a complex in which the proteolysis tag is bound to a CRISPR-Cas system.

4. The complex according to claim 1, wherein a base excision repair inhibitor is further bound to the complex.

5. A nucleic acid encoding the complex according to claim 1.

6. A method for altering a targeted site of a double stranded DNA of a bacterium, or regulating an expression of a gene encoded by a double-stranded DNA near the site, comprising a step of bringing a complex comprising a nucleic acid sequence-recognizing module specifically binding to a target nucleotide sequence in a selected double stranded DNA and a proteolysis tag at the C-terminal of the module, wherein the proteolysis tag consists of leucine-valine-alanine, leucine-alanine-alanine, alanine-alanine-valine, or alanine-serine-valine, into contact with the double stranded DNA, wherein the complex is further bound with a nucleic acid altering enzyme that converts one or more nucleotides in the target nucleotide sequence to a different nucleotide, deletes one or more nucleotides in the target nucleotide sequence, or inserts one or more nucleotides in the target nucleotide sequence, wherein the nucleic acid altering enzyme is a deaminase or a DNA glycosylase, and wherein the nucleic acid sequence-recognizing module is selected from the group consisting of CRISPR-mutant Cas, zinc finger motif, TAL effector and PPR motif.

7. The method according to claim 6, wherein the nucleic acid sequence-recognizing module is a CRISPR-Cas system in which only one of the two DNA cleavage abilities of Cas or both DNA cleavage abilities are inactivated.

8. The method according to claim 6, wherein the complex is a complex in which the proteolysis tag is bound to a CRISPR-Cas system.

9. The method according to claim 6, wherein the method employs two or more kinds of nucleic acid sequence-recognizing modules comprising said proteolysis tag, wherein each nucleic acid sequence-recognizing module specifically binds to a different target nucleotide sequence.

10. The method according to claim 9, wherein the different target nucleotide sequence is present in a different gene.

11. The method according to claim 6, wherein the nucleic acid altering enzyme is a DNA glycosylase.

12. The method according to claim 11, wherein the complex is further bound with a base excision repair inhibitor.

13. The method according to claim 6, wherein the nucleic acid base converting enzyme is deaminase.

14. The method according to claim 13, wherein the complex is further bound with a base excision repair inhibitor.

15. The method according to claim 6, wherein the double stranded DNA is brought into contact with the complex by introduction the nucleic acid encoding the complex into the bacterium having the double stranded DNA.

* * * * *

SEQUENCE LISTING

```
<160> NUMBER OF SEQ ID NOS: 340

<210> SEQ ID NO 1
<211> LENGTH: 4104
<212> TYPE: DNA
<213> ORGANISM: Streptococcus pyogenes
<220> FEATURE:
<221> NAME/KEY: CDS
<222> LOCATION: (1)..(4104)
<223> OTHER INFORMATION: dCas9 (D10A and H840A)
<220> FEATURE:
<221> NAME/KEY: mutation
<222> LOCATION: (28)..(30)
<220> FEATURE:
<221> NAME/KEY: mutation
<222> LOCATION: (2518)..(2520)

<400> SEQUENCE: 1

atg gat aag aaa tac tca ata ggc tta gct atc ggc aca aat agc gtc       48
Met Asp Lys Lys Tyr Ser Ile Gly Leu Ala Ile Gly Thr Asn Ser Val
1               5                   10                  15

gga tgg gcg gtg atc act gat gaa tat aag gtt ccg tct aaa aag ttc       96
Gly Trp Ala Val Ile Thr Asp Glu Tyr Lys Val Pro Ser Lys Lys Phe
            20                  25                  30

aag gtt ctg gga aat aca gac cgc cac agt atc aaa aaa aat ctt ata      144
Lys Val Leu Gly Asn Thr Asp Arg His Ser Ile Lys Lys Asn Leu Ile
        35                  40                  45

ggg gct ctt tta ttt gac agt gga gag aca gcg gaa gcg act cgt ctc      192
Gly Ala Leu Leu Phe Asp Ser Gly Glu Thr Ala Glu Ala Thr Arg Leu
    50                  55                  60

aaa cgg aca gct cgt aga agg tat aca cgt cgg aag aat cgt att tgt      240
Lys Arg Thr Ala Arg Arg Arg Tyr Thr Arg Arg Lys Asn Arg Ile Cys
65                  70                  75                  80

tat cta cag gag att ttt tca aat gag atg gcg aaa gta gat gat agt      288
Tyr Leu Gln Glu Ile Phe Ser Asn Glu Met Ala Lys Val Asp Asp Ser
                85                  90                  95

ttc ttt cat cga ctt gaa gag tct ttt ttg gtg gaa gaa gac aag aag      336
Phe Phe His Arg Leu Glu Glu Ser Phe Leu Val Glu Glu Asp Lys Lys
            100                 105                 110

cat gaa cgt cat cct att ttt gga aat ata gta gat gaa gtt gct tat      384
His Glu Arg His Pro Ile Phe Gly Asn Ile Val Asp Glu Val Ala Tyr
        115                 120                 125

cat gag aaa tat cca act atc tat cat ctg cga aaa aaa ttg gta gat      432
His Glu Lys Tyr Pro Thr Ile Tyr His Leu Arg Lys Lys Leu Val Asp
    130                 135                 140

tct act gat aaa gcg gat ttg cgc tta atc tat ttg gcc tta gcg cat      480
Ser Thr Asp Lys Ala Asp Leu Arg Leu Ile Tyr Leu Ala Leu Ala His
145                 150                 155                 160

atg att aag ttt cgt ggt cat ttt ttg att gag gga gat tta aat cct      528
Met Ile Lys Phe Arg Gly His Phe Leu Ile Glu Gly Asp Leu Asn Pro
                165                 170                 175

gat aat agt gat gtg gac aaa cta ttt atc cag ttg gta caa acc tac      576
```

```
Asp Asn Ser Asp Val Asp Lys Leu Phe Ile Gln Leu Val Gln Thr Tyr
            180                 185                 190

aat caa tta ttt gaa gaa aac cct att aac gca agt gga gta gat gct      624
Asn Gln Leu Phe Glu Glu Asn Pro Ile Asn Ala Ser Gly Val Asp Ala
        195                 200                 205

aaa gcg att ctt tct gca cga ttg agt aaa tca aga cga tta gaa aat      672
Lys Ala Ile Leu Ser Ala Arg Leu Ser Lys Ser Arg Arg Leu Glu Asn
    210                 215                 220

ctc att gct cag ctc ccc ggt gag aag aaa aat ggc tta ttt ggg aat      720
Leu Ile Ala Gln Leu Pro Gly Glu Lys Lys Asn Gly Leu Phe Gly Asn
225                 230                 235                 240

ctc att gct ttg tca ttg ggt ttg acc cct aat ttt aaa tca aat ttt      768
Leu Ile Ala Leu Ser Leu Gly Leu Thr Pro Asn Phe Lys Ser Asn Phe
                245                 250                 255

gat ttg gca gaa gat gct aaa tta cag ctt tca aaa gat act tac gat      816
Asp Leu Ala Glu Asp Ala Lys Leu Gln Leu Ser Lys Asp Thr Tyr Asp
            260                 265                 270

gat gat tta gat aat tta ttg gcg caa att gga gat caa tat gct gat      864
Asp Asp Leu Asp Asn Leu Leu Ala Gln Ile Gly Asp Gln Tyr Ala Asp
        275                 280                 285

ttg ttt ttg gca gct aag aat tta tca gat gct att tta ctt tca gat      912
Leu Phe Leu Ala Ala Lys Asn Leu Ser Asp Ala Ile Leu Leu Ser Asp
    290                 295                 300

atc cta aga gta aat act gaa ata act aag gct ccc cta tca gct tca      960
Ile Leu Arg Val Asn Thr Glu Ile Thr Lys Ala Pro Leu Ser Ala Ser
305                 310                 315                 320

atg att aaa cgc tac gat gaa cat cat caa gac ttg act ctt tta aaa     1008
Met Ile Lys Arg Tyr Asp Glu His His Gln Asp Leu Thr Leu Leu Lys
                325                 330                 335

gct tta gtt cga caa caa ctt cca gaa aag tat aaa gaa atc ttt ttt     1056
Ala Leu Val Arg Gln Gln Leu Pro Glu Lys Tyr Lys Glu Ile Phe Phe
            340                 345                 350

gat caa tca aaa aac gga tat gca ggt tat att gat ggg gga gct agc     1104
Asp Gln Ser Lys Asn Gly Tyr Ala Gly Tyr Ile Asp Gly Gly Ala Ser
        355                 360                 365

caa gaa gaa ttt tat aaa ttt atc aaa cca att tta gaa aaa atg gat     1152
Gln Glu Glu Phe Tyr Lys Phe Ile Lys Pro Ile Leu Glu Lys Met Asp
    370                 375                 380

ggt act gag gaa tta ttg gtg aaa cta aat cgt gaa gat ttg ctg cgc     1200
Gly Thr Glu Glu Leu Leu Val Lys Leu Asn Arg Glu Asp Leu Leu Arg
385                 390                 395                 400

aag caa cgg acc ttt gac aac ggc tct att ccc cat caa att cac ttg     1248
Lys Gln Arg Thr Phe Asp Asn Gly Ser Ile Pro His Gln Ile His Leu
                405                 410                 415

ggt gag ctg cat gct att ttg aga aga caa gaa gac ttt tat cca ttt     1296
Gly Glu Leu His Ala Ile Leu Arg Arg Gln Glu Asp Phe Tyr Pro Phe
            420                 425                 430

tta aaa gac aat cgt gag aag att gaa aaa atc ttg act ttt cga att     1344
Leu Lys Asp Asn Arg Glu Lys Ile Glu Lys Ile Leu Thr Phe Arg Ile
        435                 440                 445

cct tat tat gtt ggt cca ttg gcg cgt ggc aat agt cgt ttt gca tgg     1392
Pro Tyr Tyr Val Gly Pro Leu Ala Arg Gly Asn Ser Arg Phe Ala Trp
    450                 455                 460

atg act cgg aag tct gaa gaa aca att acc cca tgg aat ttt gaa gaa     1440
Met Thr Arg Lys Ser Glu Glu Thr Ile Thr Pro Trp Asn Phe Glu Glu
465                 470                 475                 480

gtt gtc gat aaa ggt gct tca gct caa tca ttt att gaa cgc atg aca     1488
Val Val Asp Lys Gly Ala Ser Ala Gln Ser Phe Ile Glu Arg Met Thr
                485                 490                 495
```

```
aac ttt gat aaa aat ctt cca aat gaa aaa gta cta cca aaa cat agt      1536
Asn Phe Asp Lys Asn Leu Pro Asn Glu Lys Val Leu Pro Lys His Ser
            500                 505                 510

ttg ctt tat gag tat ttt acg gtt tat aac gaa ttg aca aag gtc aaa      1584
Leu Leu Tyr Glu Tyr Phe Thr Val Tyr Asn Glu Leu Thr Lys Val Lys
        515                 520                 525

tat gtt act gaa gga atg cga aaa cca gca ttt ctt tca ggt gaa cag      1632
Tyr Val Thr Glu Gly Met Arg Lys Pro Ala Phe Leu Ser Gly Glu Gln
    530                 535                 540

aag aaa gcc att gtt gat tta ctc ttc aaa aca aat cga aaa gta acc      1680
Lys Lys Ala Ile Val Asp Leu Leu Phe Lys Thr Asn Arg Lys Val Thr
545                 550                 555                 560

gtt aag caa tta aaa gaa gat tat ttc aaa aaa ata gaa tgt ttt gat      1728
Val Lys Gln Leu Lys Glu Asp Tyr Phe Lys Lys Ile Glu Cys Phe Asp
                565                 570                 575

agt gtt gaa att tca gga gtt gaa gat aga ttt aat gct tca tta ggt      1776
Ser Val Glu Ile Ser Gly Val Glu Asp Arg Phe Asn Ala Ser Leu Gly
            580                 585                 590

acc tac cat gat ttg cta aaa att att aaa gat aaa gat ttt ttg gat      1824
Thr Tyr His Asp Leu Leu Lys Ile Ile Lys Asp Lys Asp Phe Leu Asp
        595                 600                 605

aat gaa gaa aat gaa gat atc tta gag gat att gtt tta aca ttg acc      1872
Asn Glu Glu Asn Glu Asp Ile Leu Glu Asp Ile Val Leu Thr Leu Thr
    610                 615                 620

tta ttt gaa gat agg gag atg att gag gaa aga ctt aaa aca tat gct      1920
Leu Phe Glu Asp Arg Glu Met Ile Glu Glu Arg Leu Lys Thr Tyr Ala
625                 630                 635                 640

cac ctc ttt gat gat aag gtg atg aaa cag ctt aaa cgt cgc cgt tat      1968
His Leu Phe Asp Asp Lys Val Met Lys Gln Leu Lys Arg Arg Arg Tyr
                645                 650                 655

act ggt tgg gga cgt ttg tct cga aaa ttg att aat ggt att agg gat      2016
Thr Gly Trp Gly Arg Leu Ser Arg Lys Leu Ile Asn Gly Ile Arg Asp
            660                 665                 670

aag caa tct ggc aaa aca ata tta gat ttt ttg aaa tca gat ggt ttt      2064
Lys Gln Ser Gly Lys Thr Ile Leu Asp Phe Leu Lys Ser Asp Gly Phe
        675                 680                 685

gcc aat cgc aat ttt atg cag ctg atc cat gat gat agt ttg aca ttt      2112
Ala Asn Arg Asn Phe Met Gln Leu Ile His Asp Asp Ser Leu Thr Phe
    690                 695                 700

aaa gaa gac att caa aaa gca caa gtg tct gga caa ggc gat agt tta      2160
Lys Glu Asp Ile Gln Lys Ala Gln Val Ser Gly Gln Gly Asp Ser Leu
705                 710                 715                 720

cat gaa cat att gca aat tta gct ggt agc cct gct att aaa aaa ggt      2208
His Glu His Ile Ala Asn Leu Ala Gly Ser Pro Ala Ile Lys Lys Gly
                725                 730                 735

att tta cag act gta aaa gtt gtt gat gaa ttg gtc aaa gta atg ggg      2256
Ile Leu Gln Thr Val Lys Val Val Asp Glu Leu Val Lys Val Met Gly
            740                 745                 750

cgg cat aag cca gaa aat atc gtt att gaa atg gca cgt gaa aat cag      2304
Arg His Lys Pro Glu Asn Ile Val Ile Glu Met Ala Arg Glu Asn Gln
        755                 760                 765

aca act caa aag ggc cag aaa aat tcg cga gag cgt atg aaa cga atc      2352
Thr Thr Gln Lys Gly Gln Lys Asn Ser Arg Glu Arg Met Lys Arg Ile
    770                 775                 780

gaa gaa ggt atc aaa gaa tta gga agt cag att ctt aaa gag cat cct      2400
Glu Glu Gly Ile Lys Glu Leu Gly Ser Gln Ile Leu Lys Glu His Pro
785                 790                 795                 800

gtt gaa aat act caa ttg caa aat gaa aag ctc tat ctc tat tat ctc      2448
Val Glu Asn Thr Gln Leu Gln Asn Glu Lys Leu Tyr Leu Tyr Tyr Leu
                805                 810                 815
```

```
caa aat gga aga gac atg tat gtg gac caa gaa tta gat att aat cgt     2496
Gln Asn Gly Arg Asp Met Tyr Val Asp Gln Glu Leu Asp Ile Asn Arg
            820                 825                 830

tta agt gat tat gat gtc gat gcc att gtt cca caa agt ttc ctt aaa     2544
Leu Ser Asp Tyr Asp Val Asp Ala Ile Val Pro Gln Ser Phe Leu Lys
        835                 840                 845

gac gat tca ata gac aat aag gtc tta acg cgt tct gat aaa aat cgt     2592
Asp Asp Ser Ile Asp Asn Lys Val Leu Thr Arg Ser Asp Lys Asn Arg
    850                 855                 860

ggt aaa tcg gat aac gtt cca agt gaa gaa gta gtc aaa aag atg aaa     2640
Gly Lys Ser Asp Asn Val Pro Ser Glu Glu Val Val Lys Lys Met Lys
865                 870                 875                 880

aac tat tgg aga caa ctt cta aac gcc aag tta atc act caa cgt aag     2688
Asn Tyr Trp Arg Gln Leu Leu Asn Ala Lys Leu Ile Thr Gln Arg Lys
                885                 890                 895

ttt gat aat tta acg aaa gct gaa cgt gga ggt ttg agt gaa ctt gat     2736
Phe Asp Asn Leu Thr Lys Ala Glu Arg Gly Gly Leu Ser Glu Leu Asp
            900                 905                 910

aaa gct ggt ttt atc aaa cgc caa ttg gtt gaa act cgc caa atc act     2784
Lys Ala Gly Phe Ile Lys Arg Gln Leu Val Glu Thr Arg Gln Ile Thr
        915                 920                 925

aag cat gtg gca caa att ttg gat agt cgc atg aat act aaa tac gat     2832
Lys His Val Ala Gln Ile Leu Asp Ser Arg Met Asn Thr Lys Tyr Asp
    930                 935                 940

gaa aat gat aaa ctt att cga gag gtt aaa gtg att acc tta aaa tct     2880
Glu Asn Asp Lys Leu Ile Arg Glu Val Lys Val Ile Thr Leu Lys Ser
945                 950                 955                 960

aaa tta gtt tct gac ttc cga aaa gat ttc caa ttc tat aaa gta cgt     2928
Lys Leu Val Ser Asp Phe Arg Lys Asp Phe Gln Phe Tyr Lys Val Arg
                965                 970                 975

gag att aac aat tac cat cat gcc cat gat gcg tat cta aat gcc gtc     2976
Glu Ile Asn Asn Tyr His His Ala His Asp Ala Tyr Leu Asn Ala Val
            980                 985                 990

gtt gga act gct ttg att aag aaa  tat cca aaa ctt gaa  tcg gag ttt   3024
Val Gly Thr Ala Leu Ile Lys Lys  Tyr Pro Lys Leu Glu  Ser Glu Phe
        995                 1000                1005

gtc tat  ggt gat tat aaa gtt  tat gat gtt cgt aaa  atg att gct     3069
Val Tyr  Gly Asp Tyr Lys Val  Tyr Asp Val Arg Lys  Met Ile Ala
    1010                 1015                1020

aag tct  gag caa gaa ata ggc  aaa gca acc gca aaa  tat ttc ttt     3114
Lys Ser  Glu Gln Glu Ile Gly  Lys Ala Thr Ala Lys  Tyr Phe Phe
    1025                 1030                1035

tac tct  aat atc atg aac ttc  ttc aaa aca gaa att  aca ctt gca     3159
Tyr Ser  Asn Ile Met Asn Phe  Phe Lys Thr Glu Ile  Thr Leu Ala
    1040                 1045                1050

aat gga  gag att cgc aaa cgc  cct cta atc gaa act  aat ggg gaa     3204
Asn Gly  Glu Ile Arg Lys Arg  Pro Leu Ile Glu Thr  Asn Gly Glu
    1055                 1060                1065

act gga  gaa att gtc tgg gat  aaa ggg cga gat ttt  gcc aca gtg     3249
Thr Gly  Glu Ile Val Trp Asp  Lys Gly Arg Asp Phe  Ala Thr Val
    1070                 1075                1080

cgc aaa  gta ttg tcc atg ccc  caa gtc aat att gtc  aag aaa aca     3294
Arg Lys  Val Leu Ser Met Pro  Gln Val Asn Ile Val  Lys Lys Thr
    1085                 1090                1095

gaa gta  cag aca ggc gga ttc  tcc aag gag tca att  tta cca aaa     3339
Glu Val  Gln Thr Gly Gly Phe  Ser Lys Glu Ser Ile  Leu Pro Lys
    1100                 1105                1110

aga aat  tcg gac aag ctt att  gct cgt aaa aaa gac  tgg gat cca     3384
Arg Asn  Ser Asp Lys Leu Ile  Ala Arg Lys Lys Asp  Trp Asp Pro
```

```
    1115                1120                1125

aaa aaa  tat ggt ggt ttt gat  agt cca acg gta gct  tat tca gtc      3429
Lys Lys  Tyr Gly Gly Phe Asp  Ser Pro Thr Val Ala  Tyr Ser Val
    1130                1135                1140

cta gtg  gtt gct aag gtg gaa  aaa ggg aaa tcg aag  aag tta aaa      3474
Leu Val  Val Ala Lys Val Glu  Lys Gly Lys Ser Lys  Lys Leu Lys
    1145                1150                1155

tcc gtt  aaa gag tta cta ggg  atc aca att atg gaa  aga agt tcc      3519
Ser Val  Lys Glu Leu Leu Gly  Ile Thr Ile Met Glu  Arg Ser Ser
    1160                1165                1170

ttt gaa  aaa aat ccg att gac  ttt tta gaa gct aaa  gga tat aag      3564
Phe Glu  Lys Asn Pro Ile Asp  Phe Leu Glu Ala Lys  Gly Tyr Lys
    1175                1180                1185

gaa gtt  aaa aaa gac tta atc  att aaa cta cct aaa  tat agt ctt      3609
Glu Val  Lys Lys Asp Leu Ile  Ile Lys Leu Pro Lys  Tyr Ser Leu
    1190                1195                1200

ttt gag  tta gaa aac ggt cgt  aaa cgg atg ctg gct  agt gcc gga      3654
Phe Glu  Leu Glu Asn Gly Arg  Lys Arg Met Leu Ala  Ser Ala Gly
    1205                1210                1215

gaa tta  caa aaa gga aat gag  ctg gct ctg cca agc  aaa tat gtg      3699
Glu Leu  Gln Lys Gly Asn Glu  Leu Ala Leu Pro Ser  Lys Tyr Val
    1220                1225                1230

aat ttt  tta tat tta gct agt  cat tat gaa aag ttg  aag ggt agt      3744
Asn Phe  Leu Tyr Leu Ala Ser  His Tyr Glu Lys Leu  Lys Gly Ser
    1235                1240                1245

cca gaa  gat aac gaa caa aaa  caa ttg ttt gtg gag  cag cat aag      3789
Pro Glu  Asp Asn Glu Gln Lys  Gln Leu Phe Val Glu  Gln His Lys
    1250                1255                1260

cat tat  tta gat gag att att  gag caa atc agt gaa  ttt tct aag      3834
His Tyr  Leu Asp Glu Ile Ile  Glu Gln Ile Ser Glu  Phe Ser Lys
    1265                1270                1275

cgt gtt  att tta gca gat gcc  aat tta gat aaa gtt  ctt agt gca      3879
Arg Val  Ile Leu Ala Asp Ala  Asn Leu Asp Lys Val  Leu Ser Ala
    1280                1285                1290

tat aac  aaa cat aga gac aaa  cca ata cgt gaa caa  gca gaa aat      3924
Tyr Asn  Lys His Arg Asp Lys  Pro Ile Arg Glu Gln  Ala Glu Asn
    1295                1300                1305

att att  cat tta ttt acg ttg  acg aat ctt gga gct  ccc gct gct      3969
Ile Ile  His Leu Phe Thr Leu  Thr Asn Leu Gly Ala  Pro Ala Ala
    1310                1315                1320

ttt aaa  tat ttt gat aca aca  att gat cgt aaa cga  tat acg tct      4014
Phe Lys  Tyr Phe Asp Thr Thr  Ile Asp Arg Lys Arg  Tyr Thr Ser
    1325                1330                1335

aca aaa  gaa gtt tta gat gcc  act ctt atc cat caa  tcc atc act      4059
Thr Lys  Glu Val Leu Asp Ala  Thr Leu Ile His Gln  Ser Ile Thr
    1340                1345                1350

ggt ctt  tat gaa aca cgc att  gat ttg agt cag cta  gga ggt gac      4104
Gly Leu  Tyr Glu Thr Arg Ile  Asp Leu Ser Gln Leu  Gly Gly Asp
    1355                1360                1365


<210> SEQ ID NO 2
<211> LENGTH: 1368
<212> TYPE: PRT
<213> ORGANISM: Streptococcus pyogenes

<400> SEQUENCE: 2

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30
```

```
Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445
```

```
Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
```

-continued

```
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                1005

Val Tyr  Gly Asp Tyr Lys Val  Tyr Asp Val Arg Lys  Met Ile Ala
    1010                1015                1020

Lys Ser  Glu Gln Glu Ile Gly  Lys Ala Thr Ala Lys  Tyr Phe Phe
    1025                1030                1035

Tyr Ser  Asn Ile Met Asn Phe  Phe Lys Thr Glu Ile  Thr Leu Ala
    1040                1045                1050

Asn Gly  Glu Ile Arg Lys Arg  Pro Leu Ile Glu Thr  Asn Gly Glu
    1055                1060                1065

Thr Gly  Glu Ile Val Trp Asp  Lys Gly Arg Asp Phe  Ala Thr Val
    1070                1075                1080

Arg Lys  Val Leu Ser Met Pro  Gln Val Asn Ile Val  Lys Lys Thr
    1085                1090                1095

Glu Val  Gln Thr Gly Gly Phe  Ser Lys Glu Ser Ile  Leu Pro Lys
    1100                1105                1110

Arg Asn  Ser Asp Lys Leu Ile  Ala Arg Lys Lys Asp  Trp Asp Pro
    1115                1120                1125

Lys Lys  Tyr Gly Gly Phe Asp  Ser Pro Thr Val Ala  Tyr Ser Val
    1130                1135                1140

Leu Val  Val Ala Lys Val Glu  Lys Gly Lys Ser Lys  Lys Leu Lys
    1145                1150                1155

Ser Val  Lys Glu Leu Leu Gly  Ile Thr Ile Met Glu  Arg Ser Ser
    1160                1165                1170

Phe Glu  Lys Asn Pro Ile Asp  Phe Leu Glu Ala Lys  Gly Tyr Lys
    1175                1180                1185

Glu Val  Lys Lys Asp Leu Ile  Ile Lys Leu Pro Lys  Tyr Ser Leu
    1190                1195                1200

Phe Glu  Leu Glu Asn Gly Arg  Lys Arg Met Leu Ala  Ser Ala Gly
    1205                1210                1215

Glu Leu  Gln Lys Gly Asn Glu  Leu Ala Leu Pro Ser  Lys Tyr Val
    1220                1225                1230

Asn Phe  Leu Tyr Leu Ala Ser  His Tyr Glu Lys Leu  Lys Gly Ser
    1235                1240                1245

Pro Glu  Asp Asn Glu Gln Lys  Gln Leu Phe Val Glu  Gln His Lys
    1250                1255                1260

His Tyr  Leu Asp Glu Ile Ile  Glu Gln Ile Ser Glu  Phe Ser Lys
    1265                1270                1275
```

```
Arg Val  Ile Leu Ala Asp Ala  Asn Leu Asp Lys Val  Leu Ser Ala
    1280                 1285                 1290

Tyr Asn  Lys His Arg Asp Lys  Pro Ile Arg Glu Gln  Ala Glu Asn
    1295                 1300                 1305

Ile Ile  His Leu Phe Thr Leu  Thr Asn Leu Gly Ala  Pro Ala Ala
    1310                 1315                 1320

Phe Lys  Tyr Phe Asp Thr Thr  Ile Asp Arg Lys Arg  Tyr Thr Ser
    1325                 1330                 1335

Thr Lys  Glu Val Leu Asp Ala  Thr Leu Ile His Gln  Ser Ile Thr
    1340                 1345                 1350

Gly Leu  Tyr Glu Thr Arg Ile  Asp Leu Ser Gln Leu  Gly Gly Asp
    1355                 1360                 1365


<210> SEQ ID NO 3
<211> LENGTH: 624
<212> TYPE: DNA
<213> ORGANISM: Perkinsus marinus
<220> FEATURE:
<221> NAME/KEY: CDS
<222> LOCATION: (1)..(624)
<223> OTHER INFORMATION: PmCDA1

<400> SEQUENCE: 3

atg acc gac gct gag tac gtg aga atc cat gag aag ttg gac atc tac       48
Met Thr Asp Ala Glu Tyr Val Arg Ile His Glu Lys Leu Asp Ile Tyr
1               5                   10                  15

acg ttt aag aaa cag ttt ttc aac aac aaa aaa tcc gtg tcg cat aga       96
Thr Phe Lys Lys Gln Phe Phe Asn Asn Lys Lys Ser Val Ser His Arg
            20                  25                  30

tgc tac gtt ctc ttt gaa tta aaa cga cgg ggt gaa cgt aga gcg tgt      144
Cys Tyr Val Leu Phe Glu Leu Lys Arg Arg Gly Glu Arg Arg Ala Cys
        35                  40                  45

ttt tgg ggc tat gct gtg aat aaa cca cag agc ggg aca gaa cgt ggc      192
Phe Trp Gly Tyr Ala Val Asn Lys Pro Gln Ser Gly Thr Glu Arg Gly
    50                  55                  60

att cac gcc gaa atc ttt agc att aga aaa gtc gaa gaa tac ctg cgc      240
Ile His Ala Glu Ile Phe Ser Ile Arg Lys Val Glu Glu Tyr Leu Arg
65                  70                  75                  80

gac aac ccc gga caa ttc acg ata aat tgg tac tca tcc tgg agt cct      288
Asp Asn Pro Gly Gln Phe Thr Ile Asn Trp Tyr Ser Ser Trp Ser Pro
                85                  90                  95

tgt gca gat tgc gct gaa aag atc tta gaa tgg tat aac cag gag ctg      336
Cys Ala Asp Cys Ala Glu Lys Ile Leu Glu Trp Tyr Asn Gln Glu Leu
            100                 105                 110

cgg ggg aac ggc cac act ttg aaa atc tgg gct tgc aaa ctc tat tac      384
Arg Gly Asn Gly His Thr Leu Lys Ile Trp Ala Cys Lys Leu Tyr Tyr
        115                 120                 125

gag aaa aat gcg agg aat caa att ggg ctg tgg aat ctc aga gat aac      432
Glu Lys Asn Ala Arg Asn Gln Ile Gly Leu Trp Asn Leu Arg Asp Asn
    130                 135                 140

ggg gtt ggg ttg aat gta atg gta agt gaa cac tac caa tgt tgc agg      480
Gly Val Gly Leu Asn Val Met Val Ser Glu His Tyr Gln Cys Cys Arg
145                 150                 155                 160

aaa ata ttc atc caa tcg tcg cac aat caa ttg aat gag aat aga tgg      528
Lys Ile Phe Ile Gln Ser Ser His Asn Gln Leu Asn Glu Asn Arg Trp
                165                 170                 175

ctt gag aag act ttg aag cga gct gaa aaa cga cgg agc gag ttg tcc      576
Leu Glu Lys Thr Leu Lys Arg Ala Glu Lys Arg Arg Ser Glu Leu Ser
            180                 185                 190
```

```
att atg att cag gta aaa ata ctc cac acc act aag agt cct gct gtt      624
Ile Met Ile Gln Val Lys Ile Leu His Thr Thr Lys Ser Pro Ala Val
        195                 200                 205


<210> SEQ ID NO 4
<211> LENGTH: 208
<212> TYPE: PRT
<213> ORGANISM: Perkinsus marinus

<400> SEQUENCE: 4

Met Thr Asp Ala Glu Tyr Val Arg Ile His Glu Lys Leu Asp Ile Tyr
1               5                   10                  15

Thr Phe Lys Lys Gln Phe Phe Asn Asn Lys Lys Ser Val Ser His Arg
            20                  25                  30

Cys Tyr Val Leu Phe Glu Leu Lys Arg Arg Gly Glu Arg Arg Ala Cys
        35                  40                  45

Phe Trp Gly Tyr Ala Val Asn Lys Pro Gln Ser Gly Thr Glu Arg Gly
    50                  55                  60

Ile His Ala Glu Ile Phe Ser Ile Arg Lys Val Glu Glu Tyr Leu Arg
65                  70                  75                  80

Asp Asn Pro Gly Gln Phe Thr Ile Asn Trp Tyr Ser Ser Trp Ser Pro
                85                  90                  95

Cys Ala Asp Cys Ala Glu Lys Ile Leu Glu Trp Tyr Asn Gln Glu Leu
            100                 105                 110

Arg Gly Asn Gly His Thr Leu Lys Ile Trp Ala Cys Lys Leu Tyr Tyr
        115                 120                 125

Glu Lys Asn Ala Arg Asn Gln Ile Gly Leu Trp Asn Leu Arg Asp Asn
    130                 135                 140

Gly Val Gly Leu Asn Val Met Val Ser Glu His Tyr Gln Cys Cys Arg
145                 150                 155                 160

Lys Ile Phe Ile Gln Ser Ser His Asn Gln Leu Asn Glu Asn Arg Trp
                165                 170                 175

Leu Glu Lys Thr Leu Lys Arg Ala Glu Lys Arg Arg Ser Glu Leu Ser
            180                 185                 190

Ile Met Ile Gln Val Lys Ile Leu His Thr Thr Lys Ser Pro Ala Val
        195                 200                 205


<210> SEQ ID NO 5
<211> LENGTH: 363
<212> TYPE: DNA
<213> ORGANISM: Artificial Sequence
<220> FEATURE:
<223> OTHER INFORMATION: Synthetic Sequence - linker region
<220> FEATURE:
<221> NAME/KEY: CDS
<222> LOCATION: (1)..(363)
<220> FEATURE:
<221> NAME/KEY: misc_feature
<222> LOCATION: (31)..(201)
<223> OTHER INFORMATION: SH3 domain
<220> FEATURE:
<221> NAME/KEY: misc_feature
<222> LOCATION: (208)..(273)
<223> OTHER INFORMATION: 3xFLAG tag
<220> FEATURE:
<221> NAME/KEY: misc_feature
<222> LOCATION: (292)..(357)
<223> OTHER INFORMATION: 3xFLAG tag

<400> SEQUENCE: 5

ggt gga gga ggt tct gga ggt gga ggt tct gct gag tat gtg cga gcc       48
Gly Gly Gly Gly Ser Gly Gly Gly Gly Ser Ala Glu Tyr Val Arg Ala
1               5                   10                  15
```

```
ctc ttt gac ttt aat ggg aat gat gaa gag gat ctt ccc ttt aag aaa       96
Leu Phe Asp Phe Asn Gly Asn Asp Glu Glu Asp Leu Pro Phe Lys Lys
            20                  25                  30

gga gac atc ctg aga atc cgg gat aag cct gag gag cag tgg tgg aat      144
Gly Asp Ile Leu Arg Ile Arg Asp Lys Pro Glu Glu Gln Trp Trp Asn
        35                  40                  45

gca gag gac agc gaa gga aag agg ggg atg att cct gtc cct tac gtg      192
Ala Glu Asp Ser Glu Gly Lys Arg Gly Met Ile Pro Val Pro Tyr Val
    50                  55                  60

gag aag tat tcc gga gac tat aag gac cac gac gga gac tac aag gat      240
Glu Lys Tyr Ser Gly Asp Tyr Lys Asp His Asp Gly Asp Tyr Lys Asp
65                  70                  75                  80

cat gat att gat tac aaa gac gat gac gat aag tct agg ctc gag tcc      288
His Asp Ile Asp Tyr Lys Asp Asp Asp Asp Lys Ser Arg Leu Glu Ser
                85                  90                  95

gga gac tat aag gac cac gac gga gac tac aag gat cat gat att gat      336
Gly Asp Tyr Lys Asp His Asp Gly Asp Tyr Lys Asp His Asp Ile Asp
            100                 105                 110

tac aaa gac gat gac gat aag tct agg                                  363
Tyr Lys Asp Asp Asp Asp Lys Ser Arg
        115                 120
```

<210> SEQ ID NO 6
<211> LENGTH: 121
<212> TYPE: PRT
<213> ORGANISM: Artificial Sequence
<220> FEATURE:
<223> OTHER INFORMATION: Synthetic Construct

<400> SEQUENCE: 6

```
Gly Gly Gly Gly Ser Gly Gly Gly Gly Ser Ala Glu Tyr Val Arg Ala
1               5                   10                  15

Leu Phe Asp Phe Asn Gly Asn Asp Glu Glu Asp Leu Pro Phe Lys Lys
            20                  25                  30

Gly Asp Ile Leu Arg Ile Arg Asp Lys Pro Glu Glu Gln Trp Trp Asn
        35                  40                  45

Ala Glu Asp Ser Glu Gly Lys Arg Gly Met Ile Pro Val Pro Tyr Val
    50                  55                  60

Glu Lys Tyr Ser Gly Asp Tyr Lys Asp His Asp Gly Asp Tyr Lys Asp
65                  70                  75                  80

His Asp Ile Asp Tyr Lys Asp Asp Asp Asp Lys Ser Arg Leu Glu Ser
                85                  90                  95

Gly Asp Tyr Lys Asp His Asp Gly Asp Tyr Lys Asp His Asp Ile Asp
            100                 105                 110

Tyr Lys Asp Asp Asp Asp Lys Ser Arg
        115                 120
```

<210> SEQ ID NO 7
<211> LENGTH: 171
<212> TYPE: DNA
<213> ORGANISM: Artificial Sequence
<220> FEATURE:
<223> OTHER INFORMATION: Synthetic Sequence - SH3 domain
<220> FEATURE:
<221> NAME/KEY: CDS
<222> LOCATION: (1)..(171)

<400> SEQUENCE: 7

```
gct gag tat gtg cga gcc ctc ttt gac ttt aat ggg aat gat gaa gag       48
Ala Glu Tyr Val Arg Ala Leu Phe Asp Phe Asn Gly Asn Asp Glu Glu
1               5                   10                  15
```

```
gat ctt ccc ttt aag aaa gga gac atc ctg aga atc cgg gat aag cct       96
Asp Leu Pro Phe Lys Lys Gly Asp Ile Leu Arg Ile Arg Asp Lys Pro
            20                  25                  30

gag gag cag tgg tgg aat gca gag gac agc gaa gga aag agg ggg atg      144
Glu Glu Gln Trp Trp Asn Ala Glu Asp Ser Glu Gly Lys Arg Gly Met
        35                  40                  45

att cct gtc cct tac gtg gag aag tat                                  171
Ile Pro Val Pro Tyr Val Glu Lys Tyr
    50                  55


<210> SEQ ID NO 8
<211> LENGTH: 57
<212> TYPE: PRT
<213> ORGANISM: Artificial Sequence
<220> FEATURE:
<223> OTHER INFORMATION: Synthetic Construct

<400> SEQUENCE: 8

Ala Glu Tyr Val Arg Ala Leu Phe Asp Phe Asn Gly Asn Asp Glu Glu
1               5                   10                  15

Asp Leu Pro Phe Lys Lys Gly Asp Ile Leu Arg Ile Arg Asp Lys Pro
            20                  25                  30

Glu Glu Gln Trp Trp Asn Ala Glu Asp Ser Glu Gly Lys Arg Gly Met
        35                  40                  45

Ile Pro Val Pro Tyr Val Glu Lys Tyr
    50                  55


<210> SEQ ID NO 9
<211> LENGTH: 66
<212> TYPE: DNA
<213> ORGANISM: Artificial Sequence
<220> FEATURE:
<223> OTHER INFORMATION: Synthetic Sequence - 3xFLAG tag
<220> FEATURE:
<221> NAME/KEY: CDS
<222> LOCATION: (1)..(66)

<400> SEQUENCE: 9

gac tat aag gac cac gac gga gac tac aag gat cat gat att gat tac       48
Asp Tyr Lys Asp His Asp Gly Asp Tyr Lys Asp His Asp Ile Asp Tyr
1               5                   10                  15

aaa gac gat gac gat aag                                               66
Lys Asp Asp Asp Asp Lys
            20


<210> SEQ ID NO 10
<211> LENGTH: 22
<212> TYPE: PRT
<213> ORGANISM: Artificial Sequence
<220> FEATURE:
<223> OTHER INFORMATION: Synthetic Construct

<400> SEQUENCE: 10

Asp Tyr Lys Asp His Asp Gly Asp Tyr Lys Asp His Asp Ile Asp Tyr
1               5                   10                  15

Lys Asp Asp Asp Asp Lys
            20


<210> SEQ ID NO 11
<211> LENGTH: 24
<212> TYPE: DNA
<213> ORGANISM: Artificial Sequence
<220> FEATURE:
<223> OTHER INFORMATION: Synthetic Sequence - FLAG tag
```

```
<220> FEATURE:
<221> NAME/KEY: CDS
<222> LOCATION: (1)..(24)

<400> SEQUENCE: 11

gat tac aaa gac gat gac gat aag                                          24
Asp Tyr Lys Asp Asp Asp Asp Lys
1               5


<210> SEQ ID NO 12
<211> LENGTH: 8
<212> TYPE: PRT
<213> ORGANISM: Artificial Sequence
<220> FEATURE:
<223> OTHER INFORMATION: Synthetic Construct

<400> SEQUENCE: 12

Asp Tyr Lys Asp Asp Asp Asp Lys
1               5


<210> SEQ ID NO 13
<211> LENGTH: 252
<212> TYPE: DNA
<213> ORGANISM: Myocastor coypus
<220> FEATURE:
<221> NAME/KEY: CDS
<222> LOCATION: (1)..(252)
<223> OTHER INFORMATION: PBS2-derived UGI

<400> SEQUENCE: 13

atg acc aac ctt tcc gac atc ata gag aag gaa aca ggc aaa cag ttg          48
Met Thr Asn Leu Ser Asp Ile Ile Glu Lys Glu Thr Gly Lys Gln Leu
1               5                   10                  15

gtc atc caa gag tcg ata ctc atg ctt cct gaa gaa gtt gag gag gtc          96
Val Ile Gln Glu Ser Ile Leu Met Leu Pro Glu Glu Val Glu Glu Val
            20                  25                  30

att ggg aat aag ccg gaa agt gac att ctc gta cac act gcg tat gat         144
Ile Gly Asn Lys Pro Glu Ser Asp Ile Leu Val His Thr Ala Tyr Asp
        35                  40                  45

gag agc acc gat gag aac gtg atg ctg ctc acg tca gat gcc cca gag         192
Glu Ser Thr Asp Glu Asn Val Met Leu Leu Thr Ser Asp Ala Pro Glu
    50                  55                  60

tac aaa ccc tgg gct ctg gtg att cag gac tct aat gga gag aac aag         240
Tyr Lys Pro Trp Ala Leu Val Ile Gln Asp Ser Asn Gly Glu Asn Lys
65                  70                  75                  80

atc aag atg cta                                                         252
Ile Lys Met Leu


<210> SEQ ID NO 14
<211> LENGTH: 84
<212> TYPE: PRT
<213> ORGANISM: Myocastor coypus

<400> SEQUENCE: 14

Met Thr Asn Leu Ser Asp Ile Ile Glu Lys Glu Thr Gly Lys Gln Leu
1               5                   10                  15

Val Ile Gln Glu Ser Ile Leu Met Leu Pro Glu Glu Val Glu Glu Val
            20                  25                  30

Ile Gly Asn Lys Pro Glu Ser Asp Ile Leu Val His Thr Ala Tyr Asp
        35                  40                  45

Glu Ser Thr Asp Glu Asn Val Met Leu Leu Thr Ser Asp Ala Pro Glu
    50                  55                  60

Tyr Lys Pro Trp Ala Leu Val Ile Gln Asp Ser Asn Gly Glu Asn Lys
```

65 70 75 80

Ile Lys Met Leu

<210> SEQ ID NO 15
<211> LENGTH: 484
<212> TYPE: DNA
<213> ORGANISM: Artificial Sequence
<220> FEATURE:
<223> OTHER INFORMATION: synthetic oligonucleotide: J23119-sgRNA-units
<220> FEATURE:
<221> NAME/KEY: promoter
<222> LOCATION: (59)..(93)
<223> OTHER INFORMATION: J23119 promoter
<220> FEATURE:
<221> NAME/KEY: misc_structure
<222> LOCATION: (94)..(113)
<223> OTHER INFORMATION: minimal CRISPR array
<220> FEATURE:
<221> NAME/KEY: misc_structure
<222> LOCATION: (114)..(196)
<223> OTHER INFORMATION: gRNA scaffold
<220> FEATURE:
<221> NAME/KEY: promoter
<222> LOCATION: (269)..(303)
<223> OTHER INFORMATION: J23119 promoter
<220> FEATURE:
<221> NAME/KEY: misc_structure
<222> LOCATION: (304)..(323)
<223> OTHER INFORMATION: minimal CRISPR array
<220> FEATURE:
<221> NAME/KEY: misc_structure
<222> LOCATION: (324)..(406)
<223> OTHER INFORMATION: gRNA scaffold

<400> SEQUENCE: 15
gataacaatt gagcaagaat cttcatcgat gcatcagaaa attattttaa atttcctctt 60
gacagctagc tcagtcctag gtataatgct agcagagacc cgggatggtc tcagttttag 120
agctagaaat agcaagttaa aataaggcta gtccgttatc aacttgaaaa agtggcaccg 180
agtcggtgct ttttttccga aaaaaaaacc ccgcccctga cagggcgggg ttttttttaa 240
ttaacagaaa attattttaa atttcctctt gacagctagc tcagtcctag gtataatgct 300
agcagaagag ccggcgctct tcagttttag agctagaaat agcaagttaa aataaggcta 360
gtccgttatc aacttgaaaa agtggcaccg agtcggtgct ttttttccga aaaaaaaacc 420
ccgcccctga cagggcgggg ttttttttc tagaccgcaa aaatcagcgc gcaaatacgc 480
atac 484

<210> SEQ ID NO 16
<211> LENGTH: 35
<212> TYPE: DNA
<213> ORGANISM: Artificial Sequence
<220> FEATURE:
<223> OTHER INFORMATION: Synthetic Sequence - J23119 promoter

<400> SEQUENCE: 16
ttgacagcta gctcagtcct aggtataatg ctagc 35

<210> SEQ ID NO 17
<211> LENGTH: 20
<212> TYPE: DNA
<213> ORGANISM: Streptococcus pyogenes
<220> FEATURE:
<221> NAME/KEY: misc_feature
<222> LOCATION: (1)..(20)
<223> OTHER INFORMATION: minimal CRISPR array

<400> SEQUENCE: 17
agagacccgg gatggtctca 20

<210> SEQ ID NO 18
<211> LENGTH: 83
<212> TYPE: DNA
<213> ORGANISM: Streptococcus pyogenes
<220> FEATURE:
<221> NAME/KEY: misc_structure
<222> LOCATION: (1)..(83)
<223> OTHER INFORMATION: gRNA scaffold

<400> SEQUENCE: 18
gttttagagc tagaaatagc aagttaaaat aaggctagtc cgttatcaac ttgaaaaagt 60
ggcaccgagt cggtgctttt ttt 83

<210> SEQ ID NO 19
<211> LENGTH: 19
<212> TYPE: RNA
<213> ORGANISM: Streptococcus pyogenes
<220> FEATURE:
<221> NAME/KEY: misc_structure
<222> LOCATION: (1)..(19)
<223> OTHER INFORMATION: crRNA direct repeat sequence.

<400> SEQUENCE: 19
aauuucuacu guuguagau 19

<210> SEQ ID NO 20
<211> LENGTH: 74
<212> TYPE: DNA
<213> ORGANISM: Artificial Sequence
<220> FEATURE:
<223> OTHER INFORMATION: PCR Primer

<400> SEQUENCE: 20
gctactctag aaaaaaaaac cccgccctgt caggggcggg gtttttttt cggggtttag 60 caagatggca gcgc 74

<210> SEQ ID NO 21
<211> LENGTH: 91
<212> TYPE: DNA
<213> ORGANISM: Artificial Sequence
<220> FEATURE:
<223> OTHER INFORMATION: PCR Primer

<400> SEQUENCE: 21
gcctgatcga tgcatcagaa aattatttta aatttcctct tgacagctag ctcagtccta 60
ggtataatgc tagcagagac ccgggatggt c 91

<210> SEQ ID NO 22
<211> LENGTH: 52
<212> TYPE: DNA
<213> ORGANISM: Artificial Sequence
<220> FEATURE:
<223> OTHER INFORMATION: PCR Primer

<400> SEQUENCE: 22 gatcctttttt gataatctcg tcgacataac aattgagcaa gaatcttcat cg 52

<210> SEQ ID NO 23
<211> LENGTH: 51
<212> TYPE: DNA
<213> ORGANISM: Artificial Sequence
<220> FEATURE:

<223> OTHER INFORMATION: PCR Primer

<400> SEQUENCE: 23
ctcacgttaa gggattttgg tcatctgcag tgtatgcgta tttgcgcgct g 51

<210> SEQ ID NO 24
<211> LENGTH: 57
<212> TYPE: DNA
<213> ORGANISM: Artificial Sequence
<220> FEATURE:
<223> OTHER INFORMATION: PCR Primer

<400> SEQUENCE: 24
gaagattctt gctcaattgt tatgtcgacg agattatcaa aaaggatctt cacctag 57

<210> SEQ ID NO 25
<211> LENGTH: 51
<212> TYPE: DNA
<213> ORGANISM: Artificial Sequence
<220> FEATURE:
<223> OTHER INFORMATION: PCR Primer

<400> SEQUENCE: 25
cagcgcgcaa atacgcatac actgcagatg accaaaatcc cttaacgtga g 51

<210> SEQ ID NO 26
<211> LENGTH: 20
<212> TYPE: DNA
<213> ORGANISM: Artificial Sequence
<220> FEATURE:
<223> OTHER INFORMATION: PCR Primer

<400> SEQUENCE: 26
ctgcacgcgc acttttatcc 20

<210> SEQ ID NO 27
<211> LENGTH: 21
<212> TYPE: DNA
<213> ORGANISM: Artificial Sequence
<220> FEATURE:
<223> OTHER INFORMATION: PCR Primer

<400> SEQUENCE: 27
ctctgtttgc caacgcattt g 21

<210> SEQ ID NO 28
<211> LENGTH: 20
<212> TYPE: DNA
<213> ORGANISM: Artificial Sequence
<220> FEATURE:
<223> OTHER INFORMATION: PCR Primer

<400> SEQUENCE: 28
caatggtgac atcacgcagg 20

<210> SEQ ID NO 29
<211> LENGTH: 21
<212> TYPE: DNA
<213> ORGANISM: Artificial Sequence
<220> FEATURE:
<223> OTHER INFORMATION: PCR Primer

<400> SEQUENCE: 29
cctgggcgat aacgtagttg c 21

<210> SEQ ID NO 30
<211> LENGTH: 20
<212> TYPE: DNA
<213> ORGANISM: Artificial Sequence
<220> FEATURE:
<223> OTHER INFORMATION: PCR Primer

<400> SEQUENCE: 30
cctcggcaac cgtcgtatcc 20

<210> SEQ ID NO 31
<211> LENGTH: 20
<212> TYPE: DNA
<213> ORGANISM: Artificial Sequence
<220> FEATURE:
<223> OTHER INFORMATION: PCR Primer

<400> SEQUENCE: 31
ccggttatcg gtagcgatac 20

<210> SEQ ID NO 32
<211> LENGTH: 20
<212> TYPE: DNA
<213> ORGANISM: Artificial Sequence
<220> FEATURE:
<223> OTHER INFORMATION: PCR Primer

<400> SEQUENCE: 32
gcctggggat tattgtgtgg 20

<210> SEQ ID NO 33
<211> LENGTH: 19
<212> TYPE: DNA
<213> ORGANISM: Artificial Sequence
<220> FEATURE:
<223> OTHER INFORMATION: PCR Primer

<400> SEQUENCE: 33
gcggctccag gttacttcc 19

<210> SEQ ID NO 34
<211> LENGTH: 17
<212> TYPE: DNA
<213> ORGANISM: Artificial Sequence
<220> FEATURE:
<223> OTHER INFORMATION: PCR Primer

<400> SEQUENCE: 34
gccatcactt ccagcgc 17

<210> SEQ ID NO 35
<211> LENGTH: 18
<212> TYPE: DNA
<213> ORGANISM: Artificial Sequence
<220> FEATURE:
<223> OTHER INFORMATION: PCR Primer

<400> SEQUENCE: 35
gccaaatcgg cggtaacg 18

<210> SEQ ID NO 36
<211> LENGTH: 20
<212> TYPE: DNA
<213> ORGANISM: Artificial Sequence
<220> FEATURE:
<223> OTHER INFORMATION: PCR Primer

<400> SEQUENCE: 36
ccatttcgta accgccagtc 20

<210> SEQ ID NO 37
<211> LENGTH: 20
<212> TYPE: DNA
<213> ORGANISM: Artificial Sequence
<220> FEATURE:
<223> OTHER INFORMATION: PCR Primer

<400> SEQUENCE: 37
ctctcgtatt cgagcagatg 20

<210> SEQ ID NO 38
<211> LENGTH: 17
<212> TYPE: DNA
<213> ORGANISM: Artificial Sequence
<220> FEATURE:
<223> OTHER INFORMATION: PCR Primer

<400> SEQUENCE: 38
ccgcccatag caaccag 17

<210> SEQ ID NO 39
<211> LENGTH: 16
<212> TYPE: DNA
<213> ORGANISM: Artificial Sequence
<220> FEATURE:
<223> OTHER INFORMATION: PCR Primer

<400> SEQUENCE: 39
ggggcggcca tcttcc 16

<210> SEQ ID NO 40
<211> LENGTH: 18
<212> TYPE: DNA
<213> ORGANISM: Artificial Sequence
<220> FEATURE:
<223> OTHER INFORMATION: PCR Primer

<400> SEQUENCE: 40
cagccgagga aattcagg 18

<210> SEQ ID NO 41
<211> LENGTH: 49
<212> TYPE: DNA
<213> ORGANISM: Artificial Sequence
<220> FEATURE:
<223> OTHER INFORMATION: PCR Primer

<400> SEQUENCE: 41
tctttcccta cacgacgctc ttccgatctc cgcagaacag gcagcagag 49

<210> SEQ ID NO 42
<211> LENGTH: 54
<212> TYPE: DNA
<213> ORGANISM: Artificial Sequence
<220> FEATURE:
<223> OTHER INFORMATION: PCR Primer

<400> SEQUENCE: 42
gtgactggag ttcagacgtg tgctcttccg atctgacaat gggcgcatcg aggg 54

<210> SEQ ID NO 43
<211> LENGTH: 49

<212> TYPE: DNA
<213> ORGANISM: Artificial Sequence
<220> FEATURE:
<223> OTHER INFORMATION: PCR Primer

<400> SEQUENCE: 43
tctttcccta cacgacgctc ttccgatctc acaccgacta caacgacgg 49

<210> SEQ ID NO 44
<211> LENGTH: 54
<212> TYPE: DNA
<213> ORGANISM: Artificial Sequence
<220> FEATURE:
<223> OTHER INFORMATION: PCR Primer

<400> SEQUENCE: 44
gtgactggag ttcagacgtg tgctcttccg atctgctgct gcaatacggt tccg 54

<210> SEQ ID NO 45
<211> LENGTH: 49
<212> TYPE: DNA
<213> ORGANISM: Artificial Sequence
<220> FEATURE:
<223> OTHER INFORMATION: PCR Primer

<400> SEQUENCE: 45
tctttcccta cacgacgctc ttccgatctc ttcggcggcg tggacatgg 49

<210> SEQ ID NO 46
<211> LENGTH: 55
<212> TYPE: DNA
<213> ORGANISM: Artificial Sequence
<220> FEATURE:
<223> OTHER INFORMATION: PCR Primer

<400> SEQUENCE: 46
gtgactggag ttcagacgtg tgctcttccg atctacgaca gccacacctt tgggc 55

<210> SEQ ID NO 47
<211> LENGTH: 52
<212> TYPE: DNA
<213> ORGANISM: Artificial Sequence
<220> FEATURE:
<223> OTHER INFORMATION: PCR Primer

<400> SEQUENCE: 47
tctttcccta cacgacgctc ttccgatctg gcggtggaaa cgggtaccgt cg 52

<210> SEQ ID NO 48
<211> LENGTH: 54
<212> TYPE: DNA
<213> ORGANISM: Artificial Sequence
<220> FEATURE:
<223> OTHER INFORMATION: PCR Primer

<400> SEQUENCE: 48
gtgactggag ttcagacgtg tgctcttccg atctcgccca ccagcgatag cgtt 54

<210> SEQ ID NO 49
<211> LENGTH: 49
<212> TYPE: DNA
<213> ORGANISM: Artificial Sequence
<220> FEATURE:
<223> OTHER INFORMATION: PCR Primer

<400> SEQUENCE: 49
tctttcccta cacgacgctc ttccgatctg gcgctcttga ttttcgccg 49

<210> SEQ ID NO 50
<211> LENGTH: 54
<212> TYPE: DNA
<213> ORGANISM: Artificial Sequence
<220> FEATURE:
<223> OTHER INFORMATION: PCR Primer

<400> SEQUENCE: 50
gtgactggag ttcagacgtg tgctcttccg atctggatgg cacgctggca atgc 54

<210> SEQ ID NO 51
<211> LENGTH: 49
<212> TYPE: DNA
<213> ORGANISM: Artificial Sequence
<220> FEATURE:
<223> OTHER INFORMATION: PCR Primer

<400> SEQUENCE: 51
tctttcccta cacgacgctc ttccgatctg cctccctgtg ctgttttgc 49

<210> SEQ ID NO 52
<211> LENGTH: 54
<212> TYPE: DNA
<213> ORGANISM: Artificial Sequence
<220> FEATURE:
<223> OTHER INFORMATION: PCR Primer

<400> SEQUENCE: 52
gtgactggag ttcagacgtg tgctcttccg atctgctcaa cacccacgtt cgcc 54

<210> SEQ ID NO 53
<211> LENGTH: 20
<212> TYPE: DNA
<213> ORGANISM: Artificial Sequence
<220> FEATURE:
<223> OTHER INFORMATION: PCR Primer

<400> SEQUENCE: 53
gctcattatt tgcccgcttg 20

<210> SEQ ID NO 54
<211> LENGTH: 19
<212> TYPE: DNA
<213> ORGANISM: Artificial Sequence
<220> FEATURE:
<223> OTHER INFORMATION: PCR Primer

<400> SEQUENCE: 54
tgccggttgc cagatagtc 19

<210> SEQ ID NO 55
<211> LENGTH: 19
<212> TYPE: DNA
<213> ORGANISM: Artificial Sequence
<220> FEATURE:
<223> OTHER INFORMATION: PCR Primer

<400> SEQUENCE: 55
ggtcttcagg aaatcaccg 19

<210> SEQ ID NO 56
<211> LENGTH: 20
<212> TYPE: DNA
<213> ORGANISM: Artificial Sequence
<220> FEATURE:
<223> OTHER INFORMATION: PCR Primer

<400> SEQUENCE: 56
cgttcaacca cttcagtgtc 20

<210> SEQ ID NO 57
<211> LENGTH: 20
<212> TYPE: DNA
<213> ORGANISM: Artificial Sequence
<220> FEATURE:
<223> OTHER INFORMATION: PCR Primer

<400> SEQUENCE: 57
cacaaagctg taaatcagcg 20

<210> SEQ ID NO 58
<211> LENGTH: 20
<212> TYPE: DNA
<213> ORGANISM: Artificial Sequence
<220> FEATURE:
<223> OTHER INFORMATION: PCR Primer

<400> SEQUENCE: 58
gtcaatgcaa cacccctttc 20

<210> SEQ ID NO 59
<211> LENGTH: 20
<212> TYPE: DNA
<213> ORGANISM: Artificial Sequence
<220> FEATURE:
<223> OTHER INFORMATION: PCR Primer

<400> SEQUENCE: 59
ctacaaccag gtcgagtcag 20

<210> SEQ ID NO 60
<211> LENGTH: 21
<212> TYPE: DNA
<213> ORGANISM: Artificial Sequence
<220> FEATURE:
<223> OTHER INFORMATION: PCR Primer

<400> SEQUENCE: 60
gtaatcctgc acctccatca c 21

<210> SEQ ID NO 61
<211> LENGTH: 20
<212> TYPE: DNA
<213> ORGANISM: Artificial Sequence
<220> FEATURE:
<223> OTHER INFORMATION: PCR Primer

<400> SEQUENCE: 61
gccagtagta cccgtcgttg 20

<210> SEQ ID NO 62
<211> LENGTH: 21
<212> TYPE: DNA
<213> ORGANISM: Artificial Sequence
<220> FEATURE:
<223> OTHER INFORMATION: PCR Primer

<400> SEQUENCE: 62
cacaagtcgt atttccagag g 21

<210> SEQ ID NO 63
<211> LENGTH: 20
<212> TYPE: DNA
<213> ORGANISM: Artificial Sequence
<220> FEATURE:
<223> OTHER INFORMATION: PCR Primer

<400> SEQUENCE: 63
ctgcaataag cagaaccacc 20

<210> SEQ ID NO 64
<211> LENGTH: 20
<212> TYPE: DNA
<213> ORGANISM: Artificial Sequence
<220> FEATURE:
<223> OTHER INFORMATION: PCR Primer

<400> SEQUENCE: 64
tgttgtgcgg taagtgtctg 20

<210> SEQ ID NO 65
<211> LENGTH: 21
<212> TYPE: DNA
<213> ORGANISM: Artificial Sequence
<220> FEATURE:
<223> OTHER INFORMATION: PCR Primer

<400> SEQUENCE: 65
gagcaatgga tggattcgaa g 21

<210> SEQ ID NO 66
<211> LENGTH: 22
<212> TYPE: DNA
<213> ORGANISM: Artificial Sequence
<220> FEATURE:
<223> OTHER INFORMATION: PCR Primer

<400> SEQUENCE: 66
tgaacaactg tccatgattt cg 22

<210> SEQ ID NO 67
<211> LENGTH: 19
<212> TYPE: DNA
<213> ORGANISM: Artificial Sequence
<220> FEATURE:
<223> OTHER INFORMATION: PCR Primer

<400> SEQUENCE: 67
ggtactttcc gggcaaccg 19

<210> SEQ ID NO 68
<211> LENGTH: 18
<212> TYPE: DNA
<213> ORGANISM: Artificial Sequence
<220> FEATURE:
<223> OTHER INFORMATION: PCR Primer

<400> SEQUENCE: 68
ctgccattag cgcagcca 18

<210> SEQ ID NO 69
<211> LENGTH: 19
<212> TYPE: DNA
<213> ORGANISM: Artificial Sequence
<220> FEATURE:
<223> OTHER INFORMATION: PCR Primer

<400> SEQUENCE: 69
catagctcta cacgccagg 19

<210> SEQ ID NO 70
<211> LENGTH: 22
<212> TYPE: DNA
<213> ORGANISM: Artificial Sequence
<220> FEATURE:
<223> OTHER INFORMATION: PCR Primer

<400> SEQUENCE: 70
atcatgggct ccttttagtt gc 22

<210> SEQ ID NO 71
<211> LENGTH: 19
<212> TYPE: DNA
<213> ORGANISM: Artificial Sequence
<220> FEATURE:
<223> OTHER INFORMATION: PCR Primer

<400> SEQUENCE: 71
gatattgccc gccggacac 19

<210> SEQ ID NO 72
<211> LENGTH: 18
<212> TYPE: DNA
<213> ORGANISM: Artificial Sequence
<220> FEATURE:
<223> OTHER INFORMATION: PCR Primer

<400> SEQUENCE: 72
cgatctaaag cgcgcagc 18

<210> SEQ ID NO 73
<211> LENGTH: 22
<212> TYPE: DNA
<213> ORGANISM: Artificial Sequence
<220> FEATURE:
<223> OTHER INFORMATION: PCR Primer

<400> SEQUENCE: 73
gacgttgttg aaaatgtagg gt 22

<210> SEQ ID NO 74
<211> LENGTH: 21
<212> TYPE: DNA
<213> ORGANISM: Artificial Sequence
<220> FEATURE:
<223> OTHER INFORMATION: PCR Primer

<400> SEQUENCE: 74
gcctaacgcc tttaattcag g 21

<210> SEQ ID NO 75
<211> LENGTH: 19
<212> TYPE: DNA
<213> ORGANISM: Artificial Sequence
<220> FEATURE:
<223> OTHER INFORMATION: PCR Primer

<400> SEQUENCE: 75
tgttgtggag cctgaacgg 19

<210> SEQ ID NO 76

<211> LENGTH: 19
<212> TYPE: DNA
<213> ORGANISM: Artificial Sequence
<220> FEATURE:
<223> OTHER INFORMATION: PCR Primer

<400> SEQUENCE: 76
gcaactgttc cggcagatg 19

<210> SEQ ID NO 77
<211> LENGTH: 23
<212> TYPE: DNA
<213> ORGANISM: Artificial Sequence
<220> FEATURE:
<223> OTHER INFORMATION: PCR Primer

<400> SEQUENCE: 77
cggattaatg ataagtggat cag 23

<210> SEQ ID NO 78
<211> LENGTH: 21
<212> TYPE: DNA
<213> ORGANISM: Artificial Sequence
<220> FEATURE:
<223> OTHER INFORMATION: PCR Primer

<400> SEQUENCE: 78
cttagtgaat atttgccgac g 21

<210> SEQ ID NO 79
<211> LENGTH: 22
<212> TYPE: DNA
<213> ORGANISM: Artificial Sequence
<220> FEATURE:
<223> OTHER INFORMATION: PCR Primer

<400> SEQUENCE: 79
gctgataagt tacctcctga cc 22

<210> SEQ ID NO 80
<211> LENGTH: 22
<212> TYPE: DNA
<213> ORGANISM: Artificial Sequence
<220> FEATURE:
<223> OTHER INFORMATION: PCR Primer

<400> SEQUENCE: 80
gcgactatac aggttattga cc 22

<210> SEQ ID NO 81
<211> LENGTH: 20
<212> TYPE: DNA
<213> ORGANISM: Artificial Sequence
<220> FEATURE:
<223> OTHER INFORMATION: PCR Primer

<400> SEQUENCE: 81
acattacaga gaagccgatg 20

<210> SEQ ID NO 82
<211> LENGTH: 19
<212> TYPE: DNA
<213> ORGANISM: Artificial Sequence
<220> FEATURE:
<223> OTHER INFORMATION: PCR Primer

<400> SEQUENCE: 82
gtgatagtta gcgatgccg 19

<210> SEQ ID NO 83
<211> LENGTH: 22
<212> TYPE: DNA
<213> ORGANISM: Artificial Sequence
<220> FEATURE:
<223> OTHER INFORMATION: PCR Primer

<400> SEQUENCE: 83
ggacgaataa acgcataatt ac 22

<210> SEQ ID NO 84
<211> LENGTH: 19
<212> TYPE: DNA
<213> ORGANISM: Artificial Sequence
<220> FEATURE:
<223> OTHER INFORMATION: PCR Primer

<400> SEQUENCE: 84
tcccaacctt ctgtcacag 19

<210> SEQ ID NO 85
<211> LENGTH: 19
<212> TYPE: DNA
<213> ORGANISM: Artificial Sequence
<220> FEATURE:
<223> OTHER INFORMATION: PCR Primer

<400> SEQUENCE: 85
caattttcgc accggaatc 19

<210> SEQ ID NO 86
<211> LENGTH: 20
<212> TYPE: DNA
<213> ORGANISM: Artificial Sequence
<220> FEATURE:
<223> OTHER INFORMATION: PCR Primer

<400> SEQUENCE: 86
atggagatac gacaatcagc 20

<210> SEQ ID NO 87
<211> LENGTH: 21
<212> TYPE: DNA
<213> ORGANISM: Artificial Sequence
<220> FEATURE:
<223> OTHER INFORMATION: PCR Primer

<400> SEQUENCE: 87
caattcctgg aacattatcc g 21

<210> SEQ ID NO 88
<211> LENGTH: 19
<212> TYPE: DNA
<213> ORGANISM: Artificial Sequence
<220> FEATURE:
<223> OTHER INFORMATION: PCR Primer

<400> SEQUENCE: 88
tgagtgatgt tttggcgac 19

<210> SEQ ID NO 89
<211> LENGTH: 19
<212> TYPE: DNA

<213> ORGANISM: Artificial Sequence
<220> FEATURE:
<223> OTHER INFORMATION: PCR Primer

<400> SEQUENCE: 89
ctgtactcac agggtgatg 19

<210> SEQ ID NO 90
<211> LENGTH: 18
<212> TYPE: DNA
<213> ORGANISM: Artificial Sequence
<220> FEATURE:
<223> OTHER INFORMATION: PCR Primer

<400> SEQUENCE: 90
ggcagacagt ttgaaacc 18

<210> SEQ ID NO 91
<211> LENGTH: 19
<212> TYPE: DNA
<213> ORGANISM: Artificial Sequence
<220> FEATURE:
<223> OTHER INFORMATION: PCR Primer

<400> SEQUENCE: 91
cgccacgaac gtagttagc 19

<210> SEQ ID NO 92
<211> LENGTH: 22
<212> TYPE: DNA
<213> ORGANISM: Artificial Sequence
<220> FEATURE:
<223> OTHER INFORMATION: PCR Primer

<400> SEQUENCE: 92
gattggtgaa cacaccgact ac 22

<210> SEQ ID NO 93
<211> LENGTH: 20
<212> TYPE: DNA
<213> ORGANISM: Artificial Sequence
<220> FEATURE:
<223> OTHER INFORMATION: PCR Primer

<400> SEQUENCE: 93
ggtcaggtgg tttggaaagc 20

<210> SEQ ID NO 94
<211> LENGTH: 21
<212> TYPE: DNA
<213> ORGANISM: Artificial Sequence
<220> FEATURE:
<223> OTHER INFORMATION: PCR Primer

<400> SEQUENCE: 94
aagtggacac gctatacctg c 21

<210> SEQ ID NO 95
<211> LENGTH: 20
<212> TYPE: DNA
<213> ORGANISM: Artificial Sequence
<220> FEATURE:
<223> OTHER INFORMATION: PCR Primer

<400> SEQUENCE: 95
cactcaacac ataccgtgcc 20

<210> SEQ ID NO 96
<211> LENGTH: 21
<212> TYPE: DNA
<213> ORGANISM: Artificial Sequence
<220> FEATURE:
<223> OTHER INFORMATION: PCR Primer

<400> SEQUENCE: 96
caacaccaaa ctggaacacg g 21

<210> SEQ ID NO 97
<211> LENGTH: 22
<212> TYPE: DNA
<213> ORGANISM: Artificial Sequence
<220> FEATURE:
<223> OTHER INFORMATION: PCR Primer

<400> SEQUENCE: 97
cggaggaaac agaatcagtg tg 22

<210> SEQ ID NO 98
<211> LENGTH: 21
<212> TYPE: DNA
<213> ORGANISM: Artificial Sequence
<220> FEATURE:
<223> OTHER INFORMATION: PCR Primer

<400> SEQUENCE: 98
gagatggtgg agatcctctc g 21

<210> SEQ ID NO 99
<211> LENGTH: 19
<212> TYPE: DNA
<213> ORGANISM: Artificial Sequence
<220> FEATURE:
<223> OTHER INFORMATION: PCR Primer

<400> SEQUENCE: 99
gatagttagc gatgccggg 19

<210> SEQ ID NO 100
<211> LENGTH: 22
<212> TYPE: DNA
<213> ORGANISM: Artificial Sequence
<220> FEATURE:
<223> OTHER INFORMATION: PCR Primer

<400> SEQUENCE: 100
ggagaatccc caggttatct gg 22

<210> SEQ ID NO 101
<211> LENGTH: 20
<212> TYPE: DNA
<213> ORGANISM: Artificial Sequence
<220> FEATURE:
<223> OTHER INFORMATION: PCR Primer

<400> SEQUENCE: 101
tgaaacgtgc gggtctcaac 20

<210> SEQ ID NO 102
<211> LENGTH: 23
<212> TYPE: DNA
<213> ORGANISM: Artificial Sequence
<220> FEATURE:

<223> OTHER INFORMATION: PCR Primer

<400> SEQUENCE: 102
ggatagtggt taatggtggc gtc 23

<210> SEQ ID NO 103
<211> LENGTH: 20
<212> TYPE: DNA
<213> ORGANISM: Artificial Sequence
<220> FEATURE:
<223> OTHER INFORMATION: PCR Primer

<400> SEQUENCE: 103
cgtgctgagg gctatttacc 20

<210> SEQ ID NO 104
<211> LENGTH: 22
<212> TYPE: DNA
<213> ORGANISM: Artificial Sequence
<220> FEATURE:
<223> OTHER INFORMATION: PCR Primer

<400> SEQUENCE: 104
gacgtcatca tttagccaga tg 22

<210> SEQ ID NO 105
<211> LENGTH: 22
<212> TYPE: DNA
<213> ORGANISM: Artificial Sequence
<220> FEATURE:
<223> OTHER INFORMATION: PCR Primer

<400> SEQUENCE: 105
ggttctcagg ttaatgtttc gg 22

<210> SEQ ID NO 106
<211> LENGTH: 20
<212> TYPE: DNA
<213> ORGANISM: Artificial Sequence
<220> FEATURE:
<223> OTHER INFORMATION: PCR Primer

<400> SEQUENCE: 106
caccagatac tacgttaccg 20

<210> SEQ ID NO 107
<211> LENGTH: 20
<212> TYPE: DNA
<213> ORGANISM: Artificial Sequence
<220> FEATURE:
<223> OTHER INFORMATION: PCR Primer

<400> SEQUENCE: 107
ttcggactga aaggagcaag 20

<210> SEQ ID NO 108
<211> LENGTH: 20
<212> TYPE: DNA
<213> ORGANISM: Artificial Sequence
<220> FEATURE:
<223> OTHER INFORMATION: PCR Primer

<400> SEQUENCE: 108
agattcgtgc tcacctttcc 20

<210> SEQ ID NO 109
<211> LENGTH: 22
<212> TYPE: DNA
<213> ORGANISM: Artificial Sequence
<220> FEATURE:
<223> OTHER INFORMATION: PCR Primer

<400> SEQUENCE: 109
gattagtatt ggcgctgttg tg 22

<210> SEQ ID NO 110
<211> LENGTH: 21
<212> TYPE: DNA
<213> ORGANISM: Artificial Sequence
<220> FEATURE:
<223> OTHER INFORMATION: PCR Primer

<400> SEQUENCE: 110
cagtccattt caccgtatga g 21

<210> SEQ ID NO 111
<211> LENGTH: 21
<212> TYPE: DNA
<213> ORGANISM: Artificial Sequence
<220> FEATURE:
<223> OTHER INFORMATION: PCR Primer

<400> SEQUENCE: 111
acagacgacc agagtaatgt c 21

<210> SEQ ID NO 112
<211> LENGTH: 19
<212> TYPE: DNA
<213> ORGANISM: Artificial Sequence
<220> FEATURE:
<223> OTHER INFORMATION: PCR Primer

<400> SEQUENCE: 112
tggttacgcg ctttcatgg 19

<210> SEQ ID NO 113
<211> LENGTH: 21
<212> TYPE: DNA
<213> ORGANISM: Artificial Sequence
<220> FEATURE:
<223> OTHER INFORMATION: PCR Primer

<400> SEQUENCE: 113
caggctgaac atggataaga c 21

<210> SEQ ID NO 114
<211> LENGTH: 22
<212> TYPE: DNA
<213> ORGANISM: Artificial Sequence
<220> FEATURE:
<223> OTHER INFORMATION: PCR Primer

<400> SEQUENCE: 114
acgtatggac atctaaacat cc 22

<210> SEQ ID NO 115
<211> LENGTH: 21
<212> TYPE: DNA
<213> ORGANISM: Artificial Sequence
<220> FEATURE:
<223> OTHER INFORMATION: PCR Primer

<400> SEQUENCE: 115
gcaaggttgt gcttctaaag g 21

<210> SEQ ID NO 116
<211> LENGTH: 23
<212> TYPE: DNA
<213> ORGANISM: Artificial Sequence
<220> FEATURE:
<223> OTHER INFORMATION: PCR Primer

<400> SEQUENCE: 116
cctgcaatct aaaggtaagg atc 23

<210> SEQ ID NO 117
<211> LENGTH: 20
<212> TYPE: DNA
<213> ORGANISM: Artificial Sequence
<220> FEATURE:
<223> OTHER INFORMATION: PCR Primer

<400> SEQUENCE: 117
gattgctgtg gcaggtttac 20

<210> SEQ ID NO 118
<211> LENGTH: 20
<212> TYPE: DNA
<213> ORGANISM: Artificial Sequence
<220> FEATURE:
<223> OTHER INFORMATION: PCR Primer

<400> SEQUENCE: 118
cagtacaacc tagttgcacc 20

<210> SEQ ID NO 119
<211> LENGTH: 20
<212> TYPE: DNA
<213> ORGANISM: Artificial Sequence
<220> FEATURE:
<223> OTHER INFORMATION: PCR Primer

<400> SEQUENCE: 119
tgaagattcc gtgcgtaacc 20

<210> SEQ ID NO 120
<211> LENGTH: 19
<212> TYPE: DNA
<213> ORGANISM: Artificial Sequence
<220> FEATURE:
<223> OTHER INFORMATION: PCR Primer

<400> SEQUENCE: 120
cacgatgaaa ccgtcagtg 19

<210> SEQ ID NO 121
<211> LENGTH: 19
<212> TYPE: DNA
<213> ORGANISM: Artificial Sequence
<220> FEATURE:
<223> OTHER INFORMATION: PCR Primer

<400> SEQUENCE: 121
atgctactgc cggaacaac 19

<210> SEQ ID NO 122
<211> LENGTH: 20

<212> TYPE: DNA
<213> ORGANISM: Artificial Sequence
<220> FEATURE:
<223> OTHER INFORMATION: PCR Primer

<400> SEQUENCE: 122
tgatgtcagc gagaagatgg 20

<210> SEQ ID NO 123
<211> LENGTH: 21
<212> TYPE: DNA
<213> ORGANISM: Artificial Sequence
<220> FEATURE:
<223> OTHER INFORMATION: PCR Primer

<400> SEQUENCE: 123
agcacaggtc aatatcttca c 21

<210> SEQ ID NO 124
<211> LENGTH: 21
<212> TYPE: DNA
<213> ORGANISM: Artificial Sequence
<220> FEATURE:
<223> OTHER INFORMATION: PCR Primer

<400> SEQUENCE: 124
aatatagacc cgcagatgat g 21

<210> SEQ ID NO 125
<211> LENGTH: 20
<212> TYPE: DNA
<213> ORGANISM: Artificial Sequence
<220> FEATURE:
<223> OTHER INFORMATION: PCR Primer

<400> SEQUENCE: 125
tccgccagga ttgattttcg 20

<210> SEQ ID NO 126
<211> LENGTH: 19
<212> TYPE: DNA
<213> ORGANISM: Artificial Sequence
<220> FEATURE:
<223> OTHER INFORMATION: PCR Primer

<400> SEQUENCE: 126
ctccgggtat ggagctatg 19

<210> SEQ ID NO 127
<211> LENGTH: 20
<212> TYPE: DNA
<213> ORGANISM: Artificial Sequence
<220> FEATURE:
<223> OTHER INFORMATION: PCR Primer

<400> SEQUENCE: 127
gatcaggacg ctcatattcg 20

<210> SEQ ID NO 128
<211> LENGTH: 20
<212> TYPE: DNA
<213> ORGANISM: Artificial Sequence
<220> FEATURE:
<223> OTHER INFORMATION: PCR Primer

<400> SEQUENCE: 128
ctgtcatgtc ggttagttcc 20

<210> SEQ ID NO 129
<211> LENGTH: 20
<212> TYPE: DNA
<213> ORGANISM: Artificial Sequence
<220> FEATURE:
<223> OTHER INFORMATION: PCR Primer

<400> SEQUENCE: 129
acaggatgaa agtctttgcc 20

<210> SEQ ID NO 130
<211> LENGTH: 20
<212> TYPE: DNA
<213> ORGANISM: Artificial Sequence
<220> FEATURE:
<223> OTHER INFORMATION: PCR Primer

<400> SEQUENCE: 130
gcaatttccg cttttgctcg 20

<210> SEQ ID NO 131
<211> LENGTH: 20
<212> TYPE: DNA
<213> ORGANISM: Artificial Sequence
<220> FEATURE:
<223> OTHER INFORMATION: PCR Primer

<400> SEQUENCE: 131
aactgcttct cctcaccatc 20

<210> SEQ ID NO 132
<211> LENGTH: 18
<212> TYPE: DNA
<213> ORGANISM: Artificial Sequence
<220> FEATURE:
<223> OTHER INFORMATION: PCR Primer

<400> SEQUENCE: 132
agaatcgtct ggcggttg 18

<210> SEQ ID NO 133
<211> LENGTH: 19
<212> TYPE: DNA
<213> ORGANISM: Artificial Sequence
<220> FEATURE:
<223> OTHER INFORMATION: PCR Primer

<400> SEQUENCE: 133
catcagaatc aatgctgcg 19

<210> SEQ ID NO 134
<211> LENGTH: 19
<212> TYPE: DNA
<213> ORGANISM: Artificial Sequence
<220> FEATURE:
<223> OTHER INFORMATION: PCR Primer

<400> SEQUENCE: 134
tcgctgactt cagtttcgc 19

<210> SEQ ID NO 135
<211> LENGTH: 20
<212> TYPE: DNA
<213> ORGANISM: Artificial Sequence
<220> FEATURE:
<223> OTHER INFORMATION: PCR Primer

<400> SEQUENCE: 135
gcctgccaga tgatatggtc 20

<210> SEQ ID NO 136
<211> LENGTH: 19
<212> TYPE: DNA
<213> ORGANISM: Artificial Sequence
<220> FEATURE:
<223> OTHER INFORMATION: PCR Primer

<400> SEQUENCE: 136
accagaccgt ggttgttag 19

<210> SEQ ID NO 137
<211> LENGTH: 25
<212> TYPE: DNA
<213> ORGANISM: Artificial Sequence
<220> FEATURE:
<223> OTHER INFORMATION: PCR Primer

<400> SEQUENCE: 137
tttgttatcc agccatgatg ttttc 25

<210> SEQ ID NO 138
<211> LENGTH: 25
<212> TYPE: DNA
<213> ORGANISM: Artificial Sequence
<220> FEATURE:
<223> OTHER INFORMATION: PCR Primer

<400> SEQUENCE: 138
ttcctgtata cctgaaacga caatg 25

<210> SEQ ID NO 139
<211> LENGTH: 20
<212> TYPE: DNA
<213> ORGANISM: Artificial Sequence
<220> FEATURE:
<223> OTHER INFORMATION: PCR Primer

<400> SEQUENCE: 139
cacgcacata caacggaggg 20

<210> SEQ ID NO 140
<211> LENGTH: 20
<212> TYPE: DNA
<213> ORGANISM: Artificial Sequence
<220> FEATURE:
<223> OTHER INFORMATION: PCR Primer

<400> SEQUENCE: 140
ttgactgtgc gcaacatccc 20

<210> SEQ ID NO 141
<211> LENGTH: 18
<212> TYPE: DNA
<213> ORGANISM: Artificial Sequence
<220> FEATURE:
<223> OTHER INFORMATION: PCR Primer

<400> SEQUENCE: 141
cctattccgc ccatgacc 18

<210> SEQ ID NO 142
<211> LENGTH: 20
<212> TYPE: DNA
<213> ORGANISM: Artificial Sequence
<220> FEATURE:
<223> OTHER INFORMATION: PCR Primer

<400> SEQUENCE: 142
caaaggtcca ggcttttggg 20

<210> SEQ ID NO 143
<211> LENGTH: 20
<212> TYPE: DNA
<213> ORGANISM: Escherichia coli

<400> SEQUENCE: 143
catccatatc accacgtcaa 20

<210> SEQ ID NO 144
<211> LENGTH: 20
<212> TYPE: DNA
<213> ORGANISM: Escherichia coli

<400> SEQUENCE: 144
ggtggcatcg cccacgtcaa 20

<210> SEQ ID NO 145
<211> LENGTH: 20
<212> TYPE: DNA
<213> ORGANISM: Escherichia coli

<400> SEQUENCE: 145
gtccattagc accacgtcaa 20

<210> SEQ ID NO 146
<211> LENGTH: 20
<212> TYPE: DNA
<213> ORGANISM: Escherichia coli

<400> SEQUENCE: 146
tgcaatcgcc ttcacgtcaa 20

<210> SEQ ID NO 147
<211> LENGTH: 20
<212> TYPE: DNA
<213> ORGANISM: Escherichia coli

<400> SEQUENCE: 147
atagcggtag gccacgtcaa 20

<210> SEQ ID NO 148
<211> LENGTH: 20
<212> TYPE: DNA
<213> ORGANISM: Escherichia coli

<400> SEQUENCE: 148
tgggcgctgt tgcacgtcaa 20

<210> SEQ ID NO 149
<211> LENGTH: 20
<212> TYPE: DNA
<213> ORGANISM: Escherichia coli

<400> SEQUENCE: 149

```
accaccgcgt accacgtcaa                                                20


<210> SEQ ID NO 150
<211> LENGTH: 20
<212> TYPE: DNA
<213> ORGANISM: Escherichia coli

<400> SEQUENCE: 150

agccactcca ctggagacga                                                20


<210> SEQ ID NO 151
<211> LENGTH: 20
<212> TYPE: DNA
<213> ORGANISM: Escherichia coli

<400> SEQUENCE: 151

gatcttgtga ccggagacga                                                20


<210> SEQ ID NO 152
<211> LENGTH: 20
<212> TYPE: DNA
<213> ORGANISM: Escherichia coli

<400> SEQUENCE: 152

cccgttttgc caggagacga                                                20


<210> SEQ ID NO 153
<211> LENGTH: 20
<212> TYPE: DNA
<213> ORGANISM: Escherichia coli

<400> SEQUENCE: 153

catctctgct ctggagacga                                                20


<210> SEQ ID NO 154
<211> LENGTH: 20
<212> TYPE: DNA
<213> ORGANISM: Escherichia coli

<400> SEQUENCE: 154

accacgtata ccagccgctg                                                20


<210> SEQ ID NO 155
<211> LENGTH: 20
<212> TYPE: DNA
<213> ORGANISM: Escherichia coli

<400> SEQUENCE: 155

aattatctcc acagccgctg                                                20


<210> SEQ ID NO 156
<211> LENGTH: 20
<212> TYPE: DNA
<213> ORGANISM: Escherichia coli

<400> SEQUENCE: 156

gaagtgttga tgagccgctg                                                20


<210> SEQ ID NO 157
<211> LENGTH: 20
<212> TYPE: DNA
<213> ORGANISM: Escherichia coli
```

<400> SEQUENCE: 157
aaaagccgag gcagccgctg 20

<210> SEQ ID NO 158
<211> LENGTH: 20
<212> TYPE: DNA
<213> ORGANISM: Escherichia coli

<400> SEQUENCE: 158
aacgttgaag tcagccgctg 20

<210> SEQ ID NO 159
<211> LENGTH: 20
<212> TYPE: DNA
<213> ORGANISM: Escherichia coli

<400> SEQUENCE: 159
cagagcaggt tcagccgctg 20

<210> SEQ ID NO 160
<211> LENGTH: 20
<212> TYPE: DNA
<213> ORGANISM: Escherichia coli

<400> SEQUENCE: 160
catgccaata tcagccgctg 20

<210> SEQ ID NO 161
<211> LENGTH: 20
<212> TYPE: DNA
<213> ORGANISM: Escherichia coli

<400> SEQUENCE: 161
tctgctgctg ccagccgctg 20

<210> SEQ ID NO 162
<211> LENGTH: 20
<212> TYPE: DNA
<213> ORGANISM: Escherichia coli

<400> SEQUENCE: 162
aagaagagat caagccgctg 20

<210> SEQ ID NO 163
<211> LENGTH: 20
<212> TYPE: DNA
<213> ORGANISM: Escherichia coli

<400> SEQUENCE: 163
gacaacagtc ttagccgctg 20

<210> SEQ ID NO 164
<211> LENGTH: 20
<212> TYPE: DNA
<213> ORGANISM: Escherichia coli

<400> SEQUENCE: 164
agacatacag ccagccgctg 20

<210> SEQ ID NO 165
<211> LENGTH: 20
<212> TYPE: DNA
<213> ORGANISM: Escherichia coli

<400> SEQUENCE: 165
ttactaaaaa aaagccgctg 20

<210> SEQ ID NO 166
<211> LENGTH: 20
<212> TYPE: DNA
<213> ORGANISM: Escherichia coli

<400> SEQUENCE: 166
gtgtaaaaaa cgagccgctg 20

<210> SEQ ID NO 167
<211> LENGTH: 20
<212> TYPE: DNA
<213> ORGANISM: Escherichia coli

<400> SEQUENCE: 167
cgcatagctg gaagccgctg 20

<210> SEQ ID NO 168
<211> LENGTH: 20
<212> TYPE: DNA
<213> ORGANISM: Escherichia coli

<400> SEQUENCE: 168
aattagtggt gcagccgctg 20

<210> SEQ ID NO 169
<211> LENGTH: 20
<212> TYPE: DNA
<213> ORGANISM: Escherichia coli

<400> SEQUENCE: 169
tgctggtctt tgagccgctg 20

<210> SEQ ID NO 170
<211> LENGTH: 20
<212> TYPE: DNA
<213> ORGANISM: Escherichia coli

<400> SEQUENCE: 170
ttccggatag ttagccgctg 20

<210> SEQ ID NO 171
<211> LENGTH: 20
<212> TYPE: DNA
<213> ORGANISM: Escherichia coli

<400> SEQUENCE: 171
agcatatcgt gcagccgctg 20

<210> SEQ ID NO 172
<211> LENGTH: 20
<212> TYPE: DNA
<213> ORGANISM: Escherichia coli

<400> SEQUENCE: 172
ggcgggtttt ttagccgctg 20

<210> SEQ ID NO 173
<211> LENGTH: 20
<212> TYPE: DNA

<213> ORGANISM: Escherichia coli

<400> SEQUENCE: 173
cggctcgctc gcagccgctg 20

<210> SEQ ID NO 174
<211> LENGTH: 20
<212> TYPE: DNA
<213> ORGANISM: Escherichia coli

<400> SEQUENCE: 174
ctgcgattcc tcagccgctg 20

<210> SEQ ID NO 175
<211> LENGTH: 20
<212> TYPE: DNA
<213> ORGANISM: Escherichia coli

<400> SEQUENCE: 175
acacgtcgat atagccgctg 20

<210> SEQ ID NO 176
<211> LENGTH: 20
<212> TYPE: DNA
<213> ORGANISM: Escherichia coli

<400> SEQUENCE: 176
gtgccactga ttgcctttct 20

<210> SEQ ID NO 177
<211> LENGTH: 20
<212> TYPE: DNA
<213> ORGANISM: Escherichia coli

<400> SEQUENCE: 177
gtacctgtat ttgcctttct 20

<210> SEQ ID NO 178
<211> LENGTH: 20
<212> TYPE: DNA
<213> ORGANISM: Escherichia coli

<400> SEQUENCE: 178
ttatcggcct gagcctttct 20

<210> SEQ ID NO 179
<211> LENGTH: 20
<212> TYPE: DNA
<213> ORGANISM: Escherichia coli

<400> SEQUENCE: 179
cttaacgtcc gcgcctttct 20

<210> SEQ ID NO 180
<211> LENGTH: 20
<212> TYPE: DNA
<213> ORGANISM: Escherichia coli

<400> SEQUENCE: 180
ctgaccgata atgcctttct 20

<210> SEQ ID NO 181
<211> LENGTH: 10

<212> TYPE: PRT
<213> ORGANISM: Artificial Sequence
<220> FEATURE:
<223> OTHER INFORMATION: Synthetic Sequence - protein degradation tag

<400> SEQUENCE: 181

Ala Asn Asp Glu Asn Tyr Ala Leu Ala Ala
1 5 10

<210> SEQ ID NO 182
<211> LENGTH: 11
<212> TYPE: PRT
<213> ORGANISM: Artificial Sequence
<220> FEATURE:
<223> OTHER INFORMATION: Synthetic Sequence - protein degradation tag

<400> SEQUENCE: 182

Ala Ala Asn Asp Glu Asn Tyr Ala Leu Ala Ala
1 5 10

<210> SEQ ID NO 183
<211> LENGTH: 10
<212> TYPE: PRT
<213> ORGANISM: Artificial Sequence
<220> FEATURE:
<223> OTHER INFORMATION: Synthetic Sequence - protein degradation tag

<400> SEQUENCE: 183

Gly Lys Gln Asn Asn Leu Ser Leu Ala Ala
1 5 10

<210> SEQ ID NO 184
<211> LENGTH: 11
<212> TYPE: PRT
<213> ORGANISM: Artificial Sequence
<220> FEATURE:
<223> OTHER INFORMATION: Synthetic Sequence - protein degradation tag

<400> SEQUENCE: 184

Gly Lys Ser Asn Asn Asn Phe Ala Leu Ala Ala
1 5 10

<210> SEQ ID NO 185
<211> LENGTH: 11
<212> TYPE: PRT
<213> ORGANISM: Artificial Sequence
<220> FEATURE:
<223> OTHER INFORMATION: protein degradation tag

<400> SEQUENCE: 185

Gly Lys Glu Asn Asn Asn Phe Ala Leu Ala Ala
1 5 10

<210> SEQ ID NO 186
<211> LENGTH: 14
<212> TYPE: PRT
<213> ORGANISM: Artificial Sequence
<220> FEATURE:
<223> OTHER INFORMATION: Synthetic Sequence - protein degradation tag

<400> SEQUENCE: 186

Gly Lys Thr Asn Ser Phe Asn Gln Asn Val Ala Leu Ala Ala
1 5 10

<210> SEQ ID NO 187
<211> LENGTH: 11
<212> TYPE: PRT

<213> ORGANISM: Artificial Sequence
<220> FEATURE:
<223> OTHER INFORMATION: Synthetic Sequence - protein degradation tag

<400> SEQUENCE: 187

Gly Lys Ser Asn Gln Asn Leu Ala Leu Ala Ala
1               5                   10

<210> SEQ ID NO 188
<211> LENGTH: 9
<212> TYPE: PRT
<213> ORGANISM: Artificial Sequence
<220> FEATURE:
<223> OTHER INFORMATION: Synthetic Sequence - protein degradation tag

<400> SEQUENCE: 188

Gly Lys Gln Asn Tyr Ala Leu Ala Ala
1               5

<210> SEQ ID NO 189
<211> LENGTH: 10
<212> TYPE: PRT
<213> ORGANISM: Artificial Sequence
<220> FEATURE:
<223> OTHER INFORMATION: Synthetic Sequence - protein degradation tag

<400> SEQUENCE: 189

Ala Asn Asp Asp Asn Tyr Ala Leu Ala Ala
1               5                   10

<210> SEQ ID NO 190
<211> LENGTH: 12
<212> TYPE: PRT
<213> ORGANISM: Artificial Sequence
<220> FEATURE:
<223> OTHER INFORMATION: Synthetic Sequence - protein degradation tag

<400> SEQUENCE: 190

Ala Asn Asp Asp Gln Tyr Gly Ala Ala Leu Ala Ala
1               5                   10

<210> SEQ ID NO 191
<211> LENGTH: 14
<212> TYPE: PRT
<213> ORGANISM: Artificial Sequence
<220> FEATURE:
<223> OTHER INFORMATION: Synthetic Sequence - protein degradation tag

<400> SEQUENCE: 191

Ala Asn Asp Glu Asn Tyr Gly Gln Glu Phe Ala Leu Ala Ala
1               5                   10

<210> SEQ ID NO 192
<211> LENGTH: 13
<212> TYPE: PRT
<213> ORGANISM: Artificial Sequence
<220> FEATURE:
<223> OTHER INFORMATION: Synthetic Sequence - protein degradation tag

<400> SEQUENCE: 192

Ala Asn Asp Glu Thr Tyr Gly Asp Tyr Ala Leu Ala Ala
1               5                   10

<210> SEQ ID NO 193
<211> LENGTH: 13
<212> TYPE: PRT
<213> ORGANISM: Artificial Sequence
<220> FEATURE:
<223> OTHER INFORMATION: Synthetic Sequence - protein degradation tag

<400> SEQUENCE: 193

Ala Asn Asp Glu Thr Tyr Gly Glu Tyr Ala Leu Ala Ala
1 5 10

<210> SEQ ID NO 194
<211> LENGTH: 15
<212> TYPE: PRT
<213> ORGANISM: Artificial Sequence
<220> FEATURE:
<223> OTHER INFORMATION: Synthetic Sequence - protein degradation tag

<400> SEQUENCE: 194

Ala Asn Asp Glu Thr Tyr Gly Glu Glu Thr Tyr Ala Leu Ala Ala
1 5 10 15

<210> SEQ ID NO 195
<211> LENGTH: 14
<212> TYPE: PRT
<213> ORGANISM: Artificial Sequence
<220> FEATURE:
<223> OTHER INFORMATION: Synthetic Sequence - protein degradation tag

<400> SEQUENCE: 195

Ala Asn Asp Glu Asn Tyr Gly Ala Glu Tyr Lys Leu Ala Ala
1 5 10

<210> SEQ ID NO 196
<211> LENGTH: 12
<212> TYPE: PRT
<213> ORGANISM: Artificial Sequence
<220> FEATURE:
<223> OTHER INFORMATION: Synthetic Sequence - protein degradation tag

<400> SEQUENCE: 196

Ala Asn Asp Glu Asn Tyr Gly Ala Gln Leu Ala Ala
1 5 10

<210> SEQ ID NO 197
<211> LENGTH: 11
<212> TYPE: PRT
<213> ORGANISM: Artificial Sequence
<220> FEATURE:
<223> OTHER INFORMATION: Synthetic Sequence - protein degradation tag

<400> SEQUENCE: 197

Ala Lys Asn Thr Asn Ser Tyr Ala Leu Ala Ala
1 5 10

<210> SEQ ID NO 198
<211> LENGTH: 11
<212> TYPE: PRT
<213> ORGANISM: Artificial Sequence
<220> FEATURE:
<223> OTHER INFORMATION: Synthetic Sequence - protein degradation tag

<400> SEQUENCE: 198

Ala Lys Asn Thr Asn Ser Tyr Ala Val Ala Ala
1 5 10

<210> SEQ ID NO 199
<211> LENGTH: 11
<212> TYPE: PRT
<213> ORGANISM: Artificial Sequence
<220> FEATURE:

<223> OTHER INFORMATION: Synthetic Sequence - protein degradation tag

<400> SEQUENCE: 199

Ala Lys Asn Asn Thr Thr Tyr Ala Leu Ala Ala
1 5 10

<210> SEQ ID NO 200
<211> LENGTH: 11
<212> TYPE: PRT
<213> ORGANISM: Artificial Sequence
<220> FEATURE:
<223> OTHER INFORMATION: Synthetic Sequence - protein degradation tag

<400> SEQUENCE: 200

Ala Lys Asn Thr Asn Thr Tyr Ala Leu Ala Ala
1 5 10

<210> SEQ ID NO 201
<211> LENGTH: 11
<212> TYPE: PRT
<213> ORGANISM: Artificial Sequence
<220> FEATURE:
<223> OTHER INFORMATION: Synthetic Sequence - protein degradation tag

<400> SEQUENCE: 201

Ala Lys Asn Asn Thr Ser Tyr Ala Leu Ala Ala
1 5 10

<210> SEQ ID NO 202
<211> LENGTH: 52
<212> TYPE: DNA
<213> ORGANISM: Escherichia coli

<400> SEQUENCE: 202
gcgtggtgaa acatctgcaa ctgcgtaaca acagcttcgg cggcgtggac at 52

<210> SEQ ID NO 203
<211> LENGTH: 52
<212> TYPE: DNA
<213> ORGANISM: Escherichia coli

<400> SEQUENCE: 203
atgtccacgc cgccgaagct gttgttacgc agttgcagat gtttcaccac gc 52

<210> SEQ ID NO 204
<211> LENGTH: 16
<212> TYPE: PRT
<213> ORGANISM: Escherichia coli

<400> SEQUENCE: 204

Val Val Lys His Leu Gln Leu Arg Asn Asn Ser Phe Gly Gly Val Asp
1 5 10 15

<210> SEQ ID NO 205
<211> LENGTH: 52
<212> TYPE: DNA
<213> ORGANISM: Escherichia coli

<400> SEQUENCE: 205
gcgtggtgaa acatctgtaa ttgcgtaaca acagcttcgg cggcgtggac at 52

<210> SEQ ID NO 206
<211> LENGTH: 52
<212> TYPE: DNA
<213> ORGANISM: Escherichia coli

<400> SEQUENCE: 206
gcgtggtgaa acatctgtaa ctgcgtaaca acagcttcgg cggcgtggac at 52

<210> SEQ ID NO 207
<211> LENGTH: 5
<212> TYPE: PRT
<213> ORGANISM: Escherichia coli

<400> SEQUENCE: 207

Val Val Lys His Leu
1 5

<210> SEQ ID NO 208
<211> LENGTH: 50
<212> TYPE: DNA
<213> ORGANISM: Escherichia coli

<400> SEQUENCE: 208
cttcggttcc agccagctgt ctcagtttat ggaccagaac aacccgctgt 50

<210> SEQ ID NO 209
<211> LENGTH: 50
<212> TYPE: DNA
<213> ORGANISM: Escherichia coli

<400> SEQUENCE: 209
acagcgggtt gttctggtcc ataaactgag acagctggct ggaaccgaag 50

<210> SEQ ID NO 210
<211> LENGTH: 16
<212> TYPE: PRT
<213> ORGANISM: Escherichia coli

<400> SEQUENCE: 210

Phe Gly Ser Ser Gln Leu Ser Gln Phe Met Asp Gln Asn Asn Pro Leu
1 5 10 15

<210> SEQ ID NO 211
<211> LENGTH: 50
<212> TYPE: DNA
<213> ORGANISM: Escherichia coli

<400> SEQUENCE: 211
cttcggttcc agccagctgt ctcagtttat gaaccagaac aacccgctgt 50

<210> SEQ ID NO 212
<211> LENGTH: 16
<212> TYPE: PRT
<213> ORGANISM: Escherichia coli

<400> SEQUENCE: 212

Phe Gly Ser Ser Gln Leu Ser Gln Phe Met Asn Gln Asn Asn Pro Leu
1 5 10 15

<210> SEQ ID NO 213
<211> LENGTH: 50
<212> TYPE: DNA
<213> ORGANISM: Escherichia coli

<400> SEQUENCE: 213
cttcggttcc agccagctgt ctcagtttat aaaccagaac aacccgctgt 50

<210> SEQ ID NO 214
<211> LENGTH: 16
<212> TYPE: PRT
<213> ORGANISM: Escherichia coli

<400> SEQUENCE: 214

Phe Gly Ser Ser Gln Leu Ser Gln Phe Ile Asn Gln Asn Asn Pro Leu
1 5 10 15

<210> SEQ ID NO 215
<211> LENGTH: 51
<212> TYPE: DNA
<213> ORGANISM: Escherichia coli

<400> SEQUENCE: 215
acattaagtt caccgtcgcc agcatcaccg atatagatat agcggaaagc t 51

<210> SEQ ID NO 216
<211> LENGTH: 51
<212> TYPE: DNA
<213> ORGANISM: Escherichia coli

<400> SEQUENCE: 216
gtgaaaggca aaaaaacggc ctcccgatag ggaagccgta gcaaagtgcg c 51

<210> SEQ ID NO 217
<211> LENGTH: 51
<212> TYPE: DNA
<213> ORGANISM: Escherichia coli

<400> SEQUENCE: 217
ggtggaccga ttggtggcat gatttcagat aagatcctga aatcgccaag t 51

<210> SEQ ID NO 218
<211> LENGTH: 30
<212> TYPE: DNA
<213> ORGANISM: Escherichia coli

<400> SEQUENCE: 218
ctatcaatgg gctaactacg ttcgtggcgt 30

<210> SEQ ID NO 219
<211> LENGTH: 30
<212> TYPE: DNA
<213> ORGANISM: Escherichia coli

<400> SEQUENCE: 219
ctatcaatgg gctaactacg ttcgtggcgt 30

<210> SEQ ID NO 220
<211> LENGTH: 32
<212> TYPE: DNA
<213> ORGANISM: Escherichia coli

<400> SEQUENCE: 220
attgcagcag ctttatcatc tgccgctgga cg 32

<210> SEQ ID NO 221
<211> LENGTH: 32
<212> TYPE: DNA
<213> ORGANISM: Escherichia coli

<400> SEQUENCE: 221
attgcagcag ctttatcatc tgccgctgga cg 32

<210> SEQ ID NO 222
<211> LENGTH: 30
<212> TYPE: DNA
<213> ORGANISM: Escherichia coli

<400> SEQUENCE: 222
tctgcaactg cgtaacaaca gcttcggcgg 30

<210> SEQ ID NO 223
<211> LENGTH: 30
<212> TYPE: DNA
<213> ORGANISM: Escherichia coli

<400> SEQUENCE: 223
tctgcaactg cgtaacaaca gcttcggcgg 30

<210> SEQ ID NO 224
<211> LENGTH: 30
<212> TYPE: DNA
<213> ORGANISM: Escherichia coli

<400> SEQUENCE: 224
aaaccagttt gtaggctgta actgcgggat 30

<210> SEQ ID NO 225
<211> LENGTH: 30
<212> TYPE: DNA
<213> ORGANISM: Escherichia coli

<400> SEQUENCE: 225
aaaccagttt gtaggctgta actgcgggat 30

<210> SEQ ID NO 226
<211> LENGTH: 20
<212> TYPE: DNA
<213> ORGANISM: Escherichia coli

<400> SEQUENCE: 226
tctctgtttg ccaacgcatt 20

<210> SEQ ID NO 227
<211> LENGTH: 20
<212> TYPE: DNA
<213> ORGANISM: Escherichia coli

<400> SEQUENCE: 227
ccctgccact cacaccattc 20

<210> SEQ ID NO 228
<211> LENGTH: 20
<212> TYPE: DNA
<213> ORGANISM: Escherichia coli

<400> SEQUENCE: 228
actcacacca ttcaggcgcc 20

<210> SEQ ID NO 229
<211> LENGTH: 20
<212> TYPE: DNA
<213> ORGANISM: Escherichia coli

<400> SEQUENCE: 229
cctggccgcg tgaatttgat 20

<210> SEQ ID NO 230
<211> LENGTH: 20
<212> TYPE: DNA
<213> ORGANISM: Escherichia coli

<400> SEQUENCE: 230
ctgccatcac gcgaacttta 20

<210> SEQ ID NO 231
<211> LENGTH: 20
<212> TYPE: DNA
<213> ORGANISM: Escherichia coli

<400> SEQUENCE: 231
tgcgacaatg ggcgcatcga 20

<210> SEQ ID NO 232
<211> LENGTH: 20
<212> TYPE: DNA
<213> ORGANISM: Escherichia coli

<400> SEQUENCE: 232
tcgcacatga aaactatcaa 20

<210> SEQ ID NO 233
<211> LENGTH: 20
<212> TYPE: DNA
<213> ORGANISM: Escherichia coli

<400> SEQUENCE: 233
caatgggcta actacgttcg 20

<210> SEQ ID NO 234
<211> LENGTH: 21
<212> TYPE: DNA
<213> ORGANISM: Escherichia coli

<400> SEQUENCE: 234
tcaatgggct aactacgttc g 21

<210> SEQ ID NO 235
<211> LENGTH: 20
<212> TYPE: DNA
<213> ORGANISM: Escherichia coli

<400> SEQUENCE: 235
caactgcgta acaacagctt 20

<210> SEQ ID NO 236
<211> LENGTH: 21
<212> TYPE: DNA
<213> ORGANISM: Escherichia coli

<400> SEQUENCE: 236
gcaactgcgt aacaacagct t 21

<210> SEQ ID NO 237
<211> LENGTH: 20
<212> TYPE: DNA
<213> ORGANISM: Escherichia coli

<400> SEQUENCE: 237
gaccgcgact tccagtgaag 20

<210> SEQ ID NO 238
<211> LENGTH: 20
<212> TYPE: DNA
<213> ORGANISM: Escherichia coli

<400> SEQUENCE: 238
gcagctttat catctgccgc 20

<210> SEQ ID NO 239
<211> LENGTH: 23
<212> TYPE: DNA
<213> ORGANISM: Escherichia coli

<400> SEQUENCE: 239
gcagcagctt tatcatctgc cgc 23

<210> SEQ ID NO 240
<211> LENGTH: 20
<212> TYPE: DNA
<213> ORGANISM: Escherichia coli

<400> SEQUENCE: 240
acaaatcgcg cttaacggtc 20

<210> SEQ ID NO 241
<211> LENGTH: 20
<212> TYPE: DNA
<213> ORGANISM: Escherichia coli

<400> SEQUENCE: 241
cagtttgtag gctgtaactg 20

<210> SEQ ID NO 242
<211> LENGTH: 21
<212> TYPE: DNA
<213> ORGANISM: Escherichia coli

<400> SEQUENCE: 242
ccagtttgta ggctgtaact g 21

<210> SEQ ID NO 243
<211> LENGTH: 20
<212> TYPE: DNA
<213> ORGANISM: Escherichia coli

<400> SEQUENCE: 243
gatcagctaa tttccgcgct 20

<210> SEQ ID NO 244
<211> LENGTH: 35
<212> TYPE: DNA
<213> ORGANISM: Escherichia coli

<400> SEQUENCE: 244
gaaacaggcc ccccccatcg agcagaaaac ggtgg 35

<210> SEQ ID NO 245
<211> LENGTH: 35
<212> TYPE: DNA
<213> ORGANISM: Escherichia coli

<400> SEQUENCE: 245
acaggccccc cccatcgagc agaaaacggt ggtgg 35

<210> SEQ ID NO 246
<211> LENGTH: 35
<212> TYPE: DNA
<213> ORGANISM: Escherichia coli

<400> SEQUENCE: 246
ggcccccccc atcgagcaga aaacggtggt ggatg 35

<210> SEQ ID NO 247
<211> LENGTH: 34
<212> TYPE: DNA
<213> ORGANISM: Escherichia coli

<400> SEQUENCE: 247
caaccgccca acgcgttggg ccggggggga agcg 34

<210> SEQ ID NO 248
<211> LENGTH: 34
<212> TYPE: DNA
<213> ORGANISM: Escherichia coli

<400> SEQUENCE: 248
cgcttccccc ccggcccaac gcgttgggcg gttg 34

<210> SEQ ID NO 249
<211> LENGTH: 34
<212> TYPE: DNA
<213> ORGANISM: Escherichia coli

<400> SEQUENCE: 249
ggtccacgcg cgttcgaagt gggggggag gttc 34

<210> SEQ ID NO 250
<211> LENGTH: 34
<212> TYPE: DNA
<213> ORGANISM: Escherichia coli

<400> SEQUENCE: 250
gaacctcccc ccccacttcg aacgcgcgtg gacc 34

<210> SEQ ID NO 251
<211> LENGTH: 29
<212> TYPE: DNA
<213> ORGANISM: Escherichia coli

<400> SEQUENCE: 251
cttccgcttc actggaagtc gcggtcgga 29

<210> SEQ ID NO 252
<211> LENGTH: 29
<212> TYPE: DNA
<213> ORGANISM: Escherichia coli

<400> SEQUENCE: 252
tccgaccgcg acttccagtg aagcggaag 29

<210> SEQ ID NO 253
<211> LENGTH: 29
<212> TYPE: DNA
<213> ORGANISM: Escherichia coli

<400> SEQUENCE: 253
cttccgcttc actggaagtc acaatcgga 29

<210> SEQ ID NO 254
<211> LENGTH: 29
<212> TYPE: DNA
<213> ORGANISM: Escherichia coli

<400> SEQUENCE: 254
gcagcagctt tatcatctgc cgctggacg 29

<210> SEQ ID NO 255
<211> LENGTH: 29
<212> TYPE: DNA
<213> ORGANISM: Escherichia coli

<400> SEQUENCE: 255
cgtccagcgg cagatgataa agctgctgc 29

<210> SEQ ID NO 256
<211> LENGTH: 29
<212> TYPE: DNA
<213> ORGANISM: Escherichia coli

<400> SEQUENCE: 256
gcagtagttt tatcatctgc cgctggacg 29

<210> SEQ ID NO 257
<211> LENGTH: 30
<212> TYPE: DNA
<213> ORGANISM: Escherichia coli

<400> SEQUENCE: 257
aaaccagttt gtaggctgta actgcgggat 30

<210> SEQ ID NO 258
<211> LENGTH: 30
<212> TYPE: DNA
<213> ORGANISM: Escherichia coli

<400> SEQUENCE: 258
atcccgcagt tacagcctac aaactggttt 30

<210> SEQ ID NO 259
<211> LENGTH: 30
<212> TYPE: DNA
<213> ORGANISM: Escherichia coli

<400> SEQUENCE: 259
aaattagttt gtaggctgta actgcgggat 30

<210> SEQ ID NO 260
<211> LENGTH: 68
<212> TYPE: DNA
<213> ORGANISM: Escherichia coli

<400> SEQUENCE: 260
ttcttccgct tcactggaag tcgcggtcgg aaccgtattg cagcagcttt atcatctgcc 60
gctggacg 68

<210> SEQ ID NO 261

<211> LENGTH: 68
<212> TYPE: DNA
<213> ORGANISM: Escherichia coli

<400> SEQUENCE: 261
cgtccagcgg cagatgataa agctgctgca atacggttcc gaccgcgact tccagtgaag 60
cggaagaa 68

<210> SEQ ID NO 262
<211> LENGTH: 31
<212> TYPE: DNA
<213> ORGANISM: Escherichia coli

<400> SEQUENCE: 262
gaaaaccagt ttgtaggctg taactgcggg a 31

<210> SEQ ID NO 263
<211> LENGTH: 31
<212> TYPE: DNA
<213> ORGANISM: Escherichia coli

<400> SEQUENCE: 263
tcccgcagtt acagcctaca aactggtttt c 31

<210> SEQ ID NO 264
<211> LENGTH: 68
<212> TYPE: DNA
<213> ORGANISM: Escherichia coli

<400> SEQUENCE: 264
ttcttccgct tcactggaag tcacaatcgg aaccgtattg cagtagcttt atcatctgcc 60
gctggacg 68

<210> SEQ ID NO 265
<211> LENGTH: 68
<212> TYPE: DNA
<213> ORGANISM: Escherichia coli

<400> SEQUENCE: 265
ttcttccgct tcactgaaag tcacaatcgg aaccgtattg cagtagtttt atcatctgcc 60
gctggacg 68

<210> SEQ ID NO 266
<211> LENGTH: 68
<212> TYPE: DNA
<213> ORGANISM: Escherichia coli

<400> SEQUENCE: 266
ttcttccgct tcactggaag tcgcaatcgg aaccgtattg cagtagtttt atcatctgcc 60
gctggacg 68

<210> SEQ ID NO 267
<211> LENGTH: 68
<212> TYPE: DNA
<213> ORGANISM: Escherichia coli

<400> SEQUENCE: 267
ttcttccgct tcactggaag tcacaatcgg aaccgtattg cagtagtttt atcatctgcc 60
gctggacg 68

<210> SEQ ID NO 268
<211> LENGTH: 68
<212> TYPE: DNA
<213> ORGANISM: Escherichia coli

<400> SEQUENCE: 268
ttcttccgct tcactggaag tcacaatcgg aaccgtattg cagcagcttt atcatctgcc 60
gctggacg 68

<210> SEQ ID NO 269
<211> LENGTH: 31
<212> TYPE: DNA
<213> ORGANISM: Escherichia coli

<400> SEQUENCE: 269
gaaaactagt ttgtaggctg taactgcggg a 31

<210> SEQ ID NO 270
<211> LENGTH: 31
<212> TYPE: DNA
<213> ORGANISM: Escherichia coli

<400> SEQUENCE: 270
gaaaattagt ttgtaggctg taactgcggg a 31

<210> SEQ ID NO 271
<211> LENGTH: 50
<212> TYPE: DNA
<213> ORGANISM: Escherichia coli

<400> SEQUENCE: 271
caacgcattt ggctaccctg ccactcacac cattcaggcg cctggccgcg 50

<210> SEQ ID NO 272
<211> LENGTH: 50
<212> TYPE: DNA
<213> ORGANISM: Escherichia coli

<400> SEQUENCE: 272
cgcggccagg cgcctgaatg gtgtgagtgg cagggtagcc aaatgcgttg 50

<210> SEQ ID NO 273
<211> LENGTH: 50
<212> TYPE: DNA
<213> ORGANISM: Escherichia coli

<400> SEQUENCE: 273
caacgcattt ggctattttg ttactcacac cattcaggcg cctggccgcg 50

<210> SEQ ID NO 274
<211> LENGTH: 50
<212> TYPE: DNA
<213> ORGANISM: Escherichia coli

<400> SEQUENCE: 274
caacgcattt ggctactttg tcactcacac cattcaggcg cctggccgcg 50

<210> SEQ ID NO 275
<211> LENGTH: 50
<212> TYPE: DNA
<213> ORGANISM: Escherichia coli

<400> SEQUENCE: 275
caacgcattt ggctactttg ccactcacac cattcaggcg cctggccgcg 50

<210> SEQ ID NO 276
<211> LENGTH: 50
<212> TYPE: DNA
<213> ORGANISM: Escherichia coli

<400> SEQUENCE: 276
caacgcattt ggctattttg tcactcacac cattcaggcg cctggccgcg 50

<210> SEQ ID NO 277
<211> LENGTH: 50
<212> TYPE: DNA
<213> ORGANISM: Escherichia coli

<400> SEQUENCE: 277
ggtgctttgt tacctgaagt tgcgaaagcg tggggtatgg cgacggtgcc 50

<210> SEQ ID NO 278
<211> LENGTH: 50
<212> TYPE: DNA
<213> ORGANISM: Escherichia coli

<400> SEQUENCE: 278
ggcaccgtcg ccatacccca cgctttcgca acttcaggta acaaagcacc 50

<210> SEQ ID NO 279
<211> LENGTH: 50
<212> TYPE: DNA
<213> ORGANISM: Escherichia coli

<400> SEQUENCE: 279
ggtgctttgt tacctgaagt tgcgaaagca taaagtatgg cgacggtgcc 50

<210> SEQ ID NO 280
<211> LENGTH: 50
<212> TYPE: DNA
<213> ORGANISM: Escherichia coli

<400> SEQUENCE: 280
ggtgctttgt tacctgaagt tgcgaaagcg taaggtatgg cgacggtgcc 50

<210> SEQ ID NO 281
<211> LENGTH: 50
<212> TYPE: DNA
<213> ORGANISM: Escherichia coli

<400> SEQUENCE: 281
ggtgctttgt tacctgaagt tgcgaaagcg taaaatatgg cgacggtgcc 50

<210> SEQ ID NO 282
<211> LENGTH: 50
<212> TYPE: DNA
<213> ORGANISM: Escherichia coli

<400> SEQUENCE: 282
ggtgctttgt tacctgaagt tgcgaaagcg taaagtatgg cgacggtgcc 50

<210> SEQ ID NO 283
<211> LENGTH: 50
<212> TYPE: DNA
<213> ORGANISM: Escherichia coli

<400> SEQUENCE: 283
ggtgctttgt tacctgaagt tgcgaaagca taaaatatgg cgacggtgcc 50

<210> SEQ ID NO 284
<211> LENGTH: 50
<212> TYPE: DNA
<213> ORGANISM: Escherichia coli

<400> SEQUENCE: 284
aaatccgtcc agccagccga tggccgagct gtggatgggc gcacatccga 50

<210> SEQ ID NO 285
<211> LENGTH: 50
<212> TYPE: DNA
<213> ORGANISM: Escherichia coli

<400> SEQUENCE: 285
tcggatgtgc gcccatccac agctcggcca tcggctggct ggacggattt 50

<210> SEQ ID NO 286
<211> LENGTH: 50
<212> TYPE: DNA
<213> ORGANISM: Escherichia coli

<400> SEQUENCE: 286
aaatccgtcc agccagccga tggccgaact ataaatgggc gcacatccga 50

<210> SEQ ID NO 287
<211> LENGTH: 50
<212> TYPE: DNA
<213> ORGANISM: Escherichia coli

<400> SEQUENCE: 287
aaatccgtcc agccagccga tggccaaact ataaatgggc gcacatccga 50

<210> SEQ ID NO 288
<211> LENGTH: 50
<212> TYPE: DNA
<213> ORGANISM: Escherichia coli

<400> SEQUENCE: 288
aaatccgtcc agccagccga tggccgagct ataaatgggc gcacatccga 50

<210> SEQ ID NO 289
<211> LENGTH: 50
<212> TYPE: DNA
<213> ORGANISM: Escherichia coli

<400> SEQUENCE: 289
tgatccggcg aagctgcaag aatccagccc gctgccggtt ctcggcgctg 50

<210> SEQ ID NO 290
<211> LENGTH: 50
<212> TYPE: DNA
<213> ORGANISM: Escherichia coli

<400> SEQUENCE: 290
cagcgccgag aaccggcagc gggctggatt cttgcagctt cgccggatca 50

<210> SEQ ID NO 291
<211> LENGTH: 50
<212> TYPE: DNA
<213> ORGANISM: Escherichia coli

<400> SEQUENCE: 291
tgatccggcg aagctgtaag aatccagccc gctgccggtt ctcggcgctg 50

<210> SEQ ID NO 292
<211> LENGTH: 50
<212> TYPE: DNA
<213> ORGANISM: Escherichia coli

<400> SEQUENCE: 292
gcggctgata tcgttctgca ggctgctatc gctgccggtg ctccgaaaga 50

<210> SEQ ID NO 293
<211> LENGTH: 50
<212> TYPE: DNA
<213> ORGANISM: Escherichia coli

<400> SEQUENCE: 293
tctttcggag caccggcagc gatagcagcc tgcagaacga tatcagccgc 50

<210> SEQ ID NO 294
<211> LENGTH: 50
<212> TYPE: DNA
<213> ORGANISM: Escherichia coli

<400> SEQUENCE: 294
gcggctgata tcgttttgta ggctgctatc gctgccggtg ctccgaaaga 50

<210> SEQ ID NO 295
<211> LENGTH: 50
<212> TYPE: DNA
<213> ORGANISM: Escherichia coli

<400> SEQUENCE: 295
gcggctgata tcgttttgta ggctgctatc gctgccggtg ctccgaaaga 50

<210> SEQ ID NO 296
<211> LENGTH: 50
<212> TYPE: DNA
<213> ORGANISM: Escherichia coli

<400> SEQUENCE: 296
gcggctgata tcgttttgta ggctgttatc gctgccggtg ctccgaaaga 50

<210> SEQ ID NO 297
<211> LENGTH: 50
<212> TYPE: DNA
<213> ORGANISM: Escherichia coli

<400> SEQUENCE: 297
gcggctgata ttgttttgta ggctgctatc gctgccggtg ctccgaaaga 50

<210> SEQ ID NO 298
<211> LENGTH: 51
<212> TYPE: DNA
<213> ORGANISM: Escherichia coli

<400> SEQUENCE: 298
cgcggtactg aaaactcagg gtgctgcggc attcgaaggt gcggttatcg c 51

<210> SEQ ID NO 299
<211> LENGTH: 51
<212> TYPE: DNA
<213> ORGANISM: Escherichia coli

<400> SEQUENCE: 299
gcgataaccg caccttcgaa tgccgcagca ccctgagttt tcagtaccgc g 51

<210> SEQ ID NO 300
<211> LENGTH: 51
<212> TYPE: DNA
<213> ORGANISM: Escherichia coli

<400> SEQUENCE: 300
cgcggtactg aaaacttagg gtgctgcggc attcgaaggt gcggttatcg c 51

<210> SEQ ID NO 301
<211> LENGTH: 90
<212> TYPE: DNA
<213> ORGANISM: Escherichia coli

<400> SEQUENCE: 301
cgacgctggg gcgtcttatg agcctgctgt caccctttga cgtggtgata tggatgacgg 60
atggctggcc gctgtatgaa tcccgcctga 90

<210> SEQ ID NO 302
<211> LENGTH: 30
<212> TYPE: PRT
<213> ORGANISM: Escherichia coli

<400> SEQUENCE: 302

Ala Thr Leu Gly Arg Leu Met Ser Leu Leu Ser Pro Phe Asp Val Val
1 5 10 15

Ile Trp Met Thr Asp Gly Trp Pro Leu Tyr Glu Ser Arg Leu
20 25 30

<210> SEQ ID NO 303
<211> LENGTH: 90
<212> TYPE: DNA
<213> ORGANISM: Escherichia coli

<400> SEQUENCE: 303
cgacgctggg gcgtcttatg agcctgctgt caccctttga cgtggtgata taaataacgg 60
atggctggcc gctgtatgaa tcccgcctga 90

<210> SEQ ID NO 304
<211> LENGTH: 90
<212> TYPE: DNA
<213> ORGANISM: Escherichia coli

<400> SEQUENCE: 304
cgacgctggg gcgtcttatg agcctgctgt caccctttga cgtggtaata taaataacgg 60
atggctggcc gctgtatgaa tcccgcctga 90

<210> SEQ ID NO 305
<211> LENGTH: 90
<212> TYPE: DNA
<213> ORGANISM: Escherichia coli

<400> SEQUENCE: 305
cgacgctggg gcgtcttatg agcctgctgt caccctttga cgtagtgata taaataacgg 60
atggctggcc gctgtatgaa tcccgcctga 90

<210> SEQ ID NO 306

<211> LENGTH: 90
<212> TYPE: DNA
<213> ORGANISM: Escherichia coli

<400> SEQUENCE: 306
ggagcggtgg aacgccgctt cggcaacgat cttccgtcgt ctccagtgga gtggctgacg 60
gataatggtt catgctaccg ggctaatgaa 90

<210> SEQ ID NO 307
<211> LENGTH: 29
<212> TYPE: PRT
<213> ORGANISM: Escherichia coli

<400> SEQUENCE: 307

Gly Ala Val Glu Arg Arg Phe Gly Asn Asp Leu Pro Ser Ser Pro Val
1 5 10 15

Glu Trp Leu Thr Asp Asn Gly Ser Cys Tyr Arg Ala Asn
20 25

<210> SEQ ID NO 308
<211> LENGTH: 90
<212> TYPE: DNA
<213> ORGANISM: Escherichia coli

<400> SEQUENCE: 308
ggagcggtgg aacgccgctt cggcaacgat cttccgtcgt ctccagtgaa ataactgacg 60
gataatggtt catgctaccg ggctaatgaa 90

<210> SEQ ID NO 309
<211> LENGTH: 90
<212> TYPE: DNA
<213> ORGANISM: Escherichia coli

<400> SEQUENCE: 309
ggagcggtgg aacgccgctt cggcaacgat cttccgtcgt ctccagtgga ataactaacg 60
gataatggtt catgctaccg ggctaatgaa 90

<210> SEQ ID NO 310
<211> LENGTH: 90
<212> TYPE: DNA
<213> ORGANISM: Escherichia coli

<400> SEQUENCE: 310
ggagcggtgg aacgccgctt cggcaacgat cttccgtcgt ctccagtgga ataactgacg 60
gataatggtt catgctaccg ggctaatgaa 90

<210> SEQ ID NO 311
<211> LENGTH: 90
<212> TYPE: DNA
<213> ORGANISM: Escherichia coli

<400> SEQUENCE: 311
ggagcggtgg aacgccgctt cggcaacgat cttccgtcgt ctccagtaaa ataactgacg 60
gataatggtt catgctaccg ggctaatgaa 90

<210> SEQ ID NO 312
<211> LENGTH: 90
<212> TYPE: DNA
<213> ORGANISM: Escherichia coli

<400> SEQUENCE: 312
ggagcggtgg aacgccgctt cggcaacgat cttccgtcgt ctccagtgaa ataactaacg 60
gataatggtt catgctaccg ggctaatgaa 90

<210> SEQ ID NO 313
<211> LENGTH: 90
<212> TYPE: DNA
<213> ORGANISM: Escherichia coli

<400> SEQUENCE: 313
catcaaagca atgtgccgcg tgctccgggt ggcccgcagc ggctggtata cgtggtgtca 60
gcggcggaca aggataagca cgcgtcagca 90

<210> SEQ ID NO 314
<211> LENGTH: 30
<212> TYPE: PRT
<213> ORGANISM: Escherichia coli

<400> SEQUENCE: 314

Ile Lys Ala Met Cys Arg Val Leu Arg Val Ala Arg Ser Gly Trp Tyr
1 5 10 15

Thr Trp Cys Gly Arg Arg Thr Arg Ile Ser Thr Arg Gln Ala
20 25 30

<210> SEQ ID NO 315
<211> LENGTH: 90
<212> TYPE: DNA
<213> ORGANISM: Escherichia coli

<400> SEQUENCE: 315
catcaaagca atgtgccgcg tgctccgggt ggcccgcagc ggctggtata cataatgtca 60
gcggcggaca aggataagca cgcgtcagca 90

<210> SEQ ID NO 316
<211> LENGTH: 90
<212> TYPE: DNA
<213> ORGANISM: Escherichia coli

<400> SEQUENCE: 316
catcaaagca atgtgccgcg tgctccgggt ggcccgcagc ggctggtata cataatgtca 60
gcggcggaca aggataagca cgcgtcagca 90

<210> SEQ ID NO 317
<211> LENGTH: 90
<212> TYPE: DNA
<213> ORGANISM: Escherichia coli

<400> SEQUENCE: 317
catcaaagca atgtgccgcg tgctccgggt ggcccgcagc ggctggtata catagtgtca 60
gcggcggaca aggataagca cgcgtcagca 90

<210> SEQ ID NO 318
<211> LENGTH: 90
<212> TYPE: DNA
<213> ORGANISM: Escherichia coli

<400> SEQUENCE: 318
aagagcagca acgcgatccg gagatgcatc agaccaagaa aggcaatcag tggcactttg 60
gcatgaaggc ccacattggt gtcgatgcca 90

<210> SEQ ID NO 319
<211> LENGTH: 29
<212> TYPE: PRT
<213> ORGANISM: Escherichia coli

<400> SEQUENCE: 319

Lys Glu Gln Gln Arg Asp Pro Glu Met His Gln Thr Lys Lys Gly Asx
1               5                   10                  15

Gln Trp His Phe Gly Met Lys Ala His Ile Gly Val Asp
            20                  25

<210> SEQ ID NO 320
<211> LENGTH: 90
<212> TYPE: DNA
<213> ORGANISM: Escherichia coli

<400> SEQUENCE: 320
aagagcagca acgcgatccg gagatgcatc agaccaagaa aggcaatcag taacactttg     60
gcatgaaggc ccacattggt gtcgatgcca                                      90

<210> SEQ ID NO 321
<211> LENGTH: 90
<212> TYPE: DNA
<213> ORGANISM: Escherichia coli

<400> SEQUENCE: 321
aagagcagca acgcgatccg gagatgcatc agaccaagaa aggcaatcaa taacactttg     60
gcatgaaggc ccacattggt gtcgatgcca                                      90

<210> SEQ ID NO 322
<211> LENGTH: 90
<212> TYPE: DNA
<213> ORGANISM: Escherichia coli

<400> SEQUENCE: 322
aagagcagca acgcgatccg gagatgcatc agaccaagaa aggcaatcag tgacactttg     60
gcatgaaggc ccacattggt gtcgatgcca                                      90

<210> SEQ ID NO 323
<211> LENGTH: 90
<212> TYPE: DNA
<213> ORGANISM: Escherichia coli

<400> SEQUENCE: 323
aagagcagca acgcgatccg gaaatgcatc agaccaagaa aggcaatcaa taacactttg     60
gcatgaaggc ccacattggt gtcgatgcca                                      90

<210> SEQ ID NO 324
<211> LENGTH: 5
<212> TYPE: PRT
<213> ORGANISM: Artificial Sequence
<220> FEATURE:
<223> OTHER INFORMATION: Synthetic Sequence - protein degradation tag

<400> SEQUENCE: 324

Tyr Ala Ala Ser Val
1               5

<210> SEQ ID NO 325
<211> LENGTH: 5
<212> TYPE: PRT

```
<213> ORGANISM: Artificial Sequence
<220> FEATURE:
<223> OTHER INFORMATION: Synthetic Sequence - protein degradation tag

<400> SEQUENCE: 325

Tyr Ala Leu Ala Ala
1               5


<210> SEQ ID NO 326
<211> LENGTH: 3684
<212> TYPE: DNA
<213> ORGANISM: Lachnospiraceae bacterium
<220> FEATURE:
<221> NAME/KEY: CDS
<222> LOCATION: (1)..(3684)

<400> SEQUENCE: 326

atg agc aag ctt gag aag ttt aca aac tgc tac tcc ctg tct aag acc       48
Met Ser Lys Leu Glu Lys Phe Thr Asn Cys Tyr Ser Leu Ser Lys Thr
1               5                   10                  15

ctg agg ttc aag gcc atc cct gtg ggc aag acc cag gag aac atc gac       96
Leu Arg Phe Lys Ala Ile Pro Val Gly Lys Thr Gln Glu Asn Ile Asp
            20                  25                  30

aat aag cgg ctg ctg gtg gag gac gag aag aga gcc gag gat tat aag      144
Asn Lys Arg Leu Leu Val Glu Asp Glu Lys Arg Ala Glu Asp Tyr Lys
        35                  40                  45

ggc gtg aag aag ctg ctg gat cgc tac tat ctg tct ttt atc aac gac      192
Gly Val Lys Lys Leu Leu Asp Arg Tyr Tyr Leu Ser Phe Ile Asn Asp
    50                  55                  60

gtg ctg cac agc atc aag ctg aag aat ctg aac aat tac atc agc ctg      240
Val Leu His Ser Ile Lys Leu Lys Asn Leu Asn Asn Tyr Ile Ser Leu
65                  70                  75                  80

ttc cgg aag aaa acc aga acc gag aag gag aat aag gag ctg gag aac      288
Phe Arg Lys Lys Thr Arg Thr Glu Lys Glu Asn Lys Glu Leu Glu Asn
                85                  90                  95

ctg gag atc aat ctg cgg aag gag atc gcc aag gcc ttc aag ggc aac      336
Leu Glu Ile Asn Leu Arg Lys Glu Ile Ala Lys Ala Phe Lys Gly Asn
            100                 105                 110

gag ggc tac aag tcc ctg ttt aag aag gat atc atc gag aca atc ctg      384
Glu Gly Tyr Lys Ser Leu Phe Lys Lys Asp Ile Ile Glu Thr Ile Leu
        115                 120                 125

cca gag ttc ctg gac gat aag gac gag atc gcc ctg gtg aac agc ttc      432
Pro Glu Phe Leu Asp Asp Lys Asp Glu Ile Ala Leu Val Asn Ser Phe
    130                 135                 140

aat ggc ttt acc aca gcc ttc acc ggc ttc ttt gat aac aga gag aat      480
Asn Gly Phe Thr Thr Ala Phe Thr Gly Phe Phe Asp Asn Arg Glu Asn
145                 150                 155                 160

atg ttt tcc gag gag gcc aag agc aca tcc atc gcc ttc agg tgt atc      528
Met Phe Ser Glu Glu Ala Lys Ser Thr Ser Ile Ala Phe Arg Cys Ile
                165                 170                 175

aac gag aat ctg acc cgc tac atc tct aat atg gac atc ttc gag aag      576
Asn Glu Asn Leu Thr Arg Tyr Ile Ser Asn Met Asp Ile Phe Glu Lys
            180                 185                 190

gtg gac gcc atc ttt gat aag cac gag gtg cag gag atc aag gag aag      624
Val Asp Ala Ile Phe Asp Lys His Glu Val Gln Glu Ile Lys Glu Lys
        195                 200                 205

atc ctg aac agc gac tat gat gtg gag gat ttc ttt gag ggc gag ttc      672
Ile Leu Asn Ser Asp Tyr Asp Val Glu Asp Phe Phe Glu Gly Glu Phe
    210                 215                 220

ttt aac ttt gtg ctg aca cag gag ggc atc gac gtg tat aac gcc atc      720
Phe Asn Phe Val Leu Thr Gln Glu Gly Ile Asp Val Tyr Asn Ala Ile
225                 230                 235                 240
```

```
atc ggc ggc ttc gtg acc gag agc ggc gag aag atc aag ggc ctg aac      768
Ile Gly Gly Phe Val Thr Glu Ser Gly Glu Lys Ile Lys Gly Leu Asn
                245                 250                 255

gag tac atc aac ctg tat aat cag aaa acc aag cag aag ctg cct aag      816
Glu Tyr Ile Asn Leu Tyr Asn Gln Lys Thr Lys Gln Lys Leu Pro Lys
            260                 265                 270

ttt aag cca ctg tat aag cag gtg ctg agc gat cgg gag tct ctg agc      864
Phe Lys Pro Leu Tyr Lys Gln Val Leu Ser Asp Arg Glu Ser Leu Ser
        275                 280                 285

ttc tac ggc gag ggc tat aca tcc gat gag gag gtg ctg gag gtg ttt      912
Phe Tyr Gly Glu Gly Tyr Thr Ser Asp Glu Glu Val Leu Glu Val Phe
    290                 295                 300

aga aac acc ctg aac aag aac agc gag atc ttc agc tcc atc aag aag      960
Arg Asn Thr Leu Asn Lys Asn Ser Glu Ile Phe Ser Ser Ile Lys Lys
305                 310                 315                 320

ctg gag aag ctg ttc aag aat ttt gac gag tac tct agc gcc ggc atc     1008
Leu Glu Lys Leu Phe Lys Asn Phe Asp Glu Tyr Ser Ser Ala Gly Ile
                325                 330                 335

ttt gtg aag aac ggc ccc gcc atc agc aca atc tcc aag gat atc ttc     1056
Phe Val Lys Asn Gly Pro Ala Ile Ser Thr Ile Ser Lys Asp Ile Phe
            340                 345                 350

ggc gag tgg aac gtg atc cgg gac aag tgg aat gcc gag tat gac gat     1104
Gly Glu Trp Asn Val Ile Arg Asp Lys Trp Asn Ala Glu Tyr Asp Asp
        355                 360                 365

atc cac ctg aag aag aag gcc gtc gtg acc gag aag tac gag gac gat     1152
Ile His Leu Lys Lys Lys Ala Val Val Thr Glu Lys Tyr Glu Asp Asp
    370                 375                 380

cgg aga aag tcc ttc aag aag atc ggc tcc ttt tct ctg gag cag ctg     1200
Arg Arg Lys Ser Phe Lys Lys Ile Gly Ser Phe Ser Leu Glu Gln Leu
385                 390                 395                 400

cag gag tac gcc gac gcc gat ctg tct gtg gtg gag aag ctg aag gag     1248
Gln Glu Tyr Ala Asp Ala Asp Leu Ser Val Val Glu Lys Leu Lys Glu
                405                 410                 415

atc atc atc cag aag gtg gat gag atc tac aag gtg tat ggc tcc tct     1296
Ile Ile Ile Gln Lys Val Asp Glu Ile Tyr Lys Val Tyr Gly Ser Ser
            420                 425                 430

gag aag ctg ttc gac gcc gat ttt gtg ctg gag aag tct ctg aag aag     1344
Glu Lys Leu Phe Asp Ala Asp Phe Val Leu Glu Lys Ser Leu Lys Lys
        435                 440                 445

aac gac gcc gtg gtg gcc att atg aag gac ctg ctg gat tct gtg aag     1392
Asn Asp Ala Val Val Ala Ile Met Lys Asp Leu Leu Asp Ser Val Lys
    450                 455                 460

tct ttc gag aat tac atc aag gcc ttc ttt ggc gag ggc aag gag aca     1440
Ser Phe Glu Asn Tyr Ile Lys Ala Phe Phe Gly Glu Gly Lys Glu Thr
465                 470                 475                 480

aac agg gac gag tcc ttc tat ggc gat ttt gtg ctg gcc tac gac atc     1488
Asn Arg Asp Glu Ser Phe Tyr Gly Asp Phe Val Leu Ala Tyr Asp Ile
                485                 490                 495

ctg ctg aag gtg gac cac atc tac gat gcc atc cgc aat tat gtg acc     1536
Leu Leu Lys Val Asp His Ile Tyr Asp Ala Ile Arg Asn Tyr Val Thr
            500                 505                 510

cag aag ccc tac tct aag gat aag ttc aag ctg tat ttt cag aac cct     1584
Gln Lys Pro Tyr Ser Lys Asp Lys Phe Lys Leu Tyr Phe Gln Asn Pro
        515                 520                 525

cag ttc atg ggc ggc tgg gac aag gat aag gag aca gac tat cgg gcc     1632
Gln Phe Met Gly Gly Trp Asp Lys Asp Lys Glu Thr Asp Tyr Arg Ala
    530                 535                 540

acc atc ctg aga tac ggc tcc aag tac tat ctg gcc atc atg gat aag     1680
Thr Ile Leu Arg Tyr Gly Ser Lys Tyr Tyr Leu Ala Ile Met Asp Lys
```

```
545                 550                 555                 560

aag tac gcc aag tgc ctg cag aag atc gac aag gac gat gtg aac ggc      1728
Lys Tyr Ala Lys Cys Leu Gln Lys Ile Asp Lys Asp Asp Val Asn Gly
                565                 570                 575

aat tac gag aag atc aac tat aag ctg ctg ccc ggc cct aat aag atg      1776
Asn Tyr Glu Lys Ile Asn Tyr Lys Leu Leu Pro Gly Pro Asn Lys Met
            580                 585                 590

ctg cca aag gtg ttc ttt tct aag aag tgg atg gcc tac tat aac ccc      1824
Leu Pro Lys Val Phe Phe Ser Lys Lys Trp Met Ala Tyr Tyr Asn Pro
        595                 600                 605

agc gag gac atc cag aag atc tac aag aat ggt acc ttc aag aag ggc      1872
Ser Glu Asp Ile Gln Lys Ile Tyr Lys Asn Gly Thr Phe Lys Lys Gly
    610                 615                 620

gat atg ttt aac ctg aat gac tgt cac aag ctg atc gac ttc ttt aag      1920
Asp Met Phe Asn Leu Asn Asp Cys His Lys Leu Ile Asp Phe Phe Lys
625                 630                 635                 640

gat agc atc tcc cgg tat cca aag tgg tcc aat gcc tac gat ttc aac      1968
Asp Ser Ile Ser Arg Tyr Pro Lys Trp Ser Asn Ala Tyr Asp Phe Asn
                645                 650                 655

ttt tct gag aca gag aag tat aag gac atc gcc ggc ttt tac aga gag      2016
Phe Ser Glu Thr Glu Lys Tyr Lys Asp Ile Ala Gly Phe Tyr Arg Glu
            660                 665                 670

gtg gag gag cag ggc tat aag gtg agc ttc gag tct gcc agc aag aag      2064
Val Glu Glu Gln Gly Tyr Lys Val Ser Phe Glu Ser Ala Ser Lys Lys
        675                 680                 685

gag gtg gat aag ctg gtg gag gag ggc aag ctg tat atg ttc cag atc      2112
Glu Val Asp Lys Leu Val Glu Glu Gly Lys Leu Tyr Met Phe Gln Ile
    690                 695                 700

tat aac aag gac ttt tcc gat aag tct cac ggc aca ccc aat ctg cac      2160
Tyr Asn Lys Asp Phe Ser Asp Lys Ser His Gly Thr Pro Asn Leu His
705                 710                 715                 720

acc atg tac ttc aag ctg ctg ttt gac gag aac aat cac gga cag atc      2208
Thr Met Tyr Phe Lys Leu Leu Phe Asp Glu Asn Asn His Gly Gln Ile
                725                 730                 735

agg ctg agc gga gga gca gag ctg ttc atg agg cgc gct tcc ctg aag      2256
Arg Leu Ser Gly Gly Ala Glu Leu Phe Met Arg Arg Ala Ser Leu Lys
            740                 745                 750

aag gag gag ctg gtg gtg cac cca gcc aac tcc cct atc gcc aac aag      2304
Lys Glu Glu Leu Val Val His Pro Ala Asn Ser Pro Ile Ala Asn Lys
        755                 760                 765

aat cca gat aat ccc aag aaa acc aca acc ctg tcc tac gac gtg tat      2352
Asn Pro Asp Asn Pro Lys Lys Thr Thr Thr Leu Ser Tyr Asp Val Tyr
    770                 775                 780

aag gat aag agg ttt tct gag gac cag tac gag ctg cac atc cca atc      2400
Lys Asp Lys Arg Phe Ser Glu Asp Gln Tyr Glu Leu His Ile Pro Ile
785                 790                 795                 800

gcc atc aat aag tgc ccc aag aac atc ttc aag atc aat aca gag gtg      2448
Ala Ile Asn Lys Cys Pro Lys Asn Ile Phe Lys Ile Asn Thr Glu Val
                805                 810                 815

cgc gtg ctg ctg aag cac gac gat aac ccc tat gtg atc ggc atc gat      2496
Arg Val Leu Leu Lys His Asp Asp Asn Pro Tyr Val Ile Gly Ile Asp
            820                 825                 830

agg ggc gag cgc aat ctg ctg tat atc gtg gtg gtg gac ggc aag ggc      2544
Arg Gly Glu Arg Asn Leu Leu Tyr Ile Val Val Val Asp Gly Lys Gly
        835                 840                 845

aac atc gtg gag cag tat tcc ctg aac gag atc atc aac aac ttc aac      2592
Asn Ile Val Glu Gln Tyr Ser Leu Asn Glu Ile Ile Asn Asn Phe Asn
    850                 855                 860

ggc atc agg atc aag aca gat tac cac tct ctg ctg gac aag aag gag      2640
```

```
Gly Ile Arg Ile Lys Thr Asp Tyr His Ser Leu Leu Asp Lys Lys Glu
865                 870                 875                 880

aag gag agg ttc gag gcc cgc cag aac tgg acc tcc atc gag aat atc      2688
Lys Glu Arg Phe Glu Ala Arg Gln Asn Trp Thr Ser Ile Glu Asn Ile
                885                 890                 895

aag gag ctg aag gcc ggc tat atc tct cag gtg gtg cac aag atc tgc      2736
Lys Glu Leu Lys Ala Gly Tyr Ile Ser Gln Val Val His Lys Ile Cys
            900                 905                 910

gag ctg gtg gag aag tac gat gcc gtg atc gcc ctg gag gac ctg aac      2784
Glu Leu Val Glu Lys Tyr Asp Ala Val Ile Ala Leu Glu Asp Leu Asn
        915                 920                 925

tct ggc ttt aag aat agc cgc gtg aag gtg gag aag cag gtg tat cag      2832
Ser Gly Phe Lys Asn Ser Arg Val Lys Val Glu Lys Gln Val Tyr Gln
    930                 935                 940

aag ttc gag aag atg ctg atc gat aag ctg aac tac atg gtg gac aag      2880
Lys Phe Glu Lys Met Leu Ile Asp Lys Leu Asn Tyr Met Val Asp Lys
945                 950                 955                 960

aag tct aat cct tgt gca aca ggc ggc gcc ctg aag ggc tat cag atc      2928
Lys Ser Asn Pro Cys Ala Thr Gly Gly Ala Leu Lys Gly Tyr Gln Ile
                965                 970                 975

acc aat aag ttc gag agc ttt aag tcc atg tct acc cag aac ggc ttc      2976
Thr Asn Lys Phe Glu Ser Phe Lys Ser Met Ser Thr Gln Asn Gly Phe
            980                 985                 990

atc ttt tac atc cct gcc tgg ctg  aca tcc aag atc gat  cca tct acc    3024
Ile Phe Tyr Ile Pro Ala Trp Leu  Thr Ser Lys Ile Asp  Pro Ser Thr
        995                 1000                1005

ggc ttt  gtg aac ctg ctg aaa  acc aag tat acc agc  atc gcc gat      3069
Gly Phe  Val Asn Leu Leu Lys  Thr Lys Tyr Thr Ser  Ile Ala Asp
    1010                1015                1020

tcc aag  aag ttc atc agc tcc  ttt gac agg atc atg  tac gtg ccc      3114
Ser Lys  Lys Phe Ile Ser Ser  Phe Asp Arg Ile Met  Tyr Val Pro
    1025                1030                1035

gag gag  gat ctg ttc gag ttt  gcc ctg gac tat aag  aac ttc tct      3159
Glu Glu  Asp Leu Phe Glu Phe  Ala Leu Asp Tyr Lys  Asn Phe Ser
    1040                1045                1050

cgc aca  gac gcc gat tac atc  aag aag tgg aag ctg  tac tcc tac      3204
Arg Thr  Asp Ala Asp Tyr Ile  Lys Lys Trp Lys Leu  Tyr Ser Tyr
    1055                1060                1065

ggc aac  cgg atc aga atc ttc  cgg aat cct aag aag  aac aac gtg      3249
Gly Asn  Arg Ile Arg Ile Phe  Arg Asn Pro Lys Lys  Asn Asn Val
    1070                1075                1080

ttc gac  tgg gag gag gtg tgc  ctg acc agc gcc tat  aag gag ctg      3294
Phe Asp  Trp Glu Glu Val Cys  Leu Thr Ser Ala Tyr  Lys Glu Leu
    1085                1090                1095

ttc aac  aag tac ggc atc aat  tat cag cag ggc gat  atc aga gcc      3339
Phe Asn  Lys Tyr Gly Ile Asn  Tyr Gln Gln Gly Asp  Ile Arg Ala
    1100                1105                1110

ctg ctg  tgc gag cag tcc gac  aag gcc ttc tac tct  agc ttt atg      3384
Leu Leu  Cys Glu Gln Ser Asp  Lys Ala Phe Tyr Ser  Ser Phe Met
    1115                1120                1125

gcc ctg  atg agc ctg atg ctg  cag atg cgg aac agc  atc aca ggc      3429
Ala Leu  Met Ser Leu Met Leu  Gln Met Arg Asn Ser  Ile Thr Gly
    1130                1135                1140

cgc acc  gac gtg gat ttt ctg  atc agc cct gtg aag  aac tcc gac      3474
Arg Thr  Asp Val Asp Phe Leu  Ile Ser Pro Val Lys  Asn Ser Asp
    1145                1150                1155

ggc atc  ttc tac gat agc cgg  aac tat gag gcc cag  gag aat gcc      3519
Gly Ile  Phe Tyr Asp Ser Arg  Asn Tyr Glu Ala Gln  Glu Asn Ala
    1160                1165                1170
```

```
atc ctg  cca aag aac gcc gac  gcc aat ggc gcc tat  aac atc gcc      3564
Ile Leu  Pro Lys Asn Ala Asp  Ala Asn Gly Ala Tyr  Asn Ile Ala
    1175                 1180                 1185

aga aag  gtg ctg tgg gcc atc  ggc cag ttc aag aag  gcc gag gac      3609
Arg Lys  Val Leu Trp Ala Ile  Gly Gln Phe Lys Lys  Ala Glu Asp
    1190                 1195                 1200

gag aag  ctg gat aag gtg aag  atc gcc atc tct aac  aag gag tgg      3654
Glu Lys  Leu Asp Lys Val Lys  Ile Ala Ile Ser Asn  Lys Glu Trp
    1205                 1210                 1215

ctg gag  tac gcc cag acc agc  gtg aag cac                           3684
Leu Glu  Tyr Ala Gln Thr Ser  Val Lys His
    1220                 1225
```

<210> SEQ ID NO 327
<211> LENGTH: 1228
<212> TYPE: PRT
<213> ORGANISM: Lachnospiraceae bacterium

<400> SEQUENCE: 327

```
Met Ser Lys Leu Glu Lys Phe Thr Asn Cys Tyr Ser Leu Ser Lys Thr
1               5                   10                  15

Leu Arg Phe Lys Ala Ile Pro Val Gly Lys Thr Gln Glu Asn Ile Asp
            20                  25                  30

Asn Lys Arg Leu Leu Val Glu Asp Glu Lys Arg Ala Glu Asp Tyr Lys
        35                  40                  45

Gly Val Lys Lys Leu Leu Asp Arg Tyr Tyr Leu Ser Phe Ile Asn Asp
    50                  55                  60

Val Leu His Ser Ile Lys Leu Lys Asn Leu Asn Asn Tyr Ile Ser Leu
65                  70                  75                  80

Phe Arg Lys Lys Thr Arg Thr Glu Lys Glu Asn Lys Glu Leu Glu Asn
                85                  90                  95

Leu Glu Ile Asn Leu Arg Lys Glu Ile Ala Lys Ala Phe Lys Gly Asn
            100                 105                 110

Glu Gly Tyr Lys Ser Leu Phe Lys Lys Asp Ile Ile Glu Thr Ile Leu
        115                 120                 125

Pro Glu Phe Leu Asp Asp Lys Asp Glu Ile Ala Leu Val Asn Ser Phe
    130                 135                 140

Asn Gly Phe Thr Thr Ala Phe Thr Gly Phe Phe Asp Asn Arg Glu Asn
145                 150                 155                 160

Met Phe Ser Glu Glu Ala Lys Ser Thr Ser Ile Ala Phe Arg Cys Ile
                165                 170                 175

Asn Glu Asn Leu Thr Arg Tyr Ile Ser Asn Met Asp Ile Phe Glu Lys
            180                 185                 190

Val Asp Ala Ile Phe Asp Lys His Glu Val Gln Glu Ile Lys Glu Lys
        195                 200                 205

Ile Leu Asn Ser Asp Tyr Asp Val Glu Asp Phe Phe Glu Gly Glu Phe
    210                 215                 220

Phe Asn Phe Val Leu Thr Gln Glu Gly Ile Asp Val Tyr Asn Ala Ile
225                 230                 235                 240

Ile Gly Gly Phe Val Thr Glu Ser Gly Glu Lys Ile Lys Gly Leu Asn
                245                 250                 255

Glu Tyr Ile Asn Leu Tyr Asn Gln Lys Thr Lys Gln Lys Leu Pro Lys
            260                 265                 270

Phe Lys Pro Leu Tyr Lys Gln Val Leu Ser Asp Arg Glu Ser Leu Ser
        275                 280                 285

Phe Tyr Gly Glu Gly Tyr Thr Ser Asp Glu Glu Val Leu Glu Val Phe
```

```
    290                 295                 300

Arg Asn Thr Leu Asn Lys Asn Ser Glu Ile Phe Ser Ser Ile Lys Lys
305                 310                 315                 320

Leu Glu Lys Leu Phe Lys Asn Phe Asp Glu Tyr Ser Ser Ala Gly Ile
                325                 330                 335

Phe Val Lys Asn Gly Pro Ala Ile Ser Thr Ile Ser Lys Asp Ile Phe
            340                 345                 350

Gly Glu Trp Asn Val Ile Arg Asp Lys Trp Asn Ala Glu Tyr Asp Asp
        355                 360                 365

Ile His Leu Lys Lys Lys Ala Val Val Thr Glu Lys Tyr Glu Asp Asp
    370                 375                 380

Arg Arg Lys Ser Phe Lys Lys Ile Gly Ser Phe Ser Leu Glu Gln Leu
385                 390                 395                 400

Gln Glu Tyr Ala Asp Ala Asp Leu Ser Val Val Glu Lys Leu Lys Glu
                405                 410                 415

Ile Ile Ile Gln Lys Val Asp Glu Ile Tyr Lys Val Tyr Gly Ser Ser
            420                 425                 430

Glu Lys Leu Phe Asp Ala Asp Phe Val Leu Glu Lys Ser Leu Lys Lys
        435                 440                 445

Asn Asp Ala Val Val Ala Ile Met Lys Asp Leu Leu Asp Ser Val Lys
    450                 455                 460

Ser Phe Glu Asn Tyr Ile Lys Ala Phe Phe Gly Glu Gly Lys Glu Thr
465                 470                 475                 480

Asn Arg Asp Glu Ser Phe Tyr Gly Asp Phe Val Leu Ala Tyr Asp Ile
                485                 490                 495

Leu Leu Lys Val Asp His Ile Tyr Asp Ala Ile Arg Asn Tyr Val Thr
            500                 505                 510

Gln Lys Pro Tyr Ser Lys Asp Lys Phe Lys Leu Tyr Phe Gln Asn Pro
        515                 520                 525

Gln Phe Met Gly Gly Trp Asp Lys Asp Lys Glu Thr Asp Tyr Arg Ala
    530                 535                 540

Thr Ile Leu Arg Tyr Gly Ser Lys Tyr Tyr Leu Ala Ile Met Asp Lys
545                 550                 555                 560

Lys Tyr Ala Lys Cys Leu Gln Lys Ile Asp Lys Asp Asp Val Asn Gly
                565                 570                 575

Asn Tyr Glu Lys Ile Asn Tyr Lys Leu Leu Pro Gly Pro Asn Lys Met
            580                 585                 590

Leu Pro Lys Val Phe Phe Ser Lys Lys Trp Met Ala Tyr Tyr Asn Pro
        595                 600                 605

Ser Glu Asp Ile Gln Lys Ile Tyr Lys Asn Gly Thr Phe Lys Lys Gly
    610                 615                 620

Asp Met Phe Asn Leu Asn Asp Cys His Lys Leu Ile Asp Phe Phe Lys
625                 630                 635                 640

Asp Ser Ile Ser Arg Tyr Pro Lys Trp Ser Asn Ala Tyr Asp Phe Asn
                645                 650                 655

Phe Ser Glu Thr Glu Lys Tyr Lys Asp Ile Ala Gly Phe Tyr Arg Glu
            660                 665                 670

Val Glu Glu Gln Gly Tyr Lys Val Ser Phe Glu Ser Ala Ser Lys Lys
        675                 680                 685

Glu Val Asp Lys Leu Val Glu Glu Gly Lys Leu Tyr Met Phe Gln Ile
    690                 695                 700

Tyr Asn Lys Asp Phe Ser Asp Lys Ser His Gly Thr Pro Asn Leu His
705                 710                 715                 720
```

```
Thr Met Tyr Phe Lys Leu Leu Phe Asp Glu Asn Asn His Gly Gln Ile
                725                 730                 735

Arg Leu Ser Gly Gly Ala Glu Leu Phe Met Arg Arg Ala Ser Leu Lys
            740                 745                 750

Lys Glu Glu Leu Val Val His Pro Ala Asn Ser Pro Ile Ala Asn Lys
        755                 760                 765

Asn Pro Asp Asn Pro Lys Lys Thr Thr Thr Leu Ser Tyr Asp Val Tyr
    770                 775                 780

Lys Asp Lys Arg Phe Ser Glu Asp Gln Tyr Glu Leu His Ile Pro Ile
785                 790                 795                 800

Ala Ile Asn Lys Cys Pro Lys Asn Ile Phe Lys Ile Asn Thr Glu Val
                805                 810                 815

Arg Val Leu Leu Lys His Asp Asp Asn Pro Tyr Val Ile Gly Ile Asp
            820                 825                 830

Arg Gly Glu Arg Asn Leu Leu Tyr Ile Val Val Val Asp Gly Lys Gly
        835                 840                 845

Asn Ile Val Glu Gln Tyr Ser Leu Asn Glu Ile Ile Asn Asn Phe Asn
    850                 855                 860

Gly Ile Arg Ile Lys Thr Asp Tyr His Ser Leu Leu Asp Lys Lys Glu
865                 870                 875                 880

Lys Glu Arg Phe Glu Ala Arg Gln Asn Trp Thr Ser Ile Glu Asn Ile
                885                 890                 895

Lys Glu Leu Lys Ala Gly Tyr Ile Ser Gln Val Val His Lys Ile Cys
            900                 905                 910

Glu Leu Val Glu Lys Tyr Asp Ala Val Ile Ala Leu Glu Asp Leu Asn
        915                 920                 925

Ser Gly Phe Lys Asn Ser Arg Val Lys Val Glu Lys Gln Val Tyr Gln
    930                 935                 940

Lys Phe Glu Lys Met Leu Ile Asp Lys Leu Asn Tyr Met Val Asp Lys
945                 950                 955                 960

Lys Ser Asn Pro Cys Ala Thr Gly Gly Ala Leu Lys Gly Tyr Gln Ile
                965                 970                 975

Thr Asn Lys Phe Glu Ser Phe Lys Ser Met Ser Thr Gln Asn Gly Phe
            980                 985                 990

Ile Phe Tyr Ile Pro Ala Trp Leu  Thr Ser Lys Ile Asp  Pro Ser Thr
        995                 1000                1005

Gly Phe  Val Asn Leu Leu Lys  Thr Lys Tyr Thr Ser  Ile Ala Asp
    1010                1015                1020

Ser Lys  Lys Phe Ile Ser Ser  Phe Asp Arg Ile Met  Tyr Val Pro
    1025                1030                1035

Glu Glu  Asp Leu Phe Glu Phe  Ala Leu Asp Tyr Lys  Asn Phe Ser
    1040                1045                1050

Arg Thr  Asp Ala Asp Tyr Ile  Lys Lys Trp Lys Leu  Tyr Ser Tyr
    1055                1060                1065

Gly Asn  Arg Ile Arg Ile Phe  Arg Asn Pro Lys Lys  Asn Asn Val
    1070                1075                1080

Phe Asp  Trp Glu Glu Val Cys  Leu Thr Ser Ala Tyr  Lys Glu Leu
    1085                1090                1095

Phe Asn  Lys Tyr Gly Ile Asn  Tyr Gln Gln Gly Asp  Ile Arg Ala
    1100                1105                1110

Leu Leu  Cys Glu Gln Ser Asp  Lys Ala Phe Tyr Ser  Ser Phe Met
    1115                1120                1125
```

```
Ala Leu  Met Ser Leu Met Leu  Gln Met Arg Asn Ser  Ile Thr Gly
    1130                 1135                 1140

Arg Thr  Asp Val Asp Phe Leu  Ile Ser Pro Val Lys  Asn Ser Asp
    1145                 1150                 1155

Gly Ile  Phe Tyr Asp Ser Arg  Asn Tyr Glu Ala Gln  Glu Asn Ala
    1160                 1165                 1170

Ile Leu  Pro Lys Asn Ala Asp  Ala Asn Gly Ala Tyr  Asn Ile Ala
    1175                 1180                 1185

Arg Lys  Val Leu Trp Ala Ile  Gly Gln Phe Lys Lys  Ala Glu Asp
    1190                 1195                 1200

Glu Lys  Leu Asp Lys Val Lys  Ile Ala Ile Ser Asn  Lys Glu Trp
    1205                 1210                 1215

Leu Glu  Tyr Ala Gln Thr Ser  Val Lys His
    1220                 1225
```

<210> SEQ ID NO 328
<211> LENGTH: 11174
<212> TYPE: DNA
<213> ORGANISM: Artificial Sequence
<220> FEATURE:
<223> OTHER INFORMATION: Synthetic Sequence - synthetic oligonucleotide: Vector 3685
<220> FEATURE:
<221> NAME/KEY: misc_feature
<222> LOCATION: (70)..(573)
<223> OTHER INFORMATION: CEN/ARS
<220> FEATURE:
<221> NAME/KEY: promoter
<222> LOCATION: (610)..(714)
<223> OTHER INFORMATION: Amp Rpromoter
<220> FEATURE:
<221> NAME/KEY: gene
<222> LOCATION: (715)..(1575)
<223> OTHER INFORMATION: AmpR
<220> FEATURE:
<221> NAME/KEY: rep_origin
<222> LOCATION: (1746)..(2334)
<223> OTHER INFORMATION: ori
<220> FEATURE:
<221> NAME/KEY: promoter
<222> LOCATION: (2853)..(3510)
<223> OTHER INFORMATION: GAL1,10 promoter
<220> FEATURE:
<221> NAME/KEY: protein_bind
<222> LOCATION: (3069)..(3186)
<223> OTHER INFORMATION: UAS
<220> FEATURE:
<221> NAME/KEY: gene
<222> LOCATION: (3541)..(7224)
<223> OTHER INFORMATION: LbCpf1
<220> FEATURE:
<221> NAME/KEY: sig_peptide
<222> LOCATION: (7225)..(7272)
<223> OTHER INFORMATION: nucleoplasmin NLS
<220> FEATURE:
<221> NAME/KEY: misc_feature
<222> LOCATION: (7282)..(7296)
<223> OTHER INFORMATION: protein degradation tag
<220> FEATURE:
<221> NAME/KEY: promoter
<222> LOCATION: (7318)..(7586)
<223> OTHER INFORMATION: SNR52 promoter
<220> FEATURE:
<221> NAME/KEY: misc_structure
<222> LOCATION: (7588)..(7606)
<223> OTHER INFORMATION: Fn_crRNA
<220> FEATURE:
<221> NAME/KEY: terminator
<222> LOCATION: (7631)..(7650)
<223> OTHER INFORMATION: sup4 term
<220> FEATURE:
<221> NAME/KEY: terminator
<222> LOCATION: (7657)..(7657)
<223> OTHER INFORMATION: CYC1 terminator
<220> FEATURE:
<221> NAME/KEY: promoter
<222> LOCATION: (7680)..(7948)
<223> OTHER INFORMATION: SNR52 promoter
<220> FEATURE:
<221> NAME/KEY: misc_structure
<222> LOCATION: (7950)..(7968)
<223> OTHER INFORMATION: Fn_crRNA
<220> FEATURE:
<221> NAME/KEY: terminator
<222> LOCATION: (7993)..(8012)
<223> OTHER INFORMATION: sup4 term
<220> FEATURE:
<221> NAME/KEY: rep_origin
<222> LOCATION: (8246)..(8701)
<223> OTHER INFORMATION: f1 ori
<220> FEATURE:
<221> NAME/KEY: promoter
<222> LOCATION: (9001)..(9405)
<223> OTHER INFORMATION: LEU2 promoter
<220> FEATURE:
<221> NAME/KEY: gene
<222> LOCATION: (9418)..(10512)
<223> OTHER INFORMATION: LEU2

<400> SEQUENCE: 328
gacgaaaggg cctcgtgata cgcctatttt tataggttaa tgtcatgata ataatggttt 60
cttaggacgg atcgcttgcc tgtaacttac acgcgcctcg tatcttttaa tgatggaata 120
atttgggaat ttactctgtg tttatttatt tttatgtttt gtatttggat tttagaaagt 180
aaataaagaa ggtagaagag ttacggaatg aagaaaaaaa aataaacaaa ggtttaaaaa 240
atttcaacaa aaagcgtact ttacatatat atttattaga caagaaaagc agattaaata 300
gatatacatt cgattaacga taagtaaaat gtaaaatcac aggattttcg tgtgtggtct 360
tctacacaga caagatgaaa caattcggca ttaatacctg agagcaggaa gagcaagata 420
aaaggtagta tttgttggcg atccccctag agtcttttac atcttcggaa aacaaaaact 480 atttttttctt taatttcttt ttttactttc tatttttaat ttatatattt atattaaaaa 540
atttaaatta taattatttt tatagcacgt gatgaaaagg acccaggtgg cacttttcgg 600
ggaaatgtgc gcggaacccc tatttgttta tttttctaaa tacattcaaa tatgtatccg 660
ctcatgagac aataaccctg ataaatgctt caataatatt gaaaaaggaa gagtatgagt 720
attcaacatt tccgtgtcgc ccttattccc ttttttgcgg cattttgcct tcctgttttt 780
gctcacccag aaacgctggt gaaagtaaaa gatgctgaag atcagttggg tgcacgagtg 840
ggttacatcg aactggatct caacagcggt aagatccttg agagttttcg ccccgaagaa 900
cgttttccaa tgatgagcac ttttaaagtt ctgctatgtg gcgcggtatt atcccgtatt 960
gacgccgggc aagagcaact cggtcgccgc atacactatt ctcagaatga cttggttgag 1020
tactcaccag tcacagaaaa gcatcttacg gatggcatga cagtaagaga attatgcagt 1080
gctgccataa ccatgagtga taacactgcg gccaacttac ttctgacaac gatcggagga 1140
ccgaaggagc taaccgcttt tttgcacaac atgggggatc atgtaactcg ccttgatcgt 1200
tgggaaccgg agctgaatga agccatacca aacgacgagc gtgacaccac gatgcctgta 1260
gcaatggcaa caacgttgcg caaactatta actggcgaac tacttactct agcttcccgg 1320
caacaattaa tagactggat ggaggcggat aaagttgcag gaccacttct gcgctcggcc 1380
cttccggctg gctggtttat tgctgataaa tctggagccg gtgagcgtgg gtctcgcggt 1440
atcattgcag cactggggcc agatggtaag ccctcccgta tcgtagttat ctacacgacg 1500

-continued

```
ggcagtcagg caactatgga tgaacgaaat agacagatcg ctgagatagg tgcctcactg   1560
attaagcatt ggtaactgtc agaccaagtt tactcatata tactttagat tgatttaaaa   1620
cttcattttt aatttaaaag gatctaggtg aagatccttt ttgataatct catgaccaaa   1680
atcccttaac gtgagttttc gttccactga gcgtcagacc ccgtagaaaa gatcaaagga   1740
tcttcttgag atcctttttt tctgcgcgta atctgctgct tgcaaacaaa aaaaccaccg   1800
ctaccagcgg tggtttgttt gccggatcaa gagctaccaa ctctttttcc gaaggtaact   1860
ggcttcagca gagcgcagat accaaatact gtccttctag tgtagccgta gttaggccac   1920
cacttcaaga actctgtagc accgcctaca tacctcgctc tgctaatcct gttaccagtg   1980
gctgctgcca gtggcgataa gtcgtgtctt accgggttgg actcaagacg atagttaccg   2040
gataaggcgc agcggtcggg ctgaacgggg ggttcgtgca cacagcccag cttggagcga   2100
acgacctaca ccgaactgag atacctacag cgtgagcatt gagaaagcgc cacgcttccc   2160
gaagggagaa aggcggacag gtatccggta agcggcaggg tcggaacagg agagcgcacg   2220
agggagcttc cagggggaa cgcctggtat ctttatagtc ctgtcgggtt tcgccacctc   2280
tgacttgagc gtcgattttt gtgatgctcg tcaggggggc cgagcctatg gaaaaacgcc   2340
agcaacgcgg cctttttacg gttcctggcc ttttgctggc cttttgctca catgttcttt   2400
cctgcgttat cccctgattc tgtggataac cgtattaccg cctttgagtg agctgatacc   2460
gctcgccgca gccgaacgac cgagcgcagc gagtcagtga gcgaggaagc ggaagagcgc   2520
ccaatacgca aaccgcctct ccccgcgcgt tggccgattc attaatgcag ctggcacgac   2580
aggtttcccg actggaaagc gggcagtgag cgcaacgcaa ttaatgtgag ttacctcact   2640
cattaggcac cccaggcttt acactttatg cttccggctc ctatgttgtg tggaattgtg   2700
agcggataac aatttcacac aggaaacagc tatgaccatg attacgccaa gctcggaatt   2760
aaccctcact aaagggaaca aaagctgggt accgggcccg aattctctcc ttctcttagg   2820
tggcagagca ggtggagggt cgaccatact agtttcaaaa attcttactt ttttttgga    2880
tggacgcaaa gaagtttaat aatcatatta catggcatta ccaccatata catatccata   2940
tacatatcca tatctaatct tacttatatg ttgtggaaat gtaaagagcc ccattatctt   3000
agcctaaaaa aaccttctct ttggaacttt cagtaatacg cttaactgct cattgctata   3060
ttgaagtacg gattagaagc cgccgagcgg gtgacagccc tccgaaggaa gactctcctc   3120
cgtgcgtcct cgtcttcacc ggtcgcgttc ctgaaacgca gatgtgcctc gcgccgcact   3180
gctccgaaca ataaagattc tacaatacta gcttttatgg ttatgaagag gaaaaattgg   3240
cagtaacctg gccccacaaa ccttcaaatg aacgaatcaa attaacaacc ataggatgat   3300
aatgcgatta gttttttagc cttatttctg gggtaattaa tcagcgaagc gatgattttt   3360
gatctattaa cagatatata aatgcaaaaa ctgcataacc actttaacta atactttcaa   3420
cattttcggt ttgtattact tcttattcaa atgtaataaa agtatcaaca aaaaattgtt   3480
aatataccte tatactttaa cgtcaaggag aaaaaaccca tgggtttcga atctagcatc   3540
atgagcaagc ttgagaagtt tacaaactgc tactccctgt ctaagaccct gaggttcaag   3600
gccatccctg tgggcaagac ccaggagaac atcgacaata agcggctgct ggtggaggac   3660
gagaagagag ccgaggatta taagggcgtg aagaagctgc tggatcgcta ctatctgtct   3720
tttatcaacg acgtgctgca cagcatcaag ctgaagaatc tgaacaatta catcagcctg   3780
ttccggaaga aaaccagaac cgagaaggag aataaggagc tggagaacct ggagatcaat   3840
ctgcggaagg agatcgccaa ggccttcaag ggcaacgagg gctacaagtc cctgtttaag   3900
```

```
aaggatatca tcgagacaat cctgccagag ttcctggacg ataaggacga gatcgccctg   3960
gtgaacagct tcaatggctt taccacagcc ttcaccggct tctttgataa cagagagaat   4020
atgttttccg aggaggccaa gagcacatcc atcgccttca ggtgtatcaa cgagaatctg   4080
acccgctaca tctctaatat ggacatcttc gagaaggtgg acgccatctt tgataagcac   4140
gaggtgcagg agatcaagga gaagatcctg aacagcgact atgatgtgga ggatttcttt   4200
gagggcgagt tctttaactt tgtgctgaca caggagggca tcgacgtgta taacgccatc   4260
atcggcggct tcgtgaccga gagcggcgag aagatcaagg gcctgaacga gtacatcaac   4320
ctgtataatc agaaaaccaa gcagaagctg cctaagttta agccactgta taagcaggtg   4380
ctgagcgatc gggagtctct gagcttctac ggcgagggct atacatccga tgaggaggtg   4440
ctggaggtgt ttagaaacac cctgaacaag aacagcgaga tcttcagctc catcaagaag   4500
ctggagaagc tgttcaagaa ttttgacgag tactctagcg ccggcatctt tgtgaagaac   4560
ggccccgcca tcagcacaat ctccaaggat atcttcggcg agtggaacgt gatccgggac   4620
aagtggaatg ccgagtatga cgatatccac ctgaagaaga aggccgtcgt gaccgagaag   4680
tacgaggacg atcggagaaa gtccttcaag aagatcggct ccttttctct ggagcagctg   4740
caggagtacg ccgacgccga tctgtctgtg gtggagaagc tgaaggagat catcatccag   4800
aaggtggatg agatctacaa ggtgtatggc tcctctgaga agctgttcga cgccgatttt   4860
gtgctggaga agtctctgaa gaagaacgac gccgtggtgg ccattatgaa ggacctgctg   4920
gattctgtga agtctttcga gaattacatc aaggccttct ttggcgaggg caaggagaca   4980
aacagggacg agtccttcta tggcgatttt gtgctggcct acgacatcct gctgaaggtg   5040
gaccacatct acgatgccat ccgcaattat gtgacccaga agccctactc taaggataag   5100
ttcaagctgt attttcagaa ccctcagttc atgggcggct gggacaagga taaggagaca   5160
gactatcggg ccaccatcct gagatacggc tccaagtact atctggccat catggataag   5220
aagtacgcca agtgcctgca gaagatcgac aaggacgatg tgaacggcaa ttacgagaag   5280
atcaactata agctgctgcc cggccctaat aagatgctgc caaaggtgtt cttttctaag   5340
aagtggatgg cctactataa ccccagcgag gacatccaga agatctacaa gaatggtacc   5400
ttcaagaagg gcgatatgtt taacctgaat gactgtcaca agctgatcga cttctttaag   5460
gatagcatct cccggtatcc aaagtggtcc aatgcctacg atttcaactt ttctgagaca   5520
gagaagtata aggacatcgc cggcttttac agagaggtgg aggagcaggg ctataaggtg   5580
agcttcgagt ctgccagcaa gaaggaggtg gataagctgg tggaggaggg caagctgtat   5640
atgttccaga tctataacaa ggacttttcc gataagtctc acggcacacc caatctgcac   5700
accatgtact tcaagctgct gtttgacgag aacaatcacg gacagatcag gctgagcgga   5760
ggagcagagc tgttcatgag gcgcgcttcc ctgaagaagg aggagctggt ggtgcaccca   5820
gccaactccc ctatcgccaa caagaatcca gataatccca agaaaaccac aaccctgtcc   5880
tacgacgtgt ataaggataa gaggttttct gaggaccagt acgagctgca catcccaatc   5940
gccatcaata agtgccccaa gaacatcttc aagatcaata cagaggtgcg cgtgctgctg   6000
aagcacgacg ataacccta tgtgatcggc atcgataggg gcgagcgcaa tctgctgtat   6060
atcgtggtgg tggacggcaa gggcaacatc gtggagcagt attccctgaa cgagatcatc   6120
aacaacttca acggcatcag gatcaagaca gattaccact ctctgctgga caagaaggag   6180
aaggagaggt tcgaggcccg ccagaactgg acctccatcg agaatatcaa ggagctgaag   6240
```

```
gccggctata tctctcaggt ggtgcacaag atctgcgagc tggtggagaa gtacgatgcc   6300
gtgatcgccc tggaggacct gaactctggc tttaagaata gccgcgtgaa ggtggagaag   6360
caggtgtatc agaagttcga gaagatgctg atcgataagc tgaactacat ggtggacaag   6420
aagtctaatc cttgtgcaac aggcggcgcc ctgaagggct atcagatcac caataagttc   6480
gagagcttta agtccatgtc tacccagaac ggcttcatct tttacatccc tgcctggctg   6540
acatccaaga tcgatccatc taccggcttt gtgaacctgc tgaaaaccaa gtataccagc   6600
atcgccgatt ccaagaagtt catcagctcc tttgacagga tcatgtacgt gcccgaggag   6660
gatctgttcg agtttgccct ggactataag aacttctctc gcacagacgc cgattacatc   6720
aagaagtgga agctgtactc ctacggcaac cggatcagaa tcttccggaa tcctaagaag   6780
aacaacgtgt tcgactggga ggaggtgtgc ctgaccagcg cctataagga gctgttcaac   6840
aagtacggca tcaattatca gcagggcgat atcagagccc tgctgtgcga gcagtccgac   6900
aaggccttct actctagctt tatggccctg atgagcctga tgctgcagat gcggaacagc   6960
atcacaggcc gcaccgacgt ggattttctg atcagccctg tgaagaactc cgacggcatc   7020
ttctacgata gccggaacta tgaggcccag gagaatgcca tcctgccaaa gaacgccgac   7080
gccaatggcg cctataacat cgccagaaag gtgctgtggg ccatcggcca gttcaagaag   7140
gccgaggacg agaagctgga taaggtgaag atcgccatct ctaacaagga gtggctggag   7200
tacgcccaga ccagcgtgaa gcacaaaagg ccggcggcca cgaaaaaggc cggccaggcc   7260
aaaaagaaaa agggctctag ctacgctgca tcagtctagg gaacaaaagc tggagcttct   7320
ttgaaaagat aatgtatgat tatgctttca ctcatattta tacagaaact tgatgttttc   7380
tttcgagtat atacaaggtg attacatgta cgtttgaagt acaactctag attttgtagt   7440
gccctcttgg gctagcggta aaggtgcgca tttttcaca ccctacaatg ttctgttcaa   7500
aagattttgg tcaaacgctg tagaagtgaa agttggtgcg catgtttcgg cgttcgaaac   7560
ttctccgcag tgaaagataa atgatctaat ttctactgtt gtagattggt gctggggtta   7620
ccggcctgtt tttttttgtt ttttatgtct accggtcggc cggtaccatc ccgggtagat   7680
ctttgaaaag ataatgtatg attatgcttt cactcatatt tatacagaaa cttgatgttt   7740
tctttcgagt atatacaagg tgattacatg tacgtttgaa gtacaactct agattttgta   7800
gtgccctctt gggctagcgg taaaggtgcg catttttca caccctacaa tgttctgttc   7860
aaaagatttt ggtcaaacgc tgtagaagtg aaagttggtg cgcatgtttc ggcgttcgaa   7920
acttctccgc agtgaaagat aaatgatcta atttctactg ttgtagattc caataacgga   7980
atccaacttg tttttttttg ttttttatgt ctaccggtcg gccggtaccc aattcgccct   8040
atagcctagg agctccaatt cgccctatag tgagtcgtat tacaattcac tggccgtcgt   8100
tttacaacgt cgtgactggg aaaaccctgg cgttacccaa cttaatcgcc ttgcagcaca   8160
tccccctttc gccagctggc gtaatagcga agaggcccgc accgatcgcc cttcccaaca   8220
gttgcgcagc ctgaatggcg aatggacgcg ccctgtagcg gcgcattaag cgcggcgggt   8280
gtggtggtta cgcgcagcgt gaccgctaca cttgccagcg ccctagcgcc cgctcctttc   8340
gctttcttcc cttcctttct cgccacgttc gccggctttc cccgtcaagc tctaaatcgg   8400
gggctccctt tagggttccg atttagtgct ttacggcacc tcgaccccaa aaaacttgat   8460
tagggtgatg gttcacgtag tgggccatcg ccctgataga cggtttttcg ccctttgacg   8520
ttggagtcca cgttctttaa tagtggactc ttgttccaaa ctggaacaac actcaaccct   8580
atctcggtct attcttttga tttataaggg attttgccga tttcggccta ttggttaaaa   8640
```

```
aatgagctga tttaacaaaa atttaacgcg aattttaaca aaatattaac gtttacaatt   8700
tcctgatgcg gtattttctc cttacgcatc tgtgcggtat ttcacaccgc atatcgaccc   8760
tcgaggagaa cttctagtat atccacatac ctaatattat tgccttatta aaaatggaat   8820
cggaacaatt acatcaaaat ccacattctc ttcaaaatca attgtcctgt acttccttgt   8880
tcatgtgtgt tcaaaaacgt tatatttata ggataattat actctatttc tcaacaagta   8940
attggttgtt tggccgagcg gtctaaggcg cctgattcaa gaaatatctt gaccgcagtt   9000
aactgtggga atactcaggt atcgtaagat gcaagagttc gaatctctta gcaaccatta   9060
tttttttcct caacataacg agaacacaca ggggcgctat cgcacagaat caaattcgat   9120
gactggaaat tttttgttaa tttcagaggt cgcctgacgc atataccttt ttcaactgaa   9180
aaattgggag aaaaaggaaa ggtgagaggc cggaaccggc ttttcatata gaatagagaa   9240
gcgttcatga ctaaatgctt gcatcacaat acttgaagtt gacaatatta tttaaggacc   9300
tattgttttt tccaataggt ggttagcaat cgtcttactt tctaactttt cttacctttt   9360
acatttcagc aatatatata tatatttcaa ggatatacca ttctaatgtc tgcccctatg   9420
tctgccccta agaagatcgt cgttttgcca ggtgaccacg ttggtcaaga aatcacagcc   9480
gaagccatta aggttcttaa agctatttct gatgttcgtt ccaatgtcaa gttcgatttc   9540
gaaaatcatt taattggtgg tgctgctatc gatgctacag gtgtcccact tccagatgag   9600
gcgctggaag cctccaagaa ggttgatgcc gttttgttag gtgctgtggg tggtcctaaa   9660
tggggtaccg gtagtgttag acctgaacaa ggtttactaa aaatccgtaa agaacttcaa   9720
ttgtacgcca acttaagacc atgtaacttt gcatccgact ctcttttaga cttatctcca   9780
atcaagccac aatttgctaa aggtactgac ttcgttgttg tcagagaatt agtgggaggt   9840
atttactttg gtaagagaaa ggaagacgat ggtgatggtg tcgcttggga tagtgaacaa   9900
tacaccgttc cagaagtgca aagaatcaca agaatggccg ctttcatggc cctacaacat   9960
gagccaccat tgcctatttg gtccttggat aaagctaatg ttttggcctc ttcaagatta  10020
tggagaaaaa ctgtggagga aaccatcaag aacgaattcc ctacattgaa ggttcaacat  10080
caattgattg attctgccgc catgatccta gttaagaacc caacccacct aaatggtatt  10140
ataatcacca gcaacatgtt tggtgatatc atctccgatg aagcctccgt tatcccaggt  10200
tccttgggtt tgttgccatc tgcgtccttg gcctctttgc cagacaagaa caccgcattt  10260
ggtttgtacg aaccatgcca cggttctgct ccagatttgc caaagaataa ggttgaccct  10320
atcgccacta tcttgtctgc tgcaatgatg ttgaaattgt cattgaactt gcctgaagaa  10380
ggtaaggcca ttgaagatgc agttaaaaag gttttggatg caggtatcag aactggtgat  10440
ttaggtggtt ccaacagtac caccgaagtc ggtgatgctg tcgccgaaga agttaagaaa  10500
atccttgctt aaaaagattc tcttttttta tgatatttgt acataaactt tataaatgaa  10560
attcataata gaaacgacac gaaattacaa aatggaatat gttcataggg tagacgaaac  10620
tatatacgca atctacatac atttatcaag aaggagaaaa aggaggatag taaaggaata  10680
caggtaagca aattgatact aatggctcaa cgtgataagg aaaaagaatt gcactttaac  10740
attaatattg acaaggagga gggcaccaca caaaaagtta ggtgtaacag aaaatcatga  10800
aactacgatt cctaatttga tattggagga ttttctctaa aaaaaaaaaa atacaacaaa  10860
taaaaaacac tcaatgacct gaccatttga tggagtttaa gtcaatacct tcttgaacca  10920
tttcccataa tggtgaaagt tccctcaaga attttactct gtcagaaacg gccttacgac  10980
```

```
gtagtcgata tggtgcactc tcagtacaat ctgctctgat gccgcatagt taagccagcc  11040

ccgacacccg ccaacacccg ctgacgcgcc ctgacgggct tgtctgctcc cggcatccgc  11100

ttacagacaa gctgtgaccg tctccgggag ctgcatgtgt cagaggtttt caccgtcatc  11160

accgaaacgc gcga                                                    11174


<210> SEQ ID NO 329
<211> LENGTH: 11174
<212> TYPE: DNA
<213> ORGANISM: Artificial Sequence
<220> FEATURE:
<223> OTHER INFORMATION: Synthetic Sequence - synthetic oligonucleotide:
      Vector 3686
<220> FEATURE:
<221> NAME/KEY: misc_feature
<222> LOCATION: (70)..(573)
<223> OTHER INFORMATION: CEN/ARS
<220> FEATURE:
<221> NAME/KEY: promoter
<222> LOCATION: (610)..(714)
<223> OTHER INFORMATION: AmpR promoter
<220> FEATURE:
<221> NAME/KEY: gene
<222> LOCATION: (715)..(1575)
<223> OTHER INFORMATION: AmpR
<220> FEATURE:
<221> NAME/KEY: rep_origin
<222> LOCATION: (1746)..(2334)
<223> OTHER INFORMATION: ori
<220> FEATURE:
<221> NAME/KEY: promoter
<222> LOCATION: (2853)..(3510)
<223> OTHER INFORMATION: GAL1,10 promoter
<220> FEATURE:
<221> NAME/KEY: protein_bind
<222> LOCATION: (3069)..(3186)
<223> OTHER INFORMATION: UAS
<220> FEATURE:
<221> NAME/KEY: gene
<222> LOCATION: (3541)..(7224)
<223> OTHER INFORMATION: LbCpf1
<220> FEATURE:
<221> NAME/KEY: sig_peptide
<222> LOCATION: (7225)..(7272)
<223> OTHER INFORMATION: nucleoplasmin NLS
<220> FEATURE:
<221> NAME/KEY: misc_feature
<222> LOCATION: (7282)..(7296)
<223> OTHER INFORMATION: protein degradation tag
<220> FEATURE:
<221> NAME/KEY: promoter
<222> LOCATION: (7318)..(7586)
<223> OTHER INFORMATION: SNR52 promoter
<220> FEATURE:
<221> NAME/KEY: misc_structure
<222> LOCATION: (7588)..(7606)
<223> OTHER INFORMATION: Fn_crRNA
<220> FEATURE:
<221> NAME/KEY: terminator
<222> LOCATION: (7631)..(7650)
<223> OTHER INFORMATION: sup4 term
<220> FEATURE:
<221> NAME/KEY: terminator
<222> LOCATION: (7657)..(7657)
<223> OTHER INFORMATION: CYC1 terminator
<220> FEATURE:
<221> NAME/KEY: promoter
<222> LOCATION: (7680)..(7948)
<223> OTHER INFORMATION: SNR52 promoter
<220> FEATURE:
<221> NAME/KEY: misc_structure
<222> LOCATION: (7950)..(7968)
<223> OTHER INFORMATION: Fn_crRNA
<220> FEATURE:
<221> NAME/KEY: terminator
<222> LOCATION: (7993)..(8012)
```

<223> OTHER INFORMATION: sup4 term
<220> FEATURE:
<221> NAME/KEY: rep_origin
<222> LOCATION: (8246)..(8701)
<223> OTHER INFORMATION: f1 ori
<220> FEATURE:
<221> NAME/KEY: promoter
<222> LOCATION: (9001)..(9405)
<223> OTHER INFORMATION: LEU2 promoter
<220> FEATURE:
<221> NAME/KEY: gene
<222> LOCATION: (9418)..(10512)
<223> OTHER INFORMATION: LEU2

<400> SEQUENCE: 329
gacgaaaggg cctcgtgata cgcctatttt tataggttaa tgtcatgata ataatggttt 60
cttaggacgg atcgcttgcc tgtaacttac acgcgcctcg tatcttttaa tgatggaata 120
atttgggaat ttactctgtg tttatttatt tttatgtttt gtatttggat tttagaaagt 180
aaataaagaa ggtagaagag ttacggaatg aagaaaaaaa aataaacaaa ggtttaaaaa 240
atttcaacaa aaagcgtact ttacatatat atttattaga caagaaaagc agattaaata 300
gatatacatt cgattaacga taagtaaaat gtaaaatcac aggattttcg tgtgtggtct 360
tctacacaga caagatgaaa caattcggca ttaatacctg agagcaggaa gagcaagata 420
aaaggtagta tttgttggcg atccccctag agtcttttac atcttcggaa aacaaaaact 480
attttttctt taatttcttt ttttactttc tatttttaat ttatatattt atattaaaaa 540
atttaaatta taattatttt tatagcacgt gatgaaaagg acccaggtgg cacttttcgg 600
ggaaatgtgc gcggaacccc tatttgttta tttttctaaa tacattcaaa tatgtatccg 660
ctcatgagac aataaccctg ataaatgctt caataatatt gaaaaaggaa gagtatgagt 720
attcaacatt tccgtgtcgc ccttattccc ttttttgcgg cattttgcct tcctgttttt 780
gctcacccag aaacgctggt gaaagtaaaa gatgctgaag atcagttggg tgcacgagtg 840
ggttacatcg aactggatct caacagcggt aagatccttg agagttttcg ccccgaagaa 900
cgttttccaa tgatgagcac ttttaaagtt ctgctatgtg gcgcggtatt atcccgtatt 960
gacgccgggc aagagcaact cggtcgccgc atacactatt ctcagaatga cttggttgag 1020
tactcaccag tcacagaaaa gcatcttacg gatggcatga cagtaagaga attatgcagt 1080
gctgccataa ccatgagtga taacactgcg gccaacttac ttctgacaac gatcggagga 1140
ccgaaggagc taaccgcttt tttgcacaac atgggggatc atgtaactcg ccttgatcgt 1200
tgggaaccgg agctgaatga agccatacca aacgacgagc gtgacaccac gatgcctgta 1260
gcaatggcaa caacgttgcg caaactatta actggcgaac tacttactct agcttcccgg 1320
caacaattaa tagactggat ggaggcggat aaagttgcag gaccacttct gcgctcggcc 1380
cttccggctg gctggtttat tgctgataaa tctggagccg gtgagcgtgg gtctcgcggt 1440
atcattgcag cactggggcc agatggtaag ccctcccgta tcgtagttat ctacacgacg 1500
ggcagtcagg caactatgga tgaacgaaat agacagatcg ctgagatagg tgcctcactg 1560
attaagcatt ggtaactgtc agaccaagtt tactcatata tactttagat tgatttaaaa 1620
cttcattttt aatttaaaag gatctaggtg aagatccttt ttgataatct catgaccaaa 1680
atcccttaac gtgagttttc gttccactga gcgtcagacc ccgtagaaaa gatcaaagga 1740
tcttcttgag atcctttttt tctgcgcgta atctgctgct tgcaaacaaa aaaaccaccg 1800
ctaccagcgg tggtttgttt gccggatcaa gagctaccaa ctctttttcc gaaggtaact 1860
ggcttcagca gagcgcagat accaaatact gtccttctag tgtagccgta gttaggccac 1920

```
cacttcaaga actctgtagc accgcctaca tacctcgctc tgctaatcct gttaccagtg   1980
gctgctgcca gtggcgataa gtcgtgtctt accgggttgg actcaagacg atagttaccg   2040
gataaggcgc agcggtcggg ctgaacgggg ggttcgtgca cacagcccag cttggagcga   2100
acgacctaca ccgaactgag atacctacag cgtgagcatt gagaaagcgc cacgcttccc   2160
gaagggagaa aggcggacag gtatccggta agcggcaggg tcggaacagg agagcgcacg   2220
agggagcttc caggggggaa cgcctggtat ctttatagtc ctgtcgggtt tcgccacctc   2280
tgacttgagc gtcgattttt gtgatgctcg tcaggggggc cgagcctatg gaaaaacgcc   2340
agcaacgcgg cctttttacg gttcctggcc ttttgctggc cttttgctca catgttcttt   2400
cctgcgttat cccctgattc tgtggataac cgtattaccg cctttgagtg agctgatacc   2460
gctcgccgca gccgaacgac cgagcgcagc gagtcagtga gcgaggaagc ggaagagcgc   2520
ccaatacgca aaccgcctct ccccgcgcgt tggccgattc attaatgcag ctggcacgac   2580
aggtttcccg actggaaagc gggcagtgag cgcaacgcaa ttaatgtgag ttacctcact   2640
cattaggcac cccaggcttt acactttatg cttccggctc ctatgttgtg tggaattgtg   2700
agcggataac aatttcacac aggaaacagc tatgaccatg attacgccaa gctcggaatt   2760
aaccctcact aaagggaaca aaagctgggt accgggcccg aattctctcc ttctcttagg   2820
tggcagagca ggtggagggt cgaccatact agtttcaaaa attcttactt ttttttgga    2880
tggacgcaaa gaagtttaat aatcatatta catggcatta ccaccatata catatccata   2940
tacatatcca tatctaatct tacttatatg ttgtggaaat gtaaagagcc ccattatctt   3000
agcctaaaaa aaccttctct ttggaacttt cagtaatacg cttaactgct cattgctata   3060
ttgaagtacg gattagaagc cgccgagcgg gtgacagccc tccgaaggaa gactctcctc   3120
cgtgcgtcct cgtcttcacc ggtcgcgttc ctgaaacgca gatgtgcctc gcgccgcact   3180
gctccgaaca ataaagattc tacaatacta gcttttatgg ttatgaagag gaaaaattgg   3240
cagtaacctg gccccacaaa ccttcaaatg aacgaatcaa attaacaacc ataggatgat   3300
aatgcgatta gttttttagc cttatttctg gggtaattaa tcagcgaagc gatgattttt   3360
gatctattaa cagatatata aatgcaaaaa ctgcataacc actttaacta atactttcaa   3420
cattttcggt ttgtattact tcttattcaa atgtaataaa agtatcaaca aaaaattgtt   3480
aatatacctc tatactttaa cgtcaaggag aaaaaaccca tgggtttcga atctagcatc   3540
atgagcaagc ttgagaagtt tacaaactgc tactccctgt ctaagaccct gaggttcaag   3600
gccatccctg tgggcaagac ccaggagaac atcgacaata agcggctgct ggtggaggac   3660
gagaagagag ccgaggatta taagggcgtg aagaagctgc tggatcgcta ctatctgtct   3720
tttatcaacg acgtgctgca cagcatcaag ctgaagaatc tgaacaatta catcagcctg   3780
ttccggaaga aaaccagaac cgagaaggag aataaggagc tggagaacct ggagatcaat   3840
ctgcggaagg agatcgccaa ggccttcaag ggcaacgagg gctacaagtc cctgtttaag   3900
aaggatatca tcgagacaat cctgccagag ttcctggacg ataaggacga gatcgccctg   3960
gtgaacagct tcaatggctt taccacagcc ttcaccggct tctttgataa cagagagaat   4020
atgttttccg aggaggccaa gagcacatcc atcgccttca ggtgtatcaa cgagaatctg   4080
acccgctaca tctctaatat ggacatcttc gagaaggtgg acgccatctt tgataagcac   4140
gaggtgcagg agatcaagga gaagatcctg aacagcgact atgatgtgga ggatttcttt   4200
gagggcgagt tctttaactt tgtgctgaca caggagggca tcgacgtgta taacgccatc   4260
```

```
atcggcggct tcgtgaccga gagcggcgag aagatcaagg gcctgaacga gtacatcaac   4320
ctgtataatc agaaaaccaa gcagaagctg cctaagttta agccactgta taagcaggtg   4380
ctgagcgatc gggagtctct gagcttctac ggcgagggct atacatccga tgaggaggtg   4440
ctggaggtgt ttagaaacac cctgaacaag aacagcgaga tcttcagctc catcaagaag   4500
ctggagaagc tgttcaagaa ttttgacgag tactctagcg ccggcatctt tgtgaagaac   4560
ggccccgcca tcagcacaat ctccaaggat atcttcggcg agtggaacgt gatccgggac   4620
aagtggaatg ccgagtatga cgatatccac ctgaagaaga aggccgtcgt gaccgagaag   4680
tacgaggacg atcggagaaa gtccttcaag aagatcggct ccttttctct ggagcagctg   4740
caggagtacg ccgacgccga tctgtctgtg gtggagaagc tgaaggagat catcatccag   4800
aaggtggatg agatctacaa ggtgtatggc tcctctgaga agctgttcga cgccgatttt   4860
gtgctggaga agtctctgaa gaagaacgac gccgtggtgg ccattatgaa ggacctgctg   4920
gattctgtga agtctttcga gaattacatc aaggccttct ttggcgaggg caaggagaca   4980
aacagggacg agtccttcta tggcgatttt gtgctggcct acgacatcct gctgaaggtg   5040
gaccacatct acgatgccat ccgcaattat gtgacccaga agccctactc taaggataag   5100
ttcaagctgt attttcagaa ccctcagttc atgggcggct gggacaagga taaggagaca   5160
gactatcggg ccaccatcct gagatacggc tccaagtact atctggccat catggataag   5220
aagtacgcca agtgcctgca gaagatcgac aaggacgatg tgaacggcaa ttacgagaag   5280
atcaactata agctgctgcc cggccctaat aagatgctgc caaaggtgtt cttttctaag   5340
aagtggatgg cctactataa ccccagcgag gacatccaga agatctacaa gaatggtacc   5400
ttcaagaagg gcgatatgtt taacctgaat gactgtcaca agctgatcga cttctttaag   5460
gatagcatct cccggtatcc aaagtggtcc aatgcctacg atttcaactt ttctgagaca   5520
gagaagtata aggacatcgc cggcttttac agagaggtgg aggagcaggg ctataaggtg   5580
agcttcgagt ctgccagcaa gaaggaggtg gataagctgg tggaggaggg caagctgtat   5640
atgttccaga tctataacaa ggacttttcc gataagtctc acggcacacc caatctgcac   5700
accatgtact tcaagctgct gtttgacgag aacaatcacg gacagatcag gctgagcgga   5760
ggagcagagc tgttcatgag gcgcgcttcc ctgaagaagg aggagctggt ggtgcaccca   5820
gccaactccc ctatcgccaa caagaatcca gataatccca agaaaaccac aaccctgtcc   5880
tacgacgtgt ataaggataa gaggttttct gaggaccagt acgagctgca catcccaatc   5940
gccatcaata agtgccccaa gaacatcttc aagatcaata cagaggtgcg cgtgctgctg   6000
aagcacgacg ataaccccta tgtgatcggc atcgataggg gcgagcgcaa tctgctgtat   6060
atcgtggtgg tggacggcaa gggcaacatc gtggagcagt attccctgaa cgagatcatc   6120
aacaacttca acggcatcag gatcaagaca gattaccact ctctgctgga caagaaggag   6180
aaggagaggt tcgaggcccg ccagaactgg acctccatcg agaatatcaa ggagctgaag   6240
gccggctata tctctcaggt ggtgcacaag atctgcgagc tggtggagaa gtacgatgcc   6300
gtgatcgccc tggaggacct gaactctggc tttaagaata gccgcgtgaa ggtggagaag   6360
caggtgtatc agaagttcga gaagatgctg atcgataagc tgaactacat ggtggacaag   6420
aagtctaatc cttgtgcaac aggcggcgcc ctgaagggct atcagatcac caataagttc   6480
gagagcttta agtccatgtc tacccagaac ggcttcatct tttacatccc tgcctggctg   6540
acatccaaga tcgatccatc taccggcttt gtgaacctgc tgaaaaccaa gtataccagc   6600
atcgccgatt ccaagaagtt catcagctcc tttgacagga tcatgtacgt gcccgaggag   6660
```

```
gatctgttcg agtttgccct ggactataag aacttctctc gcacagacgc cgattacatc   6720
aagaagtgga agctgtactc ctacggcaac cggatcagaa tcttccggaa tcctaagaag   6780
aacaacgtgt tcgactggga ggaggtgtgc ctgaccagcg cctataagga gctgttcaac   6840
aagtacggca tcaattatca gcagggcgat atcagagccc tgctgtgcga gcagtccgac   6900
aaggccttct actctagctt tatggccctg atgagcctga tgctgcagat gcggaacagc   6960
atcacaggcc gcaccgacgt ggattttctg atcagccctg tgaagaactc cgacggcatc   7020
ttctacgata gccggaacta tgaggcccag gagaatgcca tcctgccaaa gaacgccgac   7080
gccaatggcg cctataacat cgccagaaag gtgctgtggg ccatcggcca gttcaagaag   7140
gccgaggacg agaagctgga taaggtgaag atcgccatct ctaacaagga gtggctggag   7200
tacgcccaga ccagcgtgaa gcacaaaagg ccggcggcca cgaaaaaggc cggccaggcc   7260
aaaaagaaaa agggctctag ctacgctcta gctgcatagg gaacaaaagc tggagcttct   7320
ttgaaaagat aatgtatgat tatgctttca ctcatattta tacagaaact tgatgttttc   7380
tttcgagtat atacaaggtg attacatgta cgtttgaagt acaactctag attttgtagt   7440
gccctcttgg gctagcggta aaggtgcgca tttttttcaca ccctacaatg ttctgttcaa   7500
aagattttgg tcaaacgctg tagaagtgaa agttggtgcg catgtttcgg cgttcgaaac   7560
ttctccgcag tgaaagataa atgatctaat ttctactgtt gtagattggt gctggggtta   7620
ccggcctgtt tttttttgtt ttttatgtct accggtcggc cggtaccatc ccgggtagat   7680
ctttgaaaag ataatgtatg attatgcttt cactcatatt tatacagaaa cttgatgttt   7740
tctttcgagt atatacaagg tgattacatg tacgtttgaa gtacaactct agattttgta   7800
gtgccctctt gggctagcgg taaaggtgcg catttttttca caccctacaa tgttctgttc   7860
aaaagatttt ggtcaaacgc tgtagaagtg aaagttggtg cgcatgtttc ggcgttcgaa   7920
acttctccgc agtgaaagat aaatgatcta atttctactg ttgtagattc caataacgga   7980
atccaacttg tttttttttg ttttttatgt ctaccggtcg gccggtaccc aattcgccct   8040
atagcctagg agctccaatt cgccctatag tgagtcgtat tacaattcac tggccgtcgt   8100
tttacaacgt cgtgactggg aaaaccctgg cgttacccaa cttaatcgcc ttgcagcaca   8160
tccccctttc gccagctggc gtaatagcga agaggcccgc accgatcgcc cttcccaaca   8220
gttgcgcagc ctgaatggcg aatggacgcg ccctgtagcg gcgcattaag cgcggcgggt   8280
gtggtggtta cgcgcagcgt gaccgctaca cttgccagcg ccctagcgcc cgctcctttc   8340
gctttcttcc cttcctttct cgccacgttc gccggctttc cccgtcaagc tctaaatcgg   8400
gggctccctt tagggttccg atttagtgct ttacggcacc tcgaccccaa aaaacttgat   8460
tagggtgatg gttcacgtag tgggccatcg ccctgataga cggtttttcg ccctttgacg   8520
ttggagtcca cgttctttaa tagtggactc ttgttccaaa ctggaacaac actcaaccct   8580
atctcggtct attcttttga tttataaggg attttgccga tttcggccta ttggttaaaa   8640
aatgagctga tttaacaaaa atttaacgcg aattttaaca aaatattaac gtttacaatt   8700
tcctgatgcg gtattttctc cttacgcatc tgtgcggtat ttcacaccgc atatcgaccc   8760
tcgaggagaa cttctagtat atccacatac ctaatattat tgccttatta aaaatggaat   8820
cggaacaatt acatcaaaat ccacattctc ttcaaaatca attgtcctgt acttccttgt   8880
tcatgtgtgt tcaaaaacgt tatatttata ggataattat actctatttc tcaacaagta   8940
attggttgtt tggccgagcg gtctaaggcg cctgattcaa gaaatatctt gaccgcagtt   9000
```

```
aactgtggga atactcaggt atcgtaagat gcaagagttc gaatctctta gcaaccatta    9060
ttttttttcct caacataacg agaacacaca ggggcgctat cgcacagaat caaattcgat    9120
gactggaaat tttttgttaa tttcagaggt cgcctgacgc atataccttt ttcaactgaa    9180
aaattgggag aaaaaggaaa ggtgagaggc cggaaccggc ttttcatata gaatagagaa    9240
gcgttcatga ctaaatgctt gcatcacaat acttgaagtt gacaatatta tttaaggacc    9300
tattgttttt tccaataggt ggttagcaat cgtcttactt tctaactttt cttacctttt    9360
acatttcagc aatatatata tatatttcaa ggatatacca ttctaatgtc tgcccctatg    9420
tctgccccta agaagatcgt cgttttgcca ggtgaccacg ttggtcaaga aatcacagcc    9480
gaagccatta aggttcttaa agctatttct gatgttcgtt ccaatgtcaa gttcgatttc    9540
gaaaatcatt taattggtgg tgctgctatc gatgctacag gtgtcccact tccagatgag    9600
gcgctggaag cctccaagaa ggttgatgcc gttttgttag gtgctgtggg tggtcctaaa    9660
tggggtaccg gtagtgttag acctgaacaa ggtttactaa aaatccgtaa agaacttcaa    9720
ttgtacgcca acttaagacc atgtaacttt gcatccgact ctcttttaga cttatctcca    9780
atcaagccac aatttgctaa aggtactgac ttcgttgttg tcagagaatt agtgggaggt    9840
atttactttg gtaagagaaa ggaagacgat ggtgatggtg tcgcttggga tagtgaacaa    9900
tacaccgttc cagaagtgca aagaatcaca agaatggccg ctttcatggc cctacaacat    9960
gagccaccat tgcctatttg gtccttggat aaagctaatg ttttggcctc ttcaagatta   10020
tggagaaaaa ctgtggagga aaccatcaag aacgaattcc ctacattgaa ggttcaacat   10080
caattgattg attctgccgc catgatccta gttaagaacc caacccacct aaatggtatt   10140
ataatcacca gcaacatgtt tggtgatatc atctccgatg aagcctccgt tatcccaggt   10200
tccttgggtt tgttgccatc tgcgtccttg gcctctttgc cagacaagaa caccgcattt   10260
ggtttgtacg aaccatgcca cggttctgct ccagatttgc caaagaataa ggttgaccct   10320
atcgccacta tcttgtctgc tgcaatgatg ttgaaattgt cattgaactt gcctgaagaa   10380
ggtaaggcca ttgaagatgc agttaaaaag gttttggatg caggtatcag aactggtgat   10440
ttaggtggtt ccaacagtac caccgaagtc ggtgatgctg tcgccgaaga agttaagaaa   10500
atccttgctt aaaaagattc tcttttttta tgatatttgt acataaactt tataaatgaa   10560
attcataata gaaacgacac gaaattacaa aatggaatat gttcataggg tagacgaaac   10620
tatatacgca atctacatac atttatcaag aaggagaaaa aggaggatag taaaggaata   10680
caggtaagca aattgatact aatggctcaa cgtgataagg aaaaagaatt gcactttaac   10740
attaatattg acaaggagga gggcaccaca caaaaagtta ggtgtaacag aaaatcatga   10800
aactacgatt cctaatttga tattggagga ttttctctaa aaaaaaaaaa atacaacaaa   10860
taaaaaacac tcaatgacct gaccatttga tggagtttaa gtcaatacct tcttgaacca   10920
tttcccataa tggtgaaagt tccctcaaga attttactct gtcagaaacg gccttacgac   10980
gtagtcgata tggtgcactc tcagtacaat ctgctctgat gccgcatagt taagccagcc   11040
ccgacacccg ccaacacccg ctgacgcgcc ctgacgggct tgtctgctcc cggcatccgc   11100
ttacagacaa gctgtgaccg tctccgggag ctgcatgtgt cagaggtttt caccgtcatc   11160
accgaaacgc gcga                                                     11174
```

<210> SEQ ID NO 330
<211> LENGTH: 11165
<212> TYPE: DNA
<213> ORGANISM: Artificial Sequence

```
<220> FEATURE:
<223> OTHER INFORMATION: Synthetic Sequence - synthetic oligonucleotide:
      Vector 3687
<220> FEATURE:
<221> NAME/KEY: misc_feature
<222> LOCATION: (70)..(573)
<223> OTHER INFORMATION: CEN/ARS
<220> FEATURE:
<221> NAME/KEY: promoter
<222> LOCATION: (610)..(714)
<223> OTHER INFORMATION: AmpR promoter
<220> FEATURE:
<221> NAME/KEY: gene
<222> LOCATION: (715)..(1575)
<223> OTHER INFORMATION: AmpR
<220> FEATURE:
<221> NAME/KEY: rep_origin
<222> LOCATION: (1746)..(2334)
<223> OTHER INFORMATION: ori
<220> FEATURE:
<221> NAME/KEY: promoter
<222> LOCATION: (2853)..(3510)
<223> OTHER INFORMATION: GAL1,10 promoter
<220> FEATURE:
<221> NAME/KEY: protein_bind
<222> LOCATION: (3069)..(3186)
<223> OTHER INFORMATION: UAS
<220> FEATURE:
<221> NAME/KEY: gene
<222> LOCATION: (3541)..(7224)
<223> OTHER INFORMATION: LbCpf1
<220> FEATURE:
<221> NAME/KEY: sig_peptide
<222> LOCATION: (7225)..(7272)
<223> OTHER INFORMATION: nucleoplasmin NLS
<220> FEATURE:
<221> NAME/KEY: misc_feature
<222> LOCATION: (7282)..(7287)
<223> OTHER INFORMATION: protein degradation tag
<220> FEATURE:
<221> NAME/KEY: promoter
<222> LOCATION: (7309)..(7577)
<223> OTHER INFORMATION: SNR52 promoter
<220> FEATURE:
<221> NAME/KEY: misc_structure
<222> LOCATION: (7579)..(7597)
<223> OTHER INFORMATION: Fn_crRNA
<220> FEATURE:
<221> NAME/KEY: terminator
<222> LOCATION: (7622)..(7641)
<223> OTHER INFORMATION: sup4 term
<220> FEATURE:
<221> NAME/KEY: terminator
<222> LOCATION: (7648)..(7648)
<223> OTHER INFORMATION: CYC1 terminator
<220> FEATURE:
<221> NAME/KEY: promoter
<222> LOCATION: (7671)..(7939)
<223> OTHER INFORMATION: SNR52 promoter
<220> FEATURE:
<221> NAME/KEY: misc_structure
<222> LOCATION: (7941)..(7959)
<223> OTHER INFORMATION: Fn_crRNA
<220> FEATURE:
<221> NAME/KEY: terminator
<222> LOCATION: (7984)..(8003)
<223> OTHER INFORMATION: sup4 term
<220> FEATURE:
<221> NAME/KEY: rep_origin
<222> LOCATION: (8237)..(8692)
<223> OTHER INFORMATION: f1 ori
<220> FEATURE:
<221> NAME/KEY: promoter
<222> LOCATION: (8992)..(9396)
<223> OTHER INFORMATION: LEU2 promoter
<220> FEATURE:
<221> NAME/KEY: gene
<222> LOCATION: (9409)..(10503)
<223> OTHER INFORMATION: LEU2
```

<400> SEQUENCE: 330

```
gacgaaaggg cctcgtgata cgcctatttt tataggttaa tgtcatgata ataatggttt     60
cttaggacgg atcgcttgcc tgtaacttac acgcgcctcg tatcttttaa tgatggaata    120
atttgggaat ttactctgtg tttatttatt tttatgtttt gtatttggat tttagaaagt    180
aaataaagaa ggtagaagag ttacggaatg aagaaaaaaa aataaacaaa ggtttaaaaa    240
atttcaacaa aaagcgtact ttacatatat atttattaga caagaaaagc agattaaata    300
gatatacatt cgattaacga taagtaaaat gtaaaatcac aggattttcg tgtgtggtct    360
tctacacaga caagatgaaa caattcggca ttaatacctg agagcaggaa gagcaagata    420
aaaggtagta tttgttggcg atccccctag agtcttttac atcttcggaa aacaaaaact    480
atttttttctt taatttcttt ttttactttc tatttttaat ttatatattt atattaaaaa    540
atttaaatta taattatttt tatagcacgt gatgaaaagg acccaggtgg cacttttcgg    600
ggaaatgtgc gcggaacccc tatttgttta tttttctaaa tacattcaaa tatgtatccg    660
ctcatgagac aataaccctg ataaatgctt caataatatt gaaaaaggaa gagtatgagt    720
attcaacatt tccgtgtcgc ccttattccc ttttttgcgg cattttgcct tcctgttttt    780
gctcacccag aaacgctggt gaaagtaaaa gatgctgaag atcagttggg tgcacgagtg    840
ggttacatcg aactggatct caacagcggt aagatccttg agagttttcg ccccgaagaa    900
cgttttccaa tgatgagcac ttttaaagtt ctgctatgtg gcgcggtatt atcccgtatt    960
gacgccgggc aagagcaact cggtcgccgc atacactatt ctcagaatga cttggttgag   1020
tactcaccag tcacagaaaa gcatcttacg gatggcatga cagtaagaga attatgcagt   1080
gctgccataa ccatgagtga taacactgcg gccaacttac ttctgacaac gatcggagga   1140
ccgaaggagc taaccgcttt tttgcacaac atgggggatc atgtaactcg ccttgatcgt   1200
tgggaaccgg agctgaatga agccatacca aacgacgagc gtgacaccac gatgcctgta   1260
gcaatggcaa caacgttgcg caaactatta actggcgaac tacttactct agcttcccgg   1320
caacaattaa tagactggat ggaggcggat aaagttgcag gaccacttct gcgctcggcc   1380
cttccggctg gctggtttat tgctgataaa tctggagccg gtgagcgtgg gtctcgcggt   1440
atcattgcag cactggggcc agatggtaag ccctcccgta tcgtagttat ctacacgacg   1500
ggcagtcagg caactatgga tgaacgaaat agacagatcg ctgagatagg tgcctcactg   1560
attaagcatt ggtaactgtc agaccaagtt tactcatata tactttagat tgatttaaaa   1620
cttcattttt aatttaaaag gatctaggtg aagatccttt ttgataatct catgaccaaa   1680
atcccttaac gtgagttttc gttccactga gcgtcagacc ccgtagaaaa gatcaaagga   1740
tcttcttgag atcctttttt tctgcgcgta atctgctgct tgcaaacaaa aaaaccaccg   1800
ctaccagcgg tggtttgttt gccggatcaa gagctaccaa ctctttttcc gaaggtaact   1860
ggcttcagca gagcgcagat accaaatact gtccttctag tgtagccgta gttaggccac   1920
cacttcaaga actctgtagc accgcctaca tacctcgctc tgctaatcct gttaccagtg   1980
gctgctgcca gtggcgataa gtcgtgtctt accgggttgg actcaagacg atagttaccg   2040
gataaggcgc agcggtcggg ctgaacgggg ggttcgtgca cacagcccag cttggagcga   2100
acgacctaca ccgaactgag atacctacag cgtgagcatt gagaaagcgc cacgcttccc   2160
gaagggagaa aggcggacag gtatccggta agcggcaggg tcggaacagg agagcgcacg   2220
agggagcttc cagggggaaa cgcctggtat ctttatagtc ctgtcgggtt tcgccacctc   2280
```

-continued

```
tgacttgagc gtcgattttt gtgatgctcg tcaggggggc cgagcctatg gaaaaacgcc   2340
agcaacgcgg cctttttacg gttcctggcc ttttgctggc cttttgctca catgttcttt   2400
cctgcgttat cccctgattc tgtggataac cgtattaccg cctttgagtg agctgatacc   2460
gctcgccgca gccgaacgac cgagcgcagc gagtcagtga gcgaggaagc ggaagagcgc   2520
ccaatacgca aaccgcctct ccccgcgcgt tggccgattc attaatgcag ctggcacgac   2580
aggtttcccg actggaaagc gggcagtgag cgcaacgcaa ttaatgtgag ttacctcact   2640
cattaggcac cccaggcttt acactttatg cttccggctc ctatgttgtg tggaattgtg   2700
agcggataac aatttcacac aggaaacagc tatgaccatg attacgccaa gctcggaatt   2760
aaccctcact aaagggaaca aaagctgggt accgggcccg aattctctcc ttctcttagg   2820
tggcagagca ggtggagggt cgaccatact agtttcaaaa attcttactt tttttttgga   2880
tggacgcaaa gaagtttaat aatcatatta catggcatta ccaccatata catatccata   2940
tacatatcca tatctaatct tacttatatg ttgtggaaat gtaaagagcc ccattatctt   3000
agcctaaaaa aaccttctct ttggaacttt cagtaatacg cttaactgct cattgctata   3060
ttgaagtacg gattagaagc cgccgagcgg gtgacagccc tccgaaggaa gactctcctc   3120
cgtgcgtcct cgtcttcacc ggtcgcgttc ctgaaacgca gatgtgcctc gcgccgcact   3180
gctccgaaca ataaagattc tacaatacta gcttttatgg ttatgaagag gaaaaattgg   3240
cagtaacctg gccccacaaa ccttcaaatg aacgaatcaa attaacaacc ataggatgat   3300
aatgcgatta gttttttagc cttatttctg gggtaattaa tcagcgaagc gatgattttt   3360
gatctattaa cagatatata aatgcaaaaa ctgcataacc actttaacta atactttcaa   3420
cattttcggt ttgtattact tcttattcaa atgtaataaa agtatcaaca aaaaattgtt   3480
aatatacctc tatactttaa cgtcaaggag aaaaaaccca tgggtttcga atctagcatc   3540
atgagcaagc ttgagaagtt tacaaactgc tactccctgt ctaagaccct gaggttcaag   3600
gccatccctg tgggcaagac ccaggagaac atcgacaata agcggctgct ggtggaggac   3660
gagaagagag ccgaggatta taagggcgtg aagaagctgc tggatcgcta ctatctgtct   3720
tttatcaacg acgtgctgca cagcatcaag ctgaagaatc tgaacaatta catcagcctg   3780
ttccggaaga aaaccagaac cgagaaggag aataaggagc tggagaacct ggagatcaat   3840
ctgcggaagg agatcgccaa ggccttcaag ggcaacgagg gctacaagtc cctgtttaag   3900
aaggatatca tcgagacaat cctgccagag ttcctggacg ataaggacga gatcgccctg   3960
gtgaacagct tcaatggctt taccacagcc ttcaccggct tctttgataa cagagagaat   4020
atgttttccg aggaggccaa gagcacatcc atcgccttca ggtgtatcaa cgagaatctg   4080
acccgctaca tctctaatat ggacatcttc gagaaggtgg acgccatctt tgataagcac   4140
gaggtgcagg agatcaagga gaagatcctg aacagcgact atgatgtgga ggatttcttt   4200
gagggcgagt tctttaactt tgtgctgaca caggagggca tcgacgtgta taacgccatc   4260
atcggcggct tcgtgaccga gagcggcgag aagatcaagg gcctgaacga gtacatcaac   4320
ctgtataatc agaaaaccaa gcagaagctg cctaagttta agccactgta taagcaggtg   4380
ctgagcgatc gggagtctct gagcttctac ggcgagggct atacatccga tgaggaggtg   4440
ctggaggtgt ttagaaacac cctgaacaag aacagcgaga tcttcagctc catcaagaag   4500
ctggagaagc tgttcaagaa ttttgacgag tactctagcg ccggcatctt tgtgaagaac   4560
ggccccgcca tcagcacaat ctccaaggat atcttcggcg agtggaacgt gatccgggac   4620
aagtggaatg ccgagtatga cgatatccac ctgaagaaga aggccgtcgt gaccgagaag   4680
```

-continued

```
tacgaggacg atcggagaaa gtccttcaag aagatcggct ccttttctct ggagcagctg   4740
caggagtacg ccgacgccga tctgtctgtg gtggagaagc tgaaggagat catcatccag   4800
aaggtggatg agatctacaa ggtgtatggc tcctctgaga agctgttcga cgccgatttt   4860
gtgctggaga agtctctgaa gaagaacgac gccgtggtgg ccattatgaa ggacctgctg   4920
gattctgtga agtctttcga gaattacatc aaggccttct ttggcgaggg caaggagaca   4980
aacagggacg agtccttcta tggcgatttt gtgctggcct acgacatcct gctgaaggtg   5040
gaccacatct acgatgccat ccgcaattat gtgacccaga agccctactc taaggataag   5100
ttcaagctgt attttcagaa ccctcagttc atgggcggct gggacaagga taaggagaca   5160
gactatcggg ccaccatcct gagatacggc tccaagtact atctggccat catggataag   5220
aagtacgcca agtgcctgca gaagatcgac aaggacgatg tgaacggcaa ttacgagaag   5280
atcaactata agctgctgcc cggccctaat aagatgctgc caaaggtgtt cttttctaag   5340
aagtggatgg cctactataa ccccagcgag gacatccaga agatctacaa gaatggtacc   5400
ttcaagaagg gcgatatgtt taacctgaat gactgtcaca agctgatcga cttctttaag   5460
gatagcatct cccggtatcc aaagtggtcc aatgcctacg atttcaactt ttctgagaca   5520
gagaagtata aggacatcgc cggcttttac agagaggtgg aggagcaggg ctataaggtg   5580
agcttcgagt ctgccagcaa gaaggaggtg gataagctgg tggaggaggg caagctgtat   5640
atgttccaga tctataacaa ggacttttcc gataagtctc acggcacacc caatctgcac   5700
accatgtact tcaagctgct gtttgacgag aacaatcacg gacagatcag gctgagcgga   5760
ggagcagagc tgttcatgag gcgcgcttcc ctgaagaagg aggagctggt ggtgcaccca   5820
gccaactccc ctatcgccaa caagaatcca gataatccca agaaaaccac aaccctgtcc   5880
tacgacgtgt ataaggataa gaggttttct gaggaccagt acgagctgca catcccaatc   5940
gccatcaata agtgccccaa gaacatcttc aagatcaata cagaggtgcg cgtgctgctg   6000
aagcacgacg ataaccccta tgtgatcggc atcgataggg gcgagcgcaa tctgctgtat   6060
atcgtggtgg tggacggcaa gggcaacatc gtggagcagt attccctgaa cgagatcatc   6120
aacaacttca acggcatcag gatcaagaca gattaccact ctctgctgga caagaaggag   6180
aaggagaggt tcgaggcccg ccagaactgg acctccatcg agaatatcaa ggagctgaag   6240
gccggctata tctctcaggt ggtgcacaag atctgcgagc tggtggagaa gtacgatgcc   6300
gtgatcgccc tggaggacct gaactctggc tttaagaata gccgcgtgaa ggtggagaag   6360
caggtgtatc agaagttcga gaagatgctg atcgataagc tgaactacat ggtggacaag   6420
aagtctaatc cttgtgcaac aggcggcgcc ctgaagggct atcagatcac caataagttc   6480
gagagcttta agtccatgtc tacccagaac ggcttcatct tttacatccc tgcctggctg   6540
acatccaaga tcgatccatc taccggcttt gtgaacctgc tgaaaaccaa gtataccagc   6600
atcgccgatt ccaagaagtt catcagctcc tttgacagga tcatgtacgt gcccgaggag   6660
gatctgttcg agtttgccct ggactataag aacttctctc gcacagacgc cgattacatc   6720
aagaagtgga agctgtactc ctacggcaac cggatcagaa tcttccggaa tcctaagaag   6780
aacaacgtgt tcgactggga ggaggtgtgc ctgaccagcg cctataagga gctgttcaac   6840
aagtacggca tcaattatca gcagggcgat atcagagccc tgctgtgcga gcagtccgac   6900
aaggccttct actctagctt tatggccctg atgagcctga tgctgcagat gcggaacagc   6960
atcacaggcc gcaccgacgt ggattttctg atcagccctg tgaagaactc cgacggcatc   7020
```

```
ttctacgata gccggaacta tgaggcccag gagaatgcca tcctgccaaa gaacgccgac   7080
gccaatggcg cctataacat cgccagaaag gtgctgtggg ccatcggcca gttcaagaag   7140
gccgaggacg agaagctgga taaggtgaag atcgccatct ctaacaagga gtggctggag   7200
tacgcccaga ccagcgtgaa gcacaaaagg ccggcggcca cgaaaaaggc cggccaggcc   7260
aaaaagaaaa agggctctag cacgcgttag ggaacaaaag ctggagcttc tttgaaaaga   7320
taatgtatga ttatgctttc actcatattt atacagaaac ttgatgtttt ctttcgagta   7380
tatacaaggt gattacatgt acgtttgaag tacaactcta gattttgtag tgccctcttg   7440
ggctagcggt aaaggtgcgc atttttttcac accctacaat gttctgttca aaagattttg   7500
gtcaaacgct gtagaagtga aagttggtgc gcatgtttcg gcgttcgaaa cttctccgca   7560
gtgaaagata aatgatctaa tttctactgt tgtagattgg tgctggggtt accggcctgt   7620
ttttttttgt tttttatgtc taccggtcgg ccggtaccat cccgggtaga tctttgaaaa   7680
gataatgtat gattatgctt tcactcatat ttatacagaa acttgatgtt ttctttcgag   7740
tatatacaag gtgattacat gtacgtttga agtacaactc tagattttgt agtgccctct   7800
tgggctagcg gtaaaggtgc gcatttttttc acaccctaca atgttctgtt caaaagattt   7860
tggtcaaacg ctgtagaagt gaaagttggt gcgcatgttt cggcgttcga aacttctccg   7920
cagtgaaaga taaatgatct aatttctact gttgtagatt ccaataacgg aatccaactt   7980
gttttttttt gtttttttatg tctaccggtc ggccggtacc caattcgccc tatagcctag   8040
gagctccaat tcgccctata gtgagtcgta ttacaattca ctggccgtcg ttttacaacg   8100
tcgtgactgg gaaaaccctg gcgttaccca acttaatcgc cttgcagcac atcccccttt   8160
cgccagctgg cgtaatagcg aagaggcccg caccgatcgc ccttcccaac agttgcgcag   8220
cctgaatggc gaatggacgc gccctgtagc ggcgcattaa gcgcggcggg tgtggtggtt   8280
acgcgcagcg tgaccgctac acttgccagc gccctagcgc ccgctccttt cgctttcttc   8340
ccttcctttc tcgccacgtt cgccggcttt ccccgtcaag ctctaaatcg gggggctccct  8400
ttagggttcc gatttagtgc tttacggcac ctcgacccca aaaaacttga ttagggtgat   8460
ggttcacgta gtgggccatc gccctgatag acggtttttc gccctttgac gttggagtcc   8520
acgttcttta atagtggact cttgttccaa actggaacaa cactcaaccc tatctcggtc   8580
tattcttttg atttataagg gattttgccg atttcggcct attggttaaa aaatgagctg   8640
atttaacaaa aatttaacgc gaattttaac aaaatattaa cgtttacaat ttcctgatgc   8700
ggtattttct ccttacgcat ctgtgcggta tttcacaccg catatcgacc ctcgaggaga   8760
acttctagta tatccacata cctaatatta ttgccttatt aaaaatggaa tcggaacaat   8820
tacatcaaaa tccacattct cttcaaaatc aattgtcctg tacttccttg ttcatgtgtg   8880
ttcaaaaacg ttatatttat aggataatta tactctattt ctcaacaagt aattggttgt   8940
ttggccgagc ggtctaaggc gcctgattca agaaatatct tgaccgcagt taactgtggg   9000
aatactcagg tatcgtaaga tgcaagagtt cgaatctctt agcaaccatt attttttttcc  9060
tcaacataac gagaacacac aggggcgcta tcgcacagaa tcaaattcga tgactggaaa   9120
tttttgtta atttcagagg tcgcctgacg catatacctt tttcaactga aaaattggga   9180
gaaaaaggaa aggtgagagg ccggaaccgg cttttcatat agaatagaga agcgttcatg   9240
actaaatgct tgcatcacaa tacttgaagt tgacaatatt atttaaggac ctattgtttt   9300
ttccaatagg tggttagcaa tcgtcttact ttctaacttt tcttaccttt tacatttcag   9360
caatatatat atatatttca aggatatacc attctaatgt ctgcccctat gtctgcccct   9420
```

```
aagaagatcg tcgttttgcc aggtgaccac gttggtcaag aaatcacagc cgaagccatt   9480

aaggttctta aagctatttc tgatgttcgt tccaatgtca agttcgattt cgaaaatcat   9540

ttaattggtg gtgctgctat cgatgctaca ggtgtcccac ttccagatga ggcgctggaa   9600

gcctccaaga aggttgatgc cgttttgtta ggtgctgtgg gtggtcctaa atggggtacc   9660

ggtagtgtta gacctgaaca aggtttacta aaaatccgta aagaacttca attgtacgcc   9720

aacttaagac catgtaactt tgcatccgac tctcttttag acttatctcc aatcaagcca   9780

caatttgcta aaggtactga cttcgttgtt gtcagagaat tagtgggagg tatttacttt   9840

ggtaagagaa aggaagacga tggtgatggt gtcgcttggg atagtgaaca atacaccgtt   9900

ccagaagtgc aaagaatcac aagaatggcc gctttcatgg ccctacaaca tgagccacca   9960

ttgcctattt ggtccttgga taaagctaat gttttggcct cttcaagatt atggagaaaa  10020

actgtggagg aaaccatcaa gaacgaattc cctacattga aggttcaaca tcaattgatt  10080

gattctgccg ccatgatcct agttaagaac ccaacccacc taaatggtat tataatcacc  10140

agcaacatgt ttggtgatat catctccgat gaagcctccg ttatcccagg ttccttgggt  10200

ttgttgccat ctgcgtcctt ggcctctttg ccagacaaga acaccgcatt tggtttgtac  10260

gaaccatgcc acggttctgc tccagatttg ccaaagaata aggttgaccc tatcgccact  10320

atcttgtctg ctgcaatgat gttgaaattg tcattgaact tgcctgaaga aggtaaggcc  10380

attgaagatg cagttaaaaa ggttttggat gcaggtatca gaactggtga tttaggtggt  10440

tccaacagta ccaccgaagt cggtgatgct gtcgccgaag aagttaagaa aatccttgct  10500

taaaaagatt ctcttttttt atgatatttg tacataaact ttataaatga aattcataat  10560

agaaacgaca cgaaattaca aaatggaata tgttcatagg gtagacgaaa ctatatacgc  10620

aatctacata catttatcaa gaaggagaaa aaggaggata gtaaaggaat acaggtaagc  10680

aaattgatac taatggctca acgtgataag gaaaaagaat tgcactttaa cattaatatt  10740

gacaaggagg agggcaccac acaaaaagtt aggtgtaaca gaaaatcatg aaactacgat  10800

tcctaatttg atattggagg attttctcta aaaaaaaaaa aatacaacaa ataaaaaaca  10860

ctcaatgacc tgaccatttg atggagttta agtcaatacc ttcttgaacc atttcccata  10920

atggtgaaag ttccctcaag aattttactc tgtcagaaac ggccttacga cgtagtcgat  10980

atggtgcact ctcagtacaa tctgctctga tgccgcatag ttaagccagc cccgacaccc  11040

gccaacaccc gctgacgcgc cctgacgggc ttgtctgctc ccggcatccg cttacagaca  11100

agctgtgacc gtctccggga gctgcatgtg tcagaggttt tcaccgtcat caccgaaacg  11160

cgcga                                                              11165
```

<210> SEQ ID NO 331
<211> LENGTH: 66
<212> TYPE: DNA
<213> ORGANISM: Escherichia coli

<400> SEQUENCE: 331

```
cttccgcttc actggaagtc gcggtcggaa ccgtattgca gcagctttat catctgccgc     60

tggacg                                                                66
```

<210> SEQ ID NO 332
<211> LENGTH: 66
<212> TYPE: DNA
<213> ORGANISM: Escherichia coli

<400> SEQUENCE: 332
cgtccagcgg cagatgataa agctgctgca atacggttcc gaccgcgact tccagtgaag 60
cggaag 66

<210> SEQ ID NO 333
<211> LENGTH: 66
<212> TYPE: DNA
<213> ORGANISM: Escherichia coli

<400> SEQUENCE: 333
cttccgcttc actggaagtc acaatcggaa ccgtattgca gtagctttat catctgccgc 60
tggacg 66

<210> SEQ ID NO 334
<211> LENGTH: 66
<212> TYPE: DNA
<213> ORGANISM: Escherichia coli

<400> SEQUENCE: 334
cttccgcttc actgaaagtc acaatcggaa ccgtattgca gtagttttat catctgccgc 60
tggacg 66

<210> SEQ ID NO 335
<211> LENGTH: 66
<212> TYPE: DNA
<213> ORGANISM: Escherichia coli

<400> SEQUENCE: 335
cttccgcttc actggaagtc gcaatcggaa ccgtattgca gtagttttat catctgccgc 60
tggacg 66

<210> SEQ ID NO 336
<211> LENGTH: 66
<212> TYPE: DNA
<213> ORGANISM: Escherichia coli

<400> SEQUENCE: 336
cttccgcttc actggaagtc acaatcggaa ccgtattgca gtagttttat catctgccgc 60
tggacg 66

<210> SEQ ID NO 337
<211> LENGTH: 66
<212> TYPE: DNA
<213> ORGANISM: Escherichia coli

<400> SEQUENCE: 337
cttccgcttc actggaagtc acaatcggaa ccgtattgca gcagctttat catctgccgc 60
tggacg 66

<210> SEQ ID NO 338
<211> LENGTH: 50
<212> TYPE: DNA
<213> ORGANISM: Escherichia coli

<400> SEQUENCE: 338
gcggctgata tcgttttgaa ggctgctatc gctgccggtg ctccgaaaga 50

<210> SEQ ID NO 339
<211> LENGTH: 90

-continued

```
<212> TYPE: DNA
<213> ORGANISM: Escherichia coli

<400> SEQUENCE: 339

cgacgctggg gcgtcttatg agcctgctgt caccctttga cgtggtaata taaatgacgg     60

atggctggcc gctgtatgaa tcccgcctga                                     90


<210> SEQ ID NO 340
<211> LENGTH: 90
<212> TYPE: DNA
<213> ORGANISM: Escherichia coli

<400> SEQUENCE: 340

catcaaagca atgtgccgcg tgctccgggt ggcccgcagc ggctagtata cataatgtca     60

gcggcggaca aggataagca cgcgtcagca                                     90
```